US007812148B2

(12) United States Patent
Crombie et al.

(10) Patent No.: US 7,812,148 B2

(45) Date of Patent: Oct. 12, 2010

(54) VECTORS COMPRISING CPG ISLANDS WITHOUT POSITION EFFECT VARIGATION AND HAVING INCREASED EXPRESSION

(75) Inventors: Robert Lachlan Crombie, Cheshire (GB); Steven Geraint Williams, Cheshire (GB)

(73) Assignee: Millipore Corporation, Billerica, MA (US)

( * ) Notice: Subject to any disclaimer, the term of this patent is extended or adjusted under 35 U.S.C. 154(b) by 488 days.

(21) Appl. No.: 10/117,960

(22) Filed: Apr. 5, 2002

(65) Prior Publication Data

US 2003/0166890 A1 Sep. 4, 2003

Related U.S. Application Data

(60) Provisional application No. 60/281,605, filed on Apr. 5, 2001, provisional application No. 60/298,675, filed on Jun. 15, 2001.

(30) Foreign Application Priority Data

Apr. 17, 2001 (GB) ................................ 0109335.0

(51) Int. Cl.

*C07H 21/02* (2006.01)
*C07H 21/04* (2006.01)
*A01N 65/00* (2009.01)
*A01N 43/04* (2006.01)
*A61K 31/70* (2006.01)

(52) U.S. Cl. .................. 536/24.1; 536/23.1; 514/44 R; 424/93.1

(58) Field of Classification Search ....................... None
See application file for complete search history.

(56) References Cited

U.S. PATENT DOCUMENTS 5,583,009 A 12/1996 Palmiter et al.
5,610,053 A 3/1997 Chung et al.
6,689,606 B2 2/2004 Antoniou et al.
6,698,606 B2 * 3/2004 Deubel et al. ............... 215/384
6,881,556 B2 * 4/2005 Antoniou et al. ........... 435/69.1
6,949,361 B2 * 9/2005 Antoniou et al. ........... 435/69.1
6,964,951 B2 11/2005 Antoniou et al.
7,442,787 B2 10/2008 Antoniou et al.

FOREIGN PATENT DOCUMENTS

WO WO94/13273 6/1994
WO WO95/33841 12/1995
WO WO 98/07876 2/1998
WO WO 00/05393 2/2000
WO WO 02/24930 3/2002
WO WO 02/081677 10/2002
WO WO 02/099089 12/2002
WO WO 03/006607 1/2003

OTHER PUBLICATIONS

Scheule, et al. (2000) Adv. Drug Deliv. Rev., 44: 119-34.*
Kress, et al. (2001) FEBS Lett., 494: 135-40.*
Antoniou, et al. (2003) Genomics, 82: 269-79.*
Williams, et al. (2005) BMC Biotechnology, 5(1): 17 (pp. 1-9).*
Stimson, et al. (2002) J. Biol. Chem., 277: 4951-58.*
El-Osta, et al. (2002) Molec. Biol. Rep., 28: 209-15.*
Gunning, et al. (1987) Proc. Natl. Acad. Sci., USA., 84: 4831-35.*
Taniguchi, et al. (1988) Nucl. Acids Res., 26(2): 679-80.*
Dulon, et al. (1999) NeuroReport, 10: 1189-93.*
Kozu, et al. (1995) Genomics, 25: 365-371.*
Klucher, et al. (1997) Nucleic Acids Research, 25(23): 4858-60.*
Linton, et al. (1989) “Dual Bidirectional Promoters at the Mouse DHFR Locus: Cloning and Characterization of two mRNA Classes of the Divergently Transcribed Rep-1 gene”, Molecular and Cellular Biology, 9(7): 3058-72.*
Antoniou, et al. (2003) Transgenes Encompassing Dual-Promoter CpG Islands From the Human TBP and HNRPA2B1 Loci are Resistant to Heterochromatin-Mediated Silencing, Genomics, 82(3): 269-79.*
Braastad, et al. “Ku86 Autoantigen Related Protein-1 Transcription Initiates from a CpG Island and is Induced by p53 Through a Nearby p53 Response Element”, Nucleic Acids Research, 30(8): 1713-24.*
Adra, CN. et al., “Cloning and expression of the mouse pgk-1 gene and the nucleotide sequence of its promoter”, *Gene*, 1987, 60, 65-74.
Allen, N.D. et al., “Transgenes as probes for active chromosomal domains in mouse development”, *Nature*, 1988, 333, 852-855.
Antequera, F. et al., “Number of CpG islands and genes in human and mouse”, *Proc. Natl. Acad. Sci. USA*, 1993, 90, 1195-1199.
Artelt, P. et al., “The prokaryotic neomycin-resistance-encoding gene acts as a transcriptional silencer in eukaryotic cells”, *Gene*, 1991, 99, 249-254.
Bender, M.A. et al., “β-globin Gene Switching and Dnase I Sensitivity of the Endogenous β-globin Locus in Mice Do Not Require the Locus Control Region”, *Mol. Cell*, 2000, 5, 387-393.
Bird, A. et al., “A Fraction of the Mouse Genome That is Derived from Islands of Nonmethylated, CpG-Rich DNA”, *Cell*, 1985, 40, 91-99.
Bonnerot, C. et al., “Patterns of expression of position-dependant integrated transgenes in mouse embryo”, *Proc. Natl. Acad. Sci. USA*, 1990, 87, 6331-6335.

(Continued)

*Primary Examiner*—Robert M Kelly
(74) *Attorney, Agent, or Firm*—Cozen O’Connor

(57) ABSTRACT

Polynucleotides and vectors comprising an expressible nucleic acid flanked by a 5' extended methylation-free CpG island and a 3' selectable marker element are disclosed. Such polynucleotides and vectors provide a means for obtaining high levels of expression of the flanked expressible nucleic acid. Preferred embodiments include combinations of 5' extended methylation-free CpG islands and 3' antibiotic resistance genes.

47 Claims, 87 Drawing Sheets

OTHER PUBLICATIONS

Bulger, M. et al., "Looping versus linking:toward a model for long-distance gene activation", *Genes Dev*, 1999, 13, 2465-2477.
Chowdhury, J. Roy., et al., "Long-term improvement of hypercholesterolemia after ex vivo gene therapy in LDLR-Deficient rabbits", *Science*, 1991, 254, 1802-1805.
Cross, S.H. et al., "CpG islands and genes", *Curr. Opin. Genet. Dev.*, 1995, 5, 309-314.
Dillon, N. et al., "Chromatin domains as potential units of eukaryotic gene function", *Curr. Opin. Genet. Dev.*, 1994, 4, 260-264.
Fraser, P. et al., "Locus control regions, chromatin activation and transcription", *Curr. Opin. Cell Biol.*, 1998, 10, 361-365.
Fussenegger, M. et al., "Genetic optimization of recombinant glycoprotein production by mammalian cells", *Trends Biotech*, 1999, 17, 35-42.
Gardiner-Garden, M. et al., "CpG Islands in Vertebrate Genomes", *J. Mol. Biol*, 1987, 196, 261-282.
Gordon, J.W. et al., "Genetic transformation of mouse embryos by microinjection of purified DNA", *Proc. Natl. Acad. Sci USA*, 1980, 77, 7380-7384.
Grosveld, F., "Activation by locus control regions", *Curr. Opin. Genet. Dev.* 1999, 9, 152-157.
Hammer, R.E. et al., "Production of transgenic rabbits, sheep and pigs by microinjection", *Nature*, 1985, 315, 680-683.
Harbers, K.et al., "Microinjection of cloned retroviral genomes into mouse zygotes: integration and expression in the animal", *Nature*, 1981, 293,538-540.
Hicks,G. et al. "Functional genomics in mice by tagged sequence mutagenesis", *Nature Genet*, 1997, 16, 338-344.
Higgs, D.R. Do LCRs open chromatin domains? *Cell*, 1998, 95, 299-302.
Kaufmann, R.J., "Selection and Coamplification of Heterologous Genes in Mammalian Cells", *Methods Enzymol*, 1990, 185, 537-566.
Kioussis, D. et al., "Locus control regions:overcoming heterochromatin-induced gene inactivation in mammals", *Curr. Opin. Genet. Dev.*, 1997, 7, 614-619.
Li, Q. et al., "Locus control regions coming of age ata a decade plus", *Trends Genet.*, 1999, 15, 403-408.
Mei, Q. et al., "The tkNeo gene, but Not the pgkPuro Gene, Can Influence the Ability of the β-Globin LCR to Enhance and Confer Position-Independent Expression onto the β-Globin Gene", *Exp Cell Research*, 2000, 260, 304-312.
Needham, M. et al., "LCR/MEL: A versatile system for high-level expression of heterologous proteins in erythroid cells", *Nucleic Acids Res*, 1992, 20(5), 997-1003.
Needham, M. et al., "Further Development of the Locus Control Regon/Murine Erythroleukemia Expression System: High Level Expression and Characterization of Recombinant Human Calcitonin Receptor", *Protein Expression & Purifacation*, 1995, 6, 124-131.
Palmiter, R.D. et al., "Germ-Line Transformation of Mice", *Ann. Ref Genet.*, 1986, 20, 465-499.
Pikaart, M.J. et al., "Loss of transcriptional activity of a transgene is accompanied by DNA methylation and histone deacetylation and is prevented by insulators", *Genes Dev.*, 1998, 12, 2852-2862.
Rice, P. et al., "EMBOSS:The European Molecular biology Open Software Suite", *Trends Genet*, 2000, 16(6), 276-277.
Tazi & Bird, "Alternative Chromatin Structure at CpG Islands", *Cell*, 1990, 60, 909-920.
Thompson C.J.et al., "Nucleotide sequence of a streptomycete aminoglycoside phosphotransferase gene and its relationship to phosphotransferases encoded by resistance plasmids", *Proc. Natl. Acad. Sci USA*, 1983, 80, 5190-5194.
Vara, J.A. et al., Expression in mammalian cells of a gene from *Streptomyces alboniger* conferring puromycin resistance,*Nucleic Acids Res*, 1986, 14(11), 4617-4624.
Verma, I.M. et al., "Gene therapy-promises,problems and prospects", *Nature*, 1997, 389, 239-242.
Wagner, T.E. et al., "Microinjection of a rabbit β-globin gene into zygotes and its subsequent expression in adult mice and their off-spring", *Proc. Natl. Acad. Sci. USA*, 1981, 78(10), 6376-6380.
Wagner, E.F. et al., "The human β-globin gene and a functional viral thymidine kinase gene in developing mice", *Proc. Natl. Acad. Sci USA*, 1981,78(8), 5016-5020.
Wilson, J.M., et al., "Clinical Protocol: Ex Vivo Gene Therapy of Familial Hypercholesterolemia", *Hum. Gene. Ther.*, 1992, 3, 179-222.
Wise & Pravtcheva, "The Undermethylated State of a CpG Island Region in Igf2 Transgenes Is Dependent on the H19 Enhancers", *Genomics*, 1999, 60, 258-271.
Ortiz et al., "Adjacent DNA elements dominantly restrict the ubiquitous activity of a novel chromatin-opening region to specific tissues," *EMBO J.*, 16(16): 5037-5045, (1997).
Zhuma et al., "Human HMG box transcription factor HBP1: a role in hCD2 LCR function," *EMBO J.*, 18(22):6396-6406, (1999).
Hardison, R., "Hemoglobins from Bacteria To Man: Evolution of Different Patterns of Gene Expression," J. of Experimental Biology 201, 1099-1117 (Mar. 1998), Cambridge, UK.
Shewchuk B. and Hardison R., "CpG Islands from the α-Globin Gene Cluster Increase Gene Expression in an Integration-Dependent Manner," Molecular and Cellular Biology 17(10), 5856-5866 (Oct. 1997), Washington, D.C.
Bonifer, "Long-distance chromatin mechanisms controlling tissue-specific gene locus activation", Gene, 238(2):277-289, Oct. 1999.
Anderson, "Human gene therapy", Nature, 392(Supp):25-30, Apr. 1998.
Corcoran et al., "High-level regulated expression of the human G6PD gene in transgenic mice", Gene, 173(2):241-246, Sep. 1996.
Biamonti et al., "Two homologous genes, originated by duplication, encode the human hnRNP proteins A2 and A1", Nucl. Acids Res., 22(11):1996-2002, Jun. 1994.
Genbank Accession No. U09120, National Library of Medicine, accessed by PTO, Jul. 5, 2000, Dec. 1994, Biamonti, et al.
Genbank Accession No. D28877, National Library of Medicine, accessed by PTO, Jul. 5, 2000, Feb. 1999, Kozu, et al.
Genbank Accession No. AL031259, version AL031259.7 GI:3676176, accessed by PTO, Jul. 13, 2000, Sep. 1998, Griffiths.
Chalut et al., "Genomic structure of the human TATA-box-binding protein (TBP)", Gene, 161(2):277-282, Aug. 1995.
Foulds et al., "Analysis of the human TATA binding protein promoter and identification of an Ets site critica for activity", Nucl. Acids Res., 25(12):2485-2494, Jun. 1997.
Chung et. al.; Characterization of the chicken β-globin insulator, 1997, Proc. Natl. Acad. Sci. vol. 94: 575-580.
Crane-Robinson, C. et al., "Chromosomal mapping of core histone acetylation by immunoselection," Methods, 1997, 12(1), 48-56 (summary only).
DiBartolomeis, S.M. et al., "A superfamily of *Drosophila* satellite related (SR) DNA repeats restricted to the X chromosome euchromatin," Nucl. Acids Res., 1992, 20(5), 1113-1116.
Duhig, T. et al., "The Human Surfeit Locus," Genomics, 1998, 52, 72-78.
Ellis, J. et al., "A dominant chromatin-opening activity in 5' hypersensitive site 3 of the human β-globin locus control region," EMBO J., 1996, 15(3), 562-568.
Ellis, J. et al., "Evaluation of β-globin gene therapy constructs in single copy transgenic mice," Nucl. Acids Res., 1997, 26(6), 1296-1302.
Gaston, K. et al., "CpG methylation has differential effects on the binding of YY1 and ETS proteins to the bi-directional promotor of the Surf-1 and Surf-2 genes" Nucl. Acids Res., 1995, 23(6), 901-909.
Gaston, K. et al., "YY1 is involved in the regulation of the bi-directional promotor of the Surf-1 and Surf-2 genes," FEBS Letts., 1994, 347, 289-294.
Garson, K. et al., "Surf5: A Gene in the Tightly Clustered Mouse Surfeit Locus is Highly Conserved and Transcribed Divergently from the rpL7a (Surf 3) Gene," Genomics, 1996, 30, 163-170.
Gavalas, A. et al., "Analysis of the chicken GPAT/AIRC bidirectional promoter for de novo purine nucleotide synthesis," J. Biol. Chem., 1995, 270(5), 2403-2410.
Lavia, P. et al., "Coincident start sites for divergent transcripts at a randomly selected CpG-rich island of mouse," EMBO J., 1987, 6, 2773-2779.

Palmiter, "The elusive function of metallothioneins," Proc. Natl. Acad. Sci. USA, 1998, 95, 8428-8430.
Talbot, D. et al., "The 5' flanking region of the rat LAP (C/EBPβ) gene can direct high-level, position-independent, copy number-dependent expression in multiple tissues in transgenic mice," Nucl. Acids Res., 1994, 22(5), 756-766.
Williams, T.J. et al., "The MES-1 Murine Enhancer Element is Closely Associated with the Heterogeneous 5' Ends of Two Divergent Transcription Units," Mol. Cell. Biol., 1986, 6(12), 4558-4569.
Winston, J. H. et al., "An intron 1 regulatory region from the murine adenosine deaminase gene can activate heterologous promoters for ubiquitous expression in transgenic mice," Som. Cell Mol. Genet., 1996, 22, 261-278.
Festenstein, R., et al., "Locus control region function and heterochromatic-induced position effect variegation," Science, 1996, 271(23), 1123-1125.
Gavalas, A., et al., "Coexpression of two closely linked avian genes for purine nucleotide synthesis from a bidirectional promoter," Mol. Cell Biol., 1983, 13(8), 4784-4792.
Huxley, C., et al., "The mouse surfeit locus contains a cluster of six genes associated with four Gp G-rich islands in 32 kilobases of genomic DNA," Mol. Cell Biol., 1990, 10(2), 605-614.
Ohbayashi, T., et al., "Promoter structure of the mouse TATA-binding protein (TBP) gene," Biochem. Biophys. Res. Commun., 1996, 225(1), 275-280.
Ryan M.T., et al., "The genes encoding mammalian chaperonin 60 and chaperonin 10 are linked head-to-head and share a bidirectional promoter," Gene: An International J on Genes and Genomes, 1997, 196(1-2), 9-17.
Ursini, et al., 1990. High levels of transcription driven by a 400 bp segment of the human G6PD promotor, Biochem. Biophys. Res. Commun., 170:1203-1209.
Larsen, F. et al., "CpG Islands as Gene Markers in the Human Genome," Genomics, 1992, 13:1095-1107.
Recillas-Targa, F. et al., "Positional enhancer-blocking activity of the chicken β-globin insulator in tranciently transfected cells," Proc. Natl. Acad. Sci. USA, 1999, 96(25):14354-14359.
Ng et al., "Evolution of the Functional Human β-Actin Gene and Its MultiPseudogene Family: Conservation of Noncoding Regions and Chromosomal Dispersion of Pseudogenes," Mol. Cell. Biol., vol. 5, 1985, pp. 2720-2732.
Bell, A.C. & Felsenfield. G., "Stopped at the border: boundaries and insulators" Curr. Opin. Genet. Dev., 1999, 9, 191-198.
Sabbattini, P., Georgiou, A., Sinclaire, C. & Dillon, N., "Analysis of mice with single and multiple copies of transgenes reveals a novel arrangement for the .lambda.5-V-preBI locus control region" Mol. Cell. Biol, 1999,19, 671-679.
Cavazzana-Calvo, M., et al., "Gene Therapy of Human Severe Combined Immunodeficiency (SCID)-X1 Disease," Science, 288:669-672, (2000).
Cheng, L., et al., "A GFP reporter system to assess gene transfer and expression in human hematopoietic progenitor cells," Gene Therapy, 4:1013-1022, (1997).
Cheng, L., et al., "Sustained Gene Expression in Retrovirally Transduced, Engrafting Human Hematopoietic Stem Cells and Their Lympho-Myeloid Progeny," Blood, 92(1):83-92, (Jul. 1, 1998).
Elwood, N.J., et al., "Retroviral Transduction of Human Progenitor Cells: Use of Granulocye Colony-Stimulating Factor Plus Stem Cell Factor to Mobilize Progenitor Cells In Vivo and Stimulation by Flt3/Flk-2 Ligand In Vitro," Blood, 88(12):4452-4462, (Dec. 15, 1996).
Lu, L., et al., "High Efficiency Retroviral Mediated Gene Trnasduction into Single Isolated Immature and Replatable CD34.sup.3+ Hematopoietic Stem/Progenitor Cells from Human Umbilical Cord Blood ," J. Exp. Med., 178:2089-2096, (Dec. 1993).
Whitwam, T., et al., "Retroviral Marking of Canine Bone Marrow: Long-Term, High-Level Expression of Human Interleukin-2 Receptor Common Gamma Chain in Canine Lymphocytes," Blood, 92(5):1565-1575, (Sep. 1, 1998).
Webpage, the National Institutes for Health for Severe Combined Immunodeficiency ("SCID") in 1990.
Juengst, "What next for human gene therapy," Brit. Med. J., vol. 326, pp. 1410-1411.
Ponger Loic et al., "CPGProD: Identifying CpG islands associated with transcription start sites in large genomic mammalian sequences", Bioinformatics (Oxford) 18(4), p. 631-633, Apr. 2002.
Database EMBL (online), "*Mus musculus* ribosomal protein S3 (Rps3) gene, complete cds, and U15a snoRNA and U15b snoRNA genes, complete sequence." EPI assession No. EM: AY043296/ Database assession No. AY043296. Lee, et al.
Database EMBL (online), "H015I23S HO *Hordeum vulgare* cDNA clone H015I23 5-Prime, mRNA sequence." EBI acession No. EM_PRO:CD057580. Database accession No. CD057580, Zierold, et al.

* cited by examiner

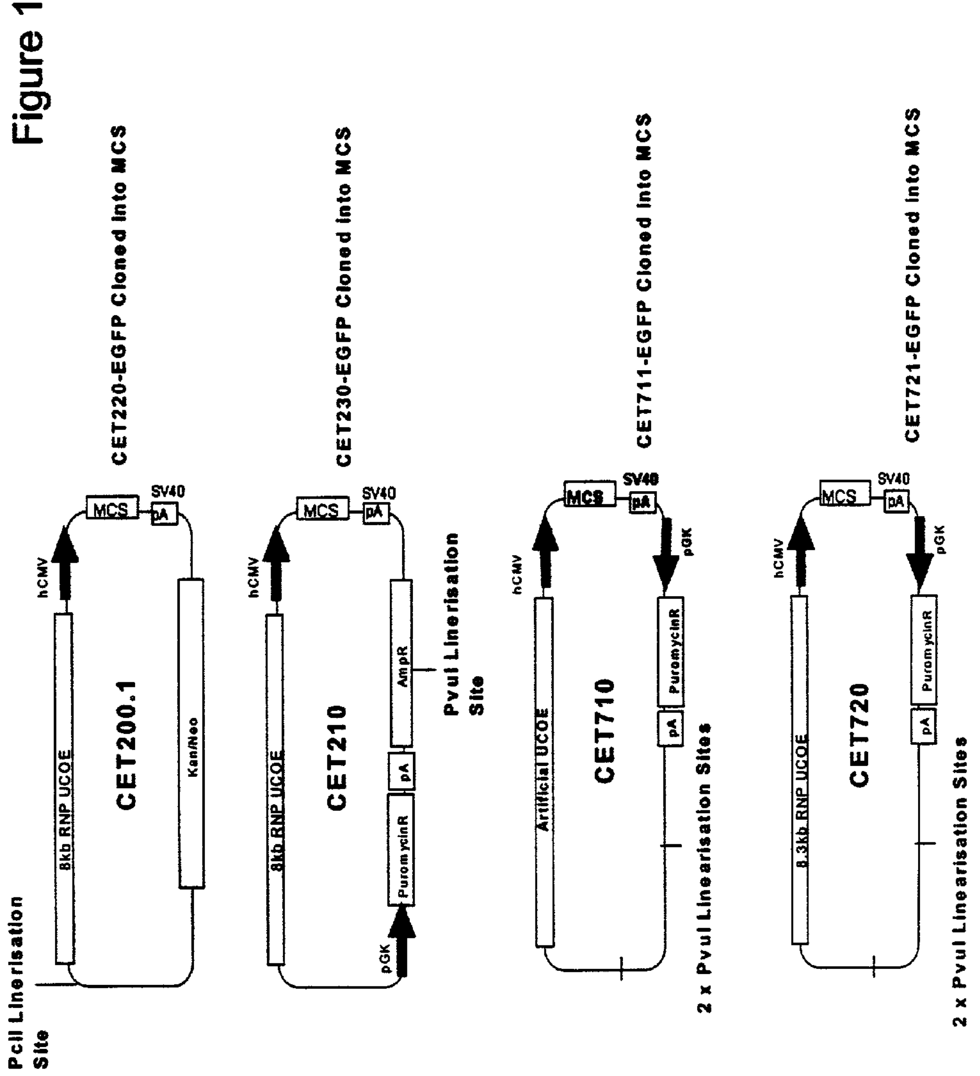
Figure 1
CET200.1
8kb RNP UCOE
hCMV
MCS
SV40
pA
Kan/Neo
Pcil Linerisation Site
CET220-EGFP Cloned into MCS
CET210
8kb RNP UCOE
hCMV
MCS
SV40
pA
AmpR
pA
PuromycinR
pGK
Pvul Linerisation Site
CET230-EGFP Cloned into MCS
CET710
Artificial UCOE
hCMV
MCS
SV40
pA
pGK
PuromycinR
pA
2 x Pvul Linearisation Sites
CET711-EGFP Cloned into MCS
CET720
8.3kb RNP UCOE
hCMV
MCS
SV40
pA
pGK
PuromycinR
pA
2 x Pvul Linearisation Sites
CET721-EGFP Cloned into MCS

Figure 10 CET710 nucleotide sequence

```
   1  GGTGGCACTT TTCGGGGAAA TGTGCGCGGA ACCCCTATTT GTTTATTTTT
      CCACCGTGAA AAGCCCCTTT ACACGCGCCT TGGGGATAAA CAAATAAAAA
  51  CTAAATACAT TCAAATATGT ATCCGCTCAT GAGACAATAA CCCTGATAAA
      GATTTATGTA AGTTTATACA TAGGCGAGTA CTCTGTTATT GGGACTATTT
 101  TGCTTCAATA ATATTGAAAA AGGAAGAGTA TGAGTATTCA ACATTTCCGT
      ACGAAGTTAT TATAACTTTT TCCTTCTCAT ACTCATAAGT TGTAAAGGCA
 151  GTCGCCCTTA TTCCCTTTTT TGCGGCATTT TGCCTTCCTG TTTTTGCTCA
      CAGCGGGAAT AAGGGAAAAA ACGCCGTAAA ACGGAAGGAC AAAAACGAGT
 201  CCCAGAAACG CTGGTGAAAG TAAAAGATGC TGAAGATCAG TTGGGTGCAC
      GGGTCTTTGC GACCACTTTC ATTTTCTACG ACTTCTAGTC AACCCACGTG
 251  GAGTGGGTTA CATCGAACTG GATCTCAACA GCGGTAAGAT CCTTGAGAGT
      CTCACCCAAT GTAGCTTGAC CTAGAGTTGT CGCCATTCTA GGAACTCTCA
 301  TTTCGCCCCG AAGAACGTTT TCCAATGATG AGCACTTTTA AAGTTCTGCT
      AAAGCGGGGC TTCTTGCAAA AGGTTACTAC TCGTGAAAAT TTCAAGACGA
 351  ATGTGGCGCG GTATTATCCC GTATTGACGC CGGGCAAGAG CAACTCGGTC
      TACACCGCGC CATAATAGGG CATAACTGCG GCCCGTTCTC GTTGAGCCAG
 401  GCCGCATACA CTATTCTCAG AATGACTTGG TTGAGTACTC ACCAGTCACA
      CGGCGTATGT GATAAGAGTC TTACTGAACC AACTCATGAG TGGTCAGTGT
 451  GAAAAGCATC TTACGGATGG CATGACAGTA AGAGAATTAT GCAGTGCTGC
      CTTTTCGTAG AATGCCTACC GTACTGTCAT TCTCTTAATA CGTCACGACG
 501  CATAACCATG AGTGATAACA CTGCGGCCAA CTTACTTCTG ACAACGATCG
      GTATTGGTAC TCACTATTGT GACGCCGGTT GAATGAAGAC TGTTGCTAGC
 551  GAGGACCGAA GGAGCTAACC GCTTTTTTGC ACAACATGGG GGATCATGTA
      CTCCTGGCTT CCTCGATTGG CGAAAAAACG TGTTGTACCC CCTAGTACAT
 601  ACTCGCCTTG ATCGTTGGGA ACCGGAGCTG AATGAAGCCA TACCAAACGA
      TGAGCGGAAC TAGCAACCCT TGGCCTCGAC TTACTTCGGT ATGGTTTGCT
 651  CGAGCGTGAC ACCACGATGC CTGTAGCAAT GGCAACAACG TTGCGCAAAC
      GCTCGCACTG TGGTGCTACG GACATCGTTA CCGTTGTTGC AACGCGTTTG
 701  TATTAACTGG CGAACTACTT ACTCTAGCTT CCCGGCAACA ATTAATAGAC
      ATAATTGACC GCTTGATGAA TGAGATCGAA GGGCCGTTGT TAATTATCTG
 751  TGGATGGAGG CGGATAAAGT TGCAGGACCA CTTCTGCGCT CGGCCCTTCC
      ACCTACCTCC GCCTATTTCA ACGTCCTGGT GAAGACGCGA GCCGGGAAGG
 801  GGCTGGCTGG TTTATTGCTG ATAAATCTGG AGCCGGTGAG CGTGGGTCTC
      CCGACCGACC AAATAACGAC TATTTAGACC TCGGCCACTC GCACCCAGAG
 851  GCGGTATCAT TGCAGCACTG GGGCCAGATG GTAAGCCCTC CCGTATCGTA
      CGCCATAGTA ACGTCGTGAC CCCGGTCTAC CATTCGGGAG GGCATAGCAT
 901  GTTATCTACA CGACGGGGAG TCAGGCAACT ATGGATGAAC GAAATAGACA
      CAATAGATGT GCTGCCCCTC AGTCCGTTGA TACCTACTTG CTTTATCTGT
 951  GATCGCTGAG ATAGGTGCCT CACTGATTAA GCATTGGTAA CTGTCAGACC
      CTAGCGACTC TATCCACGGA GTGACTAATT CGTAACCATT GACAGTCTGG
1001  AAGTTTACTC ATATATACTT TAGATTGATT TAAAACTTCA TTTTTAATTT
      TTCAAATGAG TATATATGAA ATCTAACTAA ATTTTGAAGT AAAAATTAAA
1051  AAAAGGATCT AGGTGAAGAT CCTTTTTGAT AATCTCATGA CCAAAATCCC
      TTTTCCTAGA TCCACTTCTA GGAAAAACTA TTAGAGTACT GGTTTTAGGG
1101  TTAACGTGAG TTTTCGTTCC ACTGAGCGTC AGACCCCGTA GAAAAGATCA
      AATTGCACTC AAAAGCAAGG TGACTCGCAG TCTGGGGCAT CTTTTCTAGT
1151  AAGGATCTTC TTGAGATCCT TTTTTTCTGC GCGTAATCTG CTGCTTGCAA
      TTCCTAGAAG AACTCTAGGA AAAAAAGACG CGCATTAGAC GACGAACGTT
1201  ACAAAAAAAC CACCGCTACC AGCGGTGGTT TGTTTGCCGG ATCAAGAGCT
      TGTTTTTTTG GTGGCGATGG TCGCCACCAA ACAAACGGCC TAGTTCTCGA
1251  ACCAACTCTT TTTCCGAAGG TAACTGGCTT CAGCAGAGCG CAGATACCAA
      TGGTTGAGAA AAAGGCTTCC ATTGACCGAA GTCGTCTCGC GTCTATGGTT
1301  ATACTGTCCT TCTAGTGTAG CCGTAGTTAG GCCACCACTT CAAGAACTCT
      TATGACAGGA AGATCACATC GGCATCAATC CGGTGGTGAA GTTCTTGAGA
1351  GTAGCACCGC CTACATACCT CGCTCTGCTA ATCCTGTTAC CAGTGGCTGC
      CATCGTGGCG GATGTATGGA GCGAGACGAT TAGGACAATG GTCACCGACG
1401  TGCCAGTGGC GATAAGTCGT GTCTTACCGG GTTGGACTCA AGACGATAGT
      ACGGTCACCG CTATTCAGCA CAGAATGGCC CAACCTGAGT TCTGCTATCA
1451  TACCGGATAA GGCGCAGCGG TCGGGCTGAA CGGGGGGTTC GTGCACACAG
      ATGGCCTATT CCGCGTCGCC AGCCCGACTT GCCCCCCAAG CACGTGTGTC
1501  CCCAGCTTGG AGCGAACGAC CTACACCGAA CTGAGATACC TACAGCGTGA
      GGGTCGAACC TCGCTTGCTG GATGTGGCTT GACTCTATGG ATGTCGCACT
1551  GCTATGAGAA AGCGCCACGC TTCCCGAAGG GAGAAAGGCG GACAGGTATC
```

Figure 10 cont.

```
      CGATACTCTT TCGCGGTGCG AAGGGCTTCC CTCTTTCCGC CTGTCCATAG
1601  CGGTAAGCGG CAGGGTCGGA ACAGGAGAGC GCACGAGGGA GCTTCCAGGG
      GCCATTCGCC GTCCCAGCCT TGTCCTCTCG CGTGCTCCCT CGAAGGTCCC
1651  GGAAACGCCT GGTATCTTTA TAGTCCTGTC GGGTTTCGCC ACCTCTGACT
      CCTTTGCGGA CCATAGAAAT ATCAGGACAG CCCAAAGCGG TGGAGACTGA
1701  TGAGCGTCGA TTTTTGTGAT GCTCGTCAGG GGGGCGGAGC CTATGGAAAA
      ACTCGCAGCT AAAAACACTA CGAGCAGTCC CCCCGCCTCG GATACCTTTT
1751  ACGCCAGCAA CGCGGCCTTT TTACGGTTCC TGGCCTTTTG CTGGCCTTTT
      TGCGGTCGTT GCGCCGGAAA AATGCCAAGG ACCGGAAAAC GACCGGAAAA
1801  GCTCACATGT TCTTTCCTGC GTTATCCCCT GATTCTGTGG ATAACCGTAT
      CGAGTGTACA AGAAAGGACG CAATAGGGGA CTAAGACACC TATTGGCATA
1851  TACCGCCTTT GAGTGAGCTG ATACCGCTCG CCGCAGCCGA ACGACCGAGC
      ATGGCGGAAA CTCACTCGAC TATGGCGAGC GGCGTCGGCT TGCTGGCTCG
1901  GCAGCGAGTC AGTGAGCGAG GAAGCGGAAG AGCGCCCAAT ACGCAAACCG
      CGTCGCTCAG TCACTCGCTC CTTCGCCTTC TCGCGGGTTA TGCGTTTGGC
1951  CCTCTCCCCG CGCGTTGGCC GATTCATTAA TGCAGCTGGC ACGACAGGTT
      GGAGAGGGGC GCGCAACCGG CTAAGTAATT ACGTCGACCG TGCTGTCCAA
2001  TCCCGACTGG AAAGCGGGCA GTGAGCGCAA CGCAATTAAT GTGAGTTAGC
      AGGGCTGACC TTTCGCCCGT CACTCGCGTT GCGTTAATTA CACTCAATCG
2051  TCACTCATTA GGCACCCCAG GCTTTACACT TTATGCTTCC GGCTCGTATG
      AGTGAGTAAT CCGTGGGGTC CGAAATGTGA AATACGAAGG CCGAGCATAC
2101  TTGTGTGGAA TTGTGAGCGG ATAACAATTT CACACAGGAA ACAGCTATGA
      AACACACCTT AACACTCGCC TATTGTTAAA GTGTGTCCTT TGTCGATACT
2151  CCATGATTAC GCCAAGCGCG CAATTAACCC TCACTAAAGG GAACAAAAGC
      GGTACTAATG CGGTTCGCGC GTTAATTGGG AGTGATTTCC CTTGTTTTCG
2201  TGGGTACCGG GCCCCCCCTC GAGGTCGACG GTATCGATAA GCTCGATAAG
      ACCCATGGCC CGGGGGGGAG CTCCAGCTGC CATAGCTATT CGAGCTATTC
2251  CTCATGGCAC CTGTATTGTA CTCTTATCAG TCATTATATG GACTTTAACT
      GAGTACCGTG GACATAACAT GAGAATAGTC AGTAATATAC CTGAAATTGA
2301  TCCCCAGATA TTATTTGGGC TCCTCCATAA GACTGTGAGC ATCTGACCAC
      AGGGGTCTAT AATAAACCCG AGGAGGTATT CTGACACTCG TAGACTGGTG
2351  TGGAGTGTTG CTTCCCATTA TATCCCTGTT ATCAAGCACA AGGTCAGGCA
      ACCTCACAAC GAAGGGTAAT ATAGGGACAA TAGTTCGTGT TCCAGTCCGT
2401  CAGAGTAAGA CTCAAAACAT GTTTTGGAAT GTATGACTGG TATGAACTAC
      GTCTCATTCT GAGTTTTGTA CAAAACCTTA CATACTGACC ATACTTGATG
2451  AAACCAGTAA GCTGATGTTT TCATTTTGAG TCTATAAATC TAATTTTGTG
      TTTGGTCATT CGACTACAAA AGTAAAACTC AGATATTTAG ATTAAAACAC
2501  GTGGTTTTGT GTATGGCTCA AGGCTCAAAT TGTAAAATTT AATATTATGT
      CACCAAAACA CATACCGAGT TCCGAGTTTA ACATTTTAAA TTATAATACA
2551  GACCAAAGAA AGTTATACCC AGAACCTCAA TTTCCTCACC TTCAAAATGG
      CTGGTTTCTT TCAATATGGG TCTTGGAGTT AAAGGAGTGG AAGTTTTACC
2601  GGCAGTTTCT CACTCATTGG TCTGCTGTCA CGATTTTAAT GAGCTCATGC
      CCGTCAAAGA GTGAGTAACC AGACGACAGT GCTAAAATTA CTCGAGTACG
2651  ACAAACAGCC CTTTATATAA GGTAAGTGCT GGATAAATGT TGGCTACTAT
      TGTTTGTCGG GAAATATATT CCATTCACGA CCTATTTACA ACCGATGATA
2701  AATAAAATAA GCCTCTAAGA TACTTGGTCA GCACAAGTAC TACCCAAGAG
      TTATTTTATT CGGAGATTCT ATGAACCAGT CGTGTTCATG ATGGGTTCTC
2751  TATGCACTGT AAGTAAACTG ACAAAATTGT GTATCTAAAA CTGGCCAGAT
      ATACGTGACA TTCATTTGAC TGTTTTAACA CATAGATTTT GACCGGTCTA
2801  GAAAGAGAAA CTTTTAAGGG GCCCTTCTGC GTGCCCGACA CTGTGCTAGG
      CTTTCTCTTT GAAAATTCCC CGGGAAGACG CACGGGCTGT GACACGATCC
2851  CACTCACACT ATCCCGACCC GAGAAACCGA TCTGCGACCC AGAGGAACTT
      GTGAGTGTGA TAGGGCTGGG CTCTTTGGCT AGACGCTGGG TCTCCTTGAA
2901  ACCAAGCCTC CAGCATCTTG TGCAGCCCTA CTCATGGGAC CATCTGGATA
      TGGTTCGGAG GTCGTAGAAC ACGTCGGGAT GAGTACCCTG GTAGACCTAT
2951  CCCACCCTTG TCTTTACAGG GAGCAGAACA CACCTCTTAT GTGTCAGAAA
      GGGTGGGAAC AGAAATGTCC CTCGTCTTGT GTGGAGAATA CACAGTCTTT
3001  ACAAAGTCCA GGAAGTATAT TTTTACCTGA GGCAATATCT GAAAATTGTA
      TGTTTCAGGT CCTTCATATA AAAATGGACT CCGTTATAGA CTTTTAACAT
3051  TGCTACAGCC TCCAAAGTGA GTCTTCCTCT CAGTACCTCT CTTCTAGGCA
      ACGATGTCGG AGGTTTCACT CAGAAGGAGA GTCATGGAGA GAAGATCCGT
3101  CATGGAGCCC TTTCTTCCAA GTATTATGTT TAACCACTTA ATGAATGAAG
      GTACCTCGGG AAAGAAGGTT CATAATACAA ATTGGTGAAT TACTTACTTC
3151  TCCTGAAACT GCTTACCCAT GCTCCCTATA ATCTCTGAGT AATCTTCCTT
      AGGACTTTGA CGAATGGGTA CGAGGGATAT TAGAGACTCA TTAGAAGGAA
3201  TTCCACAACC TCAGGCATAA TCTCATCTTC TGTTTCTATT ACAATTTCAA
```

Figure 10 cont.

```
      AAGGTGTTGG AGTCCGTATT AGAGTAGAAG ACAAAGATAA TGTTAAAGTT
3251  ATTCTGGAAA AAGGAAGTTG TGGTCTGGAA TTATATGGTC CAGATGATCT
      TAAGACCTTT TTCCTTCAAC ACCAGACCTT AATATACCAG GTCTACTAGA
3301  GAAACAAAAA GGACAGCACT ATTAGTAATC ATTTAGTTTT GAAGACAGTC
      CTTTGTTTTT CCTGTCGTGA TAATCATTAG TAAATCAAAA CTTCTGTCAG
3351  TAATAATTTG CTGTCTCTAA AGTACTATAT TCCCTATAGT TCTGGCATTT
      ATTATTAAAC GACAGAGATT TCATGATATA AGGGATATCA AGACCGTAAA
3401  TAGATAAAGG GTCATAAATT AAATGCCTAT ATGGTGACAT TATTCAGTGA
      ATCTATTTCC CAGTATTTAA TTTACGGATA TACCACTGTA ATAAGTCACT
3451  TTCAGACTTC ACAGCCTTTT TTTTTTTTTT ACAAAGGTGT TCCAGGCATG
      AAGTCTGAAG TGTCGGAAAA AAAAAAAAAA TGTTTCCACA AGGTCCGTAC
3501  AAAAATTTTA AAGTACTATA CCTTTCCTAA TTTTACCTTT AAAGTTGTCC
      TTTTTAAAAT TTCATGATAT GGAAAGGATT AAAATGGAAA TTTCAACAGG
3551  TGGAAATATC TGGGTTGACA AAGGCGATGA AACTGAACTG AGACTTAAAA
      ACCTTTATAG ACCCAACTGT TTCCGCTACT TTGACTTGAC TCTGAATTTT
3601  AAAAGATTAC CCACCTGGTT GTGCACAAGC CTGCTTATGT CCCAATCTCC
      TTTTCTAATG GGTGGACCAA CACGTGTTCG GACGAATACA GGGTTAGAGG
3651  AGTCTAGGGT CTGATGCTCC TTGCTGCAGT AATATGCTTT GTGGCATCTG
      TCAGATCCCA GACTACGAGG AACGACGTCA TTATACGAAA CACCGTAGAC
3701  GAGCACGTTT TGGGGCCTAA ACAGCCACAA ACCCTGCAGA GATGAGCACC
      CTCGTGCAAA ACCCCGGATT TGTCGGTGTT TGGGACGTCT CTACTCGTGG
3751  AGACTTAAGC TGGAGACACA CTGATTCTCC TGTTTCTGGG GGAGGATTCT
      TCTGAATTCG ACCTCTGTGT GACTAAGAGG ACAAAGACCC CCTCCTAAGA
3801  CAGAAGGTGG CTCATATGAG TAAAAATCGT TTTTCCTGGG TAGTTGATTC
      GTCTTCCACC GAGTATACTC ATTTTTAGCA AAAAGGACCC ATCAACTAAG
3851  CTAAAAACTA AAAAAGAATA CAGAGAAAAG TTTTATCTTC AAACAAAACA
      GATTTTTGAT TTTTTCTTAT GTCTCTTTTC AAAATAGAAG TTTGTTTTGT
3901  GCAATTCACA TATTTTATCC TCTGCACGTA AAACTGAAAA TAACAACAAC
      CGTTAAGTGT ATAAAATAGG AGACGTGCAT TTTGACTTTT ATTGTTGTTG
3951  AAAAAAGAAA TGAAAGTTTT TGCTTTCAGG AATAAGCTTT TAAAATCCAG
      TTTTTTCTTT ACTTTCAAAA ACGAAAGTCC TTATTCGAAA ATTTTAGGTC
4001  AAACTAGATT TCGTCCGGTA CACGCAACTG AGTTGCCTCC TAGAGGTGGT
      TTTGATCTAA AGCAGGCCAT GTGCGTTGAC TCAACGGAGG ATCTCCACCA
4051  TTGAGTTAAT CAAATTAATA AGACTGATCG TTAAGAACGA CTGCCAAAAA
      AACTCAATTA GTTTAATTAT TCTGACTAGC AATTCTTGCT GACGGTTTTT
4101  TACGAAAAAG CTACTGGGAT CCATCTTTCC AAGACAATTT CTATTATCTG
      ATGCTTTTTC GATGACCCTA GGTAGAAAGG TTCTGTTAAA GATAATAGAC
4151  AATTAACACC ATACCTGGTA CCCACTGATT AAAAGCTGGG GGTTACCAAT
      TTAATTGTGG TATGGACCAT GGGTGACTAA TTTTCGACCC CCAATGGTTA
4201  GCGCGTGGGC ACAGTTAGAA GCTTATGTAG CAAAAATGAG CACATCCTGG
      CGCGCACCCG TGTCAATCTT CGAATACATC GTTTTTACTC GTGTAGGACC
4251  AAGGGCCCGG GAGAAGGTGC TCCTGGGGCA GCGCGGAGAG GGAGCTCTGA
      TTCCCGGGCC CTCTTCCACG AGGACCCCGT CGCGCCTCTC CCTCGAGACT
4301  GGCTGGGGCG GCAGCGGTGC TTGCCGCCGT CCCCCTGGTC GCTCCCGGAA
      CCGACCCCGC CGTCGCCACG AACGGCGGCA GGGGGACCAG CGAGGGCCTT
4351  TTAACGCCGC GCACGCGTCG GAGGCATGGC CCCGTCCCGA CCCCGTTTGG
      AATTGCGGCG CGTGCGCAGC CTCCGTACCG GGGCAGGGCT GGGGCAAACC
4401  CGGCTCACCT CGCAGGCCGG CACAGCACGG CTGCTCGCGG CAGCAGAAGA
      GCCGAGTGGA GCGTCCGGCC GTGTCGTGCC GACGAGCGCC GTCGTCTTCT
4451  GGAAGATGCA GCGGTGGAAG GCGTCCGGGC GGCCAGGCAG CGGCGCATAC
      CCTTCTACGT CGCCACCTTC CGCAGGCCCG CCGGTCCGTC GCCGCGTATG
4501  ACCTGCAGCA GGAAGGAGAG CGGGCGGCCG CACAGCTCGC AGGCCAGGGC
      TGGACGTCGT CCTTCCTCTC GCCCGCCGGC GTGTCGAGCG TCCGGTCCCG
4551  CTGGGGCCCC GGCAGCCCGG CCGCGCCCAG CCATGCCGGC CGCCCGCCCA
      GACCCCGGGG CCGTCGGGCC GGCGCGGGTC GGTACGGCCG GCGGGCGGGT
4601  CCTTGCTGGG GAACTGCTCG CTGCGCAGTC GCCACGCCGG CGCCGACTCG
      GGAACGACCC CTTGACGAGC GACGCGTCAG CGGTGCGGCC GCGGCTGAGC
4651  GCGAAGCCCA GCTCCACAGG CCTGGCCCCG GCGGCAGCCA TGCGGGGCGC
      CGCTTCGGGT CGAGGTGTCC GGACCGGGGC CGCCGTCGGT ACGCCCCGCG
4701  GGGCTGGCGT GGGGCGCAGC CCACAGCTGG GTCGGAAGGC GGAAATCGGG
      CCCGACCGCA CCCCGCGTCG GGTGTCGACC CAGCCTTCCG CCTTTAGCCC
4751  CGCCGGGCCG GAAGGCAAGA GGCGGGCACC TTTCCGGAGG ACAGGAGGCG
      GCGGCCCGGC CTTCCGTTCT CCGCCCGTGG AAAGGCCTCC TGTCCTCCGC
4801  GAAACGCGTC TGACGGGAGC GGTTGCAGGA CCAATGCGAG GGAACGGGGC
      CTTTGCGCAG ACTGCCCTCG CCAACGTCCT GGTTACGCTC CCTTGCCCCG
4851  AGAGGAAACC TCTCGGCATC AGCCCCGCCC CTGGCGCCTC TGCCTCCGAG
```

Figure 10 cont.

```
     TCTCCTTTGG AGAGCCGTAG TCGGGGCGGG GACCGCGGAG ACGGAGGCTC
4901 CCGCTTTCCT GGTGCCTCCG GGTGCTCTGG GATGGTTCTG GTCTTTGGGA
     GGCGAAAGGA CCACGGAGGC CCACGAGACC CTACCAAGAC CAGAAACCCT
4951 GAGTGGCAGC TGGTGACGGC GCTCCGCTCA CCTCTGCACA TGTCTTGCTG
     CTCACCGTCG ACCACTGCCG CGAGGCGAGT GGAGACGTGT ACAGAACGAC
5001 TGGGCCTGCG GGTGGCCGCC AGGGAGGCAG AGCCCTCCCG CAAACCTTCC
     ACCCGGACGC CCACCGGCGG TCCCTCCGTC TCGGGAGGGC GTTTGGAAGG
5051 CTGCTGGTGT CCACCTCAGG GTGTGGGAAA CCTGTGCGCT GGCCGAGTGC
     GACGACCACA GGTGGAGTCC CACACCCTTT GGACACGCGA CCGGCTCACG
5101 TAACCAAGAG TAGGCAGTGA AAGACAAATG AAGGTTGAAC AGGTAAAGTG
     ATTGGTTCTC ATCCGTCACT TTCTGTTTAC TTCCAACTTG TCCATTTCAC
5151 AGGACCCTAC AGCGGAAACC AAGAATCCTG TGTGCCTGAG AGTAATGAAG
     TCCTGGGATG TCGCCTTTGG TTCTTAGGAC ACACGGACTC TCATTACTTC
5201 AAGCCTCTGC AGAAGAGTCT TTTCTGTCAG TCTTAAGGTC TCTGTTTTAA
     TTCGGAGACG TCTTCTCAGA AAAGACAGTC AGAATTCCAG AGACAAAATT
5251 TGTTAGTGCT GGCTTGCTGT ACCTGAATTC CAAGGGAGGA GTGTATAATG
     ACAATCACGA CCGAACGACA TGGACTTAAG GTTCCCTCCT CACATATTAC
5301 AGGCATGGCC AACCCCCACT TCCCATCATT GCCTGAACTA GTTTTTCAGG
     TCCGTACCGG TTGGGGGTGA AGGGTAGTAA CGGACTTGAT CAAAAAGTCC
5351 TTAACTTCAG AATGCCCTTG GTACCGCGGG CCCCCTCTGT GGTCCCACGC
     AATTGAAGTC TTACGGGAAC CATGGCGCCC GGGGGAGACA CCAGGGTGCG
5401 CACTGATCGC TGCATGCCCA CCACCTGGGT ACACACAGTC TGTGATTCCC
     GTGACTAGCG ACGTACGGGT GGTGGACCCA TGTGTGTCAG ACACTAAGGG
5451 GGAGCAGAAC GGACCCTGCC CACCCGGTCT TGTGTGCTAC TCAGTGGACA
     CCTCGTCTTG CCTGGGACGG GTGGGCCAGA ACACACGATG AGTCACCTGT
5501 GACCCAAGGC AAGAAAGGGT GACAAGGACA GGGTCTTCCC AGGCTGGCTT
     CTGGGTTCCG TTCTTTCCCA CTGTTCCTGT CCCAGAAGGG TCCGACCGAA
5551 TGAGTTCCTA GCACCGCCCC GCCCCCAATC CTCTGTGGCA CATGGAGTCT
     ACTCAAGGAT CGTGGCGGGG CGGGGGTTAG GAGACACCGT GTACCTCAGA
5601 TGGTCCCCAG AGTCCCCCAG CGGCCTCCAG ATGGTCTGGG AGGGCAGTTC
     ACCAGGGGTC TCAGGGGGTC GCCGGAGGTC TACCAGACCC TCCCGTCAAG
5651 AGCTGTGGCT GCGCATAGCA GACATACAAC GGACGGTGGG CCCAGACCCA
     TCGACACCGA CGCGTATCGT CTGTATGTTG CCTGCCACCC GGGTCTGGGT
5701 GGCTGTGTAG ACCCAGCCCC CCCGCCCCGC AGTGCCTAGG TCACCCACTA
     CCGACACATC TGGGTCGGGG GGGCGGGGCG TCACGGATCC AGTGGGTGAT
5751 ACGCCCCAGG CCTGGTCTTG GCTGGGCGTG ACTGTTACCC TCAAAAGCAG
     TGCGGGGTCC GGACCAGAAC CGACCCGCAC TGACAATGGG AGTTTTCGTC
5801 GCAGCTCCAG GGTAAAAGGT GCCCTGCCCT GTAGAGCCCA CTTCCTTCCC
     CGTCGAGGTC CCATTTTCCA CGGGACGGGA CATCTCGGGT GAAGGAAGGG
5851 AGGGCTGCGG CTGGGTAGGT TTGTAGCCTT CATCACGGGC CACCTCCAGC
     TCCCGACGCC GACCCATCCA AACATCGGAA GTAGTGCCCG GTGGAGGTCG
5901 CACTGGACCG CTGGCCCCTG CCCTGTCCTG GGGAGTGTGG TCCTGCGACT
     GTGACCTGGC GACCGGGGAC GGGACAGGAC CCCTCACACC AGGACGCTGA
5951 CTAATGGCCG CAAGCCACCT GACTCCCCCA ACACCACACT CTACCTCTCA
     GATTACCGGC GTTCGGTGGA CTGAGGGGGT TGTGGTGTGA GATGGAGAGT
6001 AGCCCAGGTC TCTCCCTAGT GACCCACCCA GCACATTTAG CTAGCTGAGC
     TCGGGTCCAG AGAGGGATCA CTGGGTGGGT CGTGTAAATC GATCGACTCG
6051 CCCACAGCCA GAGGTCCTCA GGCCCTGCTT TCAGGGCAGT TGCTCTGAAG
     GGGTGTCGGT CTCCAGGAGT CCGGGACGAA AGTCCCGTCA ACGAGACTTC
6101 TCGGCAAGGG GGAGTGACTG CCTGGCCACT CCATGCCCTC CAAGAGCTCC
     AGCCGTTCCC CCTCACTGAC GGACCGGTGA GGTACGGGAG GTTCTCGAGG
6151 TTCTGCAGGA GCGTACAGAA CCCAGGGCCC TGGCACCCGT GCAGACCCTG
     AAGACGTCCT CGCATGTCTT GGGTCCCGGG ACCGTGGGCA CGTCTGGGAC
6201 GCCCACCCCA CCTGGGCGCT CAGTGCCCAA GAGATGTCCA CACCTAGGAT
     CGGGTGGGGT GGACCCGCGA GTCACGGGTT CTCTACAGGT GTGGATCCTA
6251 GTCCCGCGGT GGGTGGGGGG CCCGAGAGAC GGGCAGGCCG GGGGCAGGCC
     CAGGGCGCCA CCCACCCCCC GGGCTCTCTG CCCGTCCGGC CCCCGTCCGG
6301 TGGCCATGCG GGGCCGAACC GGGCACTGCC CAGCGTGGGG CGCGGGGGCC
     ACCGGTACGC CCCGGCTTGG CCCGTGACGG GTCGCACCCC GCGCCCCCGG
6351 ACGGCGCGCG CCCCCAGCCC CCGGGCCCAG CACCCCAAGG CGGCCAACGC
     TGCCGCGCGC GGGGGTCGGG GGCCCGGGTC GTGGGGTTCC GCCGGTTGCG
6401 CAAAACTCTC CCTCCTCCTC TTCCTCAATC TCGCTCTCGC TCTTTTTTTT
     GTTTTGAGAG GGAGGAGGAG AAGGAGTTAG AGCGAGAGCG AGAAAAAAAA
6451 TTTCGCAAAA GGAGGGGAGA GGGGGTAAAA AAATGCTGCA CTGTGCGGCG
     AAAGCGTTTT CCTCCCCTCT CCCCCATTTT TTTACGACGT GACACGCCGC
6501 AAGCCGGTGA GTGAGCGGCG CGGGGCCAAT CAGCGTGCGC CGTTCCGAAA
```

Figure 10 cont.

```
      TTCGGCCACT CACTCGCCGC GCCCCGGTTA GTCGCACGCG GCAAGGCTTT
6551  GTTGCCTTTT ATGGCTCGAG CGGCCGCGGC GGCGCCCTAT AAAACCCAGC
      CAACGGAAAA TACCGAGCTC GCCGGCGCCG CCGCGGGATA TTTTGGGTCG
6601  GGCGCGACGC GCCACCACCG CCGAGACCGC GTCCGCCCGC GAGCACAGAG
      CCGCGCTGCG CGGTGGTGGC GGCTCTGGCG CAGGCGGGCG CTCGTGTCTC
6651  CCTCGCCTTT GCCGATCCGC CGCCCGTCCA CACCCGCCGC CAGGTAAGCC
      GGAGCGGAAA CGGCTAGGCG GCGGGCAGGT GTGGGCGGCG GTCCATTCGG
6701  CGGCCAGCCG ACCGGGGCAT GCGGCCGCGG CCCTTCGCCC GTGCAGAGCC
      GCCGGTCGGC TGGCCCCGTA CGCCGGCGCC GGGAAGCGGG CACGTCTCGG
6751  GCCGTCTGGG CCGCAGCGGG GGGCGCATGG GGCGGAACCG GACCGCCGTG
      CGGCAGACCC GGCGTCGCCC CCCGCGTACC CCGCCTTGGC CTGGCGGCAC
6801  GGGGGCGCGG GAGAAGCCCC TGGGCCTCCG GAGATGGGGG ACACCCCACG
      CCCCCGCGCC CTCTTCGGGG ACCCGGAGGC CTCTACCCCC TGTGGGGTGC
6851  CCAGTTCGCA GGCGCGAGGC CGCGCTCGGG CGGGCGCGCT CCGGGGGTGC
      GGTCAAGCGT CCGCGCTCCG GCGCGAGCCC GCCCGCGCGA GGCCCCCACG
6901  CGCTCTCGGG GCGGGGGCAA CCGGCGGGGT CTTTGTCTGA GCCGGGCTCT
      GCGAGAGCCC CGCCCCCGTT GGCCGCCCCA GAAACAGACT CGGCCCGAGA
6951  TGCCAATGGG GATCGCACGG TGGGCGCGGC GTAGCCCCCG TCAGGCCCGG
      ACGGTTACCC CTAGCGTGCC ACCCGCGCCG CATCGGGGGC AGTCCGGGCC
7001  TGGGGGCTGG GGCGCCATGC GCGTGCGCGC TGGTCCTTTG GGCGCTAACT
      ACCCCCGACC CCGCGGTACG CGCACGCGCG ACCAGGAAAC CCGCGATTGA
7051  GCGTGCGCGC TGGGAATTGG CGCTAATTGC GCGTGCGCGC TGGGACTCAA
      CGCACGCGCG ACCCTTAACC GCGATTAACG CGCACGCGCG ACCCTGAGTT
7101  TGGCGCTAAT CGCGCGTGCG TTCTGGGGCC CGGGCGCTTG CGCCACTTCC
      ACCGCGATTA GCGCGCACGC AAGACCCCGG GCCCGCGAAC GCGGTGAAGG
7151  TGCCCGAGCC GCTGGCGCCC GAGGGTGTGG CCGCTGCGTG CGCGCGCGCG
      ACGGGCTCGG CGACCGCGGG CTCCCACACC GGCGACGCAC GCGCGCGCGC
7201  ACCCGGTCGC TGTTTGAACC GGGCGGAGGC GGGGCTGGCG CCCGGTTGGG
      TGGGCCAGCG ACAAACTTGG CCCGCCTCCG CCCCGACCGC GGGCCAACCC
7251  AGGGGGTTGG GGCCTGGCTT CCTGCCGCGC GCCGCGGGGA CGCCTCCGAC
      TCCCCCAACC CCGGACCGAA GGACGGCGCG CGGCGCCCCT GCGGAGGCTG
7301  CAGTGTTTGC CTTTTATGGT AATAACGCGG CCGGCCCGGC TTCCTTTGTC
      GTCACAAACG GAAAATACCA TTATTGCGCC GGCCGGGCCG AAGGAAACAG
7351  CCCAATCTGG GCGCGCGCCG GCGCCCCCTG GCGGCCTAAG GACTCGGCGC
      GGGTTAGACC CGCGCGCGGC CGCGGGGGAC CGCCGGATTC CTGAGCCGCG
7401  GCCGGAAGTG GCCAGGGCGG GGGCGACTTC GGCTCACAGC GCGCCCGGCT
      CGGCCTTCAC CGGTCCCGCC CCCGCTGAAG CCGAGTGTCG CGCGGGCCGA
7451  ATTCTCGCAG CTCACCATGC CGGTCGCCAC CATGAGCTTG ATATCGAATT
      TAAGAGCGTC GAGTGGTACG GCCAGCGGTG GTACTCGAAC TATAGCTTAA
7501  CCTGCAGCCC GGGGGATCCA CTAGTTCTAG AGCTTGATTA ATAGTAATCA
      GGACGTCGGG CCCCCTAGGT GATCAAGATC TCGAACTAAT TATCATTAGT
7551  ATTACGGGGT CATTAGTTCA TAGCCCATAT ATGGAGTTCC GCGTTACATA
      TAATGCCCCA GTAATCAAGT ATCGGGTATA TACCTCAAGG CGCAATGTAT
7601  ACTTACGGTA AATGGCCCGC CTGGCTGACC GCCCAACGAC CCCCGCCCAT
      TGAATGCCAT TTACCGGGCG GACCGACTGG CGGGTTGCTG GGGGCGGGTA
7651  TGACGTCAAT AATGACGTAT GTTCCCATAG TAACGCCAAT AGGGACTTTC
      ACTGCAGTTA TTACTGCATA CAAGGGTATC ATTGCGGTTA TCCCTGAAAG
7701  CATTGACGTC AATGGGTGGA GTATTTACGG TAAACTGCCC ACTTGGCAGT
      GTAACTGCAG TTACCCACCT CATAAATGCC ATTTGACGGG TGAACCGTCA
7751  ACATCAAGTG TATCATATGC CAAGTACGCC CCCTATTGAC GTCAATGACG
      TGTAGTTCAC ATAGTATACG GTTCATGCGG GGGATAACTG CAGTTACTGC
7801  GTAAATGGCC CGCCTGGCAT TATGCCCAGT ACATGACCTT ATGGGACTTT
      CATTTACCGG GCGGACCGTA ATACGGGTCA TGTACTGGAA TACCCTGAAA
7851  CCTACTTGGC AGTACATCTA CGTATTAGTC ATCGCTATTA CCATGGTGAT
      GGATGAACCG TCATGTAGAT GCATAATCAG TAGCGATAAT GGTACCACTA
7901  GCGGTTTTGG CAGTACATCA ATGGGCGTGG ATAGCGGTTT GACTCACGGG
      CGCCAAAACC GTCATGTAGT TACCCGCACC TATCGCCAAA CTGAGTGCCC
7951  GATTTCCAAG TCTCCACCCC ATTGACGTCA ATGGGAGTTT GTTTTGGCAC
      CTAAAGGTTC AGAGGTGGGG TAACTGCAGT TACCCTCAAA CAAAACCGTG
8001  CAAAATCAAC GGGACTTTCC AAAATGTCGT AACAACTCCG CCCCATTGAC
      GTTTTAGTTG CCCTGAAAGG TTTTACAGCA TTGTTGAGGC GGGGTAACTG
8051  GCAAATGGGC GGTAGGCGTG TACGGTGGGA GGTCTATATA AGCAGAGCTG
      CGTTTACCCG CCATCCGCAC ATGCCACCCT CCAGATATAT TCGTCTCGAC
8101  GTTTAGTGAA CCGTCAGATC CGCTAGCGTT CGAAGTTTAA ACGCGGCCGC
      CAAATCACTT GGCAGTCTAG GCGATCGCAA GCTTCAAATT TGCGCCGGCG
8151  GACTCTAGAT CATAATCAGC CATACCACAT TTGTAGAGGT TTTACTTGCT
```

Figure 10 cont.

```
      CTGAGATCTA GTATTAGTCG GTATGGTGTA AACATCTCCA AAATGAACGA
8201  TTAAAAAACC TCCCACACCT CCCCCTGAAC CTGAAACATA AAATGAATGC
      AATTTTTTGG AGGGTGTGGA GGGGGACTTG GACTTTGTAT TTTACTTACG
8251  AATTGTTGTT GTTAACTTGT TTATTGCAGC TTATAATGGT TACAAATAAA
      TTAACAACAA CAATTGAACA AATAACGTCG AATATTACCA ATGTTTATTT
8301  GCAATAGCAT CACAAATTTC ACAAATAAAG CATTTTTTTC ACTGCATTCT
      CGTTATCGTA GTGTTTAAAG TGTTTATTTC GTAAAAAAAG TGACGTAAGA
8351  AGTTGTGGTT TGTCCAAACT CATCAATGTA TCTTAAATCG AATTCTACCG
      TCAACACCAA ACAGGTTTGA GTAGTTACAT AGAATTTAGC TTAAGATGGC
8401  GGTAGGGGAG GCGCTTTTCC CAAGGCAGTC TGGAGCATGC GCTTTAGCAG
      CCATCCCCTC CGCGAAAAGG GTTCCGTCAG ACCTCGTACG CGAAATCGTC
8451  CCCCGCTGGG CACTTGGCGC TACACAAGTG GCCTCTGGCC TCGCACACAT
      GGGGCGACCC GTGAACCGCG ATGTGTTCAC CGGAGACCGG AGCGTGTGTA
8501  TCCACATCCA CCGGTAGGCG CCAACCGGCT CCGTTCTTTG GTGGCCCCTT
      AGGTGTAGGT GGCCATCCGC GGTTGGCCGA GGCAAGAAAC CACCGGGGAA
8551  CGCGCCACCT TCTACTCCTC CCCTAGTCAG GAAGTTCCCC CCCGCCCCGC
      GCGCGGTGGA AGATGAGGAG GGGATCAGTC CTTCAAGGGG GGGCGGGGCG
8601  AGCTCGCGTC GTGCAGGACG TGACAAATGG AAGTAGCACG TCTCACTAGT
      TCGAGCGCAG CACGTCCTGC ACTGTTTACC TTCATCGTGC AGAGTGATCA
8651  CTCGTGCAGA TGGACAGCAC CGCTGAGCAA TGGAAGCGGG TAGGCCTTTG
      GAGCACGTCT ACCTGTCGTG GCGACTCGTT ACCTTCGCCC ATCCGGAAAC
8701  GGGCAGCGGC CAATAGCAGC TTTGCTCCTT CGCTTTCTGG GCTCAGAGGC
      CCCGTCGCCG GTTATCGTCG AAACGAGGAA GCGAAAGACC CGAGTCTCCG
8751  TGGGAAGGGG TGGGTCCGGG GGCGGGCTCA GGGGCGGGCT CAGGGGCGGG
      ACCCTTCCCC ACCCAGGCCC CCGCCCGAGT CCCCGCCCGA GTCCCCGCCC
8801  GCGGGCGCCC GAAGGTCCTC CGGAGGCCCG GCATTCTGCA CGCTTCAAAA
      CGCCCGCGGG CTTCCAGGAG GCCTCCGGGC CGTAAGACGT GCGAAGTTTT
8851  GCGCACGTCT GCCGCGCTGT TCTCCTCTTC CTCATCTCCG GGCCTTTCGA
      CGCGTGCAGA CGGCGCGACA AGAGGAGAAG GAGTAGAGGC CCGGAAAGCT
8901  CCAGCTTACC ATGACCGAGT ACAAGCCCAC GGTGCGCCTC GCCACCCGCG
      GGTCGAATGG TACTGGCTCA TGTTCGGGTG CCACGCGGAG CGGTGGGCGC
8951  ACGACGTCCC CAGGGCCGTA CGCACCCTCG CCGCCGCGTT CGCCGACTAC
      TGCTGCAGGG GTCCCGGCAT GCGTGGGAGC GGCGGCGCAA GCGGCTGATG
9001  CCCGCCACGC GCCACACCGT CGATCCGGAC CGCCACATCG AGCGGGTCAC
      GGGCGGTGCG CGGTGTGGCA GCTAGGCCTG GCGGTGTAGC TCGCCCAGTG
9051  CGAGCTGCAA GAACTCTTCC TCACGCGCGT CGGGCTCGAC ATCGGCAAGG
      GCTCGACGTT CTTGAGAAGG AGTGCGCGCA GCCCGAGCTG TAGCCGTTCC
9101  TGTGGGTCGC GGACGACGGC GCCGCGGTGG CGGTCTGGAC CACGCCGGAG
      ACACCCAGCG CCTGCTGCCG CGGCGCCACC GCCAGACCTG GTGCGGCCTC
9151  AGCGTCGAAG CGGGGGCGGT GTTCGCCGAG ATCGGCCCGC GCATGGCCGA
      TCGCAGCTTC GCCCCCGCCA CAAGCGGCTC TAGCCGGGCG CGTACCGGCT
9201  GTTGAGCGGT TCCCGGCTGG CCGCGCAGCA ACAGATGGAA GGCCTCCTGG
      CAACTCGCCA AGGGCCGACC GGCGCGTCGT TGTCTACCTT CCGGAGGACC
9251  CGCCGCACCG GCCCAAGGAG CCCGCGTGGT TCCTGGCCAC CGTCGGCGTC
      GCGGCGTGGC CGGGTTCCTC GGGCGCACCA AGGACCGGTG GCAGCCGCAG
9301  TCGCCCGACC ACCAGGGCAA GGGTCTGGGC AGCGCCGTCG TGCTCCCCGG
      AGCGGGCTGG TGGTCCCGTT CCCAGACCCG TCGCGGCAGC ACGAGGGGCC
9351  AGTGGAGGCG GCCGAGCGCG CCGGGGTGCC CGCCTTCCTG GAGACCTCCG
      TCACCTCCGC CGGCTCGCGC GGCCCCACGG GCGGAAGGAC CTCTGGAGGC
9401  CGCCCCGCAA CCTCCCCTTC TACGAGCGGC TCGGCTTCAC CGTCACCGCC
      GCGGGGCGTT GGAGGGGAAG ATGCTCGCCG AGCCGAAGTG GCAGTGGCGG
9451  GACGTCGAGG TGCCCGAAGG ACCGCGCACC TGGTGCATGA CCCGCAAGCC
      CTGCAGCTCC ACGGGCTTCC TGGCGCGTGG ACCACGTACT GGGCGTTCGG
9501  CGGTGCCTGA CGCCCGCCCC ACGACCCGCA GCGCCCGACC GAAAGGAGCG
      GCCACGGACT GCGGGCGGGG TGCTGGGCGT CGCGGGCTGG CTTTCCTCGC
9551  CACGACCCCA TGCATCGTAG AGCTCGCTGA TCAGCCTCGA CTGTGCCTTC
      GTGCTGGGGT ACGTAGCATC TCGAGCGACT AGTCGGAGCT GACACGGAAG
9601  TAGTTGCCAG CCATCTGTTG TTTGCCCCTC CCCCGTGCCT TCCTTGACCC
      ATCAACGGTC GGTAGACAAC AAACGGGGAG GGGGCACGGA AGGAACTGGG
9651  TGGAAGGTGC CACTCCCACT GTCCTTTCCT AATAAAATGA GGAAATTGCA
      ACCTTCCACG GTGAGGGTGA CAGGAAAGGA TTATTTTACT CCTTTAACGT
9701  TCGCATTGTC TGAGTAGGTG TCATTCTATT CTGGGGGGTG GGGTGGGGCA
      AGCGTAACAG ACTCATCCAC AGTAAGATAA GACCCCCCAC CCCACCCCGT
9751  GGACAGCAAG GGGGGGGATT GGGRAGACAA TAGCAGGCAT GCTGGGGGGG
      CCTGTCGTTC CCCCCCCTAA CCCYTCTGTT ATCGTCCGTA CGACCCCCCC
9801  CGGTGGGGGC TATGGCTTCT GAGGCGGAAA GAACCAGCTG GGGCTCGAGA
```

Figure 10 cont.

```
         GCCACCCCCG ATACCGAAGA CTCCGCCTTT CTTGGTCGAC CCCGAGCTCT
9851     TCCACTAGTT CTAGCCTCGA GGCTAGAGCG GCCGCCACCG CGGTGGAGCT
         AGGTGATCAA GATCGGAGCT CCGATCTCGC CGGCGGTGGC GCCACCTCGA
9901     CCAATTCGCC CTATAGTGAG TCGTATTACG CGCGCTCACT GGCCGTCGTT
         GGTTAAGCGG GATATCACTC AGCATAATGC GCGCGAGTGA CCGGCAGCAA
9951     TTACAACGTC GTGACTGGGA AAACCCTGGC GTTACCCAAC TTAATCGCCT
         AATGTTGCAG CACTGACCCT TTTGGGACCG CAATGGGTTG AATTAGCGGA
10001    TGCAGCACAT CCCCCTTTCG CCAGCTGGCG TAATAGCGAA GAGGCCCGCA
         ACGTCGTGTA GGGGGAAAGC GGTCGACCGC ATTATCGCTT CTCCGGGCGT
10051    CCGATCGCCC TTCCCAACAG TTGCGCAGCC TGAATGGCGA ATGGAAATTG
         GGCTAGCGGG AAGGGTTGTC AACGCGTCGG ACTTACCGCT TACCTTTAAC
10101    TAAGCGTTAA TATTTTGTTA AAATTCGCGT TAAATTTTTG TTAAATCAGC
         ATTCGCAATT ATAAAACAAT TTTAAGCGCA ATTTAAAAAC AATTTAGTCG
10151    TCATTTTTTA ACCAATAGGC CGAAATCGGC AAAATCCCTT ATAAATCAAA
         AGTAAAAAAT TGGTTATCCG GCTTTAGCCG TTTTAGGGAA TATTTAGTTT
10201    AGAATAGACC GAGATAGGGT TGAGTGTTGT TCCAGTTTGG AACAAGAGTC
         TCTTATCTGG CTCTATCCCA ACTCACAACA AGGTCAAACC TTGTTCTCAG
10251    CACTATTAAA GAACGTGGAC TCCAACGTCA AAGGGCGAAA AACCGTCTAT
         GTGATAATTT CTTGCACCTG AGGTTGCAGT TTCCCGCTTT TTGGCAGATA
10301    CAGGGCGATG GCCCACTACG TGAACCATCA CCCTAATCAA GTTTTTTGGG
         GTCCCGCTAC CGGGTGATGC ACTTGGTAGT GGGATTAGTT CAAAAAACCC
10351    GTCGAGGTGC CGTAAAGCAC TAAATCGGAA CCCTAAAGGG AGCCCCCGAT
         CAGCTCCACG GCATTTCGTG ATTTAGCCTT GGGATTTCCC TCGGGGGCTA
10401    TTAGAGCTTG ACGGGGAAAG CCGGCGAACG TGGCGAGAAA GGAAGGGAAG
         AATCTCGAAC TGCCCCTTTC GGCCGCTTGC ACCGCTCTTT CCTTCCCTTC
10451    AAAGCGAAAG GAGCGGGCGC TAGGGCGCTG GCAAGTGTAG CGGTCACGCT
         TTTCGCTTTC CTCGCCCGCG ATCCCGCGAC CGTTCACATC GCCAGTGCGA
10501    GCGCGTAACC ACCACACCCG CCGCGCTTAA TGCGCCGCTA CAGGGCGCGT
         CGCGCATTGG TGGTGTGGGC GGCGCGAATT ACGCGGCGAT GTCCCGCGCA
10551    CAG
         GTC
```

CET 720
13545 bp
RNP UCOE
Amp
bGHpA
Puromycin
mPGK
SV40pA
CMV IE Promoter
Pvu I (13048)
Not I (12872)
Pvu I (549)
Pci I (1806)
Sal I (2225)
Hin dIII (2240)
Not I (8948)
Hin dIII (10525)
Nhe I (11117)
Bst BI (11125)
Pme I (11133)
Not I (11139)

Figure 12 CET720 nucleotide sequence

```
1     GGTGGCACTT TTCGGGGAAA TGTGCGCGGA ACCCCTATTT GTTTATTTTT
      CCACCGTGAA AAGCCCCTTT ACACGCGCCT TGGGGATAAA CAAATAAAAA
51    CTAAATACAT TCAAATATGT ATCCGCTCAT GAGACAATAA CCCTGATAAA
      GATTTATGTA AGTTTATACA TAGGCGAGTA CTCTGTTATT GGGACTATTT
101   TGCTTCAATA ATATTGAAAA AGGAAGAGTA TGAGTATTCA ACATTTCCGT
      ACGAAGTTAT TATAACTTTT TCCTTCTCAT ACTCATAAGT TGTAAAGGCA
151   GTCGCCCTTA TTCCCTTTTT TGCGGCATTT TGCCTTCCTG TTTTTGCTCA
      CAGCGGGAAT AAGGGAAAAA ACGCCGTAAA ACGGAAGGAC AAAAACGAGT
201   CCCAGAAACG CTGGTGAAAG TAAAAGATGC TGAAGATCAG TTGGGTGCAC
      GGGTCTTTGC GACCACTTTC ATTTTCTACG ACTTCTAGTC AACCCACGTG
251   GAGTGGGTTA CATCGAACTG GATCTCAACA GCGGTAAGAT CCTTGAGAGT
      CTCACCCAAT GTAGCTTGAC CTAGAGTTGT CGCCATTCTA GGAACTCTCA
301   TTTCGCCCCG AAGAACGTTT TCCAATGATG AGCACTTTTA AAGTTCTGCT
      AAAGCGGGGC TTCTTGCAAA AGGTTACTAC TCGTGAAAAT TTCAAGACGA
351   ATGTGGCGCG GTATTATCCC GTATTGACGC CGGGCAAGAG CAACTCGGTC
      TACACCGCGC CATAATAGGG CATAACTGCG GCCCGTTCTC GTTGAGCCAG
401   GCCGCATACA CTATTCTCAG AATGACTTGG TTGAGTACTC ACCAGTCACA
      CGGCGTATGT GATAAGAGTC TTACTGAACC AACTCATGAG TGGTCAGTGT
451   GAAAAGCATC TTACGGATGG CATGACAGTA AGAGAATTAT GCAGTGCTGC
      CTTTTCGTAG AATGCCTACC GTACTGTCAT TCTCTTAATA CGTCACGACG
501   CATAACCATG AGTGATAACA CTGCGGCCAA CTTACTTCTG ACAACGATCG
      GTATTGGTAC TCACTATTGT GACGCCGGTT GAATGAAGAC TGTTGCTAGC
551   GAGGACCGAA GGAGCTAACC GCTTTTTTGC ACAACATGGG GGATCATGTA
      CTCCTGGCTT CCTCGATTGG CGAAAAAACG TGTTGTACCC CCTAGTACAT
601   ACTCGCCTTG ATCGTTGGGA ACCGGAGCTG AATGAAGCCA TACCAAACGA
      TGAGCGGAAC TAGCAACCCT TGGCCTCGAC TTACTTCGGT ATGGTTTGCT
651   CGAGCGTGAC ACCACGATGC CTGTAGCAAT GGCAACAACG TTGCGCAAAC
      GCTCGCACTG TGGTGCTACG GACATCGTTA CCGTTGTTGC AACGCGTTTG
701   TATTAACTGG CGAACTACTT ACTCTAGCTT CCCGGCAACA ATTAATAGAC
      ATAATTGACC GCTTGATGAA TGAGATCGAA GGGCCGTTGT TAATTATCTG
751   TGGATGGAGG CGGATAAAGT TGCAGGACCA CTTCTGCGCT CGGCCCTTCC
      ACCTACCTCC GCCTATTTCA ACGTCCTGGT GAAGACGCGA GCCGGGAAGG
801   GGCTGGCTGG TTTATTGCTG ATAAATCTGG AGCCGGTGAG CGTGGGTCTC
      CCGACCGACC AAATAACGAC TATTTAGACC TCGGCCACTC GCACCCAGAG
851   GCGGTATCAT TGCAGCACTG GGGCCAGATG GTAAGCCCTC CCGTATCGTA
      CGCCATAGTA ACGTCGTGAC CCCGGTCTAC CATTCGGGAG GGCATAGCAT
901   GTTATCTACA CGACGGGGAG TCAGGCAACT ATGGATGAAC GAAATAGACA
      CAATAGATGT GCTGCCCCTC AGTCCGTTGA TACCTACTTG CTTTATCTGT
951   GATCGCTGAG ATAGGTGCCT CACTGATTAA GCATTGGTAA CTGTCAGACC
      CTAGCGACTC TATCCACGGA GTGACTAATT CGTAACCATT GACAGTCTGG
1001  AAGTTTACTC ATATATACTT TAGATTGATT TAAAACTTCA TTTTTAATTT
      TTCAAATGAG TATATATGAA ATCTAACTAA ATTTTGAAGT AAAAATTAAA
1051  AAAAGGATCT AGGTGAAGAT CCTTTTTGAT AATCTCATGA CCAAAATCCC
      TTTTCCTAGA TCCACTTCTA GGAAAAACTA TTAGAGTACT GGTTTTAGGG
1101  TTAACGTGAG TTTTCGTTCC ACTGAGCGTC AGACCCCGTA GAAAAGATCA
      AATTGCACTC AAAAGCAAGG TGACTCGCAG TCTGGGGCAT CTTTTCTAGT
1151  AAGGATCTTC TTGAGATCCT TTTTTTCTGC GCGTAATCTG CTGCTTGCAA
      TTCCTAGAAG AACTCTAGGA AAAAAAGACG CGCATTAGAC GACGAACGTT
1201  ACAAAAAAAC CACCGCTACC AGCGGTGGTT TGTTTGCCGG ATCAAGAGCT
      TGTTTTTTTG GTGGCGATGG TCGCCACCAA ACAAACGGCC TAGTTCTCGA
1251  ACCAACTCTT TTTCCGAAGG TAACTGGCTT CAGCAGAGCG CAGATACCAA
      TGGTTGAGAA AAAGGCTTCC ATTGACCGAA GTCGTCTCGC GTCTATGGTT
1301  ATACTGTCCT TCTAGTGTAG CCGTAGTTAG GCCACCACTT CAAGAACTCT
      TATGACAGGA AGATCACATC GGCATCAATC CGGTGGTGAA GTTCTTGAGA
1351  GTAGCACCGC CTACATACCT CGCTCTGCTA ATCCTGTTAC CAGTGGCTGC
      CATCGTGGCG GATGTATGGA GCGAGACGAT TAGGACAATG GTCACCGACG
1401  TGCCAGTGGC GATAAGTCGT GTCTTACCGG GTTGGACTCA AGACGATAGT
      ACGGTCACCG CTATTCAGCA CAGAATGGCC CAACCTGAGT TCTGCTATCA
1451  TACCGGATAA GGCGCAGCGG TCGGGCTGAA CGGGGGGTTC GTGCACACAG
      ATGGCCTATT CCGCGTCGCC AGCCCGACTT GCCCCCCAAG CACGTGTGTC
1501  CCCAGCTTGG AGCGAACGAC CTACACCGAA CTGAGATACC TACAGCGTGA
      GGGTCGAACC TCGCTTGCTG GATGTGGCTT GACTCTATGG ATGTCGCACT
1551  GCTATGAGAA AGCGCCACGC TTCCCGAAGG GAGAAAGGCG GACAGGTATC
```

Figure 12 cont.

```
      CGATACTCTT TCGCGGTGCG AAGGGCTTCC CTCTTTCCGC CTGTCCATAG
1601  CGGTAAGCGG CAGGGTCGGA ACAGGAGAGC GCACGAGGGA GCTTCCAGGG
      GCCATTCGCC GTCCCAGCCT TGTCCTCTCG CGTGCTCCCT CGAAGGTCCC
1651  GGAAACGCCT GGTATCTTTA TAGTCCTGTC GGGTTTCGCC ACCTCTGACT
      CCTTTGCGGA CCATAGAAAT ATCAGGACAG CCCAAAGCGG TGGAGACTGA
1701  TGAGCGTCGA TTTTTGTGAT GCTCGTCAGG GGGGCGGAGC CTATGGAAAA
      ACTCGCAGCT AAAAACACTA CGAGCAGTCC CCCCGCCTCG GATACCTTTT
1751  ACGCCAGCAA CGCGGCCTTT TTACGGTTCC TGGCCTTTTG CTGGCCTTTT
      TGCGGTCGTT GCGCCGGAAA AATGCCAAGG ACCGGAAAAC GACCGGAAAA
1801  GCTCACATGT TCTTTCCTGC GTTATCCCCT GATTCTGTGG ATAACCGTAT
      CGAGTGTACA AGAAAGGACG CAATAGGGGA CTAAGACACC TATTGGCATA
1851  TACCGCCTTT GAGTGAGCTG ATACCGCTCG CCGCAGCCGA ACGACCGAGC
      ATGGCGGAAA CTCACTCGAC TATGGCGAGC GGCGTCGGCT TGCTGGCTCG
1901  GCAGCGAGTC AGTGAGCGAG GAAGCGGAAG AGCGCCCAAT ACGCAAACCG
      CGTCGCTCAG TCACTCGCTC CTTCGCCTTC TCGCGGGTTA TGCGTTTGGC
1951  CCTCTCCCCG CGCGTTGGCC GATTCATTAA TGCAGCTGGC ACGACAGGTT
      GGAGAGGGGC GCGCAACCGG CTAAGTAATT ACGTCGACCG TGCTGTCCAA
2001  TCCCGACTGG AAAGCGGGCA GTGAGCGCAA CGCAATTAAT GTGAGTTAGC
      AGGGCTGACC TTTCGCCCGT CACTCGCGTT GCGTTAATTA CACTCAATCG
2051  TCACTCATTA GGCACCCCAG GCTTTACACT TTATGCTTCC GGCTCGTATG
      AGTGAGTAAT CCGTGGGGTC CGAAATGTGA AATACGAAGG CCGAGCATAC
2101  TTGTGTGGAA TTGTGAGCGG ATAACAATTT CACACAGGAA ACAGCTATGA
      AACACACCTT AACACTCGCC TATTGTTAAA GTGTGTCCTT TGTCGATACT
2151  CCATGATTAC GCCAAGCGCG CAATTAACCC TCACTAAAGG GAACAAAAGC
      GGTACTAATG CGGTTCGCGC GTTAATTGGG AGTGATTTCC CTTGTTTTCG
2201  TGGGTACCGG GCCCCCCCTC GAGGTCGACG GTATCGATAA GCTTCAATGT
      ACCCATGGCC CGGGGGGGAG CTCCAGCTGC CATAGCTATT CGAAGTTACA
2251  TTTTAGCACC CTCTGTGTGG AGGAAAATAA TGCAGATTAT TCTAATTAGT
      AAAATCGTGG GAGACACACC TCCTTTTATT ACGTCTAATA AGATTAATCA
2301  GTAATATCTA ACCACATTAA AATATATTAC ATAGTAAACT ACACTCCATA
      CATTATAGAT TGGTGTAATT TTATATAATG TATCATTTGA TGTGAGGTAT
2351  ATTTTATAAA TTTGACTCCC CAGGGTAATA AACTAGTCTC TAGTCTGCTC
      TAAAATATTT AAACTGAGGG GTCCCATTAT TTGATCAGAG ATCAGACGAG
2401  ACCTTCAACT GTACAATAAA GTCTTGGTTC TTTTGAAATA GACCTCAAAT
      TGGAAGTTGA CATGTTATTT CAGAACCAAG AAAACTTTAT CTGGAGTTTA
2451  GAGACACCTA AAATTCAAAG TGTCTTTACA TTTAAAGACA CCTACAGGAA
      CTCTGTGGAT TTTAAGTTTC ACAGAAATGT AAATTTCTGT GGATGTCCTT
2501  AGCAGGTAAA AGAGCCAGGT TAAAAACAAA TTCTAAAACC ACTTAGCTGC
      TCGTCCATTT TCTCGGTCCA ATTTTTGTTT AAGATTTTGG TGAATCGACG
2551  AGTTAAACAT ATAGTAAAGA TGCACTAAAG TTTCTTACTC TGTAAATCCC
      TCAATTTGTA TATCATTTCT ACGTGATTTC AAAGAATGAG ACATTTAGGG
2601  TTCCACTTCA GGAAATATTC CACTTTCCCA TTCACTACAC GTCGATCTAG
      AAGGTGAAGT CCTTTATAAG GTGAAAGGGT AAGTGATGTG CAGCTAGATC
2651  TACTTTTTCC ACGACAAATT CTTCAGGCTC TGCCTCTTCA ACTTTTTTAC
      ATGAAAAAGG TGCTGTTTAA GAAGTCCGAG ACGGAGAAGT TGAAAAAATG
2701  TCTTTCCATT CTGTTTTTTT CCCATTTTTT GCTAAAATAA AACAAAAGAG
      AGAAAGGTAA GACAAAAAAA GGGTAAAAAA CGATTTTATT TTGTTTTCTC
2751  AAATTAAGAA ATATTCCTCT TGAATTTTGA GCACATTTTC AAGGCTCAAT
      TTTAATTCTT TATAAGGAGA ACTTAAAACT CGTGTAAAAG TTCCGAGTTA
2801  TGCTTATATT ATTATCACAT TCGACATAAA TTTTTACTTC TATATCCCAG
      ACGAATATAA TAATAGTGTA AGCTGTATTT AAAAATGAAG ATATAGGGTC
2851  GGCAGACACC TTCTGGAAAG ATTAAAAGTC AACAGACAAT AAAATAAAAG
      CCGTCTGTGG AAGACCTTTC TAATTTTCAG TTGTCTGTTA TTTTATTTTC
2901  AATGCTTTAT CTTGTTCATT TAGTTCAAAC TTACAACCCA CCACCAAAAT
      TTACGAAATA GAACAAGTAA ATCAAGTTTG AATGTTGGGT GGTGGTTTTA
2951  AATACAATAA AAAAACACTA TCTGGAAACA GTTATTTTTT TCCAGTCTTT
      TTATGTTATT TTTTTGTGAT AGACCTTTGT CAATAAAAAA AGGTCAGAAA
3001  TTTTTTGAGA CAGGGTCTCA CACTCTTGTC GCCCAGGCTG GAGTGCAGTG
      AAAAAACTCT GTCCCAGAGT GTGAGAACAG CGGGTCCGAC CTCACGTCAC
3051  GCGTGATCTC AGCTCACTGC AACCTCCGCC TCCCCAGGTT CAAGCAGTTC
      CGCACTAGAG TCGAGTGACG TTGGAGGCGG AGGGGTCCAA GTTCGTCAAG
3101  TCATGCCTCA GCCTCCAGAG TAGCTGGGAT TATAGGCGGA TGCCACCATG
      AGTACGGAGT CGGAGGTCTC ATCGACCCTA ATATCCGCCT ACGGTGGTAC
3151  CCGGGCTAAT TTTTTTTGTG TTTTTATTAG AAACAGGGTT TCACCATGTT
      GGCCCGATTA AAAAAAACAC AAAAATAATC TTTGTCCCAA AGTGGTACAA
3201  GACCAGGCTG GTCTCAAACT CCTGACCTGA AGTGATTCAC CAGCCTGGGC
```

Figure 12 cont.

```
      CTGGTCCGAC CAGAGTTTGA GGACTGGACT TCACTAAGTG GTCGGACCCG
3251  CTCCCAAAGT GCTGGCATTA CAGGCGTGAG CCACTGCGCC CGGCCCTGTA
      GAGGGTTTCA CGACCGTAAT GTCCGCACTC GGTGACGCGG GCCGGGACAT
3301  GTCTTAAAAG ACCAAGTTTA CTAATTTTCA CTCATTTTAA CAACACTGCA
      CAGAATTTTC TGGTTCAAAT GATTAAAAGT GAGTAAAATT GTTGTGACGT
3351  ACAAACAACT ATGCAGGAAG TACCTAAAGG GTGATCCAGA GAAGCAAGTA
      TGTTTGTTGA TACGTCCTTC ATGGATTTCC CACTAGGTCT CTTCGTTCAT
3401  GTAGTGACAG GTCTTAGGTG AACCTATGAC AGACCTTGTA TCCACCCCCA
      CATCACTGTC CAGAATCCAC TTGGATACTG TCTGGAACAT AGGTGGGGGT
3451  GATGGTAAAA GCCCCAGCCC CCTTCTCAAT TCAAATATTA ATGTCAAAAG
      CTACCATTTT CGGGGTCGGG GGAAGAGTTA AGTTTATAAT TACAGTTTTC
3501  CATCAATGAT ACAGAGAAAA GATAAATGCA GAATGAAAAC ATGGTTCAAA
      GTAGTTACTA TGTCTCTTTT CTATTTACGT CTTACTTTTG TACCAAGTTT
3551  ATCCTGATAC CAACTGCAGG GTCAACTATA GAGACCACTA GGAGGTTCAA
      TAGGACTATG GTTGACGTCC CAGTTGATAT CTCTGGTGAT CCTCCAAGTT
3601  TTAAAGGACA AGATTATTTT TCCATAATCT CTGTAGATAA TATTTCCTAC
      AATTTCCTGT TCTAATAAAA AGGTATTAGA GACATCTATT ATAAAGGATG
3651  CACTTAGAAC AAAACTATAA AGCTATCACT TCAAGAGACC AACATTACAA
      GTGAATCTTG TTTTGATATT TCGATAGTGA AGTTCTCTGG TTGTAATGTT
3701  ATTTATTTTA ATTCCCTAAG GTGAAAAAAA TCCTTCCTTC CTGGTTTCTC
      TAAATAAAAT TAAGGGATTC CACTTTTTTT AGGAAGGAAG GACCAAAGAG
3751  AAGAGAAAGT CTATACTGGT AACCAAATTC ACTTTAAACA GGCATTTTCT
      TTCTCTTTCA GATATGACCA TTGGTTTAAG TGAAATTTGT CCGTAAAAGA
3801  TTGGTATGAC ACTATTTAAG AGAAGCAGGA AACCAACGTG AACCAGCTCT
      AACCATACTG TGATAAATTC TCTTCGTCCT TTGGTTGCAC TTGGTCGAGA
3851  TTCCAATGGC TCAAGATTTC CTATGAGAGG ACTAAAAATG GGGAAAATTT
      AAGGTTACCG AGTTCTAAAG GATACTCTCC TGATTTTTAC CCCTTTTAAA
3901  TTATGAGAGG ATTAAAAATG GGGGAAAAAA AACCCTGAAA TGGTTAATCA
      AATACTCTCC TAATTTTTAC CCCCTTTTTT TTGGGACTTT ACCAATTAGT
3951  GAAGATCCTA TGGGCTGAGA AGGAATCCAT CTTAACATTT CATCTTAAAG
      CTTCTAGGAT ACCCGACTCT TCCTTAGGTA GAATTGTAAA GTAGAATTTC
4001  CAAATGCTAT TGCCGGGGGC AGTGGCTCAT GCCTGTAATC CCAGCACTTT
      GTTTACGATA ACGGCCCCCG TCACCGAGTA CGGACATTAG GGTCGTGAAA
4051  GGGAGGCCGA GGTGGGCAGA TCATCTGAGG TCAGGAGTTT GAGACCAGCC
      CCCTCCGGCT CCACCCGTCT AGTAGACTCC AGTCCTCAAA CTCTGGTCGG
4101  TGACCAACAT GGAGAAACCC CGTTTCTACT AAAAATACAA AATTAGCCAG
      ACTGGTTGTA CCTCTTTGGG GCAAAGATGA TTTTTATGTT TTAATCGGTC
4151  GCATAGTGGT GCATGCCTGT AATCCCAGCT ACTTGGGAGG CTGAGGCAGG
      CGTATCACCA CGTACGGACA TTAGGGTCGA TGAACCCTCC GACTCCGTCC
4201  AGAACTGCTT GAACCCAGGA GGCTTAAGTT GCGGTGAGCC AAGATCACGC
      TCTTGACGAA CTTGGGTCCT CCGAATTCAA CGCCACTCGG TTCTAGTGCG
4251  CATTGCACTC TAGCCTGGAC AACAAGAGAA AAACTCTGTC TCAAAAAAAC
      GTAACGTGAG ATCGGACCTG TTGTTCTCTT TTTGAGACAG AGTTTTTTTG
4301  ACAAAAACAA AAAACCCAAA TACTATTTAA AAAAGATAAA CCTTAATTGC
      TGTTTTTGTT TTTTGGGTTT ATGATAAATT TTTTCTATTT GGAATTAACG
4351  TCAATCATTA AAGCCATCCC ACAAGTAAAG CAGCAAGCAG AAAAAAGTTA
      AGTTAGTAAT TTCGGTAGGG TGTTCATTTC GTCGTTCGTC TTTTTTCAAT
4401  AGAACACCTC AAGGCTACAG AAGGACATTT CAAGCTATGC AGGCATATGA
      TCTTGTGGAG TTCCGATGTC TTCCTGTAAA GTTCGATACG TCCGTATACT
4451  AGTGTGCAGA CAGATATGTA AGAAAGGCCT CAAGACTGCA AAAGGGCATT
      TCACACGTCT GTCTATACAT TCTTTCCGGA GTTCTGACGT TTTCCCGTAA
4501  TCAAGCTATG CAAGCATATA GGTAACACAT ACACACACAC AAAATAAAAT
      AGTTCGATAC GTTCGTATAT CCATTGTGTA TGTGTGTGTG TTTTATTTTA
4551  CCCCTGAAAT ACAAAAACAT GCAGCAAACA CCTGACGTTT TTGGATACCA
      GGGGACTTTA TGTTTTTGTA CGTCGTTTGT GGACTGCAAA AACCTATGGT
4601  TTTCTAAGTC AGGTGTTATG ATTCTCATTA GTCAAGATAC TTGAGTACTG
      AAAGATTCAG TCCACAATAC TAAGAGTAAT CAGTTCTATG AACTCATGAC
4651  GGCCCAAACA GCTTTCTGCC ACTGTACAGT ACAAGAAGGT AGGAATAATG
      CCGGGTTTGT CGAAAGACGG TGACATGTCA TGTTCTTCCA TCCTTATTAC
4701  GTGGGAGGAG CAAAGACAAA CTGTAATAGA CAGAAGTGTA TCAGATACCT
      CACCCTCCTC GTTTCTGTTT GACATTATCT GTCTTCACAT AGTCTATGGA
4751  ATACTACATG AAAAACAAAA CAGCTACTGC CACAAAGGGA GAAGGCTAAC
      TATGATGTAC TTTTTGTTTT GTCGATGACG GTGTTTCCCT CTTCCGATTG
4801  AAAATAAAGT CAACAATAAA TACAGAAAAT GAAAAGGATA CACACTAAGG
      TTTTATTTCA GTTGTTATTT ATGTCTTTTA CTTTTCCTAT GTGTGATTCC
4851  TTTACAAAAA AAAAAAGGCA GACAAAATGC CATACAGTAT TCATTCACTA
```

Figure 12 cont.

```
      AAATGTTTTT TTTTTTCCGT CTGTTTTACG GTATGTCATA AGTAAGTGAT
4901  CTATGGCATT CATAAGCTAG TTTCAAATGC TCACTATTTT CTTTTATAGT
      GATACCGTAA GTATTCGATC AAAGTTTACG AGTGATAAAA GAAAATATCA
4951  ATATATTTGC CTTAACCCAG CACTTTTTTC CAAAAGTGGA TGAGTCAAAA
      TATATAAACG GAATTGGGTC GTGAAAAAAG GTTTTCACCT ACTCAGTTTT
5001  TAAATTTCCC ATTATTTAAG TGAAATTAAC AGCACACATA TCTCACAACA
      ATTTAAAGGG TAATAAATTC ACTTTAATTG TCGTGTGTAT AGAGTGTTGT
5051  CTAATGAATT TTTAAAATGG AAAGTTAAGA ACTTTTAAAG TGGCCAACCT
      GATTACTTAA AAATTTTACC TTTCAATTCT TGAAAATTTC ACCGGTTGGA
5101  GTGATCCTTC ACAAAATAAA CTAAATACAA TAACAGACCC CAAAGGCTAT
      CACTAGGAAG TGTTTTATTT GATTTATGTT ATTGTCTGGG GTTTCCGATA
5151  CAATTGCGTG CAAAAACAAC TTCTGTTTTC CAGGGTAAAC AGAATCTAAT
      GTTAACGCAC GTTTTTGTTG AAGACAAAAG GTCCCATTTG TCTTAGATTA
5201  GCAGAATCTA ATGCAGGGTA AACAGACTTA ATGCAGAATC TAATGATGGC
      CGTCTTAGAT TACGTCCCAT TTGTCTGAAT TACGTCTTAG ATTACTACCG
5251  ACAAATTAAA AATCACTAAC GTGCCCTTTT TAGTGTGAAA CCCAGAGAGA
      TGTTTAATTT TTAGTGATTG CACGGGAAAA ATCACACTTT GGGTCTCTCT
5301  GCACATACAA GCCAAAAACA AATGCTTTAT TTTACCTAGG AGACATTAAC
      CGTGTATGTT CGGTTTTTGT TTACGAAATA AAATGGATCC TCTGTAATTG
5351  ATTCACCTTT ACGTGTTTAA GATTAATGCA ATGTTAAATA TTGTGAAAAC
      TAAGTGGAAA TGCACAAATT CTAATTACGT TACAATTTAT AACACTTTTG
5401  TGTAACTTTG AATTTCATGA TTTTTATGTG AATATTCCAG GGTTTAAAAA
      ACATTGAAAC TTAAAGTACT AAAAATACAC TTATAAGGTC CCAAATTTTT
5451  AACTTGTAAC ATGACATGGC TGAATAAGAT AAAAAAAAAA TCTAGCCTTT
      TTGAACATTG TACTGTACCG ACTTATTCTA TTTTTTTTTT AGATCGGAAA
5501  TCTCCCTTCT GGCTCATATT TGCGATTTCG ATCATTTTGT TTAAAAAACA
      AGAGGGAAGA CCGAGTATAA ACGCTAAAGC TAGTAAAACA AATTTTTTGT
5551  AAACACTGCA ATGAATTAAA CTTAATATTC TTCTATGTTT TAGAGTAAGT
      TTTGTGACGT TACTTAATTT GAATTATAAG AAGATACAAA ATCTCATTCA
5601  TAAAACAAGA TAAAGTGACC AAAGTAATTT GAAAGATTCA ATGACTTTTG
      ATTTTGTTCT ATTTCACTGG TTTCATTAAA CTTTCTAAGT TACTGAAAAC
5651  CTCCAACCTA GGTGCACAAG GTACCTTGTT CTTTAAATTG GGCTTTAATG
      GAGGTTGGAT CCACGTGTTC CATGGAACAA GAAATTTAAC CCGAAATTAC
5701  AAAATACTTC TCCAGAATTC TGGGGATTTA AGAAAAAATTA TGCCAACCAA
      TTTTATGAAG AGGTCTTAAG ACCCCTAAAT TCTTTTTAAT ACGGTTGGTT
5751  CAAGGGCTTT ACCATTTTAT GTAACATTTT TCAACGCTGC AAAAATGTGT
      GTTCCCGAAA TGGTAAAATA CATTGTAAAA AGTTGCGACG TTTTTACACA
5801  GTATTTCTAT TTGAAGATAA AAATCCTCAG CAAAATCCAC ATTGCACTGT
      CATAAAGATA AACTTCTATT TTTAGGAGTC GTTTTAGGTG TAACGTGACA
5851  CCTTCAAAGA TTAGCCTTCT TTGAACTAGT TAAGACACTA TTAAGCCAAG
      GGAAGTTTCT AATCGGAAGA AACTTGATCA ATTCTGTGAT AATTCGGTTC
5901  CCAGTATCTC CCTGTAATGA ATTCGTTTTT CTCTTAATTT TCCCCTGTAA
      GGTCATAGAG GGACATTACT TAAGCAAAAA GAGAATTAAA AGGGGACATT
5951  TTTACACTGG GAGAGCTGGG AAATATGTGG ATGTAAATTT CTCAGCCACA
      AAATGTGACC CTCTCGACCC TTTATACACC TACATTTAAA GAGTCGGTGT
6001  GAGATGCAAA GTTATACTGT GGGGAAAAAA AACTTGAGTT AAATCCTTAC
      CTCTACGTTT CAATATGACA CCCCTTTTTT TTGAACTCAA TTTAGGAATG
6051  ATATTTTAGG TTTTCATTAA CTTACCAATG TAGTTTTGTT GGAGGCCATT
      TATAAAATCC AAAAGTAATT GAATGGTTAC ATCAAAACAA CCTCCGGTAA
6101  TTTTTTATTG CAGACTTGAA GAGCTATTAC TAGAAAAATG CATGACAGTT
      AAAAAATAAC GTCTGAACTT CTCGATAATG ATCTTTTTAC GTACTGTCAA
6151  AAGGTAAGTT TGCATGACAC AAAAAAGGTA ACTAAATACA AATTCTGTTT
      TTCCATTCAA ACGTACTGTG TTTTTTCCAT TGATTTATGT TTAAGACAAA
6201  GGATTCCAAC CCCCAAGTAG AGAGCGCACA CTTTCAAACG TGAATACAAA
      CCTAAGGTTG GGGGTTCATC TCTCGCGTGT GAAAGTTTGC ACTTATGTTT
6251  TCCAGAGTAG ATCTGCGCTC CTACCTACAT TGCTTATGAT GTACTTAAGT
      AGGTCTCATC TAGACGCGAG GATGGATGTA ACGAATACTA CATGAATTCA
6301  ACGTGTCCTA ACCATGTGAG TCTAGAAAGA CTTTACTGGG GATCCTGGTA
      TGCACAGGAT TGGTACACTC AGATCTTTCT GAAATGACCC CTAGGACCAT
6351  CCTAAAACAG CTTCACATGG CTTAAAATAG GGGACCAATG TCTTTTCCAA
      GGATTTTGTC GAAGTGTACC GAATTTTATC CCCTGGTTAC AGAAAAGGTT
6401  TCTAAGTCCC ATTTATAATA AAGTCCATGT TCCATTTTTA AAGGACAATC
      AGATTCAGGG TAAATATTAT TTCAGGTACA AGGTAAAAAT TTCCTGTTAG
6451  CTTTCGGTTT AAAACCAGGC ACGATTACCC AAACAACTCA CAACGGTAAA
      GAAAGCCAAA TTTTGGTCCG TGCTAATGGG TTTGTTGAGT GTTGCCATTT
6501  GCACTGTGAA TCTTCTCTGT TCTGCAATCC CAACTTGGTT TCTGCTCAGA
```

Figure 12 cont.

```
      CGTGACACTT AGAAGAGACA AGACGTTAGG GTTGAACCAA AGACGAGTCT
6551  AACCCTCCCT CTTTCCAATC GGTAATTAAA TAACAAAAGG AAAAAACTTA
      TTGGGAGGGA GAAAGGTTAG CCATTAATTT ATTGTTTTCC TTTTTTGAAT
6601  AGATGCTTCA ACCCCGTTTC GTGACACTTT GAAAAAAGAA TCACCTCTTG
      TCTACGAAGT TGGGGCAAAG CACTGTGAAA CTTTTTTCTT AGTGGAGAAC
6651  CAAACACCCG CTCCCGACCC CCGCCGCTGA AGCCCGGCGT CCAGAGGCCT
      GTTTGTGGGC GAGGGCTGGG GGCGGCGACT TCGGGCCGCA GGTCTCCGGA
6701  AAGCGCGGGT GCCCGCCCCC ACCCGGGAGC GCGGGCCTCG TGGTCAGCGC
      TTCGCGCCCA CGGGCGGGGG TGGGCCCTCG CGCCCGGAGC ACCAGTCGCG
6751  ATCCGCGGGG AGAAACAAAG GCCGCGGCAC GGGGGCTCAA GGGCACTGCG
      TAGGCGCCCC TCTTTGTTTC CGGCGCCGTG CCCCCGAGTT CCCGTGACGC
6801  CCACACCGCA CGCGCCTACC CCCGCGCGGC CACGTTAACT GGCGGTCGCC
      GGTGTGGCGT GCGCGGATGG GGGCGCGCCG GTGCAATTGA CCGCCAGCGG
6851  GCAGCCTCGG GACAGCCGGC CGCGCGCCGC CAGGCTCGCG GACGCGGGAC
      CGTCGGAGCC CTGTCGGCCG GCGCGCGGCG GTCCGAGCGC CTGCGCCCTG
6901  CACGCGCCGC CCTCCGGGAG GCCCAAGTCT CGACCCAGCC CCGCGTGGCG
      GTGCGCGGCG GGAGGCCCTC CGGGTTCAGA GCTGGGTCGG GGCGCACCGC
6951  CTGGGGGAGG GGGCGCCTCC GCCGGAACGC GGGTGGGGGA GGGGAGGGGG
      GACCCCCTCC CCCGCGGAGG CGGCCTTGCG CCCACCCCCT CCCCTCCCCC
7001  AAATGCGCTT TGTCTCGAAA TGGGGCAACC GTCGCCACAG CTCCCTACCC
      TTTACGCGAA ACAGAGCTTT ACCCCGTTGG CAGCGGTGTC GAGGGATGGG
7051  CCTCGAGGGC AGAGCAGTCC CCCCACTAAC TACCGGGCTG GCCGCGCGCC
      GGAGCTCCCG TCTCGTCAGG GGGGTGATTG ATGGCCCGAC CGGCGCGCGG
7101  AGGCCAGCCG CGAGGCCACC GCCCGACCCT CCACTCCTTC CCGCAGCTCC
      TCCGGTCGGC GCTCCGGTGG CGGGCTGGGA GGTGAGGAAG GGCGTCGAGG
7151  CGGCGCGGGG TCCGGCGAGA AGGGGAGGGG AGGGGAGCGG AGAACCGGGC
      GCCGCGCCCC AGGCCGCTCT TCCCCTCCCC TCCCCTCGCC TCTTGGCCCG
7201  CCCCGGGACG CGTGTGGCAT CTGAAGCACC ACCAGCGAGC GAGAGCTAGA
      GGGGCCCTGC GCACACCGTA GACTTCGTGG TGGTCGCTCG CTCTCGATCT
7251  GAGAAGGAAA GCCACCGACT TCACCGCCTC CGAGCTGCTC CGGGTCGCGG
      CTCTTCCTTT CGGTGGCTGA AGTGGCGGAG GCTCGACGAG GCCCAGCGCC
7301  GTCTGCAGCG TCTCCGGCCC TCCGCGCCTA CAGCTCAAGC CACATCCGAA
      CAGACGTCGC AGAGGCCGGG AGGCGCGGAT GTCGAGTTCG GTGTAGGCTT
7351  GGGGGAGGGA GCCGGGAGCT GCGCGCGGGG CCGCCGGGGG GAGGGGTGGC
      CCCCCTCCCT CGGCCCTCGA CGCGCGCCCC GGCGGCCCCC CTCCCCACCG
7401  ACCGCCCACG CCGGGCGGCC ACGAAGGGCG GGGCAGCGGG CGCGCGCGCG
      TGGCGGGTGC GGCCCGCCGG TGCTTCCCGC CCCGTCGCCC GCGCGCGCGC
7451  GCGGGGGGAG GGGCCGGCGC CGCGCCCGCT GGGAATTGGG GCCCTAGGGG
      CGCCCCCCTC CCCGGCCGCG GCGCGGGCGA CCCTTAACCC CGGGATCCCC
7501  GAGGGCGGAG GCGCCGACGA CCGCGGCACT TACCGTTCGC GGCGTGGCGC
      CTCCCGCCTC CGCGGCTGCT GGCGCCGTGA ATGGCAAGCG CCGCACCGCG
7551  CCGGTGGTCC CCAAGGGGAG GGAAGGGGGA GGCGGGGCGA GGACAGTGAC
      GGCCACCAGG GGTTCCCCTC CCTTCCCCCT CCGCCCCGCT CCTGTCACTG
7601  CGGAGTCTCC TCAGCGGTGG CTTTTCTGCT TGGCAGCCTC AGCGGCTGGC
      GCCTCAGAGG AGTCGCCACC GAAAAGACGA ACCGTCGGAG TCGCCGACCG
7651  GCCAAAACCG GACTCCGCCC ACTTCCTCGC CCGCCGGTGC GAGGGTGTGG
      CGGTTTTGGC CTGAGGCGGG TGAAGGAGCG GGCGGCCACG CTCCCACACC
7701  AATCCTCCAG ACGCTGGGGG AGGGGGAGTT GGGAGCTTAA AAACTAGTAC
      TTAGGAGGTC TGCGACCCCC TCCCCCTCAA CCCTCGAATT TTTGATCATG
7751  CCCTTTGGGA CCACTTTCAG CAGCGAACTC TCCTGTACAC CAGGGGTCAG
      GGGAAACCCT GGTGAAAGTC GTCGCTTGAG AGGACATGTG GTCCCCAGTC
7801  TTCCACAGAC GCGGGCCAGG GGTGGGTCAT TGCGGCGTGA ACAATAATTT
      AAGGTGTCTG CGCCCGGTCC CCACCCAGTA ACGCCGCACT TGTTATTAAA
7851  GACTAGAAGT TGATTCGGGT GTTTCCGGAA GGGGCCGAGT CAATCCGCCG
      CTGATCTTCA ACTAAGCCCA CAAAGGCCTT CCCCGGCTCA GTTAGGCGGC
7901  AGTTGGGGCA CGGAAAACAA AAAGGGAAGG CTACTAAGAT TTTTCTGGCG
      TCAACCCCGT GCCTTTTGTT TTTCCCTTCC GATGATTCTA AAAAGACCGC
7951  GGGGTTATCA TTGGCGTAAC TGCAGGGACC ACCTCCCGGG TTGAGGGGGC
      CCCCAATAGT AACCGCATTG ACGTCCCTGG TGGAGGGCCC AACTCCCCCG
8001  TGGATCTCCA GGCTGCGGAT TAAGCCCCTC CCGTCGGCGT TAATTTCAAA
      ACCTAGAGGT CCGACGCCTA ATTCGGGGAG GGCAGCCGCA ATTAAAGTTT
8051  CTGCGCGACG TTTCTCACCT GCCTTCGCCA AGGCAGGGGC CGGGACCCTA
      GACGCGCTGC AAAGAGTGGA CGGAAGCGGT TCCGTCCCCG GCCCTGGGAT
8101  TTCCAAGAGG TAGTAACTAG CAGGACTCTA GCCTTCCGCA ATTCATTGAG
      AAGGTTCTCC ATCATTGATC GTCCTGAGAT CGGAAGGCGT TAAGTAACTC
8151  CGCATTTACG GAAGTAACGT CGGGTACTGT CTCTGGCCGC AAGGGTGGGA
```

Figure 12 cont.

```
      GCGTAAATGC CTTCATTGCA GCCCATGACA GAGACCGGCG TTCCCACCCT
8201  GGAGTACGCA TTTGGCGTAA GGTGGGGCGT AGAGCCTTCC CGCCATTGGC
      CCTCATGCGT AAACCGCATT CCACCCCGCA TCTCGGAAGG GCGGTAACCG
8251  GGCGGATAGG GCGTTTACGC GACGGCCTGA CGTAGCGGAA GACGCGTTAG
      CCGCCTATCC CGCAAATGCG CTGCCGGACT GCATCGCCTT CTGCGCAATC
8301  TGGGGGGGAA GGTTCTAGAA AAGCGGCGGC AGCGGCTCTA GCGGCAGTAG
      ACCCCCCCTT CCAAGATCTT TTCGCCGCCG TCGCCGAGAT CGCCGTCATC
8351  CAGCAGCGCC GGGTCCCGTG CGGAGGTGCT CCTCGCAGAG TTGTTTCTCG
      GTCGTCGCGG CCCAGGGCAC GCCTCCACGA GGAGCGTCTC AACAAAGAGC
8401  AGCAGCGGCA GTTCTCACTA CAGCGCCAGG ACGAGTCCGG TTCGTGTTCG
      TCGTCGCCGT CAAGAGTGAT GTCGCGGTCC TGCTCAGGCC AAGCACAAGC
8451  TCCGCGGAGA TCTCTCTCAT CTCGCTCGGC TGCGGGAAAT CGGGCTGAAG
      AGGCGCCTCT AGAGAGAGTA GAGCGAGCCG ACGCCCTTTA GCCCGACTTC
8501  CGACTGAGTC CGCGATGGAG GTAACGGGTT TGAAATCAAT GAGTTATTGA
      GCTGACTCAG GCGCTACCTC CATTGCCCAA ACTTTAGTTA CTCAATAACT
8551  AAAGGGCATG GCGAGGCCGT TGGCGCCTCA GTGGAAGTCG GCCAGCCGCC
      TTTCCCGTAC CGCTCCGGCA ACCGCGGAGT CACCTTCAGC CGGTCGGCGG
8601  TCCGTGGGAG AGAGGCAGGA AATCGGACCA ATTCAGTAGC AGTGGGGCTT
      AGGCACCCTC TCTCCGTCCT TTAGCCTGGT TAAGTCATCG TCACCCCGAA
8651  AAGGTTTATG AACGGGGTCT TGAGCGGAGG CCTGAGCGTA CAAACAGCTT
      TTCCAAATAC TTGCCCCAGA ACTCGCCTCC GGACTCGCAT GTTTGTCGAA
8701  CCCCACCCTC AGCCTCCCGG CGCCATTTCC CTTCACTGGG GGTGGGGGAT
      GGGGTGGGAG TCGGAGGGCC GCGGTAAAGG GAAGTGACCC CCACCCCCTA
8751  GGGGAGCTTT CACATGGCGG ACGCTGCCCC GCTGGGGTGA AAGTGGGGCG
      CCCCTCGAAA GTGTACCGCC TGCGACGGGG CGACCCCACT TTCACCCCGC
8801  CGGAGGCGGG AATTCTTATT CCCTTTCTAA AGCACGCTGC TTCGGGGGCC
      GCCTCCGCCC TTAAGAATAA GGGAAAGATT TCGTGCGACG AAGCCCCCGG
8851  ACGGCGTCTC CTCGGCGAGC GTTTCGGCGG GCAGCAGGTC CTCGTGAGCG
      TGCCGCAGAG GAGCCGCTCG CAAAGCCGCC CGTCGTCCAG GAGCACTCGC
8901  AGGCTGCGGA GCTTCCCCTC CCCCTCTCTC CCGGGAACCG ATTTGGCGGC
      TCCGACGCCT CGAAGGGGAG GGGGAGAGAG GGCCCTTGGC TAAACCGCCG
8951  CGCCATTTTC ATGGCTCGCC TTCCTCTCAG CGTTTTCCTT ATAACTCTTT
      GCGGTAAAAG TACCGAGCGG AAGGAGAGTC GCAAAAGGAA TATTGAGAAA
9001  TATTTTCTTA GTGTGCTTTC TCTATCAAGA AGTAGAAGTG GTTAACTATT
      ATAAAAGAAT CACACGAAAG AGATAGTTCT TCATCTTCAC CAATTGATAA
9051  TTTTTTTTCT TCTCGGGCTG TTTTCATATC GTTTCGAGGT GGATTTGGAG
      AAAAAAAAGA AGAGCCCGAC AAAAGTATAG CAAAGCTCCA CCTAAACCTC
9101  TGTTTTGTGA GCTTGGATCT TTAGAGTCCT GCGCACCTCA TTAAAGGCGC
      ACAAAACACT CGAACCTAGA AATCTCAGGA CGCGTGGAGT AATTTCCGCG
9151  TCAGCCTTCC CCTCGATGAA ATGGCGCCAT TGCGTTCGGA AGCCACACCG
      AGTCGGAAGG GGAGCTACTT TACCGCGGTA ACGCAAGCCT TCGGTGTGGC
9201  AAGAGCGGGG AGGGGGGGTG CTCCGGGTTT GCGGGCCCGG TTTCAGAGAA
      TTCTCGCCCC TCCCCCCCAC GAGGCCCAAA CGCCCGGGCC AAAGTCTCTT
9251  GATATCACCA CCCAGGGCGT CGGGCCGGGT TCAATGCGAG CCGTAGGACA
      CTATAGTGGT GGGTCCCGCA GCCCGGCCCA AGTTACGCTC GGCATCCTGT
9301  AAGAAACCAT TTTATGTTTT TCCTGTCTTT TTTTTCCTTT GAGTAACGGT
      TTCTTTGGTA AAATACAAAA AGGACAGAAA AAAAAGGAAA CTCATTGCCA
9351  TTTATCTGGG TCTGCAGTCA GTAAAACGAC AGATGAACCG CGGCAAAATA
      AAATAGACCC AGACGTCAGT CATTTTGCTG TCTACTTGGC GCCGTTTTAT
9401  AACATAAATT GGAAGCCATC GGCCACGAGG GGCAGGGACG AAGGTGGTTT
      TTGTATTTAA CCTTCGGTAG CCGGTGCTCC CCGTCCCTGC TTCCACCAAA
9451  TCTGGGCGGG GGAGGGATAT TCGCGTCAGA ATCCTTTACT GTTCTTAAGG
      AGACCCGCCC CCTCCCTATA AGCGCAGTCT TAGGAAATGA CAAGAATTCC
9501  ATTCCGTTTA AGTTGTAGAG CTGACTCATT TTAAGTAATG TTGTTACTGA
      TAAGGCAAAT TCAACATCTC GACTGAGTAA AATTCATTAC AACAATGACT
9551  GAAGTTTAAC CCTTACGGGA CAGATCCATG GACCTTTATA GATGATTACG
      CTTCAAATTG GGAATGCCCT GTCTAGGTAC CTGGAAATAT CTACTAATGC
9601  AGGAAAGTGA AATAACGATT TTGTCCTTAG TTATACTTCG ATTAAAACAT
      TCCTTTCACT TTATTGCTAA AACAGGAATC AATATGAAGC TAATTTTGTA
9651  GGCTTCAGAG GCTCCTTCCT GTAATGCGTA TGGATTGATG TGCAAAACTG
      CCGAAGTCTC CGAGGAAGGA CATTACGCAT ACCTAACTAC ACGTTTTGAC
9701  TTTTGGGCCT GGGCCGCTCT GTATTTGAAC TTTGTTACTT TTCTCATTTT
      AAAACCCGGA CCCGGCGAGA CATAAACTTG AAACAATGAA AAGAGTAAAA
9751  GTTTGCAATC TTGGTTGAAC ATTACATTGA TAAGCATAAG GTCTCAAGCG
      CAAACGTTAG AACCAACTTG TAATGTAACT ATTCGTATTC CAGAGTTCGC
9801  AAGGGGGTCT ACCTGGTTAT TTTTCTTTGA CCCTAAGCAC GTTTATAAAA
```

Figure 12 cont.

```
       TTCCCCCAGA TGGACCAATA AAAAGAAACT GGGATTCGTG CAAATATTTT
 9851  TAACATTGTT TAAAATCGAT AGTGGACATC GGGTAAGTTT GGATAAATTG
       ATTGTAACAA ATTTTAGCTA TCACCTGTAG CCCATTCAAA CCTATTTAAC
 9901  TGAGGTAAGT AATGAGTTTT TGCTTTTTGT TAGTGATTTG TAAAACTTGT
       ACTCCATTCA TTACTCAAAA ACGAAAAACA ATCACTAAAC ATTTTGAACA
 9951  TATAAATGTA CATTATCCGT AATTTCAGTT TAGAGATAAC CTATGTGCTG
       ATATTTACAT GTAATAGGCA TTAAAGTCAA ATCTCTATTG GATACACGAC
10001  ACGACAATTA AGAATAAAAA CTAGCTGAAA AAATGAAAAT AACTATCGTG
       TGCTGTTAAT TCTTATTTTT GATCGACTTT TTTACTTTTA TTGATAGCAC
10051  ACAAGTAACC ATTTCAAAAG ACTGCTTTGT GTCTCATAGG AGCTAGTTTG
       TGTTCATTGG TAAAGTTTTC TGACGAAACA CAGAGTATCC TCGATCAAAC
10101  ATCATTTCAG TTAATTTTTT CTTTAATTTT TACGAGTCAT GAAAACTACA
       TAGTAAAGTC AATTAAAAAA GAAATTAAAA ATGCTCAGTA CTTTTGATGT
10151  GGAAAAAAAA TCTGAACTGG GTTTTACCAC TACTTTTTAG GAGTTGGGAG
       CCTTTTTTTT AGACTTGACC CAAAATGGTG ATGAAAAATC CTCAACCCTC
10201  CATGCGAATG GAGGGAGAGC TCCGTAGAAC TGGGATGAGA GCAGCAATTA
       GTACGCTTAC CTCCCTCTCG AGGCATCTTG ACCCTACTCT CGTCGTTAAT
10251  ATGCTGCTTG CTAGGAACAA AAAATAATTG ATTGAAAATT ACGTGTGACT
       TACGACGAAC GATCCTTGTT TTTTATTAAC TAACTTTTAA TGCACACTGA
10301  TTTTAGTTTG CATTATGCGT TTGTAGCAGT TGGTCCTGGA TATCACTTTC
       AAAATCAAAC GTAATACGCA AACATCGTCA ACCAGGACCT ATAGTGAAAG
10351  TCTCGTTTGA GGTTTTTTAA CCTAGTTAAC TTTTAAGACA GGTTTCCTTA
       AGAGCAAACT CCAAAAAATT GGATCAATTG AAAATTCTGT CCAAAGGAAT
10401  ACATTCATAA GTGCCCAGAA TACAGCTGTG TAGTACAGCA TATAAAGATT
       TGTAAGTATT CACGGGTCTT ATGTCGACAC ATCATGTCGT ATATTTCTAA
10451  TCAGCTCTGA GGTTTTTCCT ATTGACTTGG AAAATTGTTT TGTGCCTGTC
       AGTCGAGACT CCAAAAAGGA TAACTGAACC TTTTAACAAA ACACGGACAG
10501  GCTTGCCACA TGGCCAATCA AGTAAGCTTG ATTAATAGTA ATCAATTACG
       CGAACGGTGT ACCGGTTAGT TCATTCGAAC TAATTATCAT TAGTTAATGC
10551  GGGTCATTAG TTCATAGCCC ATATATGGAG TTCCGCGTTA CATAACTTAC
       CCCAGTAATC AAGTATCGGG TATATACCTC AAGGCGCAAT GTATTGAATG
10601  GGTAAATGGC CCGCCTGGCT GACCGCCCAA CGACCCCCGC CCATTGACGT
       CCATTTACCG GGCGGACCGA CTGGCGGGTT GCTGGGGGCG GGTAACTGCA
10651  CAATAATGAC GTATGTTCCC ATAGTAACGC CAATAGGGAC TTTCCATTGA
       GTTATTACTG CATACAAGGG TATCATTGCG GTTATCCCTG AAAGGTAACT
10701  CGTCAATGGG TGGAGTATTT ACGGTAAACT GCCCACTTGG CAGTACATCA
       GCAGTTACCC ACCTCATAAA TGCCATTTGA CGGGTGAACC GTCATGTAGT
10751  AGTGTATCAT ATGCCAAGTA CGCCCCCTAT TGACGTCAAT GACGGTAAAT
       TCACATAGTA TACGGTTCAT GCGGGGGATA ACTGCAGTTA CTGCCATTTA
10801  GGCCCGCCTG GCATTATGCC CAGTACATGA CCTTATGGGA CTTTCCTACT
       CCGGGCGGAC CGTAATACGG GTCATGTACT GGAATACCCT GAAAGGATGA
10851  TGGCAGTACA TCTACGTATT AGTCATCGCT ATTACCATGG TGATGCGGTT
       ACCGTCATGT AGATGCATAA TCAGTAGCGA TAATGGTACC ACTACGCCAA
10901  TTGGCAGTAC ATCAATGGGC GTGGATAGCG GTTTGACTCA CGGGGATTTC
       AACCGTCATG TAGTTACCCG CACCTATCGC CAAACTGAGT GCCCCTAAAG
10951  CAAGTCTCCA CCCCATTGAC GTCAATGGGA GTTTGTTTTG GCACCAAAAT
       GTTCAGAGGT GGGGTAACTG CAGTTACCCT CAAACAAAAC CGTGGTTTTA
11001  CAACGGGACT TTCCAAAATG TCGTAACAAC TCCGCCCCAT TGACGCAAAT
       GTTGCCCTGA AAGGTTTTAC AGCATTGTTG AGGCGGGGTA ACTGCGTTTA
11051  GGGCGGTAGG CGTGTACGGT GGGAGGTCTA TATAAGCAGA GCTGGTTTAG
       CCCGCCATCC GCACATGCCA CCCTCCAGAT ATATTCGTCT CGACCAAATC
11101  TGAACCGTCA GATCCGCTAG CGTTCGAAGT TTAAACGCGG CCGCGACTCT
       ACTTGGCAGT CTAGGCGATC GCAAGCTTCA AATTTGCGCC GGCGCTGAGA
11151  AGATCATAAT CAGCCATACC ACATTTGTAG AGGTTTTACT TGCTTTAAAA
       TCTAGTATTA GTCGGTATGG TGTAAACATC TCCAAAATGA ACGAAATTTT
11201  AACCTCCCAC ACCTCCCCCT GAACCTGAAA CATAAAATGA ATGCAATTGT
       TTGGAGGGTG TGGAGGGGGA CTTGGACTTT GTATTTTACT TACGTTAACA
11251  TGTTGTTAAC TTGTTTATTG CAGCTTATAA TGGTTACAAA TAAAGCAATA
       ACAACAATTG AACAAATAAC GTCGAATATT ACCAATGTTT ATTTCGTTAT
11301  GCATCACAAA TTTCACAAAT AAAGCATTTT TTTCACTGCA TTCTAGTTGT
       CGTAGTGTTT AAAGTGTTTA TTTCGTAAAA AAAGTGACGT AAGATCAACA
11351  GGTTTGTCCA AACTCATCAA TGTATCTTAA ATCGAATTCT ACCGGGTAGG
       CCAAACAGGT TTGAGTAGTT ACATAGAATT TAGCTTAAGA TGGCCCATCC
11401  GGAGGCGCTT TTCCCAAGGC AGTCTGGAGC ATGCGCTTTA GCAGCCCCGC
       CCTCCGCGAA AAGGGTTCCG TCAGACCTCG TACGCGAAAT CGTCGGGGCG
11451  TGGGCACTTG GCGCTACACA AGTGGCCTCT GGCCTCGCAC ACATTCCACA
```

Figure 12 cont.

```
       ACCCGTGAAC CGCGATGTGT TCACCGGAGA CCGGAGCGTG TGTAAGGTGT
11501  TCCACCGGTA GGCGCCAACC GGCTCCGTTC TTTGGTGGCC CCTTCGCGCC
       AGGTGGCCAT CCGCGGTTGG CCGAGGCAAG AAACCACCGG GGAAGCGCGG
11551  ACCTTCTACT CCTCCCCTAG TCAGGAAGTT CCCCCCCGCC CCGCAGCTCG
       TGGAAGATGA GGAGGGGATC AGTCCTTCAA GGGGGGGCGG GGCGTCGAGC
11601  CGTCGTGCAG GACGTGACAA ATGGAAGTAG CACGTCTCAC TAGTCTCGTG
       GCAGCACGTC CTGCACTGTT TACCTTCATC GTGCAGAGTG ATCAGAGCAC
11651  CAGATGGACA GCACCGCTGA GCAATGGAAG CGGGTAGGCC TTTGGGGCAG
       GTCTACCTGT CGTGGCGACT CGTTACCTTC GCCCATCCGG AAACCCCGTC
11701  CGGCCAATAG CAGCTTTGCT CCTTCGCTTT CTGGGCTCAG AGGCTGGGAA
       GCCGGTTATC GTCGAAACGA GGAAGCGAAA GACCCGAGTC TCCGACCCTT
11751  GGGGTGGGTC CGGGGGCGGG CTCAGGGGCG GGCTCAGGGG CGGGGCGGGC
       CCCCACCCAG GCCCCCGCCC GAGTCCCCGC CCGAGTCCCC GCCCCGCCCG
11801  GCCCGAAGGT CCTCCGGAGG CCCGGCATTC TGCACGCTTC AAAAGCGCAC
       CGGGCTTCCA GGAGGCCTCC GGGCCGTAAG ACGTGCGAAG TTTTCGCGTG
11851  GTCTGCCGCG CTGTTCTCCT CTTCCTCATC TCCGGGCCTT TCGACCAGCT
       CAGACGGCGC GACAAGAGGA GAAGGAGTAG AGGCCCGGAA AGCTGGTCGA
11901  TACCATGACC GAGTACAAGC CCACGGTGCG CCTCGCCACC CGCGACGACG
       ATGGTACTGG CTCATGTTCG GGTGCCACGC GGAGCGGTGG GCGCTGCTGC
11951  TCCCCAGGGC CGTACGCACC CTCGCCGCCG CGTTCGCCGA CTACCCCGCC
       AGGGGTCCCG GCATGCGTGG GAGCGGCGGC GCAAGCGGCT GATGGGGCGG
12001  ACGCGCCACA CCGTCGATCC GGACCGCCAC ATCGAGCGGG TCACCGAGCT
       TGCGCGGTGT GGCAGCTAGG CCTGGCGGTG TAGCTCGCCC AGTGGCTCGA
12051  GCAAGAACTC TTCCTCACGC GCGTCGGGCT CGACATCGGC AAGGTGTGGG
       CGTTCTTGAG AAGGAGTGCG CGCAGCCCGA GCTGTAGCCG TTCCACACCC
12101  TCGCGGACGA CGGCGCCGCG GTGGCGGTCT GGACCACGCC GGAGAGCGTC
       AGCGCCTGCT GCCGCGGCGC CACCGCCAGA CCTGGTGCGG CCTCTCGCAG
12151  GAAGCGGGGG CGGTGTTCGC CGAGATCGGC CCGCGCATGG CCGAGTTGAG
       CTTCGCCCCC GCCACAAGCG GCTCTAGCCG GGCGCGTACC GGCTCAACTC
12201  CGGTTCCCGG CTGGCCGCGC AGCAACAGAT GGAAGGCCTC CTGGCGCCGC
       GCCAAGGGCC GACCGGCGCG TCGTTGTCTA CCTTCCGGAG GACCGCGGCG
12251  ACCGGCCCAA GGAGCCCGCG TGGTTCCTGG CCACCGTCGG CGTCTCGCCC
       TGGCCGGGTT CCTCGGGCGC ACCAAGGACC GGTGGCAGCC GCAGAGCGGG
12301  GACCACCAGG GCAAGGGTCT GGGCAGCGCC GTCGTGCTCC CCGGAGTGGA
       CTGGTGGTCC CGTTCCCAGA CCCGTCGCGG CAGCACGAGG GGCCTCACCT
12351  GGCGGCCGAG CGCGCCGGGG TGCCCGCCTT CCTGGAGACC TCCGCGCCCC
       CCGCCGGCTC GCGCGGCCCC ACGGGCGGAA GGACCTCTGG AGGCGCGGGG
12401  GCAACCTCCC CTTCTACGAG CGGCTCGGCT TCACCGTCAC CGCCGACGTC
       CGTTGGAGGG GAAGATGCTC GCCGAGCCGA AGTGGCAGTG GCGGCTGCAG
12451  GAGGTGCCCG AAGGACCGCG CACCTGGTGC ATGACCCGCA AGCCCGGTGC
       CTCCACGGGC TTCCTGGCGC GTGGACCACG TACTGGGCGT TCGGGCCACG
12501  CTGACGCCCG CCCCACGACC CGCAGCGCCC GACCGAAAGG AGCGCACGAC
       GACTGCGGGC GGGGTGCTGG GCGTCGCGGG CTGGCTTTCC TCGCGTGCTG
12551  CCCATGCATC GTAGAGCTCG CTGATCAGCC TCGACTGTGC CTTCTAGTTG
       GGGTACGTAG CATCTCGAGC GACTAGTCGG AGCTGACACG GAAGATCAAC
12601  CCAGCCATCT GTTGTTTGCC CCTCCCCCGT GCCTTCCTTG ACCCTGGAAG
       GGTCGGTAGA CAACAAACGG GGAGGGGGCA CGGAAGGAAC TGGGACCTTC
12651  GTGCCACTCC CACTGTCCTT TCCTAATAAA ATGAGGAAAT TGCATCGCAT
       CACGGTGAGG GTGACAGGAA AGGATTATTT TACTCCTTTA ACGTAGCGTA
12701  TGTCTGAGTA GGTGTCATTC TATTCTGGGG GGTGGGGTGG GGCAGGACAG
       ACAGACTCAT CCACAGTAAG ATAAGACCCC CCACCCCACC CCGTCCTGTC
12751  CAAGGGGGGG GATTGGGRAG ACAATAGCAG GCATGCTGGG GGGGCGGTGG
       GTTCCCCCCC CTAACCCYTC TGTTATCGTC CGTACGACCC CCCCGCCACC
12801  GGGCTATGGC TTCTGAGGCG GAAAGAACCA GCTGGGGCTC GAGATCCACT
       CCCGATACCG AAGACTCCGC CTTTCTTGGT CGACCCCGAG CTCTAGGTGA
12851  AGTTCTAGCC TCGAGGCTAG AGCGGCCGCC ACCGCGGTGG AGCTCCAATT
       TCAAGATCGG AGCTCCGATC TCGCCGGCGG TGGCGCCACC TCGAGGTTAA
12901  CGCCCTATAG TGAGTCGTAT TACGCGCGCT CACTGGCCGT CGTTTTACAA
       GCGGGATATC ACTCAGCATA ATGCGCGCGA GTGACCGGCA GCAAAATGTT
12951  CGTCGTGACT GGGAAAACCC TGGCGTTACC CAACTTAATC GCCTTGCAGC
       GCAGCACTGA CCCTTTTGGG ACCGCAATGG GTTGAATTAG CGGAACGTCG
13001  ACATCCCCCT TTCGCCAGCT GGCGTAATAG CGAAGAGGCC CGCACCGATC
       TGTAGGGGGA AAGCGGTCGA CCGCATTATC GCTTCTCCGG GCGTGGCTAG
13051  GCCCTTCCCA ACAGTTGCGC AGCCTGAATG GCGAATGGAA ATTGTAAGCG
       CGGGAAGGGT TGTCAACGCG TCGGACTTAC CGCTTACCTT TAACATTCGC
13101  TTAATATTTT GTTAAAATTC GCGTTAAATT TTTGTTAAAT CAGCTCATTT
```

Figure 12 cont.

```
       AATTATAAAA CAATTTTAAG CGCAATTTAA AAACAATTTA GTCGAGTAAA
13151  TTTAACCAAT AGGCCGAAAT CGGCAAAATC CCTTATAAAT CAAAAGAATA
       AAATTGGTTA TCCGGCTTTA GCCGTTTTAG GGAATATTTA GTTTTCTTAT
13201  GACCGAGATA GGGTTGAGTG TTGTTCCAGT TTGGAACAAG AGTCCACTAT
       CTGGCTCTAT CCCAACTCAC AACAAGGTCA AACCTTGTTC TCAGGTGATA
13251  TAAAGAACGT GGACTCCAAC GTCAAAGGGC GAAAAACCGT CTATCAGGGC
       ATTTCTTGCA CCTGAGGTTG CAGTTTCCCG CTTTTTGGCA GATAGTCCCG
13301  GATGGCCCAC TACGTGAACC ATCACCCTAA TCAAGTTTTT TGGGGTCGAG
       CTACCGGGTG ATGCACTTGG TAGTGGGATT AGTTCAAAAA ACCCCAGCTC
13351  GTGCCGTAAA GCACTAAATC GGAACCCTAA AGGGAGCCCC CGATTTAGAG
       CACGGCATTT CGTGATTTAG CCTTGGGATT TCCCTCGGGG GCTAAATCTC
13401  CTTGACGGGG AAAGCCGGCG AACGTGGCGA GAAAGGAAGG GAAGAAAGCG
       GAACTGCCCC TTTCGGCCGC TTGCACCGCT CTTTCCTTCC CTTCTTTCGC
13451  AAAGGAGCGG GCGCTAGGGC GCTGGCAAGT GTAGCGGTCA CGCTGCGCGT
       TTTCCTCGCC CGCGATCCCG CGACCGTTCA CATCGCCAGT GCGACGCGCA
13501  AACCACCACA CCCGCCGCGC TTAATGCGCC GCTACAGGGC GCGTCAG
       TTGGTGGTGT GGGCGGCGCG AATTACGCGG CGATGTCCCG CGCAGTC
```

Figure 13

*S alboniger* puromycin N-acetyl transferase nucleotide sequence

```
  1   ATGACCGAGT ACAAGCCCAC GGTGCGCCTC GCCACCCGCG ACGACGTCCC
      TACTGGCTCA TGTTCGGGTG CCACGCGGAG CGGTGGGCGC TGCTGCAGGG
 51   CAGGGCCGTA CGCACCCTCG CCGCCGCGTT CGCCGACTAC CCCGCCACGC
      GTCCCGGCAT GCGTGGGAGC GGCGGCGCAA GCGGCTGATG GGGCGGTGCG
101   GCCACACCGT CGATCCGGAC CGCCACATCG AGCGGGTCAC CGAGCTGCAA
      CGGTGTGGCA GCTAGGCCTG GCGGTGTAGC TCGCCCAGTG GCTCGACGTT
151   GAACTCTTCC TCACGCGCGT CGGGCTCGAC ATCGGCAAGG TGTGGGTCGC
      CTTGAGAAGG AGTGCGCGCA GCCCGAGCTG TAGCCGTTCC ACACCCAGCG
201   GGACGACGGC GCCGCGGTGG CGGTCTGGAC CACGCCGGAG AGCGTCGAAG
      CCTGCTGCCG CGGCGCCACC GCCAGACCTG GTGCGGCCTC TCGCAGCTTC
251   CGGGGGCGGT GTTCGCCGAG ATCGGCCCGC GCATGGCCGA GTTGAGCGGT
      GCCCCCGCCA CAAGCGGCTC TAGCCGGGCG CGTACCGGCT CAACTCGCCA
301   TCCCGGCTGG CCGCGCAGCA ACAGATGGAA GGCCTCCTGG CGCCGCACCG
      AGGGCCGACC GGCGCGTCGT TGTCTACCTT CCGGAGGACC GCGGCGTGGC
351   GCCCAAGGAG CCCGCGTGGT TCCTGGCCAC CGTCGGCGTC TCGCCCGACC
      CGGGTTCCTC GGGCGCACCA AGGACCGGTG GCAGCCGCAG AGCGGGCTGG
401   ACCAGGGCAA GGGTCTGGGC AGCGCCGTCG TGCTCCCCGG AGTGGAGGCG
      TGGTCCCGTT CCCAGACCCG TCGCGGCAGC ACGAGGGGCC TCACCTCCGC
451   GCCGAGCGCG CCGGGGTGCC CGCCTTCCTG GAGACCTCCG CGCCCCGCAA
      CGGCTCGCGC GGCCCCACGG GCGGAAGGAC CTCTGGAGGC GCGGGGCGTT
501   CCTCCCCTTC TACGAGCGGC TCGGCTTCAC CGTCACCGCC GACGTCGAGG
      GGAGGGGAAG ATGCTCGCCG AGCCGAAGTG GCAGTGGCGG CTGCAGCTCC
551   TGCCCGAAGG ACCGCGCACC TGGTGCATGA CCCGCAAGCC CGGTGCCTGA
      ACGGGCTTCC TGGCGCGTGG ACCACGTACT GGGCGTTCGG GCCACGGACT
```

Figure 14

Modified *S alboniger* puromycin N-acetyl transferase nucleotide sequence

```
  1  ATGACTGAAT ACAAACCAAC TGTTCGCCTG GCAACTCGTG ATGATGTTCC
     TACTGACTTA TGTTTGGTTG ACAAGCGGAC CGTTGAGCAC TACTACAAGG
 51  ACGTGCAGTT CGCACCCTGG CTGCTGCATT TGCTGACTAC CCTGCAACCC
     TGCACGTCAA GCGTGGGACC GACGACGTAA ACGACTGATG GGACGTTGGG
101  GTCACACTGT GGACCCAGAC CGCCACATTG AACGTGTGAC TGAACTGCAG
     CAGTGTGACA CCTGGGTCTG GCGGTGTAAC TTGCACACTG ACTTGACGTC
151  GAGCTGTTCC TGACCCGTGT GGGCCTGGAC ATTGGCAAAG TGTGGGTGGC
     CTCGACAAGG ACTGGGCACA CCCGGACCTG TAACCGTTTC ACACCCACCG
201  AGATGATGGT GCTGCTGTGG CAGTGTGGAC CACCCCTGAA TCTGTTGAAG
     TCTACTACCA CGACGACACC GTCACACCTG GTGGGGACTT AGACAACTTC
251  CTGGTGCAGT GTTTGCTGAG ATTGGCCCAC GCATGGCAGA ACTGTCTGGC
     GACCACGTCA CAAACGACTC TAACCGGGTG CGTACCGTCT TGACAGACCG
301  AGCCGCCTGG CAGCACAACA GCAGATGGAA GGTCTGCTGG CACCACACCG
     TCGGCGGACC GTCGTGTTGT CGTCTACCTT CCAGACGACC GTGGTGTGGC
351  CCCAAAAGAA CCTGCTTGGT TCCTGGCAAC TGTGGGTGTG AGCCCTGACC
     GGGTTTTCTT GGACGAACCA AGGACCGTTG ACACCCACAC TCGGGACTGG
401  ACCAGGGTAA GGGCCTGGGC TCTGCAGTGG TGCTGCCTGG TGTGGAAGCA
     TGGTCCCATT CCCGGACCCG AGACGTCACC ACGACGGACC ACACCTTCGT
451  GCTGAACGTG CAGGTGTGCC TGCTTTCCTG GAGACCTCAG CTCCACGCAA
     CGACTTGCAC GTCCACACGG ACGAAAGGAC CTCTGGAGTC GAGGTGCGTT
501  CCTGCCTTTC TATGAACGCC TGGGCTTCAC TGTGACTGCT GATGTGGAAG
     GGACGGAAAG ATACTTGCGG ACCCGAAGTG ACACTGACGA CTACACCTTC
551  TGCCAGAAGG CCCACGCACT TGGTGCATGA CTCGCAAACC AGGTGCTTAA
     ACGGTCTTCC GGGTGCGTGA ACCACGTACT GAGCGTTTGG TCCACGAATT
```

Figure 15 *S fradiae* aminoglycoside phosphotransferase nucleotide sequence

```
  1  ATGGACGACA GCACGTTGCG CCGGAAGTAC CCGCACCACG AGTGGCACGC
     TACCTGCTGT CGTGCAACGC GGCCTTCATG GGCGTGGTGC TCACCGTGCG
 51  AGTGAACGAA GGAGACTCGG GCGCCTTCGT CTACCAGCTC ACCGGCGGCC
     TCACTTGCTT CCTCTGAGCC CGCGGAAGCA GATGGTCGAG TGGCCGCCGG
101  CCGAGCCCCA GCCCGAGCTC TACGCGAAGA TCGCCCCCCG CGCCCCCGAG
     GGCTCGGGGT CGGGCTCGAG ATGCGCTTCT AGCGGGGGGC GCGGGGGCTC
151  AACTCCGCCT TCGACCTGTC CGGCGAGGCC GACCGGCTGG AGTGGCTCCA
     TTGAGGCGGA AGCTGGACAG GCCGCTCCGG CTGGCCGACC TCACCGAGGT
201  CCGCCACGGG ATCCCCGTCC CCCGCGTCGT CGAGCGCGGT GCCGACGACA
     GGCGGTGCCC TAGGGGCAGG GGGCGCAGCA GCTCGCGCCA CGGCTGCTGT
251  CCGCCGCGTG GCTCGTCACG GAGGCCGTCC CCGGCGTCGC GGCGGCCGAG
     GGCGGCGCAC CGAGCAGTGC CTCCGGCAGG GGCCGCAGCG CCGCCGGCTC
301  GAGTGGCCCG AGCACCAGCG GTTCGCCGTG GTCGAGGCGA TGGCGGAGCT
     CTCACCGGGC TCGTGGTCGC CAAGCGGCAC CAGCTCCGCT ACCGCCTCGA
351  GGCCCGCGCC CTCCACGAGC TGCCCGTGGA GGACTGCCCC TCCGACCGGC
     CCGGGCGCGG GAGGTGCTCG ACGGGCACCT CCTGACGGGG AGGCTGGCCG
401  GCCTCGACGC GGCGGTCGCC GAGGCCCGGC GGAACGTCGC CGAGGGCTTG
     CGGAGCTGCG CCGCCAGCGG CTCCGGGCCG CCTTGCAGCG GCTCCCGAAC
451  GTGGACCTCG ACGACCTGCA GGAGGAGCGG GCCGGGTGGA CCGGCGACCA
     CACCTGGAGC TGCTGGACGT CCTCCTCGCC CGGCCCACCT GGCCGCTGGT
501  GCTCCTGGCG GAGCTCGACC GCACCCGTCC CGAGAAGGAG GACCTGGTCG
     CGAGGACCGC CTCGAGCTGG CGTGGGCAGG GCTCTTCCTC CTGGACCAGC
551  TCTGCCATGG CGACCTGTGC CCCAACAACG TCCTGCTCGA CCCCGGGACC
     AGACGGTACC GCTGGACACG GGGTTGTTGC AGGACGAGCT GGGGCCCTGG
601  TGCCGGGTCA CCGGCGTGAT CGACGTCGGC CGCCTCGGGG TCGCCGACCG
     ACGGCCCAGT GGCCGCACTA GCTGCAGCCG GCGGAGCCCC AGCGGCTGGC
651  CCACGCCGAC ATCGCCTTGG CCGCCCGCGA GCTGGAGATC GACGAGGACC
     GGTGCGGCTG TAGCGGAACC GGCGGGCGCT CGACCTCTAG CTGCTCCTGG
701  CCTGGTTCGG CCCCGCCTAC GCCGAGCGGT TCCTGGAGCG GTACGGCGCC
     GGACCAAGCC GGGGCGGATG CGGCTCGCCA AGGACCTCGC CATGCCGCGG
751  CACCGCGTCG ACAAGGAGAA GCTGGCCTTC TACCAGCTTC TCGACGAGTT
     GTGGCGCAGC TGTTCCTCTT CGACCGGAAG ATGGTCGAAG AGCTGCTCAA
801  CTTCTAG
     GAAGATC
```

Figure 16 *S hygroscopicus* hygromycin phosphotransferase nucleotide sequence

```
  1   ATGACACAAG AATCCCTGTT ACTTCTCGAC CGTATTGATT CGGATGATTC
      TACTGTGTTC TTAGGGACAA TGAAGAGCTG GCATAACTAA GCCTACTAAG
 51   CTACGCGAGC CTGCGGAACG ACCAGGAATT CTGGGAGCCG CTGGCCCGCC
      GATGCGCTCG GACGCCTTGC TGGTCCTTAA GACCCTCGGC GACCGGGCGG
101   GAGCCCTGGA GGAGCTCGGG CTGCCGGTGC CGCCGGTGCT GCGGGTGCCC
      CTCGGGACCT CCTCGAGCCC GACGGCCACG GCGGCCACGA CGCCCACGGG
151   GGCGAGAGCA CCAACCCCGT ACTGGTCGGC GAGCCCGACC CGGTGATCAA
      CCGCTCTCGT GGTTGGGGCA TGACCAGCCG CTCGGGCTGG GCCACTAGTT
201   GCTGTTCGGC GAGCACTGGT GCGGTCCGGA GAGCCTCGCG TCGGAGTCGG
      CGACAAGCCG CTCGTGACCA CGCCAGGCCT CTCGGAGCGC AGCCTCAGCC
251   AGGCGTACGC GGTCCTGGCG GACGCCCCGG TGCCGGTGCC CCGCCTCCTC
      TCCGCATGCG CCAGGACCGC CTGCGGGGCC ACGGCCACGG GGCGGAGGAG
301   GGCCGCGGCG AGCTGCGGCC CGGCACCGGA GCCTGGCCGT GGCCCTACCT
      CCGGCGCCGC TCGACGCCGG GCCGTGGCCT CGGACCGGCA CCGGGATGGA
351   GGTGATGAGC CGGATGACCG GCACCACCTG GCGGTCCGCG ATGGACGGCA
      CCACTACTCG GCCTACTGGC CGTGGTGGAC CGCCAGGCGC TACCTGCCGT
401   CGACCGACCG GAACGCGCTG CTCGCCCTGG CCCGCGAACT CGGCCGGGTG
      GCTGGCTGGC CTTGCGCGAC GAGCGGGACC GGGCGCTTGA GCCGGCCCAC
451   CTCGGCCGGC TGCACAGGGT GCCGCTGACC GGGAACACCG TGCTCACCCC
      GAGCCGGCCG ACGTGTCCCA CGGCGACTGG CCCTTGTGGC ACGAGTGGGG
501   CCATTCCGAG GTCTTCCCGG AACTGCTGCG GGAACGCCGC GCGGCGACCG
      GGTAAGGCTC CAGAAGGGCC TTGACGACGC CCTTGCGGCG CGCCGCTGGC
551   TCGAGGACCA CCGCGGGTGG GGCTACCTCT CGCCCCGGCT GCTGGACCGC
      AGCTCCTGGT GGCGCCCACC CCGATGGAGA GCGGGGCCGA CGACCTGGCG
601   CTGGAGGACT GGCTGCCGGA CGTGGACACG CTGCTGGCCG GCCGCGAACC
      GACCTCCTGA CCGACGGCCT GCACCTGTGC GACGACCGGC CGGCGCTTGG
651   CCGGTTCGTC CACGGCGACC TGCACGGGAC CAACATCTTC GTGGACCTGG
      GGCCAAGCAG GTGCCGCTGG ACGTGCCCTG GTTGTAGAAG CACCTGGACC
701   CCGCGACCGA GGTCACCGGG ATCGTCGACT TCACCGACGT CTATGCGGGA
      GGCGCTGGCT CCAGTGGCCC TAGCAGCTGA AGTGGCTGCA GATACGCCCT
751   GACTCCCGCT ACAGCCTGGT GCAACTGCAT CTCAACGCCT TCCGGGGCGA
      CTGAGGGCGA TGTCGGACCA CGTTGACGTA GAGTTGCGGA AGGCCCCGCT
801   CCGCGAGATC CTGGCCGCGC TGCTCGACGG GGCGCAGTGG AAGCGGACCG
      GGCGCTCTAG GACCGGCGCG ACGAGCTGCC CCGCGTCACC TTCGCCTGGC
851   AGGACTTCGC CCGCGAACTG CTCGCCTTCA CCTTCCTGCA CGACTTCGAG
      TCCTGAAGCG GGCGCTTGAC GAGCGGAAGT GGAAGGACGT GCTGAAGCTC
901   GTGTTCGAGG AGACCCCGCT GGATCTCTCC GGCTTCACCG ATCCGGAGGA
      CACAAGCTCC TCTGGGGCGA CCTAGAGAGG CCGAAGTGGC TAGGCCTCCT
951   ACTGGCGCAG TTCCTCTGGG GGCCGCCGGA CACCGCCCCC GGCGCCTGA
      TGACCGCGTC AAGGAGACCC CCGGCGGCCT GTGGCGGGGG CCGCGGACT
```

Figure 17 *E coli* aminocyclitol phosphotransferase($hygro^{r}$)nucleotide sequence

```
1     ATGAAAAAGC CTGAACTCAC CGCGACGTCT GTCGCGAAGT TTCTGATCGA
      TACTTTTTCG GACTTGAGTG GCGCTGCAGA CAGCGCTTCA AAGACTAGCT
51    AAAGTTCGAC AGCGTCTCCG ACCTGATGCA GCTCTCGGAG GGCGAAGAAT
      TTTCAAGCTG TCGCAGAGGC TGGACTACGT CGAGAGCCTC CCGCTTCTTA
101   CTCGTGCTTT CAGCTTCGAT GTAGGAGGGC GTGGATATGT CCTGCGGGTA
      GAGCACGAAA GTCGAAGCTA CATCCTCCCG CACCTATACA GGACGCCCAT
151   AATAGCTGCG CCGATGGTTT CTACAAAGAT CGTTATGTTT ATCGGCACTT
      TTATCGACGC GGCTACCAAA GATGTTTCTA GCAATACAAA TAGCCGTGAA
201   TGCATCGGCC GCGCTCCCGA TTCCGGAAGT GCTTGACATT GGGGAATTCA
      ACGTAGCCGG CGCGAGGGCT AAGGCCTTCA CGAACTGTAA CCCCTTAAGT
251   GCGAGAGCCT GACCTATTGC ATCTCCCGCC GTGCACAGGG TGTCACGTTG
      CGCTCTCGGA CTGGATAACG TAGAGGGCGG CACGTGTCCC ACAGTGCAAC
301   CAAGACCTGC CTGAAACCGA ACTGCCCGCT GTTCTGCAAC CCGTCGCGGA
      GTTCTGGACG GACTTTGGCT TGACGGGCGA CAAGACGTTG GGCAGCGCCT
351   GCTCATGGAT GCGATCGCTG CGGCCGATCT TAGCCAGACG AGCGGGTTCG
      CGAGTACCTA CGCTAGCGAC GCCGGCTAGA ATCGGTCTGC TCGCCCAAGC
401   GCCCATTCGG ACCGCAAGGA ATCGGTCAAT ACACTACATG GCGTGATTTC
      CGGGTAAGCC TGGCGTTCCT TAGCCAGTTA TGTGATGTAC CGCACTAAAG
451   ATATGCGCGA TTGCTGATCC CCATGTGTAT CACTGGCAAA CTGTGATGGA
      TATACGCGCT AACGACTAGG GGTACACATA GTGACCGTTT GACACTACCT
501   CGACACCGTC AGTGCGTCCG TCGCGCAGGC TCTCGATGAG CTGATGCTTT
      GCTGTGGCAG TCACGCAGGC AGCGCGTCCG AGAGCTACTC GACTACGAAA
551   GGGCCGAGGA CTGCCCCGAA GTCCGGCACC TCGTGCACGC GGATTTCGGC
      CCCGGCTCCT GACGGGGCTT CAGGCCGTGG AGCACGTGCG CCTAAAGCCG
601   TCCAACAATG TCCTGACGGA CAATGGCCGC ATAACAGCGG TCATTGACTG
      AGGTTGTTAC AGGACTGCCT GTTACCGGCG TATTGTCGCC AGTAACTGAC
651   GAGCGAGGCG ATGTTCGGGG ATTCCCAATA CGAGGTCGCC AACATCTTCT
      CTCGCTCCGC TACAAGCCCC TAAGGGTTAT GCTCCAGCGG TTGTAGAAGA
701   TCTGGAGGCC GTGGTTGGCT TGTATGGAGC AGCAGACGCG CTACTTCGAG
      AGACCTCCGG CACCAACCGA ACATACCTCG TCGTCTGCGC GATGAAGCTC
751   CGGAGGCATC CGGAGCTTGC AGGATCGCCG CGGCTCCGGG CGTATATGCT
      GCCTCCGTAG GCCTCGAACG TCCTAGCGGC GCCGAGGCCC GCATATACGA
801   CCGCATTGGT CTTGACCAAC TCTATCAGAG CTTGGTTGAC GGCAATTTCG
      GGCGTAACCA GAACTGGTTG AGATAGTCTC GAACCAACTG CCGTTAAAGC
851   ATGATGCAGC TTGGGCGCAG GGTCGATGCG ACGCAATCGT CCGATCCGGA
      TACTACGTCG AACCCGCGTC CCAGCTACGC TGCGTTAGCA GGCTAGGCCT
901   GCCGGGACTG TCGGGCGTAC ACAAATCGCC CGCAGAAGCG CGGCCGTCTG
      CGGCCCTGAC AGCCCGCATG TGTTTAGCGG GCGTCTTCGC GCCGGCAGAC
951   GACCGATGGC TGTGTAGAAG TACTCGCCGA TAGTGGAAAC CGACGCCCCA
      CTGGCTACCG ACACATCTTC ATGAGCGGCT ATCACCTTTG GCTGCGGGGT
1001  GCACTCGTCC GAGGGCAAAG GAATGA
      CGTGAGCAGG CTCCCGTTTC CTTACT
```

Figure 18 Tn5 (*Klebsiella pneumoniae*) neomycin phosphotransferase nucleotide sequence

```
  1  ATGATTGAAC AAGATGGATT GCACGCAGGT TCTCCGGCCG CTTGGGTGGA
     TACTAACTTG TTCTACCTAA CGTGCGTCCA AGAGGCCGGC GAACCCACCT
 51  GAGGCTATTC GGCTATGACT GGGCACAACA GACAATCGGC TGCTCTGATG
     CTCCGATAAG CCGATACTGA CCCGTGTTGT CTGTTAGCCG ACGAGACTAC
101  CCGCCGTGTT CCGGCTGTCA GCGCAGGGGC GCCCGGTTCT TTTTGTCAAG
     GGCGGCACAA GGCCGACAGT CGCGTCCCCG CGGGCCAAGA AAAACAGTTC
151  ACCGACCTGT CCGGTGCCCT GAATGAACTG CAAGACGAGG CAGCGCGGCT
     TGGCTGGACA GGCCACGGGA CTTACTTGAC GTTCTGCTCC GTCGCGCCGA
201  ATCGTGGCTG GCCACGACGG GCGTTCCTTG CGCAGCTGTG CTCGACGTTG
     TAGCACCGAC CGGTGCTGCC CGCAAGGAAC GCGTCGACAC GAGCTGCAAC
251  TCACTGAAGC GGGAAGGGAC TGGCTGCTAT TGGGCGAAGT GCCGGGGCAG
     AGTGACTTCG CCCTTCCCTG ACCGACGATA ACCCGCTTCA CGGCCCCGTC
301  GATCTCCTGT CATCTCACCT TGCTCCTGCC GAGAAAGTAT CCATCATGGC
     CTAGAGGACA GTAGAGTGGA ACGAGGACGG CTCTTTCATA GGTAGTACCG
351  TGATGCAATG CGGCGGCTGC ATACGCTTGA TCCGGCTACC TGCCCATTCG
     ACTACGTTAC GCCGCCGACG TATGCGAACT AGGCCGATGG ACGGGTAAGC
401  ACCACCAAGC GAAACATCGC ATCGAGCGAG CACGTACTCG GATGGAAGCC
     TGGTGGTTCG CTTTGTAGCG TAGCTCGCTC GTGCATGAGC CTACCTTCGG
451  GGTCTTGTCG ATCAGGATGA TCTGGACGAA GAGCATCAGG GGCTCGCGCC
     CCAGAACAGC TAGTCCTACT AGACCTGCTT CTCGTAGTCC CCGAGCGCGG
501  AGCCGAACTG TTCGCCAGGC TCAAGGCGAG CATGCCCGAC GGCGAGGATC
     TCGGCTTGAC AAGCGGTCCG AGTTCCGCTC GTACGGGCTG CCGCTCCTAG
551  TCGTCGTGAC CCATGGCGAT GCCTGCTTGC CGAATATCAT GGTGGAAAAT
     AGCAGCACTG GGTACCGCTA CGGACGAACG GCTTATAGTA CCACCTTTTA
601  GGCCGCTTTT CTGGATTCAT CGACTGTGGC CGGCTGGGTG TGGCGGACCG
     CCGGCGAAAA GACCTAAGTA GCTGACACCG GCCGACCCAC ACCGCCTGGC
651  CTATCAGGAC ATAGCGTTGG CTACCCGTGA TATTGCTGAA GAGCTTGGCG
     GATAGTCCTG TATCGCAACC GATGGGCACT ATAACGACTT CTCGAACCGC
701  GCGAATGGGC TGACCGCTTC CTCGTGCTTT ACGGTATCGC CGCTCCCGAT
     CGCTTACCCG ACTGGCGAAG GAGCACGAAA TGCCATAGCG GCGAGGGCTA
751  TCGCAGCGCA TCGCCTTCTA TCGCCTTCTT GACGAGTTCT TCTGA
     AGCGTCGCGT AGCGGAAGAT AGCGGAAGAA CTGCTCAAGA AGACT
```

Figure 19 Mouse hnRNP *Hind*III fragment nucleotide sequence

```
   1  AAGCTTTTAA CCCTCTATCC CTTTAAACTT CCTTGATCCA GTGTAAGCAC
      TTCGAAAATT GGGAGATAGG GAAATTTGAA GGAACTAGGT CACATTCGTG
  51  CTCCTAGAAA GTCAGTAGAC AATAAAACAA AAGTTCTGCT TCACCGATTT
      GAGGATCTTT CAGTCATCTG TTATTTTGTT TTCAAGACGA AGTGGCTAAA
 101  ACATTTATAA CCAAATACCC TTCACCAATA CAATAAAAAA ACAAAACAAC
      TGTAAATATT GGTTTATGGG AAGTGGTTAT GTTATTTTTT TGTTTTGTTG
 151  AAAAAACCCC AACCATCTGA GAAATAATCT TCTCCTTTCC CAGCTTTATT
      TTTTTTGGGG TTGGTAGACT CTTTATTAGA AGAGGAAAGG GTCGAAATAA
 201  CCCAGGATTC TACATGACCA AATTACCAGA GTCACCACTC ATTTTAATCA
      GGGTCCTAAG ATGTACTGGT TTAATGGTCT CAGTGGTGAG TAAAATTAGT
 251  CAACATAGTG TCAAATAACT AGAAAACATG AGACAACAAT GGAGAGCTGA
      GTTGTATCAC AGTTTATTGA TCTTTTGTAC TCTGTTGTTA CCTCTCGACT
 301  GTAACTATTA GTAGTAGTAC TTTACCAGAG AATGGCCTCT ATAGGCTCAC
      CATTGATAAT CATCATCATG AAATGGTCTC TTACCGGAGA TATCCGAGTG
 351  ATGTAGGAAT GGTTGGTCCC CAGGTGGTAG GTAGAGCTGT TTGAGGATTA
      TACATCCTTA CCAACCAGGG GTCCACCATC CATCTCGACA AACTCCTAAT
 401  CGTGGCCTTC TTGGATGGGG GGTGGGGGTG GGGTGGGAGG GTTGGGTGGT
      GCACCGGAAG AACCTACCCC CCACCCCCAC CCCACCCTCC CAACCCACCA
 451  GGGTACTTAA GAGGTTTCAA AAGTCAATAT TGTTTGCATT TAGCTCTTCC
      CCCATGAATT CTCCAAAGTT TTCAGTTATA ACAAACGTAA ATCGAGAAGG
 501  TTGTACTTGT GGATCAAACA CAACCTGTCA GCTACTGCTT CAAATGTCAT
      AACATGAACA CCTAGTTTGT GTTGGACAGT CGATGACGAA GTTTACAGTA
 551  GCCTGCTGCC ATCTTCTCAG CAGGATGGTC ATGGCCTCAC CCTCTTCAAC
      CGGACGACGG TAGAAGAGTC GTCCTACCAG TACCGGAGTG GGAGAAGTTG
 601  TGTAAATCTT TCTTTCTTTT CTTCTTTTTC TTTTGGTTTC GAGACAGGGT
      ACATTTAGAA AGAAAGAAAA GAAGAAAAAG AAAACCAAAG CTCTGTCCCA
 651  TTCTCTGTAT AGTCCTGGCT GTCCTGGAAC TCACTTTGTA GACCAGGCTG
      AAGAGACATA TCAGGACCGA CAGGACCTTG AGTGAAACAT CTGGTCCGAC
 701  GCCTTGAACT CAGAAATCCG CCTGCCTCTG CCTCCCTAGC ACTGGGATTA
      CGGAACTTGA GTCTTTAGGC GGACGGAGAC GGAGGGATCG TGACCCTAAT
 751  AAGGCGTGCG CCACCACGCC CAGCTTTCAA CTGGAAATCT TAATAAACTT
      TTCCGCACGC GGTGGTGCGG GTCGAAAGTT GACCTTTAGA ATTATTTGAA
 801  TCCTAGAAGT GGCCTTGGTT ATGGGAGCTT ATCACAGCAA TAGAACAGCA
      AGGATCTTCA CCGGAACCAA TACCCTCGAA TAGTGTCGTT ATCTTGTCGT
 851  ATTATGACTG GAGTATGATA GTTAAAAACA AGCAAGCAAG CAAGCAAACA
      TAATACTGAC CTCATACTAT CAATTTTTGT TCGTTCGTTC GTTCGTTTGT
 901  CACACACCAA AACAACAAAA CCCCAAGACA GAGTCACATG TAGCCCAGGC
      GTGTGTGGTT TTGTTGTTTT GGGGTTCTGT CTCAGTGTAC ATCGGGTCCG
 951  TAGCCTCCAA ATTCACTATA TAACTGAAGA AGACCCCTAA TTCCCATTCC
      ATCGGAGGTT TAAGTGATAT ATTGACTTCT TCTGGGGATT AAGGGTAAGG
1001  TCTAGAATCT ATACCTCAAG TACTGAATGG CTTGGTTCAC AATACCCCAC
      AGATCTTAGA TATGGAGTTC ATGACTTACC GAACCAAGTG TTATGGGGTG
1051  TAAATGATTG GTCTTACTAA GTGCAACAAG GTAAACCTAA AACTTCAGCC
      ATTTACTAAC CAGAATGATT CACGTTGTTC CATTTGGATT TTGAAGTCGG
1101  CTCAGACATC CCTTTTCCAG TATCAATTTA TAAAATTAGA TCCCAAGGAT
      GAGTCTGTAG GGAAAAGGTC ATAGTTAAAT ATTTTAATCT AGGGTTCCTA
1151  AAAAATTAAT TGTAAAGTAA AATCAGAGTT CTAGCATCAA CTACAGGCTC
      TTTTTAATTA ACATTTCATT TTAGTCTCAA GATCGTAGTT GATGTCCGAG
1201  AACCATGGGG ACCACAAATA AACTAAAAGG GATAAGACTG GCTTCCCCAT
      TTGGTACCCC TGGTGTTTAT TTGATTTTCC CTATTCTGAC CGAAGGGGTA
1251  AATTATTACA TTTAGATAAT TTTCCTGACT ACTCAACAAA GCTAAAATAT
      TTAATAATGT AAATCTATTA AAAGGACTGA TGAGTTGTTT CGATTTTATA
1301  CACCACTGGT TTATTTTCTC CTTCTAGGGT TTAAGCTCAC TCTGAGGAGG
      GTGGTGACCA AATAAAAGAG GAAGATCCCA AATTCGAGTG AGACTCCTCC
1351  GGCATGCGGC ACACACTCAT AGCATCCAGG AAATAGAAAT ATGGTGACTA
      CCGTACGCCG TGTGTGAGTA TCGTAGGTCC TTTATCTTTA TACCACTGAT
1401  TCATGGGTTC AGGGCCAACC TAGGCTTTAG AGAAAAACCT TGTCCCACAA
      AGTACCCAAG TCCCGGTTGG ATCCGAAATC TCTTTTTGGA ACAGGGTGTT
1451  ACCAAAAATG TCTCTTTTTT ATTCTATCAG GGGTGGATGG ATTTGTTAAA
      TGGTTTTTAC AGAGAAAAAA TAAGATAGTC CCCACCTACC TAAACAATTT
```

Figure 19 cont.

```
1501  GAAGTGCTTT TAAAAACCTT GAGATGGTTA TTTAGAAGTC CCCATGGGAT
      CTTCACGAAA ATTTTTGGAA CTCTACCAAT AAATCTTCAG GGGTACCCTA
1551  ACCAAAATAA CCCACTATTT ATATGCCCAA GCATTTCACC TCCACAACAG
      TGGTTTTATT GGGTGATAAA TATACGGGTT CGTAAAGTGG AGGTGTTGTC
1601  TGCTATGCAC CCTTTAACAT TTTTGAGACA GTAGCCCAGT CTAGTCTTTA
      ACGATACGTG GGAAATTGTA AAAACTCTGT CATCGGGTCA GATCAGAAAT
1651  ACTTGCAGTG ATTTTTCCTG ATTCAGCTTC TCCCAGTGCT GGAATTATAG
      TGAACGTCAC TAAAAAGGAC TAAGTCGAAG AGGGTCACGA CCTTAATATC
1701  GTATGCACCA CCATGTGTAA CTACAGATGC TACTTAAAAA TTTTTTAAAG
      CATACGTGGT GGTACACATT GATGTCTACG ATGAATTTTT AAAAAATTTC
1751  GAATCACAAA AATAACCCCC TATCAAATGC CTAGTCCCTC TAACCATCAC
      CTTAGTGTTT TTATTGGGGG ATAGTTTACG GATCAGGGAG ATTGGTAGTG
1801  CAAGTGAAGG ATCACGCAGG AAAAAAAAAA TCACCAGCAG CACCTCAGAA
      GTTCACTTCC TAGTGCGTCC TTTTTTTTTT AGTGGTCGTC GTGGAGTCTT
1851  CCAGGATACT CAGTCCATCA GCATCCAGGG CCATACCCAC ACTCACAGCA
      GGTCCTATGA GTCAGGTAGT CGTAGGTCCC GGTATGGGTG TGAGTGTCGT
1901  TCTCCACAGT TTACCAGATG ATTCATGCTT ATCACTGTAT TGGGTCATCT
      AGAGGTGTCA AATGGTCTAC TAAGTACGAA TAGTGACATA ACCCAGTAGA
1951  AAGAGTGACC ATCAGGGCTT CTGATCACAG AATCTAGTCC ACTTTGCAGA
      TTCTCACTGG TAGTCCCGAA GACTAGTGTC TTAGATCAGG TGAAACGTCT
2001  CCAGTTGAAG TCATGCACTA TATGAGATAG AAATACCCTC TTGCTCATTT
      GGTCAACTTC AGTACGTGAT ATACTCTATC TTTATGGGAG AACGAGTAAA
2051  TGGTCAGAAA TTCAAGGATA AAAACCCATG TTTTGTTAAT GCACACCTCC
      ACCAGTCTTT AAGTTCCTAT TTTTGGGTAC AAAACAATTA CGTGTGGAGG
2101  ATATGATTGA GATCAATGTG TCCTAATTAA TGTAGAAACC ACAACTGTAA
      TATACTAACT CTAGTTACAC AGGATTAATT ACATCTTTGG TGTTGACATT
2151  ATTTCACTCT TTTGACATGA ATCTTTTTCT AGACAGGGTC TTGGATGCAG
      TAAAGTGAGA AAACTGTACT TAGAAAAAGA TCTGTCCCAG AACCTACGTC
2201  CCCCGACTAC CCAGAATTTT GGAATCCAGG CTAGCCTCAA ACTCAAGGCA
      GGGGCTGATG GGTCTTAAAA CCTTAGGTCC GATCGGAGTT TGAGTTCCGT
2251  ATCTGCTTGC TTCAGCTTCT CACAGGCTGG ATCACAAACA TACACCTTCA
      TAGACGAACG AAGTCGAAGA GTGTCCGACC TAGTGTTTGT ATGTGGAAGT
2301  GACCCATTTT TTTTTCCTCC CTCCGTTTTT GGTTTCTCTG TGTAGCCCTG
      CTGGGTAAAA AAAAAGGAGG GAGGCAAAAA CCAAAGAGAC ACATCGGGAC
2351  GGTGTCCGTG GACTCGCTGT GTAGATCTAT CTACCAGCCT CTGTCTTGGA
      CCACAGGCAC CTGAGCGACA CATCTAGATA GATGGTCGGA GACAGAACCT
2401  GTACTGGGAT TAAAGTTGTG GGCTACCACT GCCTGGCTGA CCCAGTTTTA
      CATGACCCTA ATTTCAACAC CCGATGGTGA CGGACCGACT GGGTCAAAAT
2451  TTTATTTTAA ATATAACTTG ACAAAAATAA ATTTGTCTAA CTTACTAGAA
      AAATAAAATT TATATTGAAC TGTTTTTATT TAAACAGATT GAATGATCTT
2501  ATCCCAAGAA AACTAACACT GGATTTAGCA ACAGTCAGAA ATCGCTGAAA
      TAGGGTTCTT TTGATTGTGA CCTAAATCGT TGTCAGTCTT TAGCGACTTT
2551  AGAAACAGAA TTGATCTAAC AGTCTTAGAT CACTCCTAGA CAGTTTGTAA
      TCTTTGTCTT AACTAGATTG TCAGAATCTA GTGAGGATCT GTCAAACATT
2601  TTCTTGCTCA TGGCAACGTG AGCTCTATCT AACTCACTCT CTGTGCACTA
      AAGAACGAGT ACCGTTGCAC TCGAGATAGA TTGAGTGAGA GACACGTGAT
2651  ATGAATGCTC AGTGTCTCCA GAACAGCACA GCTTCCAGGG TAATCATGCC
      TACTTACGAG TCACAGAGGT CTTGTCGTGT CGAAGGTCCC ATTAGTACGG
2701  AACCCACAAG ACTTTTATAG AGCTGTCCAC GACTCTTCCC CCATTCAGCT
      TTGGGTGTTC TGAAAATATC TCGACAGGTG CTGAGAAGGG GGTAAGTCGA
2751  CATTAACAAT ATGATGGAGC TCCTGTGTGG AAATCAAGGC ACACTCTGGT
      GTAATTGTTA TACTACCTCG AGGACACACC TTTAGTTCCG TGTGAGACCA
2801  AGAAACTTGT TTTTTCTTTC CACTTTTCCT TGGGCTCTGA AGATTGAGCT
      TCTTTGAACA AAAAAGAAAG GTGAAAAGGA ACCCGAGACT TCTAACTCGA
2851  GTTTTATAAC CCACAAACAT GCATTTTTTA CCTCAAAAGC ATCCAGCAAA
      CAAAATATTG GGTGTTTGTA CGTAAAAAAT GGAGTTTTCG TAGGTCGTTT
2901  AACTGTACAA CGCTTTTTCA AAAAAATGTA TTGTGATCCT CCTTAAGAAA
      TTGACATGTT GCGAAAAAGT TTTTTTACAT AACACTAGGA GGAATTCTTT
2951  AGCCTTACTT AGTGTTAATT CCTTTTTCTT TAGAATGCTG GTAAATACAA
      TCGGAATGAA TCACAATTAA GGAAAAAGAA ATCTTACGAC CATTTATGTT
3001  GGACTTAGGT AGGCTGGCTT CTAACAGCAA TTCACCCACT TATGATGGGA
      CCTGAATCCA TCCGACCGAA GATTGTCGTT AAGTGGGTGA ATACTACCCT
3051  TTAAAGGAAG GCACAACCAT GTCCACCACA GGTTCTAGCT CCCCCACCCA
      AATTTCCTTC CGTGTTGGTA CAGGTGGTGT CCAAGATCGA GGGGGTGGGT
3101  CACGCCCAGA GAGGGTTTTT CTGTGTAGCT CTGACTATTC TGGAATTCAC
      GTGCGGGTCT CTCCCAAAAA GACACATCGA GACTGATAAG ACCTTAAGTG
```

Figure 19 cont.

```
3151   ACTGCAGACC AGGCTGGTCT CGAACTCAGA GATCCACCAC CACATGGTTT
       TGACGTCTGG TCCGACCAGA GCTTGAGTCT CTAGGTGGTG GTGTACCAAA
3201   CTTAATTGTA ATTTTAAAGA AAAAAAAAAA TCCTTCAGTT AAGATTCTTA
       GAATTAACAT TAAAATTTCT TTTTTTTTTT AGGAAGTCAA TTCTAAGAAT
3251   TGTTCTAGGT TTTCACAAAC TTACCAATGT AGTTTTATTG GAGGCCATTT
       ACAAGATCCA AAAGTGTTTG AATGGTTACA TCAAAATAAC CTCCGGTAAA
3301   TTTAAATTTA ATCGGAGACT TGAAGAGCTA TTGCAAGAAA AAAAATGTAG
       AAATTTAAAT TAGCCTCTGA ACTTCTCGAT AACGTTCTTT TTTTTACATC
3351   GACAGTTAAA ATTTCATGAC ACACAAAAGG CAGCTACAAG TTTTGTGTGG
       CTGTCAATTT TAAAGTACTG TGTGTTTTCC GTCGATGTTC AAAACACACC
3401   ATTTCAACAT GTAAATTTCG GGTAAAAATG CAGGAAAACA GTTGAGTTCC
       TAAAGTTGTA CATTTAAAGC CCATTTTTAC GTCCTTTTGT CAACTCAAGG
3451   CGTGTTATTA GTATGTTACT AATAATTTCA GTATGTTAGT GAAAATAATC
       GCACAATAAT CATACAATGA TTATTAAAGT CATACAATCA CTTTTATTAG
3501   TTACTAAAAC ACTGGTACCT CAGACAACTT TACATGGTGA GGATTGTTAC
       AATGATTTTG TGACCATGGA GTCTGTTGAA ATGTACCACT CCTAACAATG
3551   TTTCCCAATC CATATAGAAT TTTAACAATT TTAGTGTTTA TTTTGGATGA
       AAAGGGTTAG GTATATCTTA AAATTGTTAA AATCACAAAT AAAACCTACT
3601   AAGGAAATGA CTATCTTTTG TTAGCAAATT ACCATAAGAT CTTTTTCTTT
       TTCCTTTACT GATAGAAAAC AATCGTTTAA TGGTATTCTA GAAAAAGAAA
3651   AGATTTCTGA ATACTCCAAG GAGCTCATAT AATTCCATCC TTATTTTTTC
       TCTAAAGACT TATGAGGTTC CTCGAGTATA TTAAGGTAGG AATAAAAAAG
3701   AGAGGCCCTC CCTGTTCAAT CACGGTATAA AAAAAGGAAC ACATTAAGAT
       TCTCCGGGAG GGACAAGTTA GTGCCATATT TTTTTCCTTG TGTAATTCTA
3751   GTCCCAGTCC TATTTTCTGG CTTTTTTTTT CCGGGGGTGG TGGTGCGGTA
       CAGGGTCAGG ATAAAAGACC GAAAAAAAAA GGCCCCCACC ACCACGCCAT
3801   ATCACTCTCT ATAGTCCAGT CTGGGCTTCA ACGCCTGGCA ATCCCCAGCC
       TAGTGAGAGA TATCAGGTCA GACCCGAAGT TGCGGACCGT TAGGGGTCGG
3851   TCAAGCTCCC AAGTACTGTC CTGATAAGGA TAGAAGGAGT CGACCTCCTT
       AGTTCGAGGG TTCATGACAG GACTATTCCT ATCTTCCTCA GCTGGAGGAA
3901   CACGCTCCCC TCCGAGGAGG GCTCCTTCCC AGCTCCATTC CCCGGTCGGG
       GTGCGAGGGG AGGCTCCTCC CGAGGAAGGG TCGAGGTAAG GGGCCAGCCC
3951   AGCCCGTCCC CCACCCGAGA GCGCGGGCCT CGTGGTCAGC GCCTCCGCGG
       TCGGGCAGGG GGTGGGCTCT CGCGCCCGGA GCACCAGTCG CGGAGGCGCC
4001   GGAGAAACAA AGGCGGCGGC GGGGGCTCAA GGGCACTGCG CCACGGGCCC
       CCTCTTTGTT TCCGCCGCCG CCCCCGAGTT CCCGTGACGC GGTGCCCGGG
4051   GCGCCTCCCC CATCCGGCGG CGGCCACGTA GCCGGGAGCG CGCCGCAGCC
       CGCGGAGGGG GTAGGCCGCC GCCGGTGCAT CGGCCCTCGC GCGGCGTCGG
4101   CGGAGCCTCG GGCCTCGCAG CTGCAGAGCC TGAACCGCTC TCTCCCTGCG
       GCCTCGGAGC CCGGAGCGTC GACGTCTCGG ACTTGGCGAG AGAGGGACGC
4151   GGCCTGCGAC GAGGCTGGGG GAGGGGAGGC CCGCGCTTTG TCTGGAGTCT
       CCGGACGCTG CTCCGACCCC CTCCCCTCCG GGCGCGAAAC AGACCTCAGA
4201   CGGTAGCTGT CATCCGGCTC CCACCCTCAT GCACAATTGT CCCATCTCCC
       GCCATCGACA GTAGGCCGAG GGTGGGAGTA CGTGTTAACA GGGTAGAGGG
4251   CCACGCACCG GCGCGGCGCC CGCCTCAGCG AGGCCCCAGC CGGTTTCCCG
       GGTGCGTGGC CGCGCCGCGG GCGGAGTCGC TCCGGGGTCG GCCAAAGGGC
4301   CAGCCCGCGG CCCACGGGGC TCGCAGCCTC CCCGCAAGCT CGGACGCACG
       GTCGGGCGCC GGGTGCCCCG AGCGTCGGAG GGGCGTTCGA GCCTGCGTGC
4351   GAGCATCCTA AACCCCACCA CACGCAAGAT CGAAAAAAAG CAAAGGCACG
       CTCGTAGGAT TTGGGGTGGT GTGCGTTCTA GCTTTTTTTC GTTTCCGTGC
4401   AACTTCACCG CTCCGATGCT CAGGGCCGCG GATCCTGCAG AGTCTCCCGC
       TTGAAGTGGC GAGGCTACGA GTCCCGGCGC CTAGGACGTC TCAGAGGGCG
4451   CTGCGCGCTT CGGTTCAGCC ACATCCGAGG GGAGGGGGCG CGGGCAGCTC
       GACGCGCGAA GCCAAGTCGG TGTAGGCTCC CCTCCCCCGC GCCCGTCGAG
4501   CGCCGGGGGG GAGGGGGAGC ACCGCCCACG CCCTGGCCGC GCGGGGCCCG
       GCGGCCCCCC CTCCCCCTCG TGGCGGGTGC GGGACCGGCG CGCCCCGGGC
4551   CCGGGAACGC GTCCTGCGGG GGGCGGCGCG CGCAATGCTC ACCGTCCGCG
       GGCCCTTGCG CAGGACGCCC CCCGCCGCGC GCGTTACGAG TGGCAGGCGC
4601   GCGTGGCGCC CAGGGGGTCT CCTGGCTGGG GGGAGGGGGG GGAAGGCGGG
       CGCACCGCGG GTCCCCCAGA GGACCGACCC CCCTCCCCCC CCTTCCGCCC
4651   CAGGAAGGAC CGCGGAGGCC TCTCTGCGTC TCGGAGCGCG CCAAAGCGGG
       GTCCTTCCTG GCGCCTCCGG AGAGACGCAG AGCCTCGCGC GGTTTCGCCC
4701   GCTCCACCCA CCTCCTTGCC CGGATCTTGA AGGCCGGGGA GATAAACAGC
       CGAGGTGGGT GGAGGAACGG GCCTAGAACT TCCGGCCCCT CTATTTGTCG
4751   GGGGTTCTTT AAGCACCACC TCTCACTAGG CGCGGGATCC CAAGGCTTGT
       CCCCAAGAAA TTCGTGGTGG AGAGTGATCC GCGCCCTAGG GTTCCGAACA
```

Figure 19 cont.

```
4801  GGCATCCGGG GTGGTACTTG GACTAAAAGT CCTTCTGGGA GGGACCGAGT
      CCGTAGGCCC CACCATGAAC CTGATTTTCA GGAAGACCCT CCCTGGCTCA
4851  GAGAACCCCT TTGGGACGTG TAGAAATATT TGTGTGGTTC GAGAATATTT
      CTCTTGGGGA AACCCTGCAC ATCTTTATAA ACACACCAAG CTCTTATAAA
4901  GTGCGGACGG GCTTGGCAAA GGCGTAGCTG CAGAGAGCAC GCTTGGGTGG
      CACGCCTGCC CGAACCGTTT CCGCATCGAC GTCTCTCGTG CGAACCCACC
4951  AGAGGGCCGC ACGCCCCAGC GCCGGCCTAA GCCCCTCCCG ACGGCGTTAT
      TCTCCCGGCG TGCGGGGTCG CGGCCGGATT CGGGGAGGGC TGCCGCAATA
5001  TTCAAACTGC GCGACCGTTT CTCCGCTCCC TACGCGGAGG TGGGGGCCGG
      AAGTTTGACG CGCTGGCAAA GAGGCGAGGG ATGCGCCTCC ACCCCCGGCC
5051  ACCTAGTTCC GGACGTAGTA ACACGCCGAG CGCGAGCCTT CCGCAATTCA
      TGGATCAAGG CCTGCATCAT TGTGCGGCTC GCGCTCGGAA GGCGTTAAGT
5101  CGGAACACAG TTGCGCAAGT GATGTAAAGC AGTCCCGCTG TACCTAAAGG
      GCCTTGTGTC AACGCGTTCA CTACATTTCG TCAGGGCGAC ATGGATTTCC
5151  GGGAGTGTCA CGTACTTGGC GTAAGGAGAG TGTAGGCCCT TCCCGCCATT
      CCCTCACAGT GCATGAACCG CATTCCTCTC ACATCCGGGA AGGGCGGTAA
5201  GGCGGCGGTT AGGGCGTTTA CGTAACGGCG TGACGTAAGC GGAGACGCGT
      CCGCCGCCAA TCCCGCAAAT GCATTGCCGC ACTGCATTCG CCTCTGCGCA
5251  TAGTGGGGGG AAGGTTCTAG AAAAGCGGCG GTCTCGGCTC CAGCGGCAGT
      ATCACCCCCC TTCCAAGATC TTTTCGCCGC CAGAGCCGAG GTCGCCGTCA
5301  AGCAGCGGCG CCGGTCCCGT GTGCAGGAGC TCCTTTGCGG CCCAGTTTCT
      TCGTCGCCGC GGCCAGGGCA CACGTCCTCG AGGAAACGCC GGGTCAAAGA
5351  TGGCCATCGC CTGCTCTCCC CACAGCGCCA GGACGAGTCC CGTGCGCGTC
      ACCGGTAGCG GACGAGAGGG GTGTCGCGGT CCTGCTCAGG GCACGCGCAG
5401  CGTCCGCGGA GGTCTTTCTC ATCTCGCTCG GCTGCGGGAA ATCGGGCTGA
      GCAGGCGCCT CCAGAAAGAG TAGAGCGAGC CGACGCCCTT TAGCCCGACT
5451  AGCGACTGAG TCCGCGATGG AGGTAACGGG TTTGAAATCA ATGAGTTATT
      TCGCTGACTC AGGCGCTACC TCCATTGCCC AAACTTTAGT TACTCAATAA
5501  AAAAATGGCA TGGCGAGGCC GTAGGCACCG CAATGGAAAC CGGCCACCCG
      TTTTTACCGT ACCGCTCCGG CATCCGTGGC GTTACCTTTG GCCGGTGGGC
5551  CCTCCGTGGT CCGGCGGAGG GGATGCGGCC ACTCGAGTGG CGGTTGGCCT
      GGAGGCACCA GGCCGCCTCC CCTACGCCGG TGAGCTCACC GCCAACCGGA
5601  TGGCGAGTTT CTGAGGGGTC GTTGGAGGAG GCCTCTGATT GTCCGACCGC
      ACCGCTCAAA GACTCCCCAG CAACCTCCTC CGGAGACTAA CAGGCTGGCG
5651  CTTCCCCGCC CTCAGCCGCC CGGCGCCATT TCCCTCAGTT GGGGTGGGGG
      GAAGGGGCGG GAGTCGGCGG GCCGCGGTAA AGGGAGTCAA CCCCACCCCC
5701  ATGGGAAGTG CCCGCCGCGA CCGGGCTGGA CCGCTAAAGT AGCGCGTGAG
      TACCCTTCAC GGGCGGCGCT GGCCCGACCT GGCGATTTCA TCGCGCACTC
5751  CGGGCCATCG CTGGCCTTTC GATGTGCGCG GGCCTAGGGG CTCGGTTGTG
      GCCCGGTAGC GACCGGAAAG CTACACGCGC CCGGATCCCC GAGCCAACAC
5801  TTCGCGGCGG AACGTTTCTG GGGCCCCCCC GGCTTCCCGG AGCGAGTCTG
      AAGCGCCGCC TTGCAAAGAC CCCGGGGGGG CCGAAGGGCC TCGCTCAGAC
5851  CGAAGCTAGC TTCCCCTCCC CCCTCTCCCG GGAACCGGAT TTGGCGGCCG
      GCTTCGATCG AAGGGGAGGG GGGAGAGGGC CCTTGGCCTA AACCGCCGGC
5901  CCATTTTCCC GTCTCCTTCC TCGCCACGAT TTTGCTTTCA ACGCTTTAGG
      GGTAAAAGGG CAGAGGAAGG AGCGGTGCTA AAACGAAAGT TGCGAAATCC
5951  TTTACTAGTT TGGTTTTCTT TTTTCACCAC TGCGTAGACG TGTTTAGCGA
      AAATGATCAA ACCAAAAGAA AAAAGTGGTG ACGCATCTGC ACAAATCGCT
6001  TTTTCCTTTC TTTTGGAAGT CTTCATACCG TTTCGAGGTG GATTTAGCGT
      AAAAGGAAAG AAAACCTTCA GAAGTATGGC AAAGCTCCAC CTAAATCGCA
6051  TTTGAGCTTG GGTCTTCAGC GTCCTGCGCA CCTCGCTAAA GGCTCTCTGC
      AAACTCGAAC CCAGAAGTCG CAGGACGCGT GGAGCGATTT CCGAGAGACG
6101  CTTCCCCTCG ACGAAATGGC GCCATTGCTT TCTGAAGCCA CCGAGGCGCG
      GAAGGGGAGC TGCTTTACCG CGGTAACGAA AGACTTCGGT GGCTCCGCGC
6151  GGGTGGGGGC GGGGTGGCGG CGCTCCACGA GCTTTACTGG AACAGGCAGA
      CCCACCCCCG CCCCACCGCC GCGAGGTGCT CGAAATGACC TTGTCCGTCT
6201  GAGAACGTAG TACAACCGAG GCCTGGGCGG GTGGCTGAAG GCAGCGTCGC
      CTCTTGCATC ATGTTGGCTC CGGACCCGCC CACCGACTTC CGTCGCAGCG
6251  TGCAAAGAGA CCGTTTTATT TTTCATAATA CGTAAGATTA CGGGTGCTGT
      ACGTTTCTCT GGCAAAATAA AAAGTATTAT GCATTCTAAT GCCCACGACA
6301  AGTAAAGCAC TTGAGCATTA GTATAGTAGG AGGAAGTCAA AGTGGAAAAA
      TCATTTCGTG AACTCGTAAT CATATCATCC TCCTTCAGTT TCACCTTTTT
6351  ATGGGAGCGC TCATCAGGAA GCTAGGGAGG CTATGTTGAG TGCAGGGTTA
      TACCCTCGCG AGTAGTCCTT CGATCCCTCC GATACAACTC ACGTCCCAAT
6401  CTTTCCTTTT ATTGCAGAAC TTTTATCTGC TTAAAGGATC CTCGGATCGA
      GAAAGGAAAA TAACGTCTTG AAAATAGACG AATTTCCTAG GAGCCTAGCT
```

Figure 19 cont.

```
6451  AATAATTCAA ATTATAAGCA TTTTTAAGGG AATCTTCGAA TTTGTTGGTA
      TTATTAAGTT TAATATTCGT AAAAATTCCC TTAGAAGCTT AAACAACCAT
6501  AAGTCAACGG ATCCTTAGCA CGTGGTGTTC ACTTTAAGGA AGTGAAATAG
      TTCAGTTGCC TAGGAATCGT GCACCACAAG TGAAATTCCT TCACTTTATC
6551  CTGACTTTTC ATAGTTAGCC TTCGCTTAAA GCCTGGTTCA GTGGACGAAA
      GACTGAAAAG TATCAATCGG AAGCGAATTT CGGACCAAGT CACCTGCTTT
6601  ATCCACGTCC TGGCTATATA AAAACTTAGT TTGGGGTCAC AGTGTTTGAG
      TAGGTGCAGG ACCGATATAT TTTTGAATCA AACCCCAGTG TCACAAACTC
6651  CGTGGTCATT CGGTTTTTTT ATTTTTTATT TGTTTGAAAT TATGATGCAT
      GCACCAGTAA GCCAAAAAAA TAAAAAATAA ACAAACTTTA ATACTACGTA
6701  CATTACACTG ATAAGCATTA GCTTTCGAAT TGAAAGGGGT CTCCTTGGTT
      GTAATGTGAC TATTCGTAAT CGAAAGCTTA ACTTTCCCCA GAGGAACCAA
6751  ATTTTCTTTG ACTCTAAGCA CACTTATAAA TAAAATAACC TTGTTTATAA
      TAAAAGAAAC TGAGATTCGT GTGAATATTT ATTTTATTGG AACAAATATT
6801  TCGATAGTGG ACGTCTGGTA AGTTTGGAAA AAACCCGAGG TAAGTAAAGA
      AGCTATCACC TGCAGACCAT TCAAACCTTT TTTGGGCTCC ATTCATTTCT
6851  GCTTTTGCTT TCGTTAGTGA TATGAAAAAA CAAGGTGTAT TTAATACTTG
      CGAAAACGAA AGCAATCACT ATACTTTTTT GTTCCACATA AATTATGAAC
6901  CAACTTAGTT TAAGGAAAGC CAATTTACTG ACATTTTAGT AGAGCTACCA
      GTTGAATCAA ATTCCTTTCG GTTAAATGAC TGTAAAATCA TCTCGATGGT
6951  GAAACACTAT TTGGAGTCCT GATTAAGGCT TTTGTAACTA TTTTGACTAT
      CTTTGTGATA AACCTCAGGA CTAATTCCGA AAACATTGAT AAAACTGATA
7001  TTAAAACAAT TTTGGTCGTT TTTATTAAAC ATTTCAAAAC CTAAAAATTG
      AATTTTGTTA AAACCAGCAA AAATAATTTG TAAAGTTTTG GATTTTTAAC
7051  TAAACATTGG CTTTTTGAGC ACATTTTGGA GAAACTTACA AATTTAGGCT
      ATTTGTAACC GAAAAACTCG TGTAAAACCT CTTTGAATGT TTAAATCCGA
7101  ATACAGTAAA ATAACGGATT TGTTTTATAA TTTTGCTTTT TCATTTCGTT
      TATGTCATTT TATTGCCTAA ACAAAATATT AAAACGAAAA AGTAAAGCAA
7151  GTGCAGTCAT AGGTCCTGGA TAGTATGACC TAATTTATGA ACATCTTGAT
      CACGTCAGTA TCCAGGACCT ATCATACTGG ATTAAATACT TGTAGAACTA
7201  AAGTTTTTGT ACTTAGCTAT TGGAAAGCCA GTATTAAGTG CCTGACAAAA
      TTCAAAAACA TGAATCGATA ACCTTTCGGT CATAATTCAC GGACTGTTTT
7251  CCAGATTTAA GGTGATATCT GGAGTTTCAG CATTCTTCAT GGAGCTTGTT
      GGTCTAAATT CCACTATAGA CCTCAAAGTC GTAAGAAGTA CCTCGAACAA
7301  TCAGAGTTGC AGGATTTTTT TTTTTCATCT TGAGATACTT ACAATTAACA
      AGTCTCAACG TCCTAAAAAA AAAAAGTAGA ACTCTATGAA TGTTAATTGT
7351  CCAGAGGGGG CAGCTCAGGG AAAAGCAAAT ATGCCACTTT TCAGAAACTG
      GGTCTCCCCC GTCGAGTCCC TTTTCGTTTA TACGGTGAAA AGTCTTTGAC
7401  AATCTTGGAA GTGGTGAATT TGGAAACAGG TTTTTTAAAT TTTTTTTAAA
      TTAGAACCTT CACCACTTAA ACCTTTGTCC AAAAAATTTA AAAAAAATTT
7451  TCTAAAAAGT AGTAAATTTT GGACTTGGGT TGTAGAATTT AATGAATTAC
      AGATTTTTCA TCATTTAAAA CCTGAACCCA ACATCTTAAA TTACTTAATG
7501  AAAAGAATTC TTTAATACCC TTTAAATGAC CTAAGAGCTG GGTATGGTTT
      TTTTCTTAAG AAATTATGGG AAATTTACTG GATTCTCGAC CCATACCAAA
7551  TTCTGAATTT TTTTGAAGAA AATCTAAGAA AGTTTACGTG AATTAGAAGT
      AAGACTTAAA AAAACTTCTT TTAGATTCTT TCAAATGCAC TTAATCTTCA
7601  TAGATCGAAT ATTAGTGACT TTGAAACTTG TATAGCTCAG GCAATTTTTG
      ATCTAGCTTA TAATCACTGA AACTTTGAAC ATATCGAGTC CGTTAAAAAC
7651  GTGTAACACA ACTAATATGC AGTTTAACAT ATGGTTTAAA TTTGATGTAA
      CACATTGTGT TGATTATACG TCAAATTGTA TACCAAATTT AAACTACATT
7701  GTTTTTTTTC TCCCCCCCAG AAAACTTTAG AAACTGTTCC TTTGGAGAGG
      CAAAAAAAAG AGGGGGGGTC TTTTGAAATC TTTGACAAGG AAACCTCTCC
7751  AAAAAGGTAC TCTACCAGCA GGTCACCTCA TATTTAAGAA TTTAATTTCC
      TTTTTCCATG AGATGGTCGT CCAGTGGAGT ATAAATTCTT AAATTAAAGG
7801  TGCATACAAA GAAAGTGTAA ATAAAAATTG AAATGGTATT TCCCTTTGCA
      ACGTATGTTT CTTTCACATT TATTTTTAAC TTTACCATAA AGGGAAACGT
7851  GAGAGAAAAG GAACAGTTCC GAAAGCTCTT TATTGGTGGC TTAAGCTT
      CTCTCTTTTC CTTGTCAAGG CTTTCGAGAA ATAACCACCG AATTCGAA
```

Figure 21: CET1010 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAAGCT
      TAACCCATGG CCCGGGGGGG AGCTTCAAAT TTGTAAATTT AGATCTTCGA
 101  TCAATGTTTT TAGCACCCTC TGTGTGGAGG AAAATAATGC AGATTATTCT
      AGTTACAAAA ATCGTGGGAG ACACACCTCC TTTTATTACG TCTAATAAGA
 151  AATTAGTGTA ATATCTAACC ACATTAAAAT ATATTACATA GTAAACTACA
      TTAATCACAT TATAGATTGG TGTAATTTTA TATAATGTAT CATTTGATGT
 201  CTCCATAATT TTATAAATTT GACTCCCCAG GGTAATAAAC TAGTCTCTAG
      GAGGTATTAA AATATTTAAA CTGAGGGGTC CCATTATTTG ATCAGAGATC
 251  TCTGCTCACC TTCAACTGTA CAATAAAGTC TTGGTTCTTT TGAAATAGAC
      AGACGAGTGG AAGTTGACAT GTTATTTCAG AACCAAGAAA ACTTTATCTG
 301  CTCAAATGAG ACACCTAAAA TTCAAAGTGT CTTTACATTT AAAGACACCT
      GAGTTTACTC TGTGGATTTT AAGTTTCACA GAAATGTAAA TTTCTGTGGA
 351  ACAGGAAAGC AGGTAAAAGA GCCAGGTTAA AAACAAATTC TAAAACCACT
      TGTCCTTTCG TCCATTTTCT CGGTCCAATT TTTGTTTAAG ATTTTGGTGA
 401  TAGCTGCAGT TAAACATATA GTAAAGATGC ACTAAAGTTT CTTACTCTGT
      ATCGACGTCA ATTTGTATAT CATTTCTACG TGATTTCAAA GAATGAGACA
 451  AAATCCCTTC CACTTCAGGA AATATTCCAC TTTCCCATTC ACTACACGTC
      TTTAGGGAAG GTGAAGTCCT TTATAAGGTG AAAGGGTAAG TGATGTGCAG
 501  GATCTAGTAC TTTTTCCACG ACAAATTCTT CAGGCTCTGC CTCTTCAACT
      CTAGATCATG AAAAAGGTGC TGTTTAAGAA GTCCGAGACG GAGAAGTTGA
 551  TTTTTACTCT TTCCATTCTG TTTTTTTCCC ATTTTTTGCT AAAATAAAAC
      AAAAATGAGA AAGGTAAGAC AAAAAAAGGG TAAAAAACGA TTTTATTTTG
 601  AAAAGAGAAA TTAAGAAATA TTCCTCTTGA ATTTTGAGCA CATTTTCAAG
      TTTTCTCTTT AATTCTTTAT AAGGAGAACT TAAAACTCGT GTAAAAGTTC
 651  GCTCAATTGC TTATATTATT ATCACATTCG ACATAAATTT TTACTTCTAT
      CGAGTTAACG AATATAATAA TAGTGTAAGC TGTATTTAAA AATGAAGATA
 701  ATCCCAGGGC AGACACCTTC TGGAAAGATT AAAAGTCAAC AGACAATAAA
      TAGGGTCCCG TCTGTGGAAG ACCTTTCTAA TTTTCAGTTG TCTGTTATTT
 751  ATAAAAGAAT GCTTTATCTT GTTCATTTAG TTCAAACTTA CAACCCACCA
      TATTTTCTTA CGAAATAGAA CAAGTAAATC AAGTTTGAAT GTTGGGTGGT
 801  CCAAAATAAT ACAATAAAAA AACACTATCT GGAAACAGTT ATTTTTTTCC
      GGTTTTATTA TGTTATTTTT TTGTGATAGA CCTTTGTCAA TAAAAAAAGG
 851  AGTCTTTTTT TTTGAGACAG GGTCTCACAC TCTTGTCGCC CAGGCTGGAG
      TCAGAAAAAA AAACTCTGTC CCAGAGTGTG AGAACAGCGG GTCCGACCTC
 901  TGCAGTGGCG TGATCTCAGC TCACTGCAAC CTCCGCCTCC CCAGGTTCAA
      ACGTCACCGC ACTAGAGTCG AGTGACGTTG GAGGCGGAGG GGTCCAAGTT
 951  GCAGTTCTCA TGCCTCAGCC TCCAGAGTAG CTGGGATTAT AGGCGGATGC
      CGTCAAGAGT ACGGAGTCGG AGGTCTCATC GACCCTAATA TCCGCCTACG
1001  CACCATGCCG GGCTAATTTT TTTTGTGTTT TTATTAGAAA CAGGGTTTCA
      GTGGTACGGC CCGATTAAAA AAAACACAAA AATAATCTTT GTCCCAAAGT
1051  CCATGTTGAC CAGGCTGGTC TCAAACTCCT GACCTGAAGT GATTCACCAG
      GGTACAACTG GTCCGACCAG AGTTTGAGGA CTGGACTTCA CTAAGTGGTC
1101  CCTGGGCCTC CCAAAGTGCT GGCATTACAG GCGTGAGCCA CTGCGCCCGG
      GGACCCGGAG GGTTTCACGA CCGTAATGTC CGCACTCGGT GACGCGGGCC
1151  CCCTGTAGTC TTAAAAGACC AAGTTTACTA ATTTTCACTC ATTTTAACAA
      GGGACATCAG AATTTTCTGG TTCAAATGAT TAAAAGTGAG TAAAATTGTT
1201  CACTGCAACA AACAACTATG CAGGAAGTAC CTAAAGGGTG ATCCAGAGAA
      GTGACGTTGT TTGTTGATAC GTCCTTCATG GATTTCCCAC TAGGTCTCTT
1251  GCAAGTAGTA GTGACAGGTC TTAGGTGAAC CTATGACAGA CCTTGTATCC
      CGTTCATCAT CACTGTCCAG AATCCACTTG GATACTGTCT GGAACATAGG
1301  ACCCCCAGAT GGTAAAAGCC CCAGCCCCCT TCTCAATTCA AATATTAATG
      TGGGGGTCTA CCATTTTCGG GGTCGGGGGA AGAGTTAAGT TTATAATTAC
1351  TCAAAAGCAT CAATGATACA GAGAAAAGAT AAATGCAGAA TGAAAACATG
      AGTTTTCGTA GTTACTATGT CTCTTTTCTA TTTACGTCTT ACTTTTGTAC
1401  GTTCAAAATC CTGATACCAA CTGCAGGGTC AACTATAGAG ACCACTAGGA
      CAAGTTTTAG GACTATGGTT GACGTCCCAG TTGATATCTC TGGTGATCCT
1451  GGTTCAATTA AAGGACAAGA TTATTTTTCC ATAATCTCTG TAGATAATAT
      CCAAGTTAAT TTCCTGTTCT AATAAAAAGG TATTAGAGAC ATCTATTATA
1501  TTCCTACCAC TTAGAACAAA ACTATAAAGC TATCACTTCA AGAGACCAAC
      AAGGATGGTG AATCTTGTTT TGATATTTCG ATAGTGAAGT TCTCTGGTTG
1551  ATTACAAATT TATTTTAATT CCCTAAGGTG AAAAAAATCC TTCCTTCCTG
```

Figure 21 cont.

```
      TAATGTTTAA ATAAAATTAA GGGATTCCAC TTTTTTTAGG AAGGAAGGAC
1601  GTTTCTCAAG AGAAAGTCTA TACTGGTAAC CAAATTCACT TTAAACAGGC
      CAAAGAGTTC TCTTTCAGAT ATGACCATTG GTTTAAGTGA AATTTGTCCG
1651  ATTTCTTTG  GTATGACACT ATTTAAGAGA AGCAGGAAAC CAACGTGAAC
      TAAAAGAAAC CATACTGTGA TAAATTCTCT TCGTCCTTTG GTTGCACTTG
1701  CAGCTCTTTC CAATGGCTCA AGATTTCCTA TGAGAGGACT AAAAATGGGG
      GTCGAGAAAG GTTACCGAGT TCTAAAGGAT ACTCTCCTGA TTTTTACCCC
1751  AAAATTTTTA TGAGAGGATT AAAAATGGGG GAAAAAAAAC CCTGAAATGG
      TTTTAAAAAT ACTCTCCTAA TTTTTACCCC CTTTTTTTTG GGACTTTACC
1801  TTAATCAGAA GATCCTATGG GCTGAGAAGG AATCCATCTT AACATTTCAT
      AATTAGTCTT CTAGGATACC CGACTCTTCC TTAGGTAGAA TTGTAAAGTA
1851  CTTAAAGCAA ATGCTATTGC CGGGGGCAGT GGCTCATGCC TGTAATCCCA
      GAATTTCGTT TACGATAACG GCCCCCGTCA CCGAGTACGG ACATTAGGGT
1901  GCACTTTGGG AGGCCGAGGT GGGCAGATCA TCTGAGGTCA GGAGTTTGAG
      CGTGAAACCC TCCGGCTCCA CCCGTCTAGT AGACTCCAGT CCTCAAACTC
1951  ACCAGCCTGA CCAACATGGA GAAACCCCGT TTCTACTAAA AATACAAAAT
      TGGTCGGACT GGTTGTACCT CTTTGGGGCA AAGATGATTT TTATGTTTTA
2001  TAGCCAGGCA TAGTGGTGCA TGCCTGTAAT CCCAGCTACT TGGGAGGCTG
      ATCGGTCCGT ATCACCACGT ACGGACATTA GGGTCGATGA ACCCTCCGAC
2051  AGGCAGGAGA ACTGCTTGAA CCCAGGAGGC TTAAGTTGCG GTGAGCCAAG
      TCCGTCCTCT TGACGAACTT GGGTCCTCCG AATTCAACGC CACTCGGTTC
2101  ATCACGCCAT TGCACTCTAG CCTGGACAAC AAGAGAAAAA CTCTGTCTCA
      TAGTGCGGTA ACGTGAGATC GGACCTGTTG TTCTCTTTTT GAGACAGAGT
2151  AAAAAACACA AAAACAAAAA ACCCAAATAC TATTTAAAAA AGATAAACCT
      TTTTTTGTGT TTTTGTTTTT TGGGTTTATG ATAAATTTTT TCTATTTGGA
2201  TAATTGCTCA ATCATTAAAG CCATCCCACA AGTAAAGCAG CAAGCAGAAA
      ATTAACGAGT TAGTAATTTC GGTAGGGTGT TCATTTCGTC GTTCGTCTTT
2251  AAAGTTAAGA ACACCTCAAG GCTACAGAAG GACATTTCAA GCTATGCAGG
      TTTCAATTCT TGTGGAGTTC CGATGTCTTC CTGTAAAGTT CGATACGTCC
2301  CATATGAAGT GTGCAGACAG ATATGTAAGA AAGGCCTCAA GACTGCAAAA
      GTATACTTCA CACGTCTGTC TATACATTCT TTCCGGAGTT CTGACGTTTT
2351  GGGCATTTCA AGCTATGCAA GCATATAGGT AACACATACA CACACACAAA
      CCCGTAAAGT TCGATACGTT CGTATATCCA TTGTGTATGT GTGTGTGTTT
2401  ATAAAATCCC CTGAAATACA AAAACATGCA GCAAACACCT GACGTTTTTG
      TATTTTAGGG GACTTTATGT TTTTGTACGT CGTTTGTGGA CTGCAAAAAC
2451  GATACCATTT CTAAGTCAGG TGTTATGATT CTCATTAGTC AAGATACTTG
      CTATGGTAAA GATTCAGTCC ACAATACTAA GAGTAATCAG TTCTATGAAC
2501  AGTACTGGGC CCAAACAGCT TTCTGCCACT GTACAGTACA AGAAGGTAGG
      TCATGACCCG GGTTTGTCGA AAGACGGTGA CATGTCATGT TCTTCCATCC
2551  AATAATGGTG GGAGGAGCAA AGACAAACTG TAATAGACAG AAGTGTATCA
      TTATTACCAC CCTCCTCGTT TCTGTTTGAC ATTATCTGTC TTCACATAGT
2601  GATACCTATA CTACATGAAA AACAAAACAG CTACTGCCAC AAAGGGAGAA
      CTATGGATAT GATGTACTTT TTGTTTTGTC GATGACGGTG TTTCCCTCTT
2651  GGCTAACAAA ATAAAGTCAA CAATAAATAC AGAAAATGAA AAGGATACAC
      CCGATTGTTT TATTTCAGTT GTTATTTATG TCTTTTACTT TTCCTATGTG
2701  ACTAAGGTTT ACAAAAAAAA AAAGGCAGAC AAAATGCCAT ACAGTATTCA
      TGATTCCAAA TGTTTTTTTT TTTCCGTCTG TTTTACGGTA TGTCATAAGT
2751  TTCACTACTA TGGCATTCAT AAGCTAGTTT CAAATGCTCA CTATTTTCTT
      AAGTGATGAT ACCGTAAGTA TTCGATCAAA GTTTACGAGT GATAAAAGAA
2801  TTATAGTATA TATTTGCCTT AACCCAGCAC TTTTTTCCAA AAGTGGATGA
      AATATCATAT ATAAACGGAA TTGGGTCGTG AAAAAAGGTT TTCACCTACT
2851  GTCAAAATAA ATTTCCCATT ATTTAAGTGA AATTAACAGC ACACATATCT
      CAGTTTTATT TAAAGGGTAA TAAATTCACT TTAATTGTCG TGTGTATAGA
2901  CACAACACTA ATGAATTTTT AAAATGGAAA GTTAAGAACT TTTAAAGTGG
      GTGTTGTGAT TACTTAAAAA TTTTACCTTT CAATTCTTGA AAATTTCACC
2951  CCAACCTGTG ATCCTTCACA AAATAAACTA AATACAATAA CAGACCCCAA
      GGTTGGACAC TAGGAAGTGT TTTATTTGAT TTATGTTATT GTCTGGGGTT
3001  AGGCTATCAA TTGCGTGCAA AAACAACTTC TGTTTTCCAG GGTAAACAGA
      TCCGATAGTT AACGCACGTT TTTGTTGAAG ACAAAAGGTC CCATTTGTCT
3051  ATCTAATGCA GAATCTAATG CAGGGTAAAC AGACTTAATG CAGAATCTAA
      TAGATTACGT CTTAGATTAC GTCCCATTTG TCTGAATTAC GTCTTAGATT
3101  TGATGGCACA AATTAAAAAT CACTAACGTG CCCTTTTTAG TGTGAAACCC
      ACTACCGTGT TTAATTTTTA GTGATTGCAC GGGAAAAATC ACACTTTGGG
3151  AGAGAGAGCA CATACAAGCC AAAAACAAAT GCTTTATTTT ACCTAGGAGA
      TCTCTCTCGT GTATGTTCGG TTTTTGTTTA CGAAATAAAA TGGATCCTCT
3201  CATTAACATT CACCTTTACG TGTTTAAGAT TAATGCAATG TTAAATATTG
```

Figure 21 cont.

```
      GTAATTGTAA GTGGAAATGC ACAAATTCTA ATTACGTTAC AATTTATAAC
3251  TGAAAACTGT AACTTTGAAT TTCATGATTT TTATGTGAAT ATTCCAGGGT
      ACTTTTGACA TTGAAACTTA AAGTACTAAA AATACACTTA TAAGGTCCCA
3301  TTAAAAAAAC TTGTAACATG ACATGGCTGA ATAAGATAAA AAAAAAATCT
      AATTTTTTTG AACATTGTAC TGTACCGACT TATTCTATTT TTTTTTTAGA
3351  AGCCTTTTCT CCCTTCTGGC TCATATTTGC GATTTCGATC ATTTTGTTTA
      TCGGAAAAGA GGGAAGACCG AGTATAAACG CTAAAGCTAG TAAAACAAAT
3401  AAAAACAAAA CACTGCAATG AATTAAACTT AATATTCTTC TATGTTTTAG
      TTTTTGTTTT GTGACGTTAC TTAATTTGAA TTATAAGAAG ATACAAAATC
3451  AGTAAGTTAA AACAAGATAA AGTGACCAAA GTAATTTGAA AGATTCAATG
      TCATTCAATT TTGTTCTATT TCACTGGTTT CATTAAACTT TCTAAGTTAC
3501  ACTTTTGCTC CAACCTAGGT GCACAAGGTA CCTTGTTCTT TAAATTGGGC
      TGAAAACGAG GTTGGATCCA CGTGTTCCAT GGAACAAGAA ATTTAACCCG
3551  TTTAATGAAA ATACTTCTCC AGAATTCTGG GGATTTAAGA AAAATTATGC
      AAATTACTTT TATGAAGAGG TCTTAAGACC CCTAAATTCT TTTTAATACG
3601  CAACCAACAA GGGCTTTACC ATTTTATGTA ACATTTTTCA ACGCTGCAAA
      GTTGGTTGTT CCCGAAATGG TAAAATACAT TGTAAAAAGT TGCGACGTTT
3651  AATGTGTGTA TTTCTATTTG AAGATAAAAA TCCTCAGCAA AATCCACATT
      TTACACACAT AAAGATAAAC TTCTATTTTT AGGAGTCGTT TTAGGTGTAA
3701  GCACTGTCCT TCAAAGATTA GCCTTCTTTG AACTAGTTAA GACACTATTA
      CGTGACAGGA AGTTTCTAAT CGGAAGAAAC TTGATCAATT CTGTGATAAT
3751  AGCCAAGCCA GTATCTCCCT GTAATGAATT CGTTTTTCTC TTAATTTTCC
      TCGGTTCGGT CATAGAGGGA CATTACTTAA GCAAAAAGAG AATTAAAAGG
3801  CCTGTAATTT ACACTGGGAG AGCTGGGAAA TATGTGGATG TAAATTTCTC
      GGACATTAAA TGTGACCCTC TCGACCCTTT ATACACCTAC ATTTAAAGAG
3851  AGCCACAGAG ATGCAAAGTT ATACTGTGGG GAAAAAAAAC TTGAGTTAAA
      TCGGTGTCTC TACGTTTCAA TATGACACCC CTTTTTTTTG AACTCAATTT
3901  TCCTTACATA TTTTAGGTTT TCATTAACTT ACCAATGTAG TTTTGTTGGA
      AGGAATGTAT AAAATCCAAA AGTAATTGAA TGGTTACATC AAAACAACCT
3951  GGCCATTTTT TTTATTGCAG ACTTGAAGAG CTATTACTAG AAAAATGCAT
      CCGGTAAAAA AAATAACGTC TGAACTTCTC GATAATGATC TTTTTACGTA
4001  GACAGTTAAG GTAAGTTTGC ATGACACAAA AAAGGTAACT AAATACAAAT
      CTGTCAATTC CATTCAAACG TACTGTGTTT TTTCCATTGA TTTATGTTTA
4051  TCTGTTTGGA TTCCAACCCC CAAGTAGAGA GCGCACACTT TCAAACGTGA
      AGACAAACCT AAGGTTGGGG GTTCATCTCT CGCGTGTGAA AGTTTGCACT
4101  ATACAAATCC AGAGTAGATC TGCGCTCCTA CCTACATTGC TTATGATGTA
      TATGTTTAGG TCTCATCTAG ACGCGAGGAT GGATGTAACG AATACTACAT
4151  CTTAAGTACG TGTCCTAACC ATGTGAGTCT AGAAAGACTT TACTGGGGAT
      GAATTCATGC ACAGGATTGG TACACTCAGA TCTTTCTGAA ATGACCCCTA
4201  CCTGGTACCT AAAACAGCTT CACATGGCTT AAAATAGGGG ACCAATGTCT
      GGACCATGGA TTTTGTCGAA GTGTACCGAA TTTTATCCCC TGGTTACAGA
4251  TTTCCAATCT AAGTCCCATT TATAATAAAG TCCATGTTCC ATTTTTAAAG
      AAAGGTTAGA TTCAGGGTAA ATATTATTTC AGGTACAAGG TAAAAATTTC
4301  GACAATCCTT TCGGTTTAAA ACCAGGCACG ATTACCCAAA CAACTCACAA
      CTGTTAGGAA AGCCAAATTT TGGTCCGTGC TAATGGGTTT GTTGAGTGTT
4351  CGGTAAAGCA CTGTGAATCT TCTCTGTTCT GCAATCCCAA CTTGGTTTCT
      GCCATTTCGT GACACTTAGA AGAGACAAGA CGTTAGGGTT GAACCAAAGA
4401  GCTCAGAAAC CCTCCCTCTT TCCAATCGGT AATTAAATAA CAAAAGGAAA
      CGAGTCTTTG GGAGGGAGAA AGGTTAGCCA TTAATTTATT GTTTTCCTTT
4451  AAACTTAAGA TGCTTCAACC CCGTTTCGTG ACACTTTGAA AAAAGAATCA
      TTTGAATTCT ACGAAGTTGG GGCAAAGCAC TGTGAAACTT TTTTCTTAGT
4501  CCTCTTGCAA ACACCCGCTC CCGACCCCCG CCGCTGAAGC CCGGCGTCCA
      GGAGAACGTT TGTGGGCGAG GGCTGGGGGC GGCGACTTCG GGCCGCAGGT
4551  GAGGCCTAAG CGCGGGTGCC CGCCCCCACC CGGGAGCGCG GGCCTCGTGG
      CTCCGGATTC GCGCCCACGG GCGGGGGTGG GCCCTCGCGC CCGGAGCACC
4601  TCAGCGCATC CGCGGGGAGA AACAAAGGCC GCGGCACGGG GGCTCAAGGG
      AGTCGCGTAG GCGCCCCTCT TTGTTTCCGG CGCCGTGCCC CCGAGTTCCC
4651  CACTGCGCCA CACCGCACGC GCCTACCCCC GCGCGGCCAC GTTAACTGGC
      GTGACGCGGT GTGGCGTGCG CGGATGGGGG CGCGCCGGTG CAATTGACCG
4701  GGTCGCCGCA GCCTCGGGAC AGCCGGCCGC GCGCCGCCAG GCTCGCGGAC
      CCAGCGGCGT CGGAGCCCTG TCGGCCGGCG CGCGGCGGTC CGAGCGCCTG
4751  GCGGGACCAC GCGCCGCCCT CCGGGAGGCC CAAGTCTCGA CCCAGCCCCG
      CGCCCTGGTG CGCGGCGGGA GGCCCTCCGG GTTCAGAGCT GGGTCGGGGC
4801  CGTGGCGCTG GGGGAGGGGG CGCCTCCGCC GGAACGCGGG TGGGGGAGGG
      GCACCGCGAC CCCCTCCCCC GCGGAGGCGG CCTTGCGCCC ACCCCCTCCC
4851  GAGGGGGAAA TGCGCTTTGT CTCGAAATGG GGCAACCGTC GCCACAGCTC
```

Figure 21 cont.

```
      CTCCCCCTTT ACGCGAAACA GAGCTTTACC CCGTTGGCAG CGGTGTCGAG
4901  CCTACCCCCT CGAGGGCAGA GCAGTCCCCC CACTAACTAC CGGGCTGGCC
      GGATGGGGGA GCTCCCGTCT CGTCAGGGGG GTGATTGATG GCCCGACCGG
4951  GCGCGCCAGG CCAGCCGCGA GGCCACCGCC CGACCCTCCA CTCCTTCCCG
      CGCGCGGTCC GGTCGGCGCT CCGGTGGCGG GCTGGGAGGT GAGGAAGGGC
5001  CAGCTCCCGG CGCGGGGTCC GGCGAGAAGG GGAGGGGAGG GGAGCGGAGA
      GTCGAGGGCC GCGCCCCAGG CCGCTCTTCC CCTCCCCTCC CCTCGCCTCT
5051  ACCGGGCCCC CGGGACGCGT GTGGCATCTG AAGCACCACC AGCGAGCGAG
      TGGCCCGGGG GCCCTGCGCA CACCGTAGAC TTCGTGGTGG TCGCTCGCTC
5101  AGCTAGAGAG AAGGAAAGCC ACCGACTTCA CCGCCTCCGA GCTGCTCCGG
      TCGATCTCTC TTCCTTTCGG TGGCTGAAGT GGCGGAGGCT CGACGAGGCC
5151  GTCGCGGGTC TGCAGCGTCT CCGGCCCTCC GCGCCTACAG CTCAAGCCAC
      CAGCGCCCAG ACGTCGCAGA GGCCGGGAGG CGCGGATGTC GAGTTCGGTG
5201  ATCCGAAGGG GGAGGGAGCC GGGAGCTGCG CGCGGGGCCG CCGGGGGGAG
      TAGGCTTCCC CCTCCCTCGG CCCTCGACGC GCGCCCCGGC GGCCCCCCTC
5251  GGGTGGCACC GCCCACGCCG GGCGGCCACG AAGGGCGGGG CAGCGGGCGC
      CCCACCGTGG CGGGTGCGGC CCGCCGGTGC TTCCCGCCCC GTCGCCCGCG
5301  GCGCGCGGCG GGGGGAGGGG CCGGCGCCGC GCCCGCTGGG AATTGGGGCC
      CGCGCGCCGC CCCCCTCCCC GGCCGCGGCG CGGGCGACCC TTAACCCCGG
5351  CTAGGGGGAG GGCGGAGGCG CCGACGACCG CGGCACTTAC CGTTCGCGGC
      GATCCCCCTC CCGCCTCCGC GGCTGCTGGC GCCGTGAATG GCAAGCGCCG
5401  GTGGCGCCCG GTGGTCCCCA AGGGGAGGGA AGGGGGAGGC GGGGCGAGGA
      CACCGCGGGC CACCAGGGGT TCCCCTCCCT TCCCCCTCCG CCCCGCTCCT
5451  CAGTGACCGG AGTCTCCTCA GCGGTGGCTT TTCTGCTTGG CAGCCTCAGC
      GTCACTGGCC TCAGAGGAGT CGCCACCGAA AAGACGAACC GTCGGAGTCG
5501  GGCTGGCGCC AAAACCGGAC TCCGCCCACT TCCTCGCCCG CCGGTGCGAG
      CCGACCGCGG TTTTGGCCTG AGGCGGGTGA AGGAGCGGGC GGCCACGCTC
5551  GGTGTGGAAT CCTCCAGACG CTGGGGGAGG GGGAGTTGGG AGCTTAAAAA
      CCACACCTTA GGAGGTCTGC GACCCCCTCC CCCTCAACCC TCGAATTTTT
5601  CTAGTACCCC TTTGGGACCA CTTTCAGCAG CGAACTCTCC TGTACACCAG
      GATCATGGGG AAACCCTGGT GAAAGTCGTC GCTTGAGAGG ACATGTGGTC
5651  GGGTCAGTTC CACAGACGCG GGCCAGGGGT GGGTCATTGC GGCGTGAACA
      CCCAGTCAAG GTGTCTGCGC CCGGTCCCCA CCCAGTAACG CCGCACTTGT
5701  ATAATTTGAC TAGAAGTTGA TTCGGGTGTT TCCGGAAGGG GCCGAGTCAA
      TATTAAACTG ATCTTCAACT AAGCCCACAA AGGCCTTCCC CGGCTCAGTT
5751  TCCGCCGAGT TGGGGCACGG AAAACAAAAA GGGAAGGCTA CTAAGATTTT
      AGGCGGCTCA ACCCCGTGCC TTTTGTTTTT CCCTTCCGAT GATTCTAAAA
5801  TCTGGCGGGG GTTATCATTG GCGTAACTGC AGGGACCACC TCCCGGGTTG
      AGACCGCCCC CAATAGTAAC CGCATTGACG TCCCTGGTGG AGGGCCCAAC
5851  AGGGGCTGG ATCTCCAGGC TGCGGATTAA GCCCCTCCCG TCGGCGTTAA
      TCCCCCGACC TAGAGGTCCG ACGCCTAATT CGGGGAGGGC AGCCGCAATT
5901  TTTCAAACTG CGCGACGTTT CTCACCTGCC TTCGCCAAGG CAGGGGCCGG
      AAAGTTTGAC GCGCTGCAAA GAGTGGACGG AAGCGGTTCC GTCCCCGGCC
5951  GACCCTATTC CAAGAGGTAG TAACTAGCAG GACTCTAGCC TTCCGCAATT
      CTGGGATAAG GTTCTCCATC ATTGATCGTC CTGAGATCGG AAGGCGTTAA
6001  CATTGAGCGC ATTTACGGAA GTAACGTCGG GTACTGTCTC TGGCCGCAAG
      GTAACTCGCG TAAATGCCTT CATTGCAGCC CATGACAGAG ACCGGCGTTC
6051  GGTGGGAGGA GTACGCATTT GGCGTAAGGT GGGGCGTAGA GCCTTCCCGC
      CCACCCTCCT CATGCGTAAA CCGCATTCCA CCCCGCATCT CGGAAGGGCG
6101  CATTGGCGGC GGATAGGGCG TTTACGCGAC GGCCTGACGT AGCGGAAGAC
      GTAACCGCCG CCTATCCCGC AAATGCGCTG CCGGACTGCA TCGCCTTCTG
6151  GCGTTAGTGG GGGGGAAGGT TCTAGAAAAG CGGCGGCAGC GGCTCTAGCG
      CGCAATCACC CCCCCTTCCA AGATCTTTTC GCCGCCGTCG CCGAGATCGC
6201  GCAGTAGCAG CAGCGCCGGG TCCCGTGCGG AGGTGCTCCT CGCAGAGTTG
      CGTCATCGTC GTCGCGGCCC AGGGCACGCC TCCACGAGGA GCGTCTCAAC
6251  TTTCTCGAGC AGCGGCAGTT CTCACTACAG CGCCAGGACG AGTCCGGTTC
      AAAGAGCTCG TCGCCGTCAA GAGTGATGTC GCGGTCCTGC TCAGGCCAAG
6301  GTGTTCGTCC GCGGAGATCT CTCTCATCTC GCTCGGCTGC GGGAAATCGG
      CACAAGCAGG CGCCTCTAGA GAGAGTAGAG CGAGCCGACG CCCTTTAGCC
6351  GCTGAAGCGA CTGAGTCCGC GATGGAGGTA ACGGGTTTGA AATCAATGAG
      CGACTTCGCT GACTCAGGCG CTACCTCCAT TGCCCAAACT TTAGTTACTC
6401  TTATTGAAAA GGGCATGGCG AGGCCGTTGG CGCCTCAGTG GAAGTCGGCC
      AATAACTTTT CCCGTACCGC TCCGGCAACC GCGGAGTCAC CTTCAGCCGG
6451  AGCCGCCTCC GTGGGAGAGA GGCAGGAAAT CGGACCAATT CAGTAGCAGT
      TCGGCGGAGG CACCCTCTCT CCGTCCTTTA GCCTGGTTAA GTCATCGTCA
6501  GGGGCTTAAG GTTTATGAAC GGGGTCTTGA GCGGAGGCCT GAGCGTACAA
```

Figure 21 cont.

```
      CCCCGAATTC CAAATACTTG CCCCAGAACT CGCCTCCGGA CTCGCATGTT
6551  ACAGCTTCCC CACCCTCAGC CTCCCGGCGC CATTTCCCTT CACTGGGGGT
      TGTCGAAGGG GTGGGAGTCG GAGGGCCGCG GTAAAGGGAA GTGACCCCCA
6601  GGGGGATGGG GAGCTTTCAC ATGGCGGACG CTGCCCCGCT GGGGTGAAAG
      CCCCCTACCC CTCGAAAGTG TACCGCCTGC GACGGGGCGA CCCCACTTTC
6651  TGGGGCGCGG AGGCGGGAAT TCTTATTCCC TTTCTAAAGC ACGCTGCTTC
      ACCCCGCGCC TCCGCCCTTA AGAATAAGGG AAAGATTTCG TGCGACGAAG
6701  GGGGGCCACG GCGTCTCCTC GGCGAGCGTT TCGGCGGGCA GCAGGTCCTC
      CCCCCGGTGC CGCAGAGGAG CCGCTCGCAA AGCCGCCCGT CGTCCAGGAG
6751  GTGAGCGAGG CTGCGGAGCT TCCCCTCCCC CTCTCTCCCG GGAACCGATT
      CACTCGCTCC GACGCCTCGA AGGGGAGGGG GAGAGAGGGC CCTTGGCTAA
6801  TGGCGGCCGC CATTTTCATG GCTCGCCTTC CTCTCAGCGT TTTCCTTATA
      ACCGCCGGCG GTAAAAGTAC CGAGCGGAAG GAGAGTCGCA AAAGGAATAT
6851  ACTCTTTTAT TTTCTTAGTG TGCTTTCTCT ATCAAGAAGT AGAAGTGGTT
      TGAGAAAATA AAAGAATCAC ACGAAAGAGA TAGTTCTTCA TCTTCACCAA
6901  AACTATTTTT TTTTTCTTCT CGGGCTGTTT TCATATCGTT TCGAGGTGGA
      TTGATAAAAA AAAAAGAAGA GCCCGACAAA AGTATAGCAA AGCTCCACCT
6951  TTTGGAGTGT TTTGTGAGCT TGGATCTTTA GAGTCCTGCG CACCTCATTA
      AAACCTCACA AAACACTCGA ACCTAGAAAT CTCAGGACGC GTGGAGTAAT
7001  AAGGCGCTCA GCCTTCCCCT CGATGAAATG GCGCCATTGC GTTCGGAAGC
      TTCCGCGAGT CGGAAGGGGA GCTACTTTAC CGCGGTAACG CAAGCCTTCG
7051  CACACCGAAG AGCGGGGAGG GGGGGTGCTC CGGGTTTGCG GGCCCGGTTT
      GTGTGGCTTC TCGCCCCTCC CCCCCACGAG GCCCAAACGC CCGGGCCAAA
7101  CAGAGAAGAT ATCACCACCC AGGGCGTCGG GCCGGGTTCA ATGCGAGCCG
      GTCTCTTCTA TAGTGGTGGG TCCCGCAGCC CGGCCCAAGT TACGCTCGGC
7151  TAGGACAAAG AAACCATTTT ATGTTTTTCC TGTCTTTTTT TTCCTTTGAG
      ATCCTGTTTC TTTGGTAAAA TACAAAAAGG ACAGAAAAAA AAGGAAACTC
7201  TAACGGTTTT ATCTGGGTCT GCAGTCAGTA AAACGACAGA TGAACCGCGG
      ATTGCCAAAA TAGACCCAGA CGTCAGTCAT TTTGCTGTCT ACTTGGCGCC
7251  CAAAATAAAC ATAAATTGGA AGCCATCGGC CACGAGGGGC AGGGACGAAG
      GTTTTATTTG TATTTAACCT TCGGTAGCCG GTGCTCCCCG TCCCTGCTTC
7301  GTGGTTTTCT GGGCGGGGGA GGGATATTCG CGTCAGAATC CTTTACTGTT
      CACCAAAAGA CCCGCCCCCT CCCTATAAGC GCAGTCTTAG GAAATGACAA
7351  CTTAAGGATT CCGTTTAAGT TGTAGAGCTG ACTCATTTTA AGTAATGTTG
      GAATTCCTAA GGCAAATTCA ACATCTCGAC TGAGTAAAAT TCATTACAAC
7401  TTACTGAGAA GTTTAACCCT TACGGGACAG ATCCATGGAC CTTTATAGAT
      AATGACTCTT CAAATTGGGA ATGCCCTGTC TAGGTACCTG GAAATATCTA
7451  GATTACGAGG AAAGTGAAAT AACGATTTTG TCCTTAGTTA TACTTCGATT
      CTAATGCTCC TTTCACTTTA TTGCTAAAAC AGGAATCAAT ATGAAGCTAA
7501  AAAACATGGC TTCAGAGGCT CCTTCCTGTA ATGCGTATGG ATTGATGTGC
      TTTTGTACCG AAGTCTCCGA GGAAGGACAT TACGCATACC TAACTACACG
7551  AAAACTGTTT TGGGCCTGGG CCGCTCTGTA TTTGAACTTT GTTACTTTTC
      TTTTGACAAA ACCCGGACCC GGCGAGACAT AAACTTGAAA CAATGAAAAG
7601  TCATTTTGTT TGCAATCTTG GTTGAACATT ACATTGATAA GCATAAGGTC
      AGTAAAACAA ACGTTAGAAC CAACTTGTAA TGTAACTATT CGTATTCCAG
7651  TCAAGCGAAG GGGGTCTACC TGGTTATTTT TCTTTGACCC TAAGCACGTT
      AGTTCGCTTC CCCCAGATGG ACCAATAAAA AGAAACTGGG ATTCGTGCAA
7701  TATAAAATAA CATTGTTTAA AATCGATAGT GGACATCGGG TAAGTTTGGA
      ATATTTTATT GTAACAAATT TTAGCTATCA CCTGTAGCCC ATTCAAACCT
7751  TAAATTGTGA GGTAAGTAAT GAGTTTTTGC TTTTTGTTAG TGATTTGTAA
      ATTTAACACT CCATTCATTA CTCAAAAACG AAAAACAATC ACTAAACATT
7801  AACTTGTTAT AAATGTACAT TATCCGTAAT TTCAGTTTAG AGATAACCTA
      TTGAACAATA TTTACATGTA ATAGGCATTA AAGTCAAATC TCTATTGGAT
7851  TGTGCTGACG ACAATTAAGA ATAAAAACTA GCTGAAAAAA TGAAAATAAC
      ACACGACTGC TGTTAATTCT TATTTTTGAT CGACTTTTTT ACTTTTATTG
7901  TATCGTGACA AGTAACCATT TCAAAAGACT GCTTTGTGTC TCATAGGAGC
      ATAGCACTGT TCATTGGTAA AGTTTTCTGA CGAAACACAG AGTATCCTCG
7951  TAGTTTGATC ATTTCAGTTA ATTTTTTCTT TAATTTTTAC GAGTCATGAA
      ATCAAACTAG TAAAGTCAAT TAAAAAAGAA ATTAAAAATG CTCAGTACTT
8001  AACTACAGGA AAAAAAATCT GAACTGGGTT TTACCACTAC TTTTTAGGAG
      TTGATGTCCT TTTTTTTAGA CTTGACCCAA AATGGTGATG AAAAATCCTC
8051  TTGGGAGCAT GCGAATGGAG GGAGAGCTCC GTAGAACTGG GATGAGAGCA
      AACCCTCGTA CGCTTACCTC CCTCTCGAGG CATCTTGACC CTACTCTCGT
8101  GCAATTAATG CTGCTTGCTA GGAACAAAAA ATAATTGATT GAAAATTACG
      CGTTAATTAC GACGAACGAT CCTTGTTTTT TATTAACTAA CTTTTAATGC
8151  TGTGACTTTT TAGTTTGCAT TATGCGTTTG TAGCAGTTGG TCCTGGATAT
```

Figure 21 cont.

```
     ACACTGAAAA ATCAAACGTA ATACGCAAAC ATCGTCAACC AGGACCTATA
8201 CACTTTCTCT CGTTTGAGGT TTTTTAACCT AGTTAACTTT TAAGACAGGT
     GTGAAAGAGA GCAAACTCCA AAAAATTGGA TCAATTGAAA ATTCTGTCCA
8251 TTCCTTAACA TTCATAAGTG CCCAGAATAC AGCTGTGTAG TACAGCATAT
     AAGGAATTGT AAGTATTCAC GGGTCTTATG TCGACACATC ATGTCGTATA
8301 AAAGATTTCA GCTCTGAGGT TTTTCCTATT GACTTGGAAA ATTGTTTTGT
     TTTCTAAAGT CGAGACTCCA AAAAGGATAA CTGAACCTTT TAACAAAACA
8351 GCCTGTCGCT TGCCACATGG CCAATCAAGT AAGCTTATCG ATACCGGTGG
     CGGACAGCGA ACGGTGTACC GGTTAGTTCA TTCGAATAGC TATGGCCACC
8401 CGCGCCAATT GTTAATTAAG ATCTGGCCCA ATGGGCCGTA CGAATTCCTT
     GCGCGGTTAA CAATTAATTC TAGACCGGGT TACCCGGCAT GCTTAAGGAA
8451 AGGCTACCGG GTAGGGGAGG CGCTTTTCCC AAGGCAGTCT GGAGCATGCG
     TCCGATGGCC CATCCCCTCC GCGAAAAGGG TTCCGTCAGA CCTCGTACGC
8501 CTTTAGCAGC CCCGCTGGGC ACTTGGCGCT ACACAAGTGG CCTCTGGCCT
     GAAATCGTCG GGGCGACCCG TGAACCGCGA TGTGTTCACC GGAGACCGGA
8551 CGCACACATT CCACATCCAC CGGCCGGTAG GCGCCAACCG GCTCCGTTCT
     GCGTGTGTAA GGTGTAGGTG GCCGGCCATC CGCGGTTGGC CGAGGCAAGA
8601 TTGGTGGCCC CTTCGCGCCA CCTTCTACTC CTCCCCTAGT CAGGAAGTTC
     AACCACCGGG GAAGCGCGGT GGAAGATGAG GAGGGGATCA GTCCTTCAAG
8651 CCCCCCGCCC CGCAGCTCGC GTCGTGCAGG ACGTGACAAA TGGAAGTAGC
     GGGGGGCGGG GCGTCGAGCG CAGCACGTCC TGCACTGTTT ACCTTCATCG
8701 ACGTCTCACT AGTCTCGTGC AGATGGACAG CACCGCTGAG CAATGGAAGC
     TGCAGAGTGA TCAGAGCACG TCTACCTGTC GTGGCGACTC GTTACCTTCG
8751 GGGTAGGCCT TTGGGGCAGC GGCCAATAGC AGCTTTGCTC CTTCGCTTTC
     CCCATCCGGA AACCCCGTCG CCGGTTATCG TCGAAACGAG GAAGCGAAAG
8801 TGGGCTCAGA GGCTGGGAAG GGGTGGGTCC GGGGGCGGGC TCAGGGGCGG
     ACCCGAGTCT CCGACCCTTC CCCACCCAGG CCCCCGCCCG AGTCCCCGCC
8851 GCTCAGGGGC GGGGCGGGCG CCCGAAGGTC CTCCGGAGGC CCGGCATTCT
     CGAGTCCCCG CCCCGCCCGC GGGCTTCCAG GAGGCCTCCG GGCCGTAAGA
8901 GCACGCTTCA AAAGCGCACG TCTGCCGCGC TGTTCTCCTC TTCCTCATCT
     CGTGCGAAGT TTTCGCGTGC AGACGGCGCG ACAAGAGGAG AAGGAGTAGA
8951 CCGGGCCTTT CGACCAGCTT ACCATGACCG AGTACAAGCC CACGGTGCGC
     GGCCCGGAAA GCTGGTCGAA TGGTACTGGC TCATGTTCGG GTGCCACGCG
9001 CTCGCCACCC GCGACGACGT CCCCAGGGCC GTACGCACCC TCGCCGCCGC
     GAGCGGTGGG CGCTGCTGCA GGGGTCCCGG CATGCGTGGG AGCGGCGGCG
9051 GTTCGCCGAC TACCCCGCCA CGCGCCACAC CGTCGATCCG GACCGCCACA
     CAAGCGGCTG ATGGGGCGGT GCGCGGTGTG GCAGCTAGGC CTGGCGGTGT
9101 TCGAGCGGGT CACCGAGCTG CAAGAACTCT TCCTCACGCG CGTCGGGCTC
     AGCTCGCCCA GTGGCTCGAC GTTCTTGAGA AGGAGTGCGC GCAGCCCGAG
9151 GACATCGGCA AGGTGTGGGT CGCGGACGAC GGCGCCGCGG TGGCGGTCTG
     CTGTAGCCGT TCCACACCCA GCGCCTGCTG CCGCGGCGCC ACCGCCAGAC
9201 GACCACGCCG GAGAGCGTCG AAGCGGGGGC GGTGTTCGCC GAGATCGGCC
     CTGGTGCGGC CTCTCGCAGC TTCGCCCCCG CCACAAGCGG CTCTAGCCGG
9251 CGCGCATGGC CGAGTTGAGC GGTTCCCGGC TGGCCGCGCA GCAACAGATG
     GCGCGTACCG GCTCAACTCG CCAAGGGCCG ACCGGCGCGT CGTTGTCTAC
9301 GAAGGCCTCC TGGCGCCGCA CCGGCCCAAG GAGCCCGCGT GGTTCCTGGC
     CTTCCGGAGG ACCGCGGCGT GGCCGGGTTC CTCGGGCGCA CCAAGGACCG
9351 CACCGTCGGC GTCTCGCCCG ACCACCAGGG CAAGGGTCTG GGCAGCGCCG
     GTGGCAGCCG CAGAGCGGGC TGGTGGTCCC GTTCCCAGAC CCGTCGCGGC
9401 TCGTGCTCCC CGGAGTGGAG GCGGCCGAGC GCGCCGGGGT GCCCGCCTTC
     AGCACGAGGG GCCTCACCTC CGCCGGCTCG CGCGGCCCCA CGGGCGGAAG
9451 CTGGAGACCT CCGCGCCCCG CAACCTCCCC TTCTACGAGC GGCTCGGCTT
     GACCTCTGGA GGCGCGGGGC GTTGGAGGGG AAGATGCTCG CCGAGCCGAA
9501 CACCGTCACC GCCGACGTCG AGGTGCCCGA AGGACCGCGC ACCTGGTGCA
     GTGGCAGTGG CGGCTGCAGC TCCACGGGCT TCCTGGCGCG TGGACCACGT
9551 TGACCCGCAA GCCCGGTGCC TGACGCCCGC CCCACGACCC GCAGCGCCCG
     ACTGGGCGTT CGGGCCACGG ACTGCGGGCG GGGTGCTGGG CGTCGCGGGC
9601 ACCGAAAGGA GCGCACGACC CCATGCATCG TAGAGCTCGC TGATCAGCCT
     TGGCTTTCCT CGCGTGCTGG GGTACGTAGC ATCTCGAGCG ACTAGTCGGA
9651 CGACTGTGCC TTCTAGTTGC CAGCCATCTG TTGTTTGCCC CTCCCCCGTG
     GCTGACACGG AAGATCAACG GTCGGTAGAC AACAAACGGG GAGGGGGCAC
9701 CCTTCCTTGA CCCTGGAAGG TGCCACTCCC ACTGTCCTTT CCTAATAAAA
     GGAAGGAACT GGGACCTTCC ACGGTGAGGG TGACAGGAAA GGATTATTTT
9751 TGAGGAAATT GCATCGCATT GTCTGAGTAG GTGTCATTCT ATTCTGGGGG
     ACTCCTTTAA CGTAGCGTAA CAGACTCATC CACAGTAAGA TAAGACCCCC
9801 GTGGGGTGGG GCAGGACAGC AAGGGGGGGG ATTGGRAGA CAATAGCAGG
```

Figure 21 cont.

```
      CACCCCACCC CGTCCTGTCG TTCCCCCCCC TAACCCYTCT GTTATCGTCC
 9851 CATGCTGGGG GGGCGGTGGG GGCTATGGCT TCTGAGGCGG AAAGAACCAG
      GTACGACCCC CCCGCCACCC CCGATACCGA AGACTCCGCC TTTCTTGGTC
 9901 CTGGGGCTCG AGGGCCGCCA CCGCGGTGGA GCTCCAGCTT TTGTTCCCTT
      GACCCCGAGC TCCCGGCGGT GGCGCCACCT CGAGGTCGAA AACAAGGGAA
 9951 TAGTGAGGGT TAATTTCGAG CTTGGCGTAA TCATGGTCAT AGCTGTTTCC
      ATCACTCCCA ATTAAAGCTC GAACCGCATT AGTACCAGTA TCGACAAAGG
10001 TGTGTGAAAT TGTTATCCGC TCACAATTCC ACACAACATA CGAGCCGGAA
      ACACACTTTA ACAATAGGCG AGTGTTAAGG TGTGTTGTAT GCTCGGCCTT
10051 GCATAAAGTG TAAAGCCTGG GGTGCCTAAT GAGTGAGCTA ACTCACATTA
      CGTATTTCAC ATTTCGGACC CCACGGATTA CTCACTCGAT TGAGTGTAAT
10101 ATTGCGTTGC GCTCACTGCC CGCTTTCCAG TCGGGAAACC TGTCGTGCCA
      TAACGCAACG CGAGTGACGG GCGAAAGGTC AGCCCTTTGG ACAGCACGGT
10151 GCATCGCGAG CACTTTTCGG GGAAATGTGC GCGGAACCCC TATTTGTTTA
      CGTAGCGCTC GTGAAAAGCC CCTTTACACG CGCCTTGGGG ATAAACAAAT
10201 TTTTTCTAAA TACATTCAAA TATGTATCCG CTCATGAGAC AATAACCCTG
      AAAAAGATTT ATGTAAGTTT ATACATAGGC GAGTACTCTG TTATTGGGAC
10251 ATAAATGCTT CAATAATATT GAAAAAGGAA GAGTATGAGT ATTCAACATT
      TATTTACGAA GTTATTATAA CTTTTTCCTT CTCATACTCA TAAGTTGTAA
10301 TCCGTGTCGC CCTTATTCCC TTTTTTGCGG CATTTTGCCT TCCTGTTTTT
      AGGCACAGCG GGAATAAGGG AAAAAACGCC GTAAAACGGA AGGACAAAAA
10351 GCTCACCCAG AAACGCTGGT GAAAGTAAAA GATGCTGAAG ATCAGTTGGG
      CGAGTGGGTC TTTGCGACCA CTTTCATTTT CTACGACTTC TAGTCAACCC
10401 TGCACGAGTG GGTTACATCG AACTGGATCT CAACAGCGGT AAGATCCTTG
      ACGTGCTCAC CCAATGTAGC TTGACCTAGA GTTGTCGCCA TTCTAGGAAC
10451 AGAGTTTTCG CCCCGAAGAA CGTTTTCCAA TGATGAGCAC TTTTAAAGTT
      TCTCAAAAGC GGGGCTTCTT GCAAAAGGTT ACTACTCGTG AAAATTTCAA
10501 CTGCTATGTG GCGCGGTATT ATCCCGTATT GACGCCGGGC AAGAGCAACT
      GACGATACAC CGCGCCATAA TAGGGCATAA CTGCGGCCCG TTCTCGTTGA
10551 CGGTCGCCGC ATACACTATT CTCAGAATGA CTTGGTTGAG TACTCACCAG
      GCCAGCGGCG TATGTGATAA GAGTCTTACT GAACCAACTC ATGAGTGGTC
10601 TCACAGAAAA GCATCTTACG GATGGCATGA CAGTAAGAGA ATTATGCAGT
      AGTGTCTTTT CGTAGAATGC CTACCGTACT GTCATTCTCT TAATACGTCA
10651 GCTGCCATAA CCATGAGTGA TAACACTGCG GCCAACTTAC TTCTGACAAC
      CGACGGTATT GGTACTCACT ATTGTGACGC CGGTTGAATG AAGACTGTTG
10701 GATCGGAGGA CCGAAGGAGC TAACCGCTTT TTTGCACAAC ATGGGGGATC
      CTAGCCTCCT GGCTTCCTCG ATTGGCGAAA AAACGTGTTG TACCCCCTAG
10751 ATGTAACTCG CCTTGATCGT TGGGAACCGG AGCTGAATGA AGCCATACCA
      TACATTGAGC GGAACTAGCA ACCCTTGGCC TCGACTTACT TCGGTATGGT
10801 AACGACGAGC GTGACACCAC GATGCCTGTA GCAATGGCAA CAACGTTGCG
      TTGCTGCTCG CACTGTGGTG CTACGGACAT CGTTACCGTT GTTGCAACGC
10851 CAAACTATTA ACTGGCGAAC TACTTACTCT AGCTTCCCGG CAACAATTAA
      GTTTGATAAT TGACCGCTTG ATGAATGAGA TCGAAGGGCC GTTGTTAATT
10901 TAGACTGGAT GGAGGCGGAT AAAGTTGCAG GACCACTTCT GCGCTCGGCC
      ATCTGACCTA CCTCCGCCTA TTTCAACGTC CTGGTGAAGA CGCGAGCCGG
10951 CTTCCGGCTG GCTGGTTTAT TGCTGATAAA TCTGGAGCCG GTGAGCGTGG
      GAAGGCCGAC CGACCAAATA ACGACTATTT AGACCTCGGC CACTCGCACC
11001 GTCTCGCGGT ATCATTGCAG CACTGGGGCC AGATGGTAAG CCCTCCCGTA
      CAGAGCGCCA TAGTAACGTC GTGACCCCGG TCTACCATTC GGGAGGGCAT
11051 TCGTAGTTAT CTACACGACG GGGAGTCAGG CAACTATGGA TGAACGAAAT
      AGCATCAATA GATGTGCTGC CCCTCAGTCC GTTGATACCT ACTTGCTTTA
11101 AGACAGATCG CTGAGATAGG TGCCTCACTG ATTAAGCATT GGTAACTGTC
      TCTGTCTAGC GACTCTATCC ACGGAGTGAC TAATTCGTAA CCATTGACAG
11151 AGACTCGCGA CACTGCATTA ATGAATCGGC CAACGCGCGG GGAGAGGCGG
      TCTGAGCGCT GTGACGTAAT TACTTAGCCG GTTGCGCGCC CCTCTCCGCC
11201 TTTGCGTATT GGGCGCTCTT CCGCTTCCTC GCTCACTGAC TCGCTGCGCT
      AAACGCATAA CCCGCGAGAA GGCGAAGGAG CGAGTGACTG AGCGACGCGA
11251 CGGTCGTTCG GCTGCGGCGA GCGGTATCAG CTCACTCAAA GGCGGTAATA
      GCCAGCAAGC CGACGCCGCT CGCCATAGTC GAGTGAGTTT CCGCCATTAT
11301 CGGTTATCCA CAGAATCAGG GGATAACGCA GGAAAGAACA TGTGAGCAAA
      GCCAATAGGT GTCTTAGTCC CCTATTGCGT CCTTTCTTGT ACACTCGTTT
11351 AGGCCAGCAA AAGGCCAGGA ACCGTAAAAA GGCCGCGTTG CTGGCGTTTT
      TCCGGTCGTT TTCCGGTCCT TGGCATTTTT CCGGCGCAAC GACCGCAAAA
11401 TCCATAGGCT CCGCCCCCCT GACGAGCATC ACAAAAATCG ACGCTCAAGT
      AGGTATCCGA GGCGGGGGGA CTGCTCGTAG TGTTTTTAGC TGCGAGTTCA
11451 CAGAGGTGGC GAAACCCGAC AGGACTATAA AGATACCAGG CGTTTCCCCC
```

Figure 21 cont.

```
      GTCTCCACCG CTTTGGGCTG TCCTGATATT TCTATGGTCC GCAAAGGGGG
11501 TGGAAGCTCC CTCGTGCGCT CTCCTGTTCC GACCCTGCCG CTTACCGGAT
      ACCTTCGAGG GAGCACGCGA GAGGACAAGG CTGGGACGGC GAATGGCCTA
11551 ACCTGTCCGC CTTTCTCCCT TCGGGAAGCG TGGCGCTTTC TCATAGCTCA
      TGGACAGGCG GAAAGAGGGA AGCCCTTCGC ACCGCGAAAG AGTATCGAGT
11601 CGCTGTAGGT ATCTCAGTTC GGTGTAGGTC GTTCGCTCCA AGCTGGGCTG
      GCGACATCCA TAGAGTCAAG CCACATCCAG CAAGCGAGGT TCGACCCGAC
11651 TGTGCACGAA CCCCCCGTTC AGCCCGACCG CTGCGCCTTA TCCGGTAACT
      ACACGTGCTT GGGGGGCAAG TCGGGCTGGC GACGCGGAAT AGGCCATTGA
11701 ATCGTCTTGA GTCCAACCCG GTAAGACACG ACTTATCGCC ACTGGCAGCA
      TAGCAGAACT CAGGTTGGGC CATTCTGTGC TGAATAGCGG TGACCGTCGT
11751 GCCACTGGTA ACAGGATTAG CAGAGCGAGG TATGTAGGCG GTGCTACAGA
      CGGTGACCAT TGTCCTAATC GTCTCGCTCC ATACATCCGC CACGATGTCT
11801 GTTCTTGAAG TGGTGGCCTA ACTACGGCTA CACTAGAAGG ACAGTATTTG
      CAAGAACTTC ACCACCGGAT TGATGCCGAT GTGATCTTCC TGTCATAAAC
11851 GTATCTGCGC TCTGCTGAAG CCAGTTACCT TCGGAAAAAG AGTTGGTAGC
      CATAGACGCG AGACGACTTC GGTCAATGGA AGCCTTTTTC TCAACCATCG
11901 TCTTGATCCG GCAAACAAAC CACCGCTGGT AGCGGTGGTT TTTTTGTTTG
      AGAACTAGGC CGTTTGTTTG GTGGCGACCA TCGCCACCAA AAAAACAAAC
11951 CAAGCAGCAG ATTACGCGCA GAAAAAAAGG ATCTCAAGAA GATCCTTTGA
      GTTCGTCGTC TAATGCGCGT CTTTTTTTCC TAGAGTTCTT CTAGGAAACT
12001 TCTTTTCTAC GGGGTCTGAC GCTCAGTGGA ACGAAAACTC A
      AGAAAAGATG CCCCAGACTG CGAGTCACCT TGCTTTTGAG T
```

Figure 23 CET1020 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAAGCT
      TAACCCATGG CCCGGGGGGG AGCTTCAAAT TTGTAAATTT AGATCTTCGA
 101  TTTAACCCTC TATCCCTTTA AACTTCCTTG ATCCAGTGTA AGCACCTCCT
      AAATTGGGAG ATAGGGAAAT TTGAAGGAAC TAGGTCACAT TCGTGGAGGA
 151  AGAAAGTCAG TAGACAATAA AACAAAAGTT CTGCTTCACC GATTTACATT
      TCTTTCAGTC ATCTGTTATT TTGTTTTCAA GACGAAGTGG CTAAATGTAA
 201  TATAACCAAA TACCCTTCAC CAATACAATA AAAAAACAAA ACAACAAAAA
      ATATTGGTTT ATGGGAAGTG GTTATGTTAT TTTTTTGTTT TGTTGTTTTT
 251  ACCCCAACCA TCTGAGAAAT AATCTTCTCC TTTCCCAGCT TTATTCCCAG
      TGGGGTTGGT AGACTCTTTA TTAGAAGAGG AAAGGGTCGA AATAAGGGTC
 301  GATTCTACAT GACCAAATTA CCAGAGTCAC CACTCATTTT AATCACAACA
      CTAAGATGTA CTGGTTTAAT GGTCTCAGTG GTGAGTAAAA TTAGTGTTGT
 351  TAGTGTCAAA TAACTAGAAA ACATGAGACA ACAATGGAGA GCTGAGTAAC
      ATCACAGTTT ATTGATCTTT TGTACTCTGT TGTTACCTCT CGACTCATTG
 401  TATTAGTAGT AGTACTTTAC CAGAGAATGG CCTCTATAGG CTCACATGTA
      ATAATCATCA TCATGAAATG GTCTCTTACC GGAGATATCC GAGTGTACAT
 451  GGAATGGTTG GTCCCCAGGT GGTAGGTAGA GCTGTTTGAG GATTACGTGG
      CCTTACCAAC CAGGGGTCCA CCATCCATCT CGACAAACTC CTAATGCACC
 501  CCTTCTTGGA TGGGGGGTGG GGGTGGGGTG GGAGGGTTGG GTGGTGGGTA
      GGAAGAACCT ACCCCCCACC CCCACCCCAC CCTCCCAACC CACCACCCAT
 551  CTTAAGAGGT TTCAAAAGTC AATATTGTTT GCATTTAGCT CTTCCTTGTA
      GAATTCTCCA AAGTTTTCAG TTATAACAAA CGTAAATCGA GAAGGAACAT
 601  CTTGTGGATC AAACACAACC TGTCAGCTAC TGCTTCAAAT GTCATGCCTG
      GAACACCTAG TTTGTGTTGG ACAGTCGATG ACGAAGTTTA CAGTACGGAC
 651  CTGCCATCTT CTCAGCAGGA TGGTCATGGC CTCACCCTCT TCAACTGTAA
      GACGGTAGAA GAGTCGTCCT ACCAGTACCG GAGTGGGAGA AGTTGACATT
 701  ATCTTTCTTT CTTTTCTTCT TTTTCTTTTG GTTTCGAGAC AGGGTTTCTC
      TAGAAAGAAA GAAAAGAAGA AAAAGAAAAC CAAAGCTCTG TCCCAAAGAG
 751  TGTATAGTCC TGGCTGTCCT GGAACTCACT TTGTAGACCA GGCTGGCCTT
      ACATATCAGG ACCGACAGGA CCTTGAGTGA AACATCTGGT CCGACCGGAA
 801  GAACTCAGAA ATCCGCCTGC CTCTGCCTCC CTAGCACTGG GATTAAAGGC
      CTTGAGTCTT TAGGCGGACG GAGACGGAGG GATCGTGACC CTAATTTCCG
 851  GTGCGCCACC ACGCCCAGCT TTCAACTGGA AATCTTAATA AACTTTCCTA
      CACGCGGTGG TGCGGGTCGA AAGTTGACCT TTAGAATTAT TTGAAAGGAT
 901  GAAGTGGCCT TGGTTATGGG AGCTTATCAC AGCAATAGAA CAGCAATTAT
      CTTCACCGGA ACCAATACCC TCGAATAGTG TCGTTATCTT GTCGTTAATA
 951  GACTGGAGTA TGATAGTTAA AAACAAGCAA GCAAGCAAGC AAACACACAC
      CTGACCTCAT ACTATCAATT TTTGTTCGTT CGTTCGTTCG TTTGTGTGTG
1001  ACCAAAACAA CAAAACCCCA AGACAGAGTC ACATGTAGCC CAGGCTAGCC
      TGGTTTTGTT GTTTTGGGGT TCTGTCTCAG TGTACATCGG GTCCGATCGG
1051  TCCAAATTCA CTATATAACT GAAGAAGACC CCTAATTCCC ATTCCTCTAG
      AGGTTTAAGT GATATATTGA CTTCTTCTGG GGATTAAGGG TAAGGAGATC
1101  AATCTATACC TCAAGTACTG AATGGCTTGG TTCACAATAC CCCACTAAAT
      TTAGATATGG AGTTCATGAC TTACCGAACC AAGTGTTATG GGGTGATTTA
1151  GATTGGTCTT ACTAAGTGCA ACAAGGTAAA CCTAAAACTT CAGCCCTCAG
      CTAACCAGAA TGATTCACGT TGTTCCATTT GGATTTTGAA GTCGGGAGTC
1201  ACATCCCTTT TCCAGTATCA ATTTATAAAA TTAGATCCCA AGGATAAAAA
      TGTAGGGAAA AGGTCATAGT TAAATATTTT AATCTAGGGT TCCTATTTTT
1251  TTAATTGTAA AGTAAAATCA GAGTTCTAGC ATCAACTACA GGCTCAACCA
      AATTAACATT TCATTTTAGT CTCAAGATCG TAGTTGATGT CCGAGTTGGT
1301  TGGGGACCAC AAATAAACTA AAAGGGATAA GACTGGCTTC CCCATAATTA
      ACCCCTGGTG TTTATTTGAT TTTCCCTATT CTGACCGAAG GGGTATTAAT
1351  TTACATTTAG ATAATTTTCC TGACTACTCA ACAAAGCTAA AATATCACCA
      AATGTAAATC TATTAAAAGG ACTGATGAGT TGTTTCGATT TTATAGTGGT
1401  CTGGTTTATT TTCTCCTTCT AGGGTTTAAG CTCACTCTGA GGAGGGGCAT
      GACCAAATAA AAGAGGAAGA TCCCAAATTC GAGTGAGACT CCTCCCCGTA
1451  GCGGCACACA CTCATAGCAT CCAGGAAATA GAAATATGGT GACTATCATG
      CGCCGTGTGT GAGTATCGTA GGTCCTTTAT CTTTATACCA CTGATAGTAC
1501  GGTTCAGGGC CAACCTAGGC TTTAGAGAAA AACCTTGTCC CACAAACCAA
      CCAAGTCCCG GTTGGATCCG AAATCTCTTT TTGGAACAGG GTGTTTGGTT
1551  AAATGTCTCT TTTTTATTCT ATCAGGGGTG GATGGATTTG TTAAAGAAGT
```

Figure 23 cont.

```
     TTTACAGAGA AAAAATAAGA TAGTCCCCAC CTACCTAAAC AATTTCTTCA
1601 GCTTTTAAAA ACCTTGAGAT GGTTATTTAG AAGTCCCCAT GGGATACCAA
     CGAAAATTTT TGGAACTCTA CCAATAAATC TTCAGGGGTA CCCTATGGTT
1651 AATAACCCAC TATTTATATG CCCAAGCATT TCACCTCCAC AACAGTGCTA
     TTATTGGGTG ATAAATATAC GGGTTCGTAA AGTGGAGGTG TTGTCACGAT
1701 TGCACCCTTT AACATTTTTG AGACAGTAGC CCAGTCTAGT CTTTAACTTG
     ACGTGGGAAA TTGTAAAAAC TCTGTCATCG GGTCAGATCA GAAATTGAAC
1751 CAGTGATTTT TCCTGATTCA GCTTCTCCCA GTGCTGGAAT TATAGGTATG
     GTCACTAAAA AGGACTAAGT CGAAGAGGGT CACGACCTTA ATATCCATAC
1801 CACCACCATG TGTAACTACA GATGCTACTT AAAAATTTTT TAAAGGAATC
     GTGGTGGTAC ACATTGATGT CTACGATGAA TTTTTAAAAA ATTTCCTTAG
1851 ACAAAAATAA CCCCCTATCA AATGCCTAGT CCCTCTAACC ATCACCAAGT
     TGTTTTTATT GGGGGATAGT TTACGGATCA GGGAGATTGG TAGTGGTTCA
1901 GAAGGATCAC GCAGGAAAAA AAAAATCACC AGCAGCACCT CAGAACCAGG
     CTTCCTAGTG CGTCCTTTTT TTTTTAGTGG TCGTCGTGGA GTCTTGGTCC
1951 ATACTCAGTC CATCAGCATC CAGGGCCATA CCCACACTCA CAGCATCTCC
     TATGAGTCAG GTAGTCGTAG GTCCCGGTAT GGGTGTGAGT GTCGTAGAGG
2001 ACAGTTTACC AGATGATTCA TGCTTATCAC TGTATTGGGT CATCTAAGAG
     TGTCAAATGG TCTACTAAGT ACGAATAGTG ACATAACCCA GTAGATTCTC
2051 TGACCATCAG GGCTTCTGAT CACAGAATCT AGTCCACTTT GCAGACCAGT
     ACTGGTAGTC CCGAAGACTA GTGTCTTAGA TCAGGTGAAA CGTCTGGTCA
2101 TGAAGTCATG CACTATATGA GATAGAAATA CCCTCTTGCT CATTTTGGTC
     ACTTCAGTAC GTGATATACT CTATCTTTAT GGGAGAACGA GTAAAACCAG
2151 AGAAATTCAA GGATAAAAAC CCATGTTTTG TTAATGCACA CCTCCATATG
     TCTTTAAGTT CCTATTTTTG GGTACAAAAC AATTACGTGT GGAGGTATAC
2201 ATTGAGATCA ATGTGTCCTA ATTAATGTAG AAACCACAAC TGTAAATTTC
     TAACTCTAGT TACACAGGAT TAATTACATC TTTGGTGTTG ACATTTAAAG
2251 ACTCTTTTGA CATGAATCTT TTTCTAGACA GGGTCTTGGA TGCAGCCCCG
     TGAGAAAACT GTACTTAGAA AAAGATCTGT CCCAGAACCT ACGTCGGGGC
2301 ACTACCCAGA ATTTTGGAAT CCAGGCTAGC CTCAAACTCA AGGCAATCTG
     TGATGGGTCT TAAAACCTTA GGTCCGATCG GAGTTTGAGT TCCGTTAGAC
2351 CTTGCTTCAG CTTCTCACAG GCTGGATCAC AAACATACAC CTTCAGACCC
     GAACGAAGTC GAAGAGTGTC CGACCTAGTG TTTGTATGTG GAAGTCTGGG
2401 ATTTTTTTTT CCTCCCTCCG TTTTTGGTTT CTCTGTGTAG CCCTGGGTGT
     TAAAAAAAAA GGAGGGAGGC AAAAACCAAA GAGACACATC GGGACCCACA
2451 CCGTGGACTC GCTGTGTAGA TCTATCTACC AGCCTCTGTC TTGGAGTACT
     GGCACCTGAG CGACACATCT AGATAGATGG TCGGAGACAG AACCTCATGA
2501 GGGATTAAAG TTGTGGGCTA CCACTGCCTG GCTGACCCAG TTTTATTTAT
     CCCTAATTTC AACACCCGAT GGTGACGGAC CGACTGGGTC AAAATAAATA
2551 TTTAAATATA ACTTGACAAA AATAAATTTG TCTAACTTAC TAGAAATCCC
     AAATTTATAT TGAACTGTTT TTATTTAAAC AGATTGAATG ATCTTTAGGG
2601 AAGAAAACTA ACACTGGATT TAGCAACAGT CAGAAATCGC TGAAAAGAAA
     TTCTTTTGAT TGTGACCTAA ATCGTTGTCA GTCTTTAGCG ACTTTTCTTT
2651 CAGAATTGAT CTAACAGTCT TAGATCACTC CTAGACAGTT TGTAATTCTT
     GTCTTAACTA GATTGTCAGA ATCTAGTGAG GATCTGTCAA ACATTAAGAA
2701 GCTCATGGCA ACGTGAGCTC TATCTAACTC ACTCTCTGTG CACTAATGAA
     CGAGTACCGT TGCACTCGAG ATAGATTGAG TGAGAGACAC GTGATTACTT
2751 TGCTCAGTGT CTCCAGAACA GCACAGCTTC CAGGGTAATC ATGCCAACCC
     ACGAGTCACA GAGGTCTTGT CGTGTCGAAG GTCCCATTAG TACGGTTGGG
2801 ACAAGACTTT TATAGAGCTG TCCACGACTC TTCCCCCATT CAGCTCATTA
     TGTTCTGAAA ATATCTCGAC AGGTGCTGAG AAGGGGGTAA GTCGAGTAAT
2851 ACAATATGAT GGAGCTCCTG TGTGGAAATC AAGGCACACT CTGGTAGAAA
     TGTTATACTA CCTCGAGGAC ACACCTTTAG TTCCGTGTGA GACCATCTTT
2901 CTTGTTTTTT CTTTCCACTT TTCCTTGGGC TCTGAAGATT GAGCTGTTTT
     GAACAAAAAA GAAAGGTGAA AAGGAACCCG AGACTTCTAA CTCGACAAAA
2951 ATAACCCACA AACATGCATT TTTTACCTCA AAAGCATCCA GCAAAAACTG
     TATTGGGTGT TTGTACGTAA AAAATGGAGT TTTCGTAGGT CGTTTTTGAC
3001 TACAACGCTT TTTCAAAAAA ATGTATTGTG ATCCTCCTTA AGAAAAGCCT
     ATGTTGCGAA AAAGTTTTTT TACATAACAC TAGGAGGAAT TCTTTTCGGA
3051 TACTTAGTGT TAATTCCTTT TTCTTTAGAA TGCTGGTAAA TACAAGGACT
     ATGAATCACA ATTAAGGAAA AAGAAATCTT ACGACCATTT ATGTTCCTGA
3101 TAGGTAGGCT GGCTTCTAAC AGCAATTCAC CCACTTATGA TGGGATTAAA
     ATCCATCCGA CCGAAGATTG TCGTTAAGTG GGTGAATACT ACCCTAATTT
3151 GGAAGGCACA ACCATGTCCA CCACAGGTTC TAGCTCCCCC ACCCACACGC
     CCTTCCGTGT TGGTACAGGT GGTGTCCAAG ATCGAGGGGG TGGGTGTGCG
3201 CCAGAGAGGG TTTTTCTGTG TAGCTCTGAC TATTCTGGAA TTCACACTGC
```

Figure 23 cont.

```
      GGTCTCTCCC AAAAAGACAC ATCGAGACTG ATAAGACCTT AAGTGTGACG
3251  AGACCAGGCT GGTCTCGAAC TCAGAGATCC ACCACCACAT GGTTTCTTAA
      TCTGGTCCGA CCAGAGCTTG AGTCTCTAGG TGGTGGTGTA CCAAAGAATT
3301  TTGTAATTTT AAAGAAAAAA AAAAATCCTT CAGTTAAGAT TCTTATGTTC
      AACATTAAAA TTTCTTTTTT TTTTTAGGAA GTCAATTCTA AGAATACAAG
3351  TAGGTTTTCA CAAACTTACC AATGTAGTTT TATTGGAGGC CATTTTTTAA
      ATCCAAAAGT GTTTGAATGG TTACATCAAA ATAACCTCCG GTAAAAAATT
3401  ATTTAATCGG AGACTTGAAG AGCTATTGCA AGAAAAAAAA TGTAGGACAG
      TAAATTAGCC TCTGAACTTC TCGATAACGT TCTTTTTTTT ACATCCTGTC
3451  TTAAAATTTC ATGACACACA AAAGGCAGCT ACAAGTTTTG TGTGGATTTC
      AATTTTAAAG TACTGTGTGT TTTCCGTCGA TGTTCAAAAC ACACCTAAAG
3501  AACATGTAAA TTTCGGGTAA AAATGCAGGA AAACAGTTGA GTTCCCGTGT
      TTGTACATTT AAAGCCCATT TTTACGTCCT TTTGTCAACT CAAGGGCACA
3551  TATTAGTATG TTACTAATAA TTTCAGTATG TTAGTGAAAA TAATCTTACT
      ATAATCATAC AATGATTATT AAAGTCATAC AATCACTTTT ATTAGAATGA
3601  AAAACACTGG TACCTCAGAC AACTTTACAT GGTGAGGATT GTTACTTTCC
      TTTTGTGACC ATGGAGTCTG TTGAAATGTA CCACTCCTAA CAATGAAAGG
3651  CAATCCATAT AGAATTTTAA CAATTTTAGT GTTTATTTTG GATGAAAGGA
      GTTAGGTATA TCTTAAAATT GTTAAAATCA CAAATAAAAC CTACTTTCCT
3701  AATGACTATC TTTTGTTAGC AAATTACCAT AAGATCTTTT TCTTTAGATT
      TTACTGATAG AAAACAATCG TTTAATGGTA TTCTAGAAAA AGAAATCTAA
3751  TCTGAATACT CCAAGGAGCT CATATAATTC CATCCTTATT TTTTCAGAGG
      AGACTTATGA GGTTCCTCGA GTATATTAAG GTAGGAATAA AAAAGTCTCC
3801  CCCTCCCTGT TCAATCACGG TATAAAAAAA GGAACACATT AAGATGTCCC
      GGGAGGGACA AGTTAGTGCC ATATTTTTTT CCTTGTGTAA TTCTACAGGG
3851  AGTCCTATTT TCTGGCTTTT TTTTTCCGGG GGTGGTGGTG CGGTAATCAC
      TCAGGATAAA AGACCGAAAA AAAAAGGCCC CCACCACCAC GCCATTAGTG
3901  TCTCTATAGT CCAGTCTGGG CTTCAACGCC TGGCAATCCC CAGCCTCAAG
      AGAGATATCA GGTCAGACCC GAAGTTGCGG ACCGTTAGGG GTCGGAGTTC
3951  CTCCCAAGTA CTGTCCTGAT AAGGATAGAA GGAGTCGACC TCCTTCACGC
      GAGGGTTCAT GACAGGACTA TTCCTATCTT CCTCAGCTGG AGGAAGTGCG
4001  TCCCCTCCGA GGAGGGCTCC TTCCCAGCTC CATTCCCCGG TCGGGAGCCC
      AGGGGAGGCT CCTCCCGAGG AAGGGTCGAG GTAAGGGGCC AGCCCTCGGG
4051  GTCCCCCACC CGAGAGCGCG GGCCTCGTGG TCAGCGCCTC CGCGGGGAGA
      CAGGGGGTGG GCTCTCGCGC CCGGAGCACC AGTCGCGGAG GCGCCCCTCT
4101  AACAAAGGCG GCGGCGGGGG CTCAAGGGCA CTGCGCCACG GGCCCGCGCC
      TTGTTTCCGC CGCCGCCCCC GAGTTCCCGT GACGCGGTGC CCGGGCGCGG
4151  TCCCCCATCC GGCGGCGGCC ACGTAGCCGG GAGCGCGCCG CAGCCCGGAG
      AGGGGGTAGG CCGCCGCCGG TGCATCGGCC CTCGCGCGGC GTCGGGCCTC
4201  CCTCGGGCCT CGCAGCTGCA GAGCCTGAAC CGCTCTCTCC CTGCGGGCCT
      GGAGCCCGGA GCGTCGACGT CTCGGACTTG GCGAGAGAGG GACGCCCGGA
4251  GCGACGAGGC TGGGGGAGGG GAGGCCCGCG CTTTGTCTGG AGTCTCGGTA
      CGCTGCTCCG ACCCCCTCCC CTCCGGGCGC GAAACAGACC TCAGAGCCAT
4301  GCTGTCATCC GGCTCCCACC CTCATGCACA ATTGTCCCAT CTCCCCCACG
      CGACAGTAGG CCGAGGGTGG GAGTACGTGT TAACAGGGTA GAGGGGGTGC
4351  CACCGGCGCG GCGCCCGCCT CAGCGAGGCC CCAGCCGGTT TCCCGCAGCC
      GTGGCCGCGC CGCGGGCGGA GTCGCTCCGG GGTCGGCCAA AGGGCGTCGG
4401  CGCGGCCCAC GGGGCTCGCA GCCTCCCCGC AAGCTCGGAC GCACGGAGCA
      GCGCCGGGTG CCCCGAGCGT CGGAGGGGCG TTCGAGCCTG CGTGCCTCGT
4451  TCCTAAACCC CACCACACGC AAGATCGAAA AAAAGCAAAG GCACGAACTT
      AGGATTTGGG GTGGTGTGCG TTCTAGCTTT TTTTCGTTTC CGTGCTTGAA
4501  CACCGCTCCG ATGCTCAGGG CCGCGGATCC TGCAGAGTCT CCCGCCTGCG
      GTGGCGAGGC TACGAGTCCC GGCGCCTAGG ACGTCTCAGA GGGCGGACGC
4551  CGCTTCGGTT CAGCCACATC CGAGGGGAGG GGGCGCGGGC AGCTCCGCCG
      GCGAAGCCAA GTCGGTGTAG GCTCCCCTCC CCCGCGCCCG TCGAGGCGGC
4601  GGGGGGAGGG GGAGCACCGC CCACGCCCTG GCCGCGCGGG GCCCGCCGGG
      CCCCCCTCCC CCTCGTGGCG GGTGCGGGAC CGGCGCGCCC CGGGCGGCCC
4651  AACGCGTCCT GCGGGGGGCG GCGCGCGCAA TGCTCACCGT CCGCGGCGTG
      TTGCGCAGGA CGCCCCCCGC CGCGCGCGTT ACGAGTGGCA GGCGCCGCAC
4701  GCGCCCAGGG GGTCTCCTGG CTGGGGGGAG GGGGGGAAG GCGGGCAGGA
      CGCGGGTCCC CCAGAGGACC GACCCCCCTC CCCCCCCTTC CGCCCGTCCT
4751  AGGACCGCGG AGGCCTCTCT GCGTCTCGGA GCGCGCCAAA GCGGGGCTCC
      TCCTGGCGCC TCCGGAGAGA CGCAGAGCCT CGCGCGGTTT CGCCCCGAGG
4801  ACCCACCTCC TTGCCCGGAT CTTGAAGGCC GGGGAGATAA ACAGCGGGGT
      TGGGTGGAGG AACGGGCCTA GAACTTCCGG CCCCTCTATT TGTCGCCCCA
4851  TCTTTAAGCA CCACCTCTCA CTAGGCGCGG GATCCCAAGG CTTGTGGCAT
```

Figure 23 cont.

```
      AGAAATTCGT GGTGGAGAGT GATCCGCGCC CTAGGGTTCC GAACACCGTA
4901  CCGGGGTGGT ACTTGGACTA AAAGTCCTTC TGGGAGGGAC CGAGTGAGAA
      GGCCCCACCA TGAACCTGAT TTTCAGGAAG ACCCTCCCTG GCTCACTCTT
4951  CCCCTTTGGG ACGTGTAGAA ATATTTGTGT GGTTCGAGAA TATTTGTGCG
      GGGGAAACCC TGCACATCTT TATAAACACA CCAAGCTCTT ATAAACACGC
5001  GACGGGCTTG GCAAAGGCGT AGCTGCAGAG AGCACGCTTG GGTGGAGAGG
      CTGCCCGAAC CGTTTCCGCA TCGACGTCTC TCGTGCGAAC CCACCTCTCC
5051  GCCGCACGCC CCAGCGCCGG CCTAAGCCCC TCCCGACGGC GTTATTTCAA
      CGGCGTGCGG GGTCGCGGCC GGATTCGGGG AGGGCTGCCG CAATAAAGTT
5101  ACTGCGCGAC CGTTTCTCCG CTCCCTACGC GGAGGTGGGG GCCGGACCTA
      TGACGCGCTG GCAAAGAGGC GAGGGATGCG CCTCCACCCC CGGCCTGGAT
5151  GTTCCGGACG TAGTAACACG CCGAGCGCGA GCCTTCCGCA ATTCACGGAA
      CAAGGCCTGC ATCATTGTGC GGCTCGCGCT CGGAAGGCGT TAAGTGCCTT
5201  CACAGTTGCG CAAGTGATGT AAAGCAGTCC CGCTGTACCT AAAGGGGGAG
      GTGTCAACGC GTTCACTACA TTTCGTCAGG GCGACATGGA TTTCCCCCTC
5251  TGTCACGTAC TTGGCGTAAG GAGAGTGTAG GCCCTTCCCG CCATTGGCGG
      ACAGTGCATG AACCGCATTC CTCTCACATC CGGGAAGGGC GGTAACCGCC
5301  CGGTTAGGGC GTTTACGTAA CGGCGTGACG TAAGCGGAGA CGCGTTAGTG
      GCCAATCCCG CAAATGCATT GCCGCACTGC ATTCGCCTCT GCGCAATCAC
5351  GGGGGAAGGT TCTAGAAAAG CGGCGGTCTC GGCTCCAGCG GCAGTAGCAG
      CCCCCTTCCA AGATCTTTTC GCCGCCAGAG CCGAGGTCGC CGTCATCGTC
5401  CGGCGCCGGT CCCGTGTGCA GGAGCTCCTT TGCGGCCCAG TTTCTTGGCC
      GCCGCGGCCA GGGCACACGT CCTCGAGGAA ACGCCGGGTC AAAGAACCGG
5451  ATCGCCTGCT CTCCCCACAG CGCCAGGACG AGTCCCGTGC GCGTCCGTCC
      TAGCGGACGA GAGGGGTGTC GCGGTCCTGC TCAGGGCACG CGCAGGCAGG
5501  GCGGAGGTCT TTCTCATCTC GCTCGGCTGC GGGAAATCGG GCTGAAGCGA
      CGCCTCCAGA AAGAGTAGAG CGAGCCGACG CCCTTTAGCC CGACTTCGCT
5551  CTGAGTCCGC GATGGAGGTA ACGGGTTTGA AATCAATGAG TTATTAAAAA
      GACTCAGGCG CTACCTCCAT TGCCCAAACT TTAGTTACTC AATAATTTTT
5601  TGGCATGGCG AGGCCGTAGG CACCGCAATG GAAACCGGCC ACCCGCCTCC
      ACCGTACCGC TCCGGCATCC GTGGCGTTAC CTTTGGCCGG TGGGCGGAGG
5651  GTGGTCCGGC GGAGGGGATG CGGCCACTCG AGTGGCGGTT GGCCTTGGCG
      CACCAGGCCG CCTCCCCTAC GCCGGTGAGC TCACCGCCAA CCGGAACCGC
5701  AGTTTCTGAG GGGTCGTTGG AGGAGGCCTC TGATTGTCCG ACCGCCTTCC
      TCAAAGACTC CCCAGCAACC TCCTCCGGAG ACTAACAGGC TGGCGGAAGG
5751  CCGCCCTCAG CCGCCCGGCG CCATTTCCCT CAGTTGGGGT GGGGGATGGG
      GGCGGGAGTC GGCGGGCCGC GGTAAAGGGA GTCAACCCCA CCCCCTACCC
5801  AAGTGCCCGC CGCGACCGGG CTGGACCGCT AAAGTAGCGC GTGAGCGGGC
      TTCACGGGCG GCGCTGGCCC GACCTGGCGA TTTCATCGCG CACTCGCCCG
5851  CATCGCTGGC CTTTCGATGT GCGCGGGCCT AGGGGCTCGG TTGTGTTCGC
      GTAGCGACCG GAAAGCTACA CGCGCCCGGA TCCCCGAGCC AACACAAGCG
5901  GGCGGAACGT TTCTGGGGCC CCCCCGGCTT CCCGGAGCGA GTCTGCGAAG
      CCGCCTTGCA AAGACCCCGG GGGGGCCGAA GGGCCTCGCT CAGACGCTTC
5951  CTAGCTTCCC CTCCCCCCTC TCCCGGGAAC CGGATTTGGC GGCCGCCATT
      GATCGAAGGG GAGGGGGGAG AGGGCCCTTG GCCTAAACCG CCGGCGGTAA
6001  TTCCCGTCTC CTTCCTCGCC ACGATTTTGC TTTCAACGCT TTAGGTTTAC
      AAGGGCAGAG GAAGGAGCGG TGCTAAAACG AAAGTTGCGA AATCCAAATG
6051  TAGTTTGGTT TTCTTTTTTC ACCACTGCGT AGACGTGTTT AGCGATTTTC
      ATCAAACCAA AAGAAAAAAG TGGTGACGCA TCTGCACAAA TCGCTAAAAG
6101  CTTTCTTTTG GAAGTCTTCA TACCGTTTCG AGGTGGATTT AGCGTTTTGA
      GAAAGAAAAC CTTCAGAAGT ATGGCAAAGC TCCACCTAAA TCGCAAAACT
6151  GCTTGGGTCT TCAGCGTCCT GCGCACCTCG CTAAAGGCTC TCTGCCTTCC
      CGAACCCAGA AGTCGCAGGA CGCGTGGAGC GATTTCCGAG AGACGGAAGG
6201  CCTCGACGAA ATGGCGCCAT TGCTTTCTGA AGCCACCGAG GCGCGGGGTG
      GGAGCTGCTT TACCGCGGTA ACGAAAGACT TCGGTGGCTC CGCGCCCCAC
6251  GGGGCGGGGT GGCGGCGCTC CACGAGCTTT ACTGGAACAG GCAGAGAGAA
      CCCCGCCCCA CCGCCGCGAG GTGCTCGAAA TGACCTTGTC CGTCTCTCTT
6301  CGTAGTACAA CCGAGGCCTG GGCGGGTGGC TGAAGGCAGC GTCGCTGCAA
      GCATCATGTT GGCTCCGGAC CCGCCCACCG ACTTCCGTCG CAGCGACGTT
6351  AGAGACCGTT TTATTTTTCA TAATACGTAA GATTACGGGT GCTGTAGTAA
      TCTCTGGCAA AATAAAAAGT ATTATGCATT CTAATGCCCA CGACATCATT
6401  AGCACTTGAG CATTAGTATA GTAGGAGGAA GTCAAAGTGG AAAAAATGGG
      TCGTGAACTC GTAATCATAT CATCCTCCTT CAGTTTCACC TTTTTTACCC
6451  AGCGCTCATC AGGAAGCTAG GGAGGCTATG TTGAGTGCAG GGTTACTTTC
      TCGCGAGTAG TCCTTCGATC CCTCCGATAC AACTCACGTC CCAATGAAAG
6501  CTTTTATTGC AGAACTTTTA TCTGCTTAAA GGATCCTCGG ATCGAAATAA
```

Figure 23 cont.

```
      GAAAATAACG TCTTGAAAAT AGACGAATTT CCTAGGAGCC TAGCTTTATT
6551  TTCAAATTAT AAGCATTTTT AAGGGAATCT TCGAATTTGT TGGTAAAGTC
      AAGTTTAATA TTCGTAAAAA TTCCCTTAGA AGCTTAAACA ACCATTTCAG
6601  AACGGATCCT TAGCACGTGG TGTTCACTTT AAGGAAGTGA AATAGCTGAC
      TTGCCTAGGA ATCGTGCACC ACAAGTGAAA TTCCTTCACT TTATCGACTG
6651  TTTTCATAGT TAGCCTTCGC TTAAAGCCTG GTTCAGTGGA CGAAAATCCA
      AAAAGTATCA ATCGGAAGCG AATTTCGGAC CAAGTCACCT GCTTTTAGGT
6701  CGTCCTGGCT ATATAAAAAC TTAGTTTGGG GTCACAGTGT TTGAGCGTGG
      GCAGGACCGA TATATTTTTG AATCAAACCC CAGTGTCACA AACTCGCACC
6751  TCATTCGGTT TTTTTATTTT TTATTTGTTT GAAATTATGA TGCATCATTA
      AGTAAGCCAA AAAAATAAAA AATAAACAAA CTTTAATACT ACGTAGTAAT
6801  CACTGATAAG CATTAGCTTT CGAATTGAAA GGGGTCTCCT TGGTTATTTT
      GTGACTATTC GTAATCGAAA GCTTAACTTT CCCCAGAGGA ACCAATAAAA
6851  CTTTGACTCT AAGCACACTT ATAAATAAAA TAACCTTGTT TATAATCGAT
      GAAACTGAGA TTCGTGTGAA TATTTATTTT ATTGGAACAA ATATTAGCTA
6901  AGTGGACGTC TGGTAAGTTT GGAAAAAACC CGAGGTAAGT AAAGAGCTTT
      TCACCTGCAG ACCATTCAAA CCTTTTTTGG GCTCCATTCA TTTCTCGAAA
6951  TGCTTTCGTT AGTGATATGA AAAAACAAGG TGTATTTAAT ACTTGCAACT
      ACGAAAGCAA TCACTATACT TTTTTGTTCC ACATAAATTA TGAACGTTGA
7001  TAGTTTAAGG AAAGCCAATT TACTGACATT TTAGTAGAGC TACCAGAAAC
      ATCAAATTCC TTTCGGTTAA ATGACTGTAA AATCATCTCG ATGGTCTTTG
7051  ACTATTTGGA GTCCTGATTA AGGCTTTTGT AACTATTTTG ACTATTTAAA
      TGATAAACCT CAGGACTAAT TCCGAAAACA TTGATAAAAC TGATAAATTT
7101  ACAATTTTGG TCGTTTTTAT TAAACATTTC AAAACCTAAA AATTGTAAAC
      TGTTAAAACC AGCAAAAATA ATTTGTAAAG TTTTGGATTT TTAACATTTG
7151  ATTGGCTTTT TGAGCACATT TTGGAGAAAC TTACAAATTT AGGCTATACA
      TAACCGAAAA ACTCGTGTAA AACCTCTTTG AATGTTTAAA TCCGATATGT
7201  GTAAAATAAC GGATTTGTTT TATAATTTTG CTTTTTCATT TCGTTGTGCA
      CATTTTATTG CCTAAACAAA ATATTAAAAC GAAAAAGTAA AGCAACACGT
7251  GTCATAGGTC CTGGATAGTA TGACCTAATT TATGAACATC TTGATAAGTT
      CAGTATCCAG GACCTATCAT ACTGGATTAA ATACTTGTAG AACTATTCAA
7301  TTTGTACTTA GCTATTGGAA AGCCAGTATT AAGTGCCTGA CAAAACCAGA
      AAACATGAAT CGATAACCTT TCGGTCATAA TTCACGGACT GTTTTGGTCT
7351  TTTAAGGTGA TATCTGGAGT TTCAGCATTC TTCATGGAGC TTGTTTCAGA
      AAATTCCACT ATAGACCTCA AAGTCGTAAG AAGTACCTCG AACAAAGTCT
7401  GTTGCAGGAT TTTTTTTTTT CATCTTGAGA TACTTACAAT TAACACCAGA
      CAACGTCCTA AAAAAAAAAA GTAGAACTCT ATGAATGTTA ATTGTGGTCT
7451  GGGGGCAGCT CAGGGAAAAG CAAATATGCC ACTTTTCAGA AACTGAATCT
      CCCCCGTCGA GTCCCTTTTC GTTTATACGG TGAAAAGTCT TTGACTTAGA
7501  TGGAAGTGGT GAATTTGGAA ACAGGTTTTT TAAATTTTTT TTAAATCTAA
      ACCTTCACCA CTTAAACCTT TGTCCAAAAA ATTTAAAAAA AATTTAGATT
7551  AAAGTAGTAA ATTTTGGACT TGGGTTGTAG AATTTAATGA ATTACAAAAG
      TTTCATCATT TAAAACCTGA ACCCAACATC TTAAATTACT TAATGTTTTC
7601  AATTCTTTAA TACCCTTTAA ATGACCTAAG AGCTGGGTAT GGTTTTTCTG
      TTAAGAAATT ATGGGAAATT TACTGGATTC TCGACCCATA CCAAAAAGAC
7651  AATTTTTTTG AAGAAAATCT AAGAAAGTTT ACGTGAATTA GAAGTTAGAT
      TTAAAAAAAC TTCTTTTAGA TTCTTTCAAA TGCACTTAAT CTTCAATCTA
7701  CGAATATTAG TGACTTTGAA ACTTGTATAG CTCAGGCAAT TTTTGGTGTA
      GCTTATAATC ACTGAAACTT TGAACATATC GAGTCCGTTA AAAACCACAT
7751  ACACAACTAA TATGCAGTTT AACATATGGT TTAAATTTGA TGTAAGTTTT
      TGTGTTGATT ATACGTCAAA TTGTATACCA AATTTAAACT ACATTCAAAA
7801  TTTTCTCCCC CCCAGAAAAC TTTAGAAACT GTTCCTTTGG AGAGGAAAAA
      AAAAGAGGGG GGGTCTTTTG AAATCTTTGA CAAGGAAACC TCTCCTTTTT
7851  GGTACTCTAC CAGCAGGTCA CCTCATATTT AAGAATTTAA TTTCCTGCAT
      CCATGAGATG GTCGTCCAGT GGAGTATAAA TTCTTAAATT AAAGGACGTA
7901  ACAAAGAAAG TGTAAATAAA AATTGAAATG GTATTTCCCT TTGCAGAGAG
      TGTTTCTTTC ACATTTATTT TTAACTTTAC CATAAAGGGA AACGTCTCTC
7951  AAAAGGAACA GTTCCGAAAG CTCTTTATTG GTGGCTTAAG CTTATCGATA
      TTTTCCTTGT CAAGGCTTTC GAGAAATAAC CACCGAATTC GAATAGCTAT
8001  CCGGTGGCGC GCCAATTGTT AATTAAGATC TGGCCCAATG GGCCGTACGA
      GGCCACCGCG CGGTTAACAA TTAATTCTAG ACCGGGTTAC CCGGCATGCT
8051  ATTCCTTAGG CTACCGGGTA GGGGAGGCGC TTTTCCCAAG GCAGTCTGGA
      TAAGGAATCC GATGGCCCAT CCCCTCCGCG AAAAGGGTTC CGTCAGACCT
8101  GCATGCGCTT TAGCAGCCCC GCTGGGCACT TGGCGCTACA CAAGTGGCCT
      CGTACGCGAA ATCGTCGGGG CGACCCGTGA ACCGCGATGT GTTCACCGGA
8151  CTGGCCTCGC ACACATTCCA CATCCACCGG CCGGTAGGCG CCAACCGGCT
```

Figure 23 cont.

```
      GACCGGAGCG TGTGTAAGGT GTAGGTGGCC GGCCATCCGC GGTTGGCCGA
8201  CCGTTCTTTG GTGGCCCCTT CGCGCCACCT TCTACTCCTC CCCTAGTCAG
      GGCAAGAAAC CACCGGGGAA GCGCGGTGGA AGATGAGGAG GGGATCAGTC
8251  GAAGTTCCCC CCCGCCCCGC AGCTCGCGTC GTGCAGGACG TGACAAATGG
      CTTCAAGGGG GGGCGGGGCG TCGAGCGCAG CACGTCCTGC ACTGTTTACC
8301  AAGTAGCACG TCTCACTAGT CTCGTGCAGA TGGACAGCAC CGCTGAGCAA
      TTCATCGTGC AGAGTGATCA GAGCACGTCT ACCTGTCGTG GCGACTCGTT
8351  TGGAAGCGGG TAGGCCTTTG GGGCAGCGGC CAATAGCAGC TTTGCTCCTT
      ACCTTCGCCC ATCCGGAAAC CCCGTCGCCG GTTATCGTCG AAACGAGGAA
8401  CGCTTTCTGG GCTCAGAGGC TGGGAAGGGG TGGGTCCGGG GGCGGGCTCA
      GCGAAAGACC CGAGTCTCCG ACCCTTCCCC ACCCAGGCCC CCGCCCGAGT
8451  GGGGCGGGCT CAGGGGCGGG GCGGGCGCCC GAAGGTCCTC CGGAGGCCCG
      CCCCGCCCGA GTCCCCGCCC CGCCCGCGGG CTTCCAGGAG GCCTCCGGGC
8501  GCATTCTGCA CGCTTCAAAA GCGCACGTCT GCCGCGCTGT TCTCCTCTTC
      CGTAAGACGT GCGAAGTTTT CGCGTGCAGA CGGCGCGACA AGAGGAGAAG
8551  CTCATCTCCG GGCCTTTCGA CCAGCTTACC ATGACCGAGT ACAAGCCCAC
      GAGTAGAGGC CCGGAAAGCT GGTCGAATGG TACTGGCTCA TGTTCGGGTG
8601  GGTGCGCCTC GCCACCCGCG ACGACGTCCC CAGGGCCGTA CGCACCCTCG
      CCACGCGGAG CGGTGGGCGC TGCTGCAGGG GTCCCGGCAT GCGTGGGAGC
8651  CCGCCGCGTT CGCCGACTAC CCCGCCACGC GCCACACCGT CGATCCGGAC
      GGCGGCGCAA GCGGCTGATG GGGCGGTGCG CGGTGTGGCA GCTAGGCCTG
8701  CGCCACATCG AGCGGGTCAC CGAGCTGCAA GAACTCTTCC TCACGCGCGT
      GCGGTGTAGC TCGCCCAGTG GCTCGACGTT CTTGAGAAGG AGTGCGCGCA
8751  CGGGCTCGAC ATCGGCAAGG TGTGGGTCGC GGACGACGGC GCCGCGGTGG
      GCCCGAGCTG TAGCCGTTCC ACACCCAGCG CCTGCTGCCG CGGCGCCACC
8801  CGGTCTGGAC CACGCCGGAG AGCGTCGAAG CGGGGGCGGT GTTCGCCGAG
      GCCAGACCTG GTGCGGCCTC TCGCAGCTTC GCCCCCGCCA CAAGCGGCTC
8851  ATCGGCCCGC GCATGGCCGA GTTGAGCGGT TCCCGGCTGG CCGCGCAGAA
      TAGCCGGGCG CGTACCGGCT CAACTCGCCA AGGGCCGACC GGCGCGTCTT
8901  CAGATGGAAG GCCTCCTGGC GCCGCACCGG CCCAAGGAGC CCGCGTGGTT
      GTCTACCTTC CGGAGGACCG CGGCGTGGCC GGGTTCCTCG GGCGCACCAA
8951  CCTGGCCACC GTCGCGTCTC GCCCGACCAC CAGGGCAAGG GTCTGGGCAG
      GGACCGGTGG CAGCGCAGAG CGGGCTGGTG GTCCCGTTCC CAGACCCGTC
9001  CGCCGTCGTG CTCCCCGGAG TGGAGGCGGC CGAGCGCGCC GGGGTGCCCG
      GCGGCAGCAC GAGGGGCCTC ACCTCCGCCG GCTCGCGCGG CCCCACGGGC
9051  CCTTCCTGGA GACCTCCGCG CCCCGCAACC TCCCCTTCTA CGAGCGGCTC
      GGAAGGACCT CTGGAGGCGC GGGGCGTTGG AGGGGAAGAT GCTCGCCGAG
9101  GGCTTCACCG TCACCGCCGA CGTCGAGGTG CCCGAAGGAC CGCGCACCTG
      CCGAAGTGGC AGTGGCGGCT GCAGCTCCAC GGGCTTCCTG GCGCGTGGAC
9151  GTGCATGACC CGCAAGCCCG GTGCCTGACG CCCGCCCCAC GACCCGCAGC
      CACGTACTGG GCGTTCGGGC CACGGACTGC GGGCGGGGTG CTGGGCGTCG
9201  GCCCGACCGA AAGGAGCGCA CGACCCCATG CATCGTAGAG CTCGCTGATC
      CGGGCTGGCT TTCCTCGCGT GCTGGGGTAC GTAGCATCTC GAGCGACTAG
9251  AGCCTCGACT GTGCCTTCTA GTTGCCAGCC ATCTGTTGTT TGCCCCTCCC
      TCGGAGCTGA CACGGAAGAT CAACGGTCGG TAGACAACAA ACGGGGAGGG
9301  CCGTGCCTTC CTTGACCCTG GAAGGTGCCA CTCCCACTGT CCTTTCCTAA
      GGCACGGAAG GAACTGGGAC CTTCCACGGT GAGGGTGACA GGAAAGGATT
9351  TAAAATGAGG AAATTGCATC GCATTGTCTG AGTAGGTGTC ATTCTATTCT
      ATTTTACTCC TTTAACGTAG CGTAACAGAC TCATCCACAG TAAGATAAGA
9401  GGGGGGTGGG GTGGGGCAGG ACAGCAAGGG GGGGGATTGG GRAGACAATA
      CCCCCCACCC CACCCCGTCC TGTCGTTCCC CCCCCTAACC CYTCTGTTAT
9451  GCAGGCATGC TGGGGGGGCG GTGGGGGCTA TGGCTTCTGA GGCGGAAAGA
      CGTCCGTACG ACCCCCCCGC CACCCCCGAT ACCGAAGACT CCGCCTTTCT
9501  ACCAGCTGGG GCTCGAGGGC CGCCACCGCG GTGGAGCTCC AGCTTTTGTT
      TGGTCGACCC CGAGCTCCCG GCGGTGGCGC CACCTCGAGG TCGAAAACAA
9551  CCCTTTAGTG AGGGTTAATT TCGAGCTTGG CGTAATCATG GTCATAGCTG
      GGGAAATCAC TCCCAATTAA AGCTCGAACC GCATTAGTAC CAGTATCGAC
9601  TTTCCTGTGT GAAATTGTTA TCCGCTCACA ATTCCACACA ACATACGAGC
      AAAGGACACA CTTTAACAAT AGGCGAGTGT TAAGGTGTGT TGTATGCTCG
9651  CGGAAGCATA AAGTGTAAAG CCTGGGGTGC CTAATGAGTG AGCTAACTCA
      GCCTTCGTAT TTCACATTTC GGACCCCACG GATTACTCAC TCGATTGAGT
9701  CATTAATTGC GTTGCGCTCA CTGCCCGCTT TCCAGTCGGG AAACCTGTCG
      GTAATTAACG CAACGCGAGT GACGGGCGAA AGGTCAGCCC TTTGGACAGC
9751  TGCCAGCATC GCGAGCACTT TTCGGGGAAA TGTGCGCGGA ACCCCTATTT
      ACGGTCGTAG CGCTCGTGAA AAGCCCCTTT ACACGCGCCT TGGGGATAAA
9801  GTTTATTTTT CTAAATACAT TCAAATATGT ATCCGCTCAT GAGACAATAA
```

Figure 23 cont.

```
       CAAATAAAAA GATTTATGTA AGTTTATACA TAGGCGAGTA CTCTGTTATT
 9851  CCCTGATAAA TGCTTCAATA ATATTGAAAA AGGAAGAGTA TGAGTATTCA
       GGGACTATTT ACGAAGTTAT TATAACTTTT TCCTTCTCAT ACTCATAAGT
 9901  ACATTTCCGT GTCGCCCTTA TTCCCTTTTT TGCGGCATTT TGCCTTCCTG
       TGTAAAGGCA CAGCGGGAAT AAGGGAAAAA ACGCCGTAAA ACGGAAGGAC
 9951  TTTTTGCTCA CCCAGAAACG CTGGTGAAAG TAAAAGATGC TGAAGATCAG
       AAAAACGAGT GGGTCTTTGC GACCACTTTC ATTTTCTACG ACTTCTAGTC
10001  TTGGGTGCAC GAGTGGGTTA CATCGAACTG GATCTCAACA GCGGTAAGAT
       AACCCACGTG CTCACCCAAT GTAGCTTGAC CTAGAGTTGT CGCCATTCTA
10051  CCTTGAGAGT TTTCGCCCCG AAGAACGTTT TCCAATGATG AGCACTTTTA
       GGAACTCTCA AAAGCGGGGC TTCTTGCAAA AGGTTACTAC TCGTGAAAAT
10101  AAGTTCTGCT ATGTGGCGCG GTATTATCCC GTATTGACGC CGGGCAAGAG
       TTCAAGACGA TACACCGCGC CATAATAGGG CATAACTGCG GCCCGTTCTC
10151  CAACTCGGTC GCCGCATACA CTATTCTCAG AATGACTTGG TTGAGTACTC
       GTTGAGCCAG CGGCGTATGT GATAAGAGTC TTACTGAACC AACTCATGAG
10201  ACCAGTCACA GAAAAGCATC TTACGGATGG CATGACAGTA AGAGAATTAT
       TGGTCAGTGT CTTTTCGTAG AATGCCTACC GTACTGTCAT TCTCTTAATA
10251  GCAGTGCTGC CATAACCATG AGTGATAACA CTGCGGCCAA CTTACTTCTG
       CGTCACGACG GTATTGGTAC TCACTATTGT GACGCCGGTT GAATGAAGAC
10301  ACAACGATCG GAGGACCGAA GGAGCTAACC GCTTTTTTGC ACAACATGGG
       TGTTGCTAGC CTCCTGGCTT CCTCGATTGG CGAAAAAACG TGTTGTACCC
10351  GGATCATGTA ACTCGCCTTG ATCGTTGGGA ACCGGAGCTG AATGAAGCCA
       CCTAGTACAT TGAGCGGAAC TAGCAACCCT TGGCCTCGAC TTACTTCGGT
10401  TACCAAACGA CGAGCGTGAC ACCACGATGC CTGTAGCAAT GGCAACAACG
       ATGGTTTGCT GCTCGCACTG TGGTGCTACG GACATCGTTA CCGTTGTTGC
10451  TTGCGCAAAC TATTAACTGG CGAACTACTT ACTCTAGCTT CCCGGCAACA
       AACGCGTTTG ATAATTGACC GCTTGATGAA TGAGATCGAA GGGCCGTTGT
10501  ATTAATAGAC TGGATGGAGG CGGATAAAGT TGCAGGACCA CTTCTGCGCT
       TAATTATCTG ACCTACCTCC GCCTATTTCA ACGTCCTGGT GAAGACGCGA
10551  CGGCCCTTCC GGCTGGCTGG TTTATTGCTG ATAAATCTGG AGCCGGTGAG
       GCCGGGAAGG CCGACCGACC AAATAACGAC TATTTAGACC TCGGCCACTC
10601  CGTGGGTCTC GCGGTATCAT TGCAGCACTG GGGCCAGATG GTAAGCCCTC
       GCACCCAGAG CGCCATAGTA ACGTCGTGAC CCCGGTCTAC CATTCGGGAG
10651  CCGTATCGTA GTTATCTACA CGACGGGGAG TCAGGCAACT ATGGATGAAC
       GGCATAGCAT CAATAGATGT GCTGCCCCTC AGTCCGTTGA TACCTACTTG
10701  GAAATAGACA GATCGCTGAG ATAGGTGCCT CACTGATTAA GCATTGGTAA
       CTTTATCTGT CTAGCGACTC TATCCACGGA GTGACTAATT CGTAACCATT
10751  CTGTCAGACT CGCGACACTG CATTAATGAA TCGGCCAACG CGCGGGGAGA
       GACAGTCTGA GCGCTGTGAC GTAATTACTT AGCCGGTTGC GCGCCCCTCT
10801  GGCGGTTTGC GTATTGGGCG CTCTTCCGCT TCCTCGCTCA CTGACTCGCT
       CCGCCAAACG CATAACCCGC GAGAAGGCGA AGGAGCGAGT GACTGAGCGA
10851  GCGCTCGGTC GTTCGGCTGC GGCGAGCGGT ATCAGCTCAC TCAAAGGCGG
       CGCGAGCCAG CAAGCCGACG CCGCTCGCCA TAGTCGAGTG AGTTTCCGCC
10901  TAATACGGTT ATCCACAGAA TCAGGGGATA ACGCAGGAAA GAACATGTGA
       ATTATGCCAA TAGGTGTCTT AGTCCCCTAT TGCGTCCTTT CTTGTACACT
10951  GCAAAAGGCC AGCAAAAGGC CAGGAACCGT AAAAAGGCCG CGTTGCTGGC
       CGTTTTCCGG TCGTTTTCCG GTCCTTGGCA TTTTTCCGGC GCAACGACCG
11001  GTTTTTCCAT AGGCTCCGCC CCCCTGACGA GCATCACAAA AATCGACGCT
       CAAAAAGGTA TCCGAGGCGG GGGGACTGCT CGTAGTGTTT TTAGCTGCGA
11051  CAAGTCAGAG GTGGCGAAAC CCGACAGGAC TATAAAGATA CCAGGCGTTT
       GTTCAGTCTC CACCGCTTTG GGCTGTCCTG ATATTTCTAT GGTCCGCAAA
11101  CCCCCTGGAA GCTCCCTCGT GCGCTCTCCT GTTCCGACCC TGCCGCTTAC
       GGGGGACCTT CGAGGGAGCA CGCGAGAGGA CAAGGCTGGG ACGGCGAATG
11151  CGGATACCTG TCCGCCTTTC TCCCTTCGGG AAGCGTGGCG CTTTCTCATA
       GCCTATGGAC AGGCGGAAAG AGGGAAGCCC TTCGCACCGC GAAAGAGTAT
11201  GCTCACGCTG TAGGTATCTC AGTTCGGTGT AGGTCGTTCG CTCCAAGCTG
       CGAGTGCGAC ATCCATAGAG TCAAGCCACA TCCAGCAAGC GAGGTTCGAC
11251  GGCTGTGTGC ACGAACCCCC CGTTCAGCCC GACCGCTGCG CCTTATCCGG
       CCGACACACG TGCTTGGGGG GCAAGTCGGG CTGGCGACGC GGAATAGGCC
11301  TAACTATCGT CTTGAGTCCA ACCCGGTAAG ACACGACTTA TCGCCACTGG
       ATTGATAGCA GAACTCAGGT TGGGCCATTC TGTGCTGAAT AGCGGTGACC
11351  CAGCAGCCAC TGGTAACAGG ATTAGCAGAG CGAGGTATGT AGGCGGTGCT
       GTCGTCGGTG ACCATTGTCC TAATCGTCTC GCTCCATACA TCCGCCACGA
11401  ACAGAGTTCT TGAAGTGGTG GCCTAACTAC GGCTACACTA GAAGGACAGT
       TGTCTCAAGA ACTTCACCAC CGGATTGATG CCGATGTGAT CTTCCTGTCA
11451  ATTTGGTATC TGCGCTCTGC TGAAGCCAGT TACCTTCGGA AAAAGAGTTG
```

Figure 23 cont.

```
       TAAACCATAG ACGCGAGACG ACTTCGGTCA ATGGAAGCCT TTTTCTCAAC
11501  GTAGCTCTTG ATCCGGCAAA CAAACCACCG CTGGTAGCGG TGGTTTTTTT
       CATCGAGAAC TAGGCCGTTT GTTTGGTGGC GACCATCGCC ACCAAAAAAA
11551  GTTTGCAAGC AGCAGATTAC GCGCAGAAAA AAAGGATCTC AAGAAGATCC
       CAAACGTTCG TCGTCTAATG CGCGTCTTTT TTTCCTAGAG TTCTTCTAGG
11601  TTTGATCTTT TCTACGGGGT CTGACGCTCA GTGGAACGAA AACTCA
       AAACTAGAAA AGATGCCCCA GACTGCGAGT CACCTTGCTT TTGAGT
```

Figure 25 CET1030 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAACTA
      TAACCCATGG CCCGGGGGGG AGCTTCAAAT TTGTAAATTT AGATCTTGAT
 101  GTGGATCCCC CGGGCTGCAG GAATTCGATA TCAAGCTCAT GGCACCTGTA
      CACCTAGGGG GCCCGACGTC CTTAAGCTAT AGTTCGAGTA CCGTGGACAT
 151  TTGTACTCTT ATCAGTCATT ATATGGACTT TAACTTCCCC AGATATTATT
      AACATGAGAA TAGTCAGTAA TATACCTGAA ATTGAAGGGG TCTATAATAA
 201  TGGGCTCCTC CATAAGACTG TGAGCATCTG ACCACTGGAG TGTTGCTTCC
      ACCCGAGGAG GTATTCTGAC ACTCGTAGAC TGGTGACCTC ACAACGAAGG
 251  CATTATATCC CTGTTATCAA GCACAAGGTC AGGCACAGAG TAAGACTCAA
      GTAATATAGG GACAATAGTT CGTGTTCCAG TCCGTGTCTC ATTCTGAGTT
 301  AACATGTTTT GGAATGTATG ACTGGTATGA ACTACAAACC AGTAAGCTGA
      TTGTACAAAA CCTTACATAC TGACCATACT TGATGTTTGG TCATTCGACT
 351  TGTTTTCATT TTGAGTCTAT AAATCTAATT TTGTGGTGGT TTTGTGTATG
      ACAAAAGTAA AACTCAGATA TTTAGATTAA AACACCACCA AAACACATAC
 401  GCTCAAGGCT CAAATTGTAA AATTTAATAT TATGTGACCA AAGAAAGTTA
      CGAGTTCCGA GTTTAACATT TTAAATTATA ATACACTGGT TTCTTTCAAT
 451  TACCCAGAAC CTCAATTTCC TCACCTTCAA AATGGGGCAG TTTCTCACTC
      ATGGGTCTTG GAGTTAAAGG AGTGGAAGTT TTACCCCGTC AAAGAGTGAG
 501  ATTGGTCTGC TGTCACGATT TTAATGAGCT CATGCACAAA CAGCCCTTTA
      TAACCAGACG ACAGTGCTAA AATTACTCGA GTACGTGTTT GTCGGGAAAT
 551  TATAAGGTAA GTGCTGGATA AATGTTGGCT ACTATAATAA AATAAGCCTC
      ATATTCCATT CACGACCTAT TTACAACCGA TGATATTATT TTATTCGGAG
 601  TAAGATACTT GGTCAGCACA AGTACTACCC AAGAGTATGC ACTGTAAGTA
      ATTCTATGAA CCAGTCGTGT TCATGATGGG TTCTCATACG TGACATTCAT
 651  AACTGACAAA ATTGTGTATC TAAAACTGGC CAGATGAAAG AGAAACTTTT
      TTGACTGTTT TAACACATAG ATTTTGACCG GTCTACTTTC TCTTTGAAAA
 701  AAGGGGCCCT TCTGCGTGCC CGACACTGTG CTAGGCACTC ACACTATCCC
      TTCCCCGGGA AGACGCACGG GCTGTGACAC GATCCGTGAG TGTGATAGGG
 751  GACCCGAGAA ACCGATCTGC GACCCAGAGG AACTTACCAA GCCTCCAGCA
      CTGGGCTCTT TGGCTAGACG CTGGGTCTCC TTGAATGGTT CGGAGGTCGT
 801  TCTTGTGCAG CCCTACTCAT GGGACCATCT GGATACCCAC CCTTGTCTTT
      AGAACACGTC GGGATGAGTA CCCTGGTAGA CCTATGGGTG GGAACAGAAA
 851  ACAGGGAGCA GAACACACCT CTTATGTGTC AGAAAACAAA GTCCAGGAAG
      TGTCCCTCGT CTTGTGTGGA GAATACACAG TCTTTTGTTT CAGGTCCTTC
 901  TATATTTTTA CCTGAGGCAA TATCTGAAAA TTGTATGCTA CAGCCTCCAA
      ATATAAAAAT GGACTCCGTT ATAGACTTTT AACATACGAT GTCGGAGGTT
 951  AGTGAGTCTT CCTCTCAGTA CCTCTCTTCT AGGCACATGG AGCCCTTTCT
      TCACTCAGAA GGAGAGTCAT GGAGAGAAGA TCCGTGTACC TCGGGAAAGA
1001  TCCAAGTATT ATGTTTAACC ACTTAATGAA TGAAGTCCTG AAACTGCTTA
      AGGTTCATAA TACAAATTGG TGAATTACTT ACTTCAGGAC TTTGACGAAT
1051  CCCATGCTCC CTATAATCTC TGAGTAATCT TCCTTTTCCA CAACCTCAGG
      GGGTACGAGG GATATTAGAG ACTCATTAGA AGGAAAAGGT GTTGGAGTCC
1101  CATAATCTCA TCTTCTGTTT CTATTACAAT TTCAAATTCT GGAAAAAGGA
      GTATTAGAGT AGAAGACAAA GATAATGTTA AAGTTTAAGA CCTTTTTCCT
1151  AGTTGTGGTC TGGAATTATA TGGTCCAGAT GATCTGAAAC AAAAAGGACA
      TCAACACCAG ACCTTAATAT ACCAGGTCTA CTAGACTTTG TTTTTCCTGT
1201  GCACTATTAG TAATCATTTA GTTTTGAAGA CAGTCTAATA ATTTGCTGTC
      CGTGATAATC ATTAGTAAAT CAAAACTTCT GTCAGATTAT TAAACGACAG
1251  TCTAAAGTAC TATATTCCCT ATAGTTCTGG CATTTTAGAT AAAGGGTCAT
      AGATTTCATG ATATAAGGGA TATCAAGACC GTAAAATCTA TTTCCCAGTA
1301  AAATTAAATG CCTATATGGT GACATTATTC AGTGATTCAG ACTTCACAGC
      TTTAATTTAC GGATATACCA CTGTAATAAG TCACTAAGTC TGAAGTGTCG
1351  CTTTTTTTTT TTTTTACAAA GGTGTTCCAG GCATGAAAAA TTTTAAAGTA
      GAAAAAAAAA AAAAATGTTT CCACAAGGTC CGTACTTTTT AAAATTTCAT
1401  CTATACCTTT CCTAATTTTA CCTTTAAAGT TGTCCTGGAA ATATCTGGGT
      GATATGGAAA GGATTAAAAT GGAAATTTCA ACAGGACCTT TATAGACCCA
1451  TGACAAAGGC GATGAAACTG AACTGAGACT TAAAAAAAAG ATTACCCACC
      ACTGTTTCCG CTACTTTGAC TTGACTCTGA ATTTTTTTTC TAATGGGTGG
1501  TGGTTGTGCA CAAGCCTGCT TATGTCCCAA TCTCCAGTCT AGGGTCTGAT
      ACCAACACGT GTTCGGACGA ATACAGGGTT AGAGGTCAGA TCCCAGACTA
```

Figure 25 cont.

```
1551  GCTCCTTGCT GCAGTAATAT GCTTTGTGGC ATCTGGAGCA CGTTTTGGGG
      CGAGGAACGA CGTCATTATA CGAAACACCG TAGACCTCGT GCAAAACCCC
1601  CCTAAACAGC CACAAACCCT GCAGAGATGA GCACCAGACT TAAGCTGGAG
      GGATTTGTCG GTGTTTGGGA CGTCTCTACT CGTGGTCTGA ATTCGACCTC
1651  ACACACTGAT TCTCCTGTTT CTGGGGGAGG ATTCTCAGAA GGTGGCTCAT
      TGTGTGACTA AGAGGACAAA GACCCCCTCC TAAGAGTCTT CCACCGAGTA
1701  ATGAGTAAAA ATCGTTTTTC CTGGGTAGTT GATTCCTAAA AACTAAAAAA
      TACTCATTTT TAGCAAAAAG GACCCATCAA CTAAGGATTT TTGATTTTTT
1751  GAATACAGAG AAAAGTTTTA TCTTCAAACA AAACAGCAAT TCACATATTT
      CTTATGTCTC TTTTCAAAAT AGAAGTTTGT TTTGTCGTTA AGTGTATAAA
1801  TATCCTCTGC ACGTAAAACT GAAAATAACA ACAACAAAAA AGAAATGAAA
      ATAGGAGACG TGCATTTTGA CTTTTATTGT TGTTGTTTTT TCTTTACTTT
1851  GTTTTTGCTT TCAGGAATAA GCTTTTAAAA TCCAGAAACT AGATTTCGTC
      CAAAAACGAA AGTCCTTATT CGAAAATTTT AGGTCTTTGA TCTAAAGCAG
1901  CGGTACACGC AACTGAGTTG CCTCCTAGAG GTGGTTTGAG TTAATCAAAT
      GCCATGTGCG TTGACTCAAC GGAGGATCTC CACCAAACTC AATTAGTTTA
1951  TAATAAGACT GATCGTTAAG AACGACTGCC AAAAATACGA AAAAGCTACT
      ATTATTCTGA CTAGCAATTC TTGCTGACGG TTTTTATGCT TTTTCGATGA
2001  GGGATCCATC TTTCCAAGAC AATTTCTATT ATCTGAATTA ACACCATACC
      CCCTAGGTAG AAAGGTTCTG TTAAAGATAA TAGACTTAAT TGTGGTATGG
2051  TGGTACCCAC TGATTAAAAG CTGGGGGTTA CCAATGCGCG TGGGCACAGT
      ACCATGGGTG ACTAATTTTC GACCCCCAAT GGTTACGCGC ACCCGTGTCA
2101  TAGAAGCTTA TGTAGCAAAA ATGAGCACAT CCTGGAAGGG CCCGGGAGAA
      ATCTTCGAAT ACATCGTTTT TACTCGTGTA GGACCTTCCC GGGCCCTCTT
2151  GGTGCTCCTG GGGCAGCGCG GAGAGGGAGC TCTGAGGCTG GGGCGGCAGC
      CCACGAGGAC CCCGTCGCGC CTCTCCCTCG AGACTCCGAC CCCGCCGTCG
2201  GGTGCTTGCC GCCGTCCCCC TGGTCGCTCC CGGAATTAAC GCCGCGCACG
      CCACGAACGG CGGCAGGGGG ACCAGCGAGG GCCTTAATTG CGGCGCGTGC
2251  CGTCGGAGGC ATGGCCCCGT CCCGACCCCG TTTGGCGGCT CACCTCGCAG
      GCAGCCTCCG TACCGGGGCA GGGCTGGGGC AAACCGCCGA GTGGAGCGTC
2301  GCCGGCACAG CACGGCTGCT CGCGGCAGCA GAAGAGGAAG ATGCAGCGGT
      CGGCCGTGTC GTGCCGACGA GCGCCGTCGT CTTCTCCTTC TACGTCGCCA
2351  GGAAGGCGTC CGGGCGGCCA GGCAGCGGCG CATACACCTG CAGCAGGAAG
      CCTTCCGCAG GCCCGCCGGT CCGTCGCCGC GTATGTGGAC GTCGTCCTTC
2401  GAGAGCGGGC GGCCGCACAG CTCGCAGGCC AGGGCCTGGG GCCCCGGCAG
      CTCTCGCCCG CCGGCGTGTC GAGCGTCCGG TCCCGGACCC CGGGGCCGTC
2451  CCCGGCCGCG CCCAGCCATG CCGGCCGCCC GCCCACCTTG CTGGGGAACT
      GGGCCGGCGC GGGTCGGTAC GGCCGGCGGG CGGGTGGAAC GACCCCTTGA
2501  GCTCGCTGCG CAGTCGCCAC GCCGGCGCCG ACTCGGCGAA GCCCAGCTCC
      CGAGCGACGC GTCAGCGGTG CGGCCGCGGC TGAGCCGCTT CGGGTCGAGG
2551  ACAGGCCTGG CCCCGGCGGC AGCCATGCGG GGCGCGGGCT GGCGTGGGGC
      TGTCCGGACC GGGGCCGCCG TCGGTACGCC CCGCGCCCGA CCGCACCCCG
2601  GCAGCCCACA GCTGGGTCGG AAGGCGGAAA TCGGGCGCCG GGCCGGAAGG
      CGTCGGGTGT CGACCCAGCC TTCCGCCTTT AGCCCGCGGC CCGGCCTTCC
2651  CAAGAGGCGG GCACCTTTCC GGAGGACAGG AGGCGGAAAC GCGTCTGACG
      GTTCTCCGCC CGTGGAAAGG CCTCCTGTCC TCCGCCTTTG CGCAGACTGC
2701  GGAGCGGTTG CAGGACCAAT GCGAGGGAAC GGGGCAGAGG AAACCTCTCG
      CCTCGCCAAC GTCCTGGTTA CGCTCCCTTG CCCCGTCTCC TTTGGAGAGC
2751  GCATCAGCCC CGCCCCTGGC GCCTCTGCCT CCGAGCCGCT TTCCTGGTGC
      CGTAGTCGGG GCGGGGACCG CGGAGACGGA GGCTCGGCGA AAGGACCACG
2801  CTCCGGGTGC TCTGGGATGG TTCTGGTCTT TGGGAGAGTG GCAGCTGGTG
      GAGGCCCACG AGACCCTACC AAGACCAGAA ACCCTCTCAC CGTCGACCAC
2851  ACGGCGCTCC GCTCACCTCT GCACATGTCT TGCTGTGGGC CTGCGGGTGG
      TGCCGCGAGG CGAGTGGAGA CGTGTACAGA ACGACACCCG GACGCCCACC
2901  CCGCCAGGGA GGCAGAGCCC TCCCGCAAAC CTTCCCTGCT GGTGTCCACC
      GGCGGTCCCT CCGTCTCGGG AGGGCGTTTG GAAGGGACGA CCACAGGTGG
2951  TCAGGGTGTG GGAAACCTGT GCGCTGGCCG AGTGCTAACC AAGAGTAGGC
      AGTCCCACAC CCTTTGGACA CGCGACCGGC TCACGATTGG TTCTCATCCG
3001  AGTGAAAGAC AAATGAAGGT TGAACAGGTA AAGTGAGGAC CCTACAGCGG
      TCACTTTCTG TTTACTTCCA ACTTGTCCAT TTCACTCCTG GGATGTCGCC
3051  AAACCAAGAA TCCTGTGTGC CTGAGAGTAA TGAAGAAGCC TCTGCAGAAG
      TTTGGTTCTT AGGACACACG GACTCTCATT ACTTCTTCGG AGACGTCTTC
3101  AGTCTTTTCT GTCAGTCTTA AGGTCTCTGT TTTAATGTTA GTGCTGGCTT
      TCAGAAAAGA CAGTCAGAAT TCCAGAGACA AAATTACAAT CACGACCGAA
3151  GCTGTACCTG AATTCCAAGG GAGGAGTGTA TAATGAGGCA TGGCCAACCC
      CGACATGGAC TTAAGGTTCC CTCCTCACAT ATTACTCCGT ACCGGTTGGG
```

Figure 25 cont.

```
3201  CCACTTCCCA TCATTGCCTG AACTAGTTTT TCAGGTTAAC TTCAGAATGC
      GGTGAAGGGT AGTAACGGAC TTGATCAAAA AGTCCAATTG AAGTCTTACG
3251  CCTTGGTACC GCGGGCCCCC TCTGTGGTCC CACGCCACTG ATCGCTGCAT
      GGAACCATGG CGCCCGGGGG AGACACCAGG GTGCGGTGAC TAGCGACGTA
3301  GCCCACCACC TGGGTACACA CAGTCTGTGA TTCCCGGAGC AGAACGGACC
      CGGGTGGTGG ACCCATGTGT GTCAGACACT AAGGGCCTCG TCTTGCCTGG
3351  CTGCCCACCC GGTCTTGTGT GCTACTCAGT GGACAGACCC AAGGCAAGAA
      GACGGGTGGG CCAGAACACA CGATGAGTCA CCTGTCTGGG TTCCGTTCTT
3401  AGGGTGACAA GGACAGGGTC TTCCCAGGCT GGCTTTGAGT TCCTAGCACC
      TCCCACTGTT CCTGTCCCAG AAGGGTCCGA CCGAAACTCA AGGATCGTGG
3451  GCCCCGCCCC CAATCCTCTG TGGCACATGG AGTCTTGGTC CCCAGAGTCC
      CGGGGCGGGG GTTAGGAGAC ACCGTGTACC TCAGAACCAG GGGTCTCAGG
3501  CCCAGCGGCC TCCAGATGGT CTGGGAGGGC AGTTCAGCTG TGGCTGCGCA
      GGGTCGCCGG AGGTCTACCA GACCCTCCCG TCAAGTCGAC ACCGACGCGT
3551  TAGCAGACAT ACAACGGACG GTGGGCCCAG ACCCAGGCTG TGTAGACCCA
      ATCGTCTGTA TGTTGCCTGC CACCCGGGTC TGGGTCCGAC ACATCTGGGT
3601  GCCCCCCCGC CCCGCAGTGC CTAGGTCACC CACTAACGCC CCAGGCCTGG
      CGGGGGGGCG GGGCGTCACG GATCCAGTGG GTGATTGCGG GGTCCGGACC
3651  TCTTGGCTGG GCGTGACTGT TACCCTCAAA AGCAGGCAGC TCCAGGGTAA
      AGAACCGACC CGCACTGACA ATGGGAGTTT TCGTCCGTCG AGGTCCCATT
3701  AAGGTGCCCT GCCCTGTAGA GCCCACTTCC TTCCCAGGGC TGCGGCTGGG
      TTCCACGGGA CGGGACATCT CGGGTGAAGG AAGGGTCCCG ACGCCGACCC
3751  TAGGTTTGTA GCCTTCATCA CGGGCCACCT CCAGCCACTG GACCGCTGGC
      ATCCAAACAT CGGAAGTAGT GCCCGGTGGA GGTCGGTGAC CTGGCGACCG
3801  CCCTGCCCTG TCCTGGGGAG TGTGGTCCTG CGACTCTAAT GGCCGCAAGC
      GGGACGGGAC AGGACCCCTC ACACCAGGAC GCTGAGATTA CCGGCGTTCG
3851  CACCTGACTC CCCCAACACC ACACTCTACC TCTCAAGCCC AGGTCTCTCC
      GTGGACTGAG GGGGTTGTGG TGTGAGATGG AGAGTTCGGG TCCAGAGAGG
3901  CTAGTGACCC ACCCAGCACA TTTAGCTAGC TGAGCCCCAC AGCCAGAGGT
      GATCACTGGG TGGGTCGTGT AAATCGATCG ACTCGGGGTG TCGGTCTCCA
3951  CCTCAGGCCC TGCTTTCAGG GCAGTTGCTC TGAAGTCGGC AAGGGGGAGT
      GGAGTCCGGG ACGAAAGTCC CGTCAACGAG ACTTCAGCCG TTCCCCCTCA
4001  GACTGCCTGG CCACTCCATG CCCTCCAAGA GCTCCTTCTG CAGGAGCGTA
      CTGACGGACC GGTGAGGTAC GGGAGGTTCT CGAGGAAGAC GTCCTCGCAT
4051  CAGAACCCAG GGCCCTGGCA CCCGTGCAGA CCCTGGCCCA CCCCACCTGG
      GTCTTGGGTC CCGGGACCGT GGGCACGTCT GGGACCGGGT GGGGTGGACC
4101  GCGCTCAGTG CCCAAGAGAT GTCCACACCT AGGATGTCCC GCGGTGGGTG
      CGCGAGTCAC GGGTTCTCTA CAGGTGTGGA TCCTACAGGG CGCCACCCAC
4151  GGGGGCCCGA GAGACGGGCA GGCCGGGGGC AGGCCTGGCC ATGCGGGGCC
      CCCCCGGGCT CTCTGCCCGT CCGGCCCCCG TCCGGACCGG TACGCCCCGG
4201  GAACCGGGCA CTGCCCAGCG TGGGGCGCGG GGGCCACGGC GCGCGCCCCC
      CTTGGCCCGT GACGGGTCGC ACCCCGCGCC CCCGGTGCCG CGCGCGGGGG
4251  AGCCCCCGGG CCCAGCACCC CAAGGCGGCC AACGCCAAAA CTCTCCCTCC
      TCGGGGGCCC GGGTCGTGGG GTTCCGCCGG TTGCGGTTTT GAGAGGGAGG
4301  TCCTCTTCCT CAATCTCGCT CTCGCTCTTT TTTTTTTTCG CAAAAGGAGG
      AGGAGAAGGA GTTAGAGCGA GAGCGAGAAA AAAAAAAAGC GTTTTCCTCC
4351  GGAGAGGGGG TAAAAAAATG CTGCACTGTG CGGCGAAGCC GGTGAGTGAG
      CCTCTCCCCC ATTTTTTTAC GACGTGACAC GCCGCTTCGG CCACTCACTC
4401  CGGCGCGGGG CCAATCAGCG TGCGCCGTTC CGAAAGTTGC CTTTTATGGC
      GCCGCGCCCC GGTTAGTCGC ACGCGGCAAG GCTTTCAACG GAAAATACCG
4451  TCGAGCGGCC GCGGCGGCGC CCTATAAAAC CCAGCGGCGC GACGCGCCAC
      AGCTCGCCGG CGCCGCCGCG GGATATTTTG GGTCGCCGCG CTGCGCGGTG
4501  CACCGCCGAG ACCGCGTCCG CCCGCGAGCA CAGAGCCTCG CCTTTGCCGA
      GTGGCGGCTC TGGCGCAGGC GGGCGCTCGT GTCTCGGAGC GGAAACGGCT
4551  TCCGCCGCCC GTCCACACCC GCCGCCAGGT AAGCCCGGCC AGCCGACCGG
      AGGCGGCGGG CAGGTGTGGG CGGCGGTCCA TTCGGGCCGG TCGGCTGGCC
4601  GGCATGCGGC CGCGGCCCTT CGCCCGTGCA GAGCCGCCGT CTGGGCCGCA
      CCGTACGCCG GCGCCGGGAA GCGGGCACGT CTCGGCGGCA GACCCGGCGT
4651  GCGGGGGGCG CATGGGGCGG AACCGGACCG CCGTGGGGGG CGCGGGAGAA
      CGCCCCCCGC GTACCCCGCC TTGGCCTGGC GGCACCCCCC GCGCCCTCTT
4701  GCCCCTGGGC CTCCGGAGAT GGGGGACACC CCACGCCAGT TCGCAGGCGC
      CGGGGACCCG GAGGCCTCTA CCCCCTGTGG GGTGCGGTCA AGCGTCCGCG
4751  GAGGCCGCGC TCGGGCGGGC GCGCTCCGGG GGTGCCGCTC TCGGGGCGGG
      CTCCGGCGCG AGCCCGCCCG CGCGAGGCCC CCACGGCGAG AGCCCCGCCC
4801  GGCAACCGGC GGGGTCTTTG TCTGAGCCGG GCTCTTGCCA ATGGGGATCG
      CCGTTGGCCG CCCCAGAAAC AGACTCGGCC CGAGAACGGT TACCCCTAGC
```

Figure 25 cont.

```
4851  CACGGTGGGC GCGGCGTAGC CCCCGTCAGG CCCGGTGGGG GCTGGGGCGC
      GTGCCACCCG CGCCGCATCG GGGGCAGTCC GGGCCACCCC CGACCCCGCG
4901  CATGCGCGTG CGCGCTGGTC CTTTGGGCGC TAACTGCGTG CGCGCTGGGA
      GTACGCGCAC GCGCGACCAG GAAACCCGCG ATTGACGCAC GCGCGACCCT
4951  ATTGGCGCTA ATTGCGCGTG CGCGCTGGGA CTCAATGGCG CTAATCGCGC
      TAACCGCGAT TAACGCGCAC GCGCGACCCT GAGTTACCGC GATTAGCGCG
5001  GTGCGTTCTG GGGCCCGGGC GCTTGCGCCA CTTCCTGCCC GAGCCGCTGG
      CACGCAAGAC CCCGGGCCCG CGAACGCGGT GAAGGACGGG CTCGGCGACC
5051  CGCCCGAGGG TGTGGCCGCT GCGTGCGCGC GCGCGACCCG GTCGCTGTTT
      GCGGGCTCCC ACACCGGCGA CGCACGCGCG CGCGCTGGGC CAGCGACAAA
5101  GAACCGGGCG GAGGCGGGGC TGGCGCCCGG TTGGGAGGGG GTTGGGGCCT
      CTTGGCCCGC CTCCGCCCCG ACCGCGGGCC AACCCTCCCC CAACCCCGGA
5151  GGCTTCCTGC CGCGCGCCGC GGGGACGCCT CCGACCAGTG TTTGCCTTTT
      CCGAAGGACG GCGCGCGGCG CCCCTGCGGA GGCTGGTCAC AAACGGAAAA
5201  ATGGTAATAA CGCGGCCGGC CCGGCTTCCT TTGTCCCCAA TCTGGGCGCG
      TACCATTATT GCGCCGGCCG GGCCGAAGGA AACAGGGGTT AGACCCGCGC
5251  CGCCGGCGCC CCCTGGCGGC CTAAGGACTC GGCGCGCCGG AAGTGGCCAG
      GCGGCCGCGG GGGACCGCCG GATTCCTGAG CCGCGCGGCC TTCACCGGTC
5301  GGCGGGGGCG ACTTCGGCTC ACAGCGCGCC CGGCTATTCT CGCAGCTCAC
      CCGCCCCCGC TGAAGCCGAG TGTCGCGCGG GCCGATAAGA GCGTCGAGTG
5351  CATGCCGGTC GCCACCATGA GCTTATCGAT ACCGGTGGCG CGCCAATTGT
      GTACGGCCAG CGGTGGTACT CGAATAGCTA TGGCCACCGC GCGGTTAACA
5401  TAATTAAGAT CTGGCCCAAT GGGCCGTACG AATTCCTTAG GCTACCGGGT
      ATTAATTCTA GACCGGGTTA CCCGGCATGC TTAAGGAATC CGATGGCCCA
5451  AGGGGAGGCG CTTTTCCCAA GGCAGTCTGG AGCATGCGCT TTAGCAGCCC
      TCCCCTCCGC GAAAAGGGTT CCGTCAGACC TCGTACGCGA AATCGTCGGG
5501  CGCTGGGCAC TTGGCGCTAC ACAAGTGGCC TCTGGCCTCG CACACATTCC
      GCGACCCGTG AACCGCGATG TGTTCACCGG AGACCGGAGC GTGTGTAAGG
5551  ACATCCACCG GCCGGTAGGC GCCAACCGGC TCCGTTCTTT GGTGGCCCCT
      TGTAGGTGGC CGGCCATCCG CGGTTGGCCG AGGCAAGAAA CCACCGGGGA
5601  TCGCGCCACC TTCTACTCCT CCCCTAGTCA GGAAGTTCCC CCCCGCCCCG
      AGCGCGGTGG AAGATGAGGA GGGGATCAGT CCTTCAAGGG GGGGCGGGGC
5651  CAGCTCGCGT CGTGCAGGAC GTGACAAATG GAAGTAGCAC GTCTCACTAG
      GTCGAGCGCA GCACGTCCTG CACTGTTTAC CTTCATCGTG CAGAGTGATC
5701  TCTCGTGCAG ATGGACAGCA CCGCTGAGCA ATGGAAGCGG GTAGGCCTTT
      AGAGCACGTC TACCTGTCGT GGCGACTCGT TACCTTCGCC CATCCGGAAA
5751  GGGGCAGCGG CCAATAGCAG CTTTGCTCCT TCGCTTTCTG GGCTCAGAGG
      CCCCGTCGCC GGTTATCGTC GAAACGAGGA AGCGAAAGAC CCGAGTCTCC
5801  CTGGGAAGGG GTGGGTCCGG GGGCGGGCTC AGGGGCGGGC TCAGGGGCGG
      GACCCTTCCC CACCCAGGCC CCCGCCCGAG TCCCCGCCCG AGTCCCCGCC
5851  GGCGGGCGCC CGAAGGTCCT CCGGAGGCCC GGCATTCTGC ACGCTTCAAA
      CCGCCCGCGG GCTTCCAGGA GGCCTCCGGG CCGTAAGACG TGCGAAGTTT
5901  AGCGCACGTC TGCCGCGCTG TTCTCCTCTT CCTCATCTCC GGGCCTTTCG
      TCGCGTGCAG ACGGCGCGAC AAGAGGAGAA GGAGTAGAGG CCCGGAAAGC
5951  ACCAGCTTAC CATGACCGAG TACAAGCCCA CGGTGCGCCT CGCCACCCGC
      TGGTCGAATG GTACTGGCTC ATGTTCGGGT GCCACGCGGA GCGGTGGGCG
6001  GACGACGTCC CCAGGGCCGT ACGCACCCTC GCCGCCGCGT TCGCCGACTA
      CTGCTGCAGG GGTCCCGGCA TGCGTGGGAG CGGCGGCGCA AGCGGCTGAT
6051  CCCCGCCACG CGCCACACCG TCGATCCGGA CCGCCACATC GAGCGGGTCA
      GGGGCGGTGC GCGGTGTGGC AGCTAGGCCT GGCGGTGTAG CTCGCCCAGT
6101  CCGAGCTGCA AGAACTCTTC CTCACGCGCG TCGGGCTCGA CATCGGCAAG
      GGCTCGACGT TCTTGAGAAG GAGTGCGCGC AGCCCGAGCT GTAGCCGTTC
6151  GTGTGGGTCG CGGACGACGG CGCCGCGGTG GCGGTCTGGA CCACGCCGGA
      CACACCCAGC GCCTGCTGCC GCGGCGCCAC CGCCAGACCT GGTGCGGCCT
6201  GAGCGTCGAA GCGGGGGCGG TGTTCGCCGA GATCGGCCCG CGCATGGCCG
      CTCGCAGCTT CGCCCCCGCC ACAAGCGGCT CTAGCCGGGC GCGTACCGGC
6251  AGTTGAGCGG TTCCCGGCTG GCCGCGCAGA ACAGATGGAA GGCCTCCTGG
      TCAACTCGCC AAGGGCCGAC CGGCGCGTCT TGTCTACCTT CCGGAGGACC
6301  CGCCGCACCG GCCCAAGGAG CCCGCGTGGT TCCTGGCCAC CGTCGCGTCT
      GCGGCGTGGC CGGGTTCCTC GGGCGCACCA AGGACCGGTG GCAGCGCAGA
6351  CGCCCGACCA CCAGGGCAAG GGTCTGGGCA GCGCCGTCGT GCTCCCCGGA
      GCGGGCTGGT GGTCCCGTTC CCAGACCCGT CGCGGCAGCA CGAGGGGCCT
6401  GTGGAGGCGG CCGAGCGCGC CGGGGTGCCC GCCTTCCTGG AGACCTCCGC
      CACCTCCGCC GGCTCGCGCG GCCCCACGGG CGGAAGGACC TCTGGAGGCG
6451  GCCCCGCAAC CTCCCCTTCT ACGAGCGGCT CGGCTTCACC GTCACCGCCG
      CGGGGCGTTG GAGGGGAAGA TGCTCGCCGA GCCGAAGTGG CAGTGGCGGC
```

Figure 25 cont.

```
6501  ACGTCGAGGT GCCCGAAGGA CCGCGCACCT GGTGCATGAC CCGCAAGCCC
      TGCAGCTCCA CGGGCTTCCT GGCGCGTGGA CCACGTACTG GGCGTTCGGG
6551  GGTGCCTGAC GCCCGCCCCA CGACCCGCAG CGCCCGACCG AAAGGAGCGC
      CCACGGACTG CGGGCGGGGT GCTGGGCGTC GCGGGCTGGC TTTCCTCGCG
6601  ACGACCCCAT GCATCGTAGA GCTCGCTGAT CAGCCTCGAC TGTGCCTTCT
      TGCTGGGGTA CGTAGCATCT CGAGCGACTA GTCGGAGCTG ACACGGAAGA
6651  AGTTGCCAGC CATCTGTTGT TTGCCCCTCC CCCGTGCCTT CCTTGACCCT
      TCAACGGTCG GTAGACAACA AACGGGGAGG GGGCACGGAA GGAACTGGGA
6701  GGAAGGTGCC ACTCCCACTG TCCTTTCCTA ATAAAATGAG GAAATTGCAT
      CCTTCCACGG TGAGGGTGAC AGGAAAGGAT TATTTTACTC CTTTAACGTA
6751  CGCATTGTCT GAGTAGGTGT CATTCTATTC TGGGGGGTGG GGTGGGGCAG
      GCGTAACAGA CTCATCCACA GTAAGATAAG ACCCCCCACC CCACCCCGTC
6801  GACAGCAAGG GGGGGATTG GGRAGACAAT AGCAGGCATG CTGGGGGGGC
      CTGTCGTTCC CCCCCCTAAC CCYTCTGTTA TCGTCCGTAC GACCCCCCCG
6851  GGTGGGGGCT ATGGCTTCTG AGGCGGAAAG AACCAGCTGG GGCTCGAGGG
      CCACCCCCGA TACCGAAGAC TCCGCCTTTC TTGGTCGACC CCGAGCTCCC
6901  CCGCCACCGC GGTGGAGCTC CAGCTTTTGT TCCCTTTAGT GAGGGTTAAT
      GGCGGTGGCG CCACCTCGAG GTCGAAAACA AGGGAAATCA CTCCCAATTA
6951  TTCGAGCTTG GCGTAATCAT GGTCATAGCT GTTTCCTGTG TGAAATTGTT
      AAGCTCGAAC CGCATTAGTA CCAGTATCGA CAAAGGACAC ACTTTAACAA
7001  ATCCGCTCAC AATTCCACAC AACATACGAG CCGGAAGCAT AAAGTGTAAA
      TAGGCGAGTG TTAAGGTGTG TTGTATGCTC GGCCTTCGTA TTTCACATTT
7051  GCCTGGGGTG CCTAATGAGT GAGCTAACTC ACATTAATTG CGTTGCGCTC
      CGGACCCCAC GGATTACTCA CTCGATTGAG TGTAATTAAC GCAACGCGAG
7101  ACTGCCCGCT TTCCAGTCGG GAAACCTGTC GTGCCAGCAT CGCGAGCACT
      TGACGGGCGA AAGGTCAGCC CTTTGGACAG CACGGTCGTA GCGCTCGTGA
7151  TTTCGGGGAA ATGTGCGCGG AACCCCTATT TGTTTATTTT TCTAAATACA
      AAAGCCCCTT TACACGCGCC TTGGGGATAA ACAAATAAAA AGATTTATGT
7201  TTCAAATATG TATCCGCTCA TGAGACAATA ACCCTGATAA ATGCTTCAAT
      AAGTTTATAC ATAGGCGAGT ACTCTGTTAT TGGGACTATT TACGAAGTTA
7251  AATATTGAAA AAGGAAGAGT ATGAGTATTC AACATTTCCG TGTCGCCCTT
      TTATAACTTT TTCCTTCTCA TACTCATAAG TTGTAAAGGC ACAGCGGGAA
7301  ATTCCCTTTT TTGCGGCATT TTGCCTTCCT GTTTTTGCTC ACCCAGAAAC
      TAAGGGAAAA AACGCCGTAA AACGGAAGGA CAAAAACGAG TGGGTCTTTG
7351  GCTGGTGAAA GTAAAAGATG CTGAAGATCA GTTGGGTGCA CGAGTGGGTT
      CGACCACTTT CATTTTCTAC GACTTCTAGT CAACCCACGT GCTCACCCAA
7401  ACATCGAACT GGATCTCAAC AGCGGTAAGA TCCTTGAGAG TTTTCGCCCC
      TGTAGCTTGA CCTAGAGTTG TCGCCATTCT AGGAACTCTC AAAAGCGGGG
7451  GAAGAACGTT TTCCAATGAT GAGCACTTTT AAAGTTCTGC TATGTGGCGC
      CTTCTTGCAA AAGGTTACTA CTCGTGAAAA TTTCAAGACG ATACACCGCG
7501  GGTATTATCC CGTATTGACG CCGGGCAAGA GCAACTCGGT CGCCGCATAC
      CCATAATAGG GCATAACTGC GGCCCGTTCT CGTTGAGCCA GCGGCGTATG
7551  ACTATTCTCA GAATGACTTG GTTGAGTACT CACCAGTCAC AGAAAAGCAT
      TGATAAGAGT CTTACTGAAC CAACTCATGA GTGGTCAGTG TCTTTTCGTA
7601  CTTACGGATG GCATGACAGT AAGAGAATTA TGCAGTGCTG CCATAACCAT
      GAATGCCTAC CGTACTGTCA TTCTCTTAAT ACGTCACGAC GGTATTGGTA
7651  GAGTGATAAC ACTGCGGCCA ACTTACTTCT GACAACGATC GGAGGACCGA
      CTCACTATTG TGACGCCGGT TGAATGAAGA CTGTTGCTAG CCTCCTGGCT
7701  AGGAGCTAAC CGCTTTTTTG CACAACATGG GGGATCATGT AACTCGCCTT
      TCCTCGATTG GCGAAAAAAC GTGTTGTACC CCCTAGTACA TTGAGCGGAA
7751  GATCGTTGGG AACCGGAGCT GAATGAAGCC ATACCAAACG ACGAGCGTGA
      CTAGCAACCC TTGGCCTCGA CTTACTTCGG TATGGTTTGC TGCTCGCACT
7801  CACCACGATG CCTGTAGCAA TGGCAACAAC GTTGCGCAAA CTATTAACTG
      GTGGTGCTAC GGACATCGTT ACCGTTGTTG CAACGCGTTT GATAATTGAC
7851  GCGAACTACT TACTCTAGCT TCCCGGCAAC AATTAATAGA CTGGATGGAG
      CGCTTGATGA ATGAGATCGA AGGGCCGTTG TTAATTATCT GACCTACCTC
7901  GCGGATAAAG TTGCAGGACC ACTTCTGCGC TCGGCCCTTC CGGCTGGCTG
      CGCCTATTTC AACGTCCTGG TGAAGACGCG AGCCGGGAAG GCCGACCGAC
7951  GTTTATTGCT GATAAATCTG GAGCCGGTGA GCGTGGGTCT CGCGGTATCA
      CAAATAACGA CTATTTAGAC CTCGGCCACT CGCACCCAGA GCGCCATAGT
8001  TTGCAGCACT GGGGCCAGAT GGTAAGCCCT CCCGTATCGT AGTTATCTAC
      AACGTCGTGA CCCCGGTCTA CCATTCGGGA GGGCATAGCA TCAATAGATG
8051  ACGACGGGGA GTCAGGCAAC TATGGATGAA CGAAATAGAC AGATCGCTGA
      TGCTGCCCCT CAGTCCGTTG ATACCTACTT GCTTTATCTG TCTAGCGACT
8101  GATAGGTGCC TCACTGATTA AGCATTGGTA ACTGTCAGAC TCGCGACACT
      CTATCCACGG AGTGACTAAT TCGTAACCAT TGACAGTCTG AGCGCTGTGA
```

Figure 25 cont.

```
8151  GCATTAATGA ATCGGCCAAC GCGCGGGGAG AGGCGGTTTG CGTATTGGGC
      CGTAATTACT TAGCCGGTTG CGCGCCCCTC TCCGCCAAAC GCATAACCCG
8201  GCTCTTCCGC TTCCTCGCTC ACTGACTCGC TGCGCTCGGT CGTTCGGCTG
      CGAGAAGGCG AAGGAGCGAG TGACTGAGCG ACGCGAGCCA GCAAGCCGAC
8251  CGGCGAGCGG TATCAGCTCA CTCAAAGGCG GTAATACGGT TATCCACAGA
      GCCGCTCGCC ATAGTCGAGT GAGTTTCCGC CATTATGCCA ATAGGTGTCT
8301  ATCAGGGGAT AACGCAGGAA AGAACATGTG AGCAAAAGGC CAGCAAAAGG
      TAGTCCCCTA TTGCGTCCTT TCTTGTACAC TCGTTTTCCG GTCGTTTTCC
8351  CCAGGAACCG TAAAAAGGCC GCGTTGCTGG CGTTTTTCCA TAGGCTCCGC
      GGTCCTTGGC ATTTTTCCGG CGCAACGACC GCAAAAAGGT ATCCGAGGCG
8401  CCCCCTGACG AGCATCACAA AAATCGACGC TCAAGTCAGA GGTGGCGAAA
      GGGGGACTGC TCGTAGTGTT TTTAGCTGCG AGTTCAGTCT CCACCGCTTT
8451  CCCGACAGGA CTATAAAGAT ACCAGGCGTT TCCCCCTGGA AGCTCCCTCG
      GGGCTGTCCT GATATTTCTA TGGTCCGCAA AGGGGGACCT TCGAGGGAGC
8501  TGCGCTCTCC TGTTCCGACC CTGCCGCTTA CCGGATACCT GTCCGCCTTT
      ACGCGAGAGG ACAAGGCTGG GACGGCGAAT GGCCTATGGA CAGGCGGAAA
8551  CTCCCTTCGG GAAGCGTGGC GCTTTCTCAT AGCTCACGCT GTAGGTATCT
      GAGGGAAGCC CTTCGCACCG CGAAAGAGTA TCGAGTGCGA CATCCATAGA
8601  CAGTTCGGTG TAGGTCGTTC GCTCCAAGCT GGGCTGTGTG CACGAACCCC
      GTCAAGCCAC ATCCAGCAAG CGAGGTTCGA CCCGACACAC GTGCTTGGGG
8651  CCGTTCAGCC CGACCGCTGC GCCTTATCCG GTAACTATCG TCTTGAGTCC
      GGCAAGTCGG GCTGGCGACG CGGAATAGGC CATTGATAGC AGAACTCAGG
8701  AACCCGGTAA GACACGACTT ATCGCCACTG GCAGCAGCCA CTGGTAACAG
      TTGGGCCATT CTGTGCTGAA TAGCGGTGAC CGTCGTCGGT GACCATTGTC
8751  GATTAGCAGA GCGAGGTATG TAGGCGGTGC TACAGAGTTC TTGAAGTGGT
      CTAATCGTCT CGCTCCATAC ATCCGCCACG ATGTCTCAAG AACTTCACCA
8801  GGCCTAACTA CGGCTACACT AGAAGGACAG TATTTGGTAT CTGCGCTCTG
      CCGGATTGAT GCCGATGTGA TCTTCCTGTC ATAAACCATA GACGCGAGAC
8851  CTGAAGCCAG TTACCTTCGG AAAAAGAGTT GGTAGCTCTT GATCCGGCAA
      GACTTCGGTC AATGGAAGCC TTTTTCTCAA CCATCGAGAA CTAGGCCGTT
8901  ACAAACCACC GCTGGTAGCG GTGGTTTTTT TGTTTGCAAG CAGCAGATTA
      TGTTTGGTGG CGACCATCGC CACCAAAAAA ACAAACGTTC GTCGTCTAAT
8951  CGCGCAGAAA AAAAGGATCT CAAGAAGATC CTTTGATCTT TTCTACGGGG
      GCGCGTCTTT TTTTCCTAGA GTTCTTCTAG GAAACTAGAA AAGATGCCCC
9001  TCTGACGCTC AGTGGAACGA AAACTCA
      AGACTGCGAG TCACCTTGCT TTTGAGT
```

Figure 27 CET1110 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAAGCT
      TAACCCATGG CCCGGGGGGG AGCTTCAAAT TTGTAAATTT AGATCTTCGA
 101  TCAATGTTTT TAGCACCCTC TGTGTGGAGG AAAATAATGC AGATTATTCT
      AGTTACAAAA ATCGTGGGAG ACACACCTCC TTTTATTACG TCTAATAAGA
 151  AATTAGTGTA ATATCTAACC ACATTAAAAT ATATTACATA GTAAACTACA
      TTAATCACAT TATAGATTGG TGTAATTTTA TATAATGTAT CATTTGATGT
 201  CTCCATAATT TTATAAATTT GACTCCCCAG GGTAATAAAC TAGTCTCTAG
      GAGGTATTAA AATATTTAAA CTGAGGGGTC CCATTATTTG ATCAGAGATC
 251  TCTGCTCACC TTCAACTGTA CAATAAAGTC TTGGTTCTTT TGAAATAGAC
      AGACGAGTGG AAGTTGACAT GTTATTTCAG AACCAAGAAA ACTTTATCTG
 301  CTCAAATGAG ACACCTAAAA TTCAAAGTGT CTTTACATTT AAAGACACCT
      GAGTTTACTC TGTGGATTTT AAGTTTCACA GAAATGTAAA TTTCTGTGGA
 351  ACAGGAAAGC AGGTAAAAGA GCCAGGTTAA AAACAAATTC TAAAACCACT
      TGTCCTTTCG TCCATTTTCT CGGTCCAATT TTTGTTTAAG ATTTTGGTGA
 401  TAGCTGCAGT TAAACATATA GTAAAGATGC ACTAAAGTTT CTTACTCTGT
      ATCGACGTCA ATTTGTATAT CATTTCTACG TGATTTCAAA GAATGAGACA
 451  AAATCCCTTC CACTTCAGGA AATATTCCAC TTTCCCATTC ACTACACGTC
      TTTAGGGAAG GTGAAGTCCT TTATAAGGTG AAAGGGTAAG TGATGTGCAG
 501  GATCTAGTAC TTTTTCCACG ACAAATTCTT CAGGCTCTGC CTCTTCAACT
      CTAGATCATG AAAAAGGTGC TGTTTAAGAA GTCCGAGACG GAGAAGTTGA
 551  TTTTTACTCT TTCCATTCTG TTTTTTTCCC ATTTTTTGCT AAAATAAAAC
      AAAAATGAGA AAGGTAAGAC AAAAAAAGGG TAAAAAACGA TTTTATTTTG
 601  AAAAGAGAAA TTAAGAAATA TTCCTCTTGA ATTTTGAGCA CATTTTCAAG
      TTTTCTCTTT AATTCTTTAT AAGGAGAACT TAAAACTCGT GTAAAAGTTC
 651  GCTCAATTGC TTATATTATT ATCACATTCG ACATAAATTT TTACTTCTAT
      CGAGTTAACG AATATAATAA TAGTGTAAGC TGTATTTAAA AATGAAGATA
 701  ATCCCAGGGC AGACACCTTC TGGAAAGATT AAAAGTCAAC AGACAATAAA
      TAGGGTCCCG TCTGTGGAAG ACCTTTCTAA TTTTCAGTTG TCTGTTATTT
 751  ATAAAAGAAT GCTTTATCTT GTTCATTTAG TTCAAACTTA CAACCCACCA
      TATTTTCTTA CGAAATAGAA CAAGTAAATC AAGTTTGAAT GTTGGGTGGT
 801  CCAAAATAAT ACAATAAAAA AACACTATCT GGAAACAGTT ATTTTTTTCC
      GGTTTTATTA TGTTATTTTT TTGTGATAGA CCTTTGTCAA TAAAAAAAGG
 851  AGTCTTTTTT TTTGAGACAG GGTCTCACAC TCTTGTCGCC CAGGCTGGAG
      TCAGAAAAAA AAACTCTGTC CCAGAGTGTG AGAACAGCGG GTCCGACCTC
 901  TGCAGTGGCG TGATCTCAGC TCACTGCAAC CTCCGCCTCC CCAGGTTCAA
      ACGTCACCGC ACTAGAGTCG AGTGACGTTG GAGGCGGAGG GGTCCAAGTT
 951  GCAGTTCTCA TGCCTCAGCC TCCAGAGTAG CTGGGATTAT AGGCGGATGC
      CGTCAAGAGT ACGGAGTCGG AGGTCTCATC GACCCTAATA TCCGCCTACG
1001  CACCATGCCG GGCTAATTTT TTTTGTGTTT TTATTAGAAA CAGGGTTTCA
      GTGGTACGGC CCGATTAAAA AAAACACAAA AATAATCTTT GTCCCAAAGT
1051  CCATGTTGAC CAGGCTGGTC TCAAACTCCT GACCTGAAGT GATTCACCAG
      GGTACAACTG GTCCGACCAG AGTTTGAGGA CTGGACTTCA CTAAGTGGTC
1101  CCTGGGCCTC CCAAAGTGCT GGCATTACAG GCGTGAGCCA CTGCGCCCGG
      GGACCCGGAG GGTTTCACGA CCGTAATGTC CGCACTCGGT GACGCGGGCC
1151  CCCTGTAGTC TTAAAAGACC AAGTTTACTA ATTTTCACTC ATTTTAACAA
      GGGACATCAG AATTTTCTGG TTCAAATGAT TAAAAGTGAG TAAAATTGTT
1201  CACTGCAACA AACAACTATG CAGGAAGTAC CTAAAGGGTG ATCCAGAGAA
      GTGACGTTGT TTGTTGATAC GTCCTTCATG GATTTCCCAC TAGGTCTCTT
1251  GCAAGTAGTA GTGACAGGTC TTAGGTGAAC CTATGACAGA CCTTGTATCC
      CGTTCATCAT CACTGTCCAG AATCCACTTG GATACTGTCT GGAACATAGG
1301  ACCCCCAGAT GGTAAAAGCC CCAGCCCCCT TCTCAATTCA AATATTAATG
      TGGGGGTCTA CCATTTTCGG GGTCGGGGGA AGAGTTAAGT TTATAATTAC
1351  TCAAAAGCAT CAATGATACA GAGAAAAGAT AAATGCAGAA TGAAAACATG
      AGTTTTCGTA GTTACTATGT CTCTTTTCTA TTTACGTCTT ACTTTTGTAC
1401  GTTCAAAATC CTGATACCAA CTGCAGGGTC AACTATAGAG ACCACTAGGA
      CAAGTTTTAG GACTATGGTT GACGTCCCAG TTGATATCTC TGGTGATCCT
1451  GGTTCAATTA AAGGACAAGA TTATTTTTCC ATAATCTCTG TAGATAATAT
      CCAAGTTAAT TTCCTGTTCT AATAAAAAGG TATTAGAGAC ATCTATTATA
1501  TTCCTACCAC TTAGAACAAA ACTATAAAGC TATCACTTCA AGAGACCAAC
      AAGGATGGTG AATCTTGTTT TGATATTTCG ATAGTGAAGT TCTCTGGTTG
```

Figure 27 cont.

```
1551  ATTACAAATT TATTTTAATT CCCTAAGGTG AAAAAAATCC TTCCTTCCTG
      TAATGTTTAA ATAAAATTAA GGGATTCCAC TTTTTTTAGG AAGGAAGGAC
1601  GTTTCTCAAG AGAAAGTCTA TACTGGTAAC CAAATTCACT TTAAACAGGC
      CAAAGAGTTC TCTTTCAGAT ATGACCATTG GTTTAAGTGA AATTTGTCCG
1651  ATTTTCTTTG GTATGACACT ATTTAAGAGA AGCAGGAAAC CAACGTGAAC
      TAAAAGAAAC CATACTGTGA TAAATTCTCT TCGTCCTTTG GTTGCACTTG
1701  CAGCTCTTTC CAATGGCTCA AGATTTCCTA TGAGAGGACT AAAAATGGGG
      GTCGAGAAAG GTTACCGAGT TCTAAAGGAT ACTCTCCTGA TTTTTACCCC
1751  AAAATTTTTA TGAGAGGATT AAAAATGGGG GAAAAAAAAC CCTGAAATGG
      TTTTAAAAAT ACTCTCCTAA TTTTTACCCC CTTTTTTTTG GGACTTTACC
1801  TTAATCAGAA GATCCTATGG GCTGAGAAGG AATCCATCTT AACATTTCAT
      AATTAGTCTT CTAGGATACC CGACTCTTCC TTAGGTAGAA TTGTAAAGTA
1851  CTTAAAGCAA ATGCTATTGC CGGGGGCAGT GGCTCATGCC TGTAATCCCA
      GAATTTCGTT TACGATAACG GCCCCCGTCA CCGAGTACGG ACATTAGGGT
1901  GCACTTTGGG AGGCCGAGGT GGGCAGATCA TCTGAGGTCA GGAGTTTGAG
      CGTGAAACCC TCCGGCTCCA CCCGTCTAGT AGACTCCAGT CCTCAAACTC
1951  ACCAGCCTGA CCAACATGGA GAAACCCCGT TTCTACTAAA AATACAAAAT
      TGGTCGGACT GGTTGTACCT CTTTGGGGCA AAGATGATTT TTATGTTTTA
2001  TAGCCAGGCA TAGTGGTGCA TGCCTGTAAT CCCAGCTACT TGGGAGGCTG
      ATCGGTCCGT ATCACCACGT ACGGACATTA GGGTCGATGA ACCCTCCGAC
2051  AGGCAGGAGA ACTGCTTGAA CCCAGGAGGC TTAAGTTGCG GTGAGCCAAG
      TCCGTCCTCT TGACGAACTT GGGTCCTCCG AATTCAACGC CACTCGGTTC
2101  ATCACGCCAT TGCACTCTAG CCTGGACAAC AAGAGAAAAA CTCTGTCTCA
      TAGTGCGGTA ACGTGAGATC GGACCTGTTG TTCTCTTTTT GAGACAGAGT
2151  AAAAAACACA AAAACAAAAA ACCCAAATAC TATTTAAAAA AGATAAACCT
      TTTTTTGTGT TTTTGTTTTT TGGGTTTATG ATAAATTTTT TCTATTTGGA
2201  TAATTGCTCA ATCATTAAAG CCATCCCACA AGTAAAGCAG CAAGCAGAAA
      ATTAACGAGT TAGTAATTTC GGTAGGGTGT TCATTTCGTC GTTCGTCTTT
2251  AAAGTTAAGA ACACCTCAAG GCTACAGAAG GACATTTCAA GCTATGCAGG
      TTTCAATTCT TGTGGAGTTC CGATGTCTTC CTGTAAAGTT CGATACGTCC
2301  CATATGAAGT GTGCAGACAG ATATGTAAGA AAGGCCTCAA GACTGCAAAA
      GTATACTTCA CACGTCTGTC TATACATTCT TTCCGGAGTT CTGACGTTTT
2351  GGGCATTTCA AGCTATGCAA GCATATAGGT AACACATACA CACACACAAA
      CCCGTAAAGT TCGATACGTT CGTATATCCA TTGTGTATGT GTGTGTGTTT
2401  ATAAAATCCC CTGAAATACA AAAACATGCA GCAAACACCT GACGTTTTTG
      TATTTTAGGG GACTTTATGT TTTTGTACGT CGTTTGTGGA CTGCAAAAAC
2451  GATACCATTT CTAAGTCAGG TGTTATGATT CTCATTAGTC AAGATACTTG
      CTATGGTAAA GATTCAGTCC ACAATACTAA GAGTAATCAG TTCTATGAAC
2501  AGTACTGGGC CCAAACAGCT TTCTGCCACT GTACAGTACA AGAAGGTAGG
      TCATGACCCG GGTTTGTCGA AAGACGGTGA CATGTCATGT TCTTCCATCC
2551  AATAATGGTG GGAGGAGCAA AGACAAACTG TAATAGACAG AAGTGTATCA
      TTATTACCAC CCTCCTCGTT TCTGTTTGAC ATTATCTGTC TTCACATAGT
2601  GATACCTATA CTACATGAAA AACAAAACAG CTACTGCCAC AAAGGGAGAA
      CTATGGATAT GATGTACTTT TTGTTTTGTC GATGACGGTG TTTCCCTCTT
2651  GGCTAACAAA ATAAAGTCAA CAATAAATAC AGAAAATGAA AAGGATACAC
      CCGATTGTTT TATTTCAGTT GTTATTTATG TCTTTTACTT TTCCTATGTG
2701  ACTAAGGTTT ACAAAAAAAA AAAGGCAGAC AAAATGCCAT ACAGTATTCA
      TGATTCCAAA TGTTTTTTTT TTTCCGTCTG TTTTACGGTA TGTCATAAGT
2751  TTCACTACTA TGGCATTCAT AAGCTAGTTT CAAATGCTCA CTATTTTCTT
      AAGTGATGAT ACCGTAAGTA TTCGATCAAA GTTTACGAGT GATAAAAGAA
2801  TTATAGTATA TATTTGCCTT AACCCAGCAC TTTTTTCCAA AAGTGGATGA
      AATATCATAT ATAAACGGAA TTGGGTCGTG AAAAAAGGTT TTCACCTACT
2851  GTCAAAATAA ATTTCCCATT ATTTAAGTGA AATTAACAGC ACACATATCT
      CAGTTTTATT TAAAGGGTAA TAAATTCACT TTAATTGTCG TGTGTATAGA
2901  CACAACACTA ATGAATTTTT AAAATGGAAA GTTAAGAACT TTTAAAGTGG
      GTGTTGTGAT TACTTAAAAA TTTTACCTTT CAATTCTTGA AAATTTCACC
2951  CCAACCTGTG ATCCTTCACA AAATAAACTA AATACAATAA CAGACCCCAA
      GGTTGGACAC TAGGAAGTGT TTTATTTGAT TTATGTTATT GTCTGGGGTT
3001  AGGCTATCAA TTGCGTGCAA AAACAACTTC TGTTTTCCAG GGTAAACAGA
      TCCGATAGTT AACGCACGTT TTTGTTGAAG ACAAAAGGTC CCATTTGTCT
3051  ATCTAATGCA GAATCTAATG CAGGGTAAAC AGACTTAATG CAGAATCTAA
      TAGATTACGT CTTAGATTAC GTCCCATTTG TCTGAATTAC GTCTTAGATT
3101  TGATGGCACA AATTAAAAAT CACTAACGTG CCCTTTTTAG TGTGAAACCC
      ACTACCGTGT TTAATTTTTA GTGATTGCAC GGGAAAAATC ACACTTTGGG
3151  AGAGAGAGCA CATACAAGCC AAAAACAAAT GCTTTATTTT ACCTAGGAGA
      TCTCTCTCGT GTATGTTCGG TTTTTGTTTA CGAAATAAAA TGGATCCTCT
```

Figure 27 cont.

```
3201   CATTAACATT CACCTTTACG TGTTTAAGAT TAATGCAATG TTAAATATTG
       GTAATTGTAA GTGGAAATGC ACAAATTCTA ATTACGTTAC AATTTATAAC
3251   TGAAAACTGT AACTTTGAAT TTCATGATTT TTATGTGAAT ATTCCAGGGT
       ACTTTTGACA TTGAAACTTA AAGTACTAAA AATACACTTA TAAGGTCCCA
3301   TTAAAAAAAC TTGTAACATG ACATGGCTGA ATAAGATAAA AAAAAAATCT
       AATTTTTTTG AACATTGTAC TGTACCGACT TATTCTATTT TTTTTTTAGA
3351   AGCCTTTTCT CCCTTCTGGC TCATATTTGC GATTTCGATC ATTTTGTTTA
       TCGGAAAAGA GGGAAGACCG AGTATAAACG CTAAAGCTAG TAAAACAAAT
3401   AAAAACAAAA CACTGCAATG AATTAAACTT AATATTCTTC TATGTTTTAG
       TTTTTGTTTT GTGACGTTAC TTAATTTGAA TTATAAGAAG ATACAAAATC
3451   AGTAAGTTAA AACAAGATAA AGTGACCAAA GTAATTTGAA AGATTCAATG
       TCATTCAATT TTGTTCTATT TCACTGGTTT CATTAAACTT TCTAAGTTAC
3501   ACTTTTGCTC CAACCTAGGT GCACAAGGTA CCTTGTTCTT TAAATTGGGC
       TGAAAACGAG GTTGGATCCA CGTGTTCCAT GGAACAAGAA ATTTAACCCG
3551   TTTAATGAAA ATACTTCTCC AGAATTCTGG GGATTTAAGA AAAATTATGC
       AAATTACTTT TATGAAGAGG TCTTAAGACC CCTAAATTCT TTTTAATACG
3601   CAACCAACAA GGGCTTTACC ATTTTATGTA ACATTTTTCA ACGCTGCAAA
       GTTGGTTGTT CCCGAAATGG TAAAATACAT TGTAAAAAGT TGCGACGTTT
3651   AATGTGTGTA TTTCTATTTG AAGATAAAAA TCCTCAGCAA AATCCACATT
       TTACACACAT AAAGATAAAC TTCTATTTTT AGGAGTCGTT TTAGGTGTAA
3701   GCACTGTCCT TCAAAGATTA GCCTTCTTTG AACTAGTTAA GACACTATTA
       CGTGACAGGA AGTTTCTAAT CGGAAGAAAC TTGATCAATT CTGTGATAAT
3751   AGCCAAGCCA GTATCTCCCT GTAATGAATT CGTTTTTCTC TTAATTTTCC
       TCGGTTCGGT CATAGAGGGA CATTACTTAA GCAAAAAGAG AATTAAAAGG
3801   CCTGTAATTT ACACTGGGAG AGCTGGGAAA TATGTGGATG TAAATTTCTC
       GGACATTAAA TGTGACCCTC TCGACCCTTT ATACACCTAC ATTTAAAGAG
3851   AGCCACAGAG ATGCAAAGTT ATACTGTGGG GAAAAAAAAC TTGAGTTAAA
       TCGGTGTCTC TACGTTTCAA TATGACACCC CTTTTTTTTG AACTCAATTT
3901   TCCTTACATA TTTTAGGTTT TCATTAACTT ACCAATGTAG TTTTGTTGGA
       AGGAATGTAT AAAATCCAAA AGTAATTGAA TGGTTACATC AAAACAACCT
3951   GGCCATTTTT TTTATTGCAG ACTTGAAGAG CTATTACTAG AAAAATGCAT
       CCGGTAAAAA AAATAACGTC TGAACTTCTC GATAATGATC TTTTTACGTA
4001   GACAGTTAAG GTAAGTTTGC ATGACACAAA AAAGGTAACT AAATACAAAT
       CTGTCAATTC CATTCAAACG TACTGTGTTT TTTCCATTGA TTTATGTTTA
4051   TCTGTTTGGA TTCCAACCCC CAAGTAGAGA GCGCACACTT TCAAACGTGA
       AGACAAACCT AAGGTTGGGG GTTCATCTCT CGCGTGTGAA AGTTTGCACT
4101   ATACAAATCC AGAGTAGATC TGCGCTCCTA CCTACATTGC TTATGATGTA
       TATGTTTAGG TCTCATCTAG ACGCGAGGAT GGATGTAACG AATACTACAT
4151   CTTAAGTACG TGTCCTAACC ATGTGAGTCT AGAAAGACTT TACTGGGGAT
       GAATTCATGC ACAGGATTGG TACACTCAGA TCTTTCTGAA ATGACCCCTA
4201   CCTGGTACCT AAAACAGCTT CACATGGCTT AAAATAGGGG ACCAATGTCT
       GGACCATGGA TTTTGTCGAA GTGTACCGAA TTTTATCCCC TGGTTACAGA
4251   TTTCCAATCT AAGTCCCATT TATAATAAAG TCCATGTTCC ATTTTTAAAG
       AAAGGTTAGA TTCAGGGTAA ATATTATTTC AGGTACAAGG TAAAAATTTC
4301   GACAATCCTT TCGGTTTAAA ACCAGGCACG ATTACCCAAA CAACTCACAA
       CTGTTAGGAA AGCCAAATTT TGGTCCGTGC TAATGGGTTT GTTGAGTGTT
4351   CGGTAAAGCA CTGTGAATCT TCTCTGTTCT GCAATCCCAA CTTGGTTTCT
       GCCATTTCGT GACACTTAGA AGAGACAAGA CGTTAGGGTT GAACCAAAGA
4401   GCTCAGAAAC CCTCCCTCTT TCCAATCGGT AATTAAATAA CAAAAGGAAA
       CGAGTCTTTG GGAGGGAGAA AGGTTAGCCA TTAATTTATT GTTTTCCTTT
4451   AAACTTAAGA TGCTTCAACC CCGTTTCGTG ACACTTTGAA AAAAGAATCA
       TTTGAATTCT ACGAAGTTGG GGCAAAGCAC TGTGAAACTT TTTTCTTAGT
4501   CCTCTTGCAA ACACCCGCTC CCGACCCCCG CCGCTGAAGC CCGGCGTCCA
       GGAGAACGTT TGTGGGCGAG GGCTGGGGGC GGCGACTTCG GGCCGCAGGT
4551   GAGGCCTAAG CGCGGGTGCC CGCCCCCACC CGGGAGCGCG GGCCTCGTGG
       CTCCGGATTC GCGCCCACGG GCGGGGGTGG GCCCTCGCGC CCGGAGCACC
4601   TCAGCGCATC CGCGGGGAGA AACAAAGGCC GCGGCACGGG GGCTCAAGGG
       AGTCGCGTAG GCGCCCCTCT TTGTTTCCGG CGCCGTGCCC CCGAGTTCCC
4651   CACTGCGCCA CACCGCACGC GCCTACCCCC GCGCGGCCAC GTTAACTGGC
       GTGACGCGGT GTGGCGTGCG CGGATGGGGG CGCGCCGGTG CAATTGACCG
4701   GGTCGCCGCA GCCTCGGGAC AGCCGGCCGC GCGCCGCCAG GCTCGCGGAC
       CCAGCGGCGT CGGAGCCCTG TCGGCCGGCG CGCGGCGGTC CGAGCGCCTG
4751   GCGGGACCAC GCGCCGCCCT CCGGGAGGCC CAAGTCTCGA CCCAGCCCCG
       CGCCCTGGTG CGCGGCGGGA GGCCCTCCGG GTTCAGAGCT GGGTCGGGGC
4801   CGTGGCGCTG GGGGAGGGGG CGCCTCCGCC GGAACGCGGG TGGGGGAGGG
       GCACCGCGAC CCCCTCCCCC GCGGAGGCGG CCTTGCGCCC ACCCCCTCCC
```

Figure 27 cont.

```
4851  GAGGGGGAAA TGCGCTTTGT CTCGAAATGG GGCAACCGTC GCCACAGCTC
      CTCCCCCTTT ACGCGAAACA GAGCTTTACC CCGTTGGCAG CGGTGTCGAG
4901  CCTACCCCCT CGAGGGCAGA GCAGTCCCCC CACTAACTAC CGGGCTGGCC
      GGATGGGGGA GCTCCCGTCT CGTCAGGGGG GTGATTGATG GCCCGACCGG
4951  GCGCGCCAGG CCAGCCGCGA GGCCACCGCC CGACCCTCCA CTCCTTCCCG
      CGCGCGGTCC GGTCGGCGCT CCGGTGGCGG GCTGGGAGGT GAGGAAGGGC
5001  CAGCTCCCGG CGCGGGGTCC GGCGAGAAGG GGAGGGGAGG GGAGCGGAGA
      GTCGAGGGCC GCGCCCCAGG CCGCTCTTCC CCTCCCCTCC CCTCGCCTCT
5051  ACCGGGCCCC CGGGACGCGT GTGGCATCTG AAGCACCACC AGCGAGCGAG
      TGGCCCGGGG GCCCTGCGCA CACCGTAGAC TTCGTGGTGG TCGCTCGCTC
5101  AGCTAGAGAG AAGGAAAGCC ACCGACTTCA CCGCCTCCGA GCTGCTCCGG
      TCGATCTCTC TTCCTTTCGG TGGCTGAAGT GGCGGAGGCT CGACGAGGCC
5151  GTCGCGGGTC TGCAGCGTCT CCGGCCCTCC GCGCCTACAG CTCAAGCCAC
      CAGCGCCCAG ACGTCGCAGA GGCCGGGAGG CGCGGATGTC GAGTTCGGTG
5201  ATCCGAAGGG GGAGGGAGCC GGGAGCTGCG CGCGGGGCCG CCGGGGGGAG
      TAGGCTTCCC CCTCCCTCGG CCCTCGACGC GCGCCCCGGC GGCCCCCCTC
5251  GGGTGGCACC GCCCACGCCG GGCGGCCACG AAGGGCGGGG CAGCGGGCGC
      CCCACCGTGG CGGGTGCGGC CCGCCGGTGC TTCCCGCCCC GTCGCCCGCG
5301  GCGCGCGGCG GGGGGAGGGG CCGGCGCCGC GCCCGCTGGG AATTGGGGCC
      CGCGCGCCGC CCCCCTCCCC GGCCGCGGCG CGGGCGACCC TTAACCCCGG
5351  CTAGGGGGAG GGCGGAGGCG CCGACGACCG CGGCACTTAC CGTTCGCGGC
      GATCCCCCTC CCGCCTCCGC GGCTGCTGGC GCCGTGAATG GCAAGCGCCG
5401  GTGGCGCCCG GTGGTCCCCA AGGGGAGGGA AGGGGGAGGC GGGGCGAGGA
      CACCGCGGGC CACCAGGGGT TCCCCTCCCT TCCCCCTCCG CCCCGCTCCT
5451  CAGTGACCGG AGTCTCCTCA GCGGTGGCTT TTCTGCTTGG CAGCCTCAGC
      GTCACTGGCC TCAGAGGAGT CGCCACCGAA AAGACGAACC GTCGGAGTCG
5501  GGCTGGCGCC AAAACCGGAC TCCGCCCACT TCCTCGCCCG CCGGTGCGAG
      CCGACCGCGG TTTTGGCCTG AGGCGGGTGA AGGAGCGGGC GGCCACGCTC
5551  GGTGTGGAAT CCTCCAGACG CTGGGGGAGG GGGAGTTGGG AGCTTAAAAA
      CCACACCTTA GGAGGTCTGC GACCCCCTCC CCCTCAACCC TCGAATTTTT
5601  CTAGTACCCC TTTGGGACCA CTTTCAGCAG CGAACTCTCC TGTACACCAG
      GATCATGGGG AAACCCTGGT GAAAGTCGTC GCTTGAGAGG ACATGTGGTC
5651  GGGTCAGTTC CACAGACGCG GGCCAGGGGT GGGTCATTGC GGCGTGAACA
      CCCAGTCAAG GTGTCTGCGC CCGGTCCCCA CCCAGTAACG CCGCACTTGT
5701  ATAATTTGAC TAGAAGTTGA TTCGGGTGTT TCCGGAAGGG GCCGAGTCAA
      TATTAAACTG ATCTTCAACT AAGCCCACAA AGGCCTTCCC CGGCTCAGTT
5751  TCCGCCGAGT TGGGGCACGG AAAACAAAAA GGGAAGGCTA CTAAGATTTT
      AGGCGGCTCA ACCCCGTGCC TTTTGTTTTT CCCTTCCGAT GATTCTAAAA
5801  TCTGGCGGGG GTTATCATTG GCGTAACTGC AGGGACCACC TCCCGGGTTG
      AGACCGCCCC CAATAGTAAC CGCATTGACG TCCCTGGTGG AGGGCCCAAC
5851  AGGGGGCTGG ATCTCCAGGC TGCGGATTAA GCCCCTCCCG TCGGCGTTAA
      TCCCCCGACC TAGAGGTCCG ACGCCTAATT CGGGGAGGGC AGCCGCAATT
5901  TTTCAAACTG CGCGACGTTT CTCACCTGCC TTCGCCAAGG CAGGGGCCGG
      AAAGTTTGAC GCGCTGCAAA GAGTGGACGG AAGCGGTTCC GTCCCCGGCC
5951  GACCCTATTC CAAGAGGTAG TAACTAGCAG GACTCTAGCC TTCCGCAATT
      CTGGGATAAG GTTCTCCATC ATTGATCGTC CTGAGATCGG AAGGCGTTAA
6001  CATTGAGCGC ATTTACGGAA GTAACGTCGG GTACTGTCTC TGGCCGCAAG
      GTAACTCGCG TAAATGCCTT CATTGCAGCC CATGACAGAG ACCGGCGTTC
6051  GGTGGGAGGA GTACGCATTT GGCGTAAGGT GGGGCGTAGA GCCTTCCCGC
      CCACCCTCCT CATGCGTAAA CCGCATTCCA CCCCGCATCT CGGAAGGGCG
6101  CATTGGCGGC GGATAGGGCG TTTACGCGAC GGCCTGACGT AGCGGAAGAC
      GTAACCGCCG CCTATCCCGC AAATGCGCTG CCGGACTGCA TCGCCTTCTG
6151  GCGTTAGTGG GGGGGAAGGT TCTAGAAAAG CGGCGGCAGC GGCTCTAGCG
      CGCAATCACC CCCCCTTCCA AGATCTTTTC GCCGCCGTCG CCGAGATCGC
6201  GCAGTAGCAG CAGCGCCGGG TCCCGTGCGG AGGTGCTCCT CGCAGAGTTG
      CGTCATCGTC GTCGCGGCCC AGGGCACGCC TCCACGAGGA GCGTCTCAAC
6251  TTTCTCGAGC AGCGGCAGTT CTCACTACAG CGCCAGGACG AGTCCGGTTC
      AAAGAGCTCG TCGCCGTCAA GAGTGATGTC GCGGTCCTGC TCAGGCCAAG
6301  GTGTTCGTCC GCGGAGATCT CTCTCATCTC GCTCGGCTGC GGGAAATCGG
      CACAAGCAGG CGCCTCTAGA GAGAGTAGAG CGAGCCGACG CCCTTTAGCC
6351  GCTGAAGCGA CTGAGTCCGC GATGGAGGTA ACGGGTTTGA AATCAATGAG
      CGACTTCGCT GACTCAGGCG CTACCTCCAT TGCCCAAACT TTAGTTACTC
6401  TTATTGAAAA GGGCATGGCG AGGCCGTTGG CGCCTCAGTG GAAGTCGGCC
      AATAACTTTT CCCGTACCGC TCCGGCAACC GCGGAGTCAC CTTCAGCCGG
6451  AGCCGCCTCC GTGGGAGAGA GGCAGGAAAT CGGACCAATT CAGTAGCAGT
      TCGGCGGAGG CACCCTCTCT CCGTCCTTTA GCCTGGTTAA GTCATCGTCA
```

Figure 27 cont.

```
6501  GGGGCTTAAG GTTTATGAAC GGGGTCTTGA GCGGAGGCCT GAGCGTACAA
      CCCCGAATTC CAAATACTTG CCCCAGAACT CGCCTCCGGA CTCGCATGTT
6551  ACAGCTTCCC CACCCTCAGC CTCCCGGCGC CATTTCCCTT CACTGGGGGT
      TGTCGAAGGG GTGGGAGTCG GAGGGCCGCG GTAAAGGGAA GTGACCCCCA
6601  GGGGGATGGG GAGCTTTCAC ATGGCGGACG CTGCCCCGCT GGGGTGAAAG
      CCCCCTACCC CTCGAAAGTG TACCGCCTGC GACGGGGCGA CCCCACTTTC
6651  TGGGGCGCGG AGGCGGGAAT TCTTATTCCC TTTCTAAAGC ACGCTGCTTC
      ACCCCGCGCC TCCGCCCTTA AGAATAAGGG AAAGATTTCG TGCGACGAAG
6701  GGGGGCCACG GCGTCTCCTC GGCGAGCGTT TCGGCGGGCA GCAGGTCCTC
      CCCCCGGTGC CGCAGAGGAG CCGCTCGCAA AGCCGCCCGT CGTCCAGGAG
6751  GTGAGCGAGG CTGCGGAGCT TCCCCTCCCC CTCTCTCCCG GGAACCGATT
      CACTCGCTCC GACGCCTCGA AGGGGAGGGG GAGAGAGGGC CCTTGGCTAA
6801  TGGCGGCCGC CATTTTCATG GCTCGCCTTC CTCTCAGCGT TTTCCTTATA
      ACCGCCGGCG GTAAAAGTAC CGAGCGGAAG GAGAGTCGCA AAAGGAATAT
6851  ACTCTTTTAT TTTCTTAGTG TGCTTTCTCT ATCAAGAAGT AGAAGTGGTT
      TGAGAAAATA AAAGAATCAC ACGAAAGAGA TAGTTCTTCA TCTTCACCAA
6901  AACTATTTTT TTTTTCTTCT CGGGCTGTTT TCATATCGTT TCGAGGTGGA
      TTGATAAAAA AAAAAGAAGA GCCCGACAAA AGTATAGCAA AGCTCCACCT
6951  TTTGGAGTGT TTTGTGAGCT TGGATCTTTA GAGTCCTGCG CACCTCATTA
      AAACCTCACA AAACACTCGA ACCTAGAAAT CTCAGGACGC GTGGAGTAAT
7001  AAGGCGCTCA GCCTTCCCCT CGATGAAATG GCGCCATTGC GTTCGGAAGC
      TTCCGCGAGT CGGAAGGGGA GCTACTTTAC CGCGGTAACG CAAGCCTTCG
7051  CACACCGAAG AGCGGGGAGG GGGGGTGCTC CGGGTTTGCG GGCCCGGTTT
      GTGTGGCTTC TCGCCCCTCC CCCCCACGAG GCCCAAACGC CCGGGCCAAA
7101  CAGAGAAGAT ATCACCACCC AGGGCGTCGG GCCGGGTTCA ATGCGAGCCG
      GTCTCTTCTA TAGTGGTGGG TCCCGCAGCC CGGCCCAAGT TACGCTCGGC
7151  TAGGACAAAG AAACCATTTT ATGTTTTTCC TGTCTTTTTT TTCCTTTGAG
      ATCCTGTTTC TTTGGTAAAA TACAAAAAGG ACAGAAAAAA AAGGAAACTC
7201  TAACGGTTTT ATCTGGGTCT GCAGTCAGTA AAACGACAGA TGAACCGCGG
      ATTGCCAAAA TAGACCCAGA CGTCAGTCAT TTTGCTGTCT ACTTGGCGCC
7251  CAAAATAAAC ATAAATTGGA AGCCATCGGC CACGAGGGGC AGGGACGAAG
      GTTTTATTTG TATTTAACCT TCGGTAGCCG GTGCTCCCCG TCCCTGCTTC
7301  GTGGTTTTCT GGGCGGGGGA GGGATATTCG CGTCAGAATC CTTTACTGTT
      CACCAAAAGA CCCGCCCCCT CCCTATAAGC GCAGTCTTAG GAAATGACAA
7351  CTTAAGGATT CCGTTTAAGT TGTAGAGCTG ACTCATTTTA AGTAATGTTG
      GAATTCCTAA GGCAAATTCA ACATCTCGAC TGAGTAAAAT TCATTACAAC
7401  TTACTGAGAA GTTTAACCCT TACGGGACAG ATCCATGGAC CTTTATAGAT
      AATGACTCTT CAAATTGGGA ATGCCCTGTC TAGGTACCTG GAAATATCTA
7451  GATTACGAGG AAAGTGAAAT AACGATTTTG TCCTTAGTTA TACTTCGATT
      CTAATGCTCC TTTCACTTTA TTGCTAAAAC AGGAATCAAT ATGAAGCTAA
7501  AAAACATGGC TTCAGAGGCT CCTTCCTGTA ATGCGTATGG ATTGATGTGC
      TTTTGTACCG AAGTCTCCGA GGAAGGACAT TACGCATACC TAACTACACG
7551  AAAACTGTTT TGGGCCTGGG CCGCTCTGTA TTTGAACTTT GTTACTTTTC
      TTTTGACAAA ACCCGGACCC GGCGAGACAT AAACTTGAAA CAATGAAAAG
7601  TCATTTTGTT TGCAATCTTG GTTGAACATT ACATTGATAA GCATAAGGTC
      AGTAAAACAA ACGTTAGAAC CAACTTGTAA TGTAACTATT CGTATTCCAG
7651  TCAAGCGAAG GGGGTCTACC TGGTTATTTT TCTTTGACCC TAAGCACGTT
      AGTTCGCTTC CCCCAGATGG ACCAATAAAA AGAAACTGGG ATTCGTGCAA
7701  TATAAAATAA CATTGTTTAA AATCGATAGT GGACATCGGG TAAGTTTGGA
      ATATTTTATT GTAACAAATT TTAGCTATCA CCTGTAGCCC ATTCAAACCT
7751  TAAATTGTGA GGTAAGTAAT GAGTTTTTGC TTTTTGTTAG TGATTTGTAA
      ATTTAACACT CCATTCATTA CTCAAAAACG AAAAACAATC ACTAAACATT
7801  AACTTGTTAT AAATGTACAT TATCCGTAAT TTCAGTTTAG AGATAACCTA
      TTGAACAATA TTTACATGTA ATAGGCATTA AAGTCAAATC TCTATTGGAT
7851  TGTGCTGACG ACAATTAAGA ATAAAAACTA GCTGAAAAAA TGAAAATAAC
      ACACGACTGC TGTTAATTCT TATTTTTGAT CGACTTTTTT ACTTTTATTG
7901  TATCGTGACA AGTAACCATT TCAAAAGACT GCTTTGTGTC TCATAGGAGC
      ATAGCACTGT TCATTGGTAA AGTTTTCTGA CGAAACACAG AGTATCCTCG
7951  TAGTTTGATC ATTTCAGTTA ATTTTTTCTT TAATTTTTAC GAGTCATGAA
      ATCAAACTAG TAAAGTCAAT TAAAAAAGAA ATTAAAAATG CTCAGTACTT
8001  AACTACAGGA AAAAAAATCT GAACTGGGTT TTACCACTAC TTTTTAGGAG
      TTGATGTCCT TTTTTTTAGA CTTGACCCAA AATGGTGATG AAAAATCCTC
8051  TTGGGAGCAT GCGAATGGAG GGAGAGCTCC GTAGAACTGG GATGAGAGCA
      AACCCTCGTA CGCTTACCTC CCTCTCGAGG CATCTTGACC CTACTCTCGT
8101  GCAATTAATG CTGCTTGCTA GGAACAAAAA ATAATTGATT GAAAATTACG
      CGTTAATTAC GACGAACGAT CCTTGTTTTT TATTAACTAA CTTTTAATGC
```

Figure 27 cont.

```
8151  TGTGACTTTT TAGTTTGCAT TATGCGTTTG TAGCAGTTGG TCCTGGATAT
      ACACTGAAAA ATCAAACGTA ATACGCAAAC ATCGTCAACC AGGACCTATA
8201  CACTTTCTCT CGTTTGAGGT TTTTTAACCT AGTTAACTTT TAAGACAGGT
      GTGAAAGAGA GCAAACTCCA AAAAATTGGA TCAATTGAAA ATTCTGTCCA
8251  TTCCTTAACA TTCATAAGTG CCCAGAATAC AGCTGTGTAG TACAGCATAT
      AAGGAATTGT AAGTATTCAC GGGTCTTATG TCGACACATC ATGTCGTATA
8301  AAAGATTTCA GCTCTGAGGT TTTTCCTATT GACTTGGAAA ATTGTTTTGT
      TTTCTAAAGT CGAGACTCCA AAAAGGATAA CTGAACCTTT TAACAAAACA
8351  GCCTGTCGCT TGCCACATGG CCAATCAAGT AAGCTTATCG ATACCGGTGG
      CGGACAGCGA ACGGTGTACC GGTTAGTTCA TTCGAATAGC TATGGCCACC
8401  CGCGCCAATT GTTAATTAAG ATCTGGCCCA ATGGGCCGTA CGAATTTGAG
      GCGCGGTTAA CAATTAATTC TAGACCGGGT TACCCGGCAT GCTTAAACTC
8451  GCGGAAAGAA CCAGCTGTGG AATGTGTGTC AGTTAGGGTG TGGAAAGTCC
      CGCCTTTCTT GGTCGACACC TTACACACAG TCAATCCCAC ACCTTTCAGG
8501  CCAGGCTCCC CAGCAGGCAG AAGTATGCAA AGCATGCATC TCAATTAGTC
      GGTCCGAGGG GTCGTCCGTC TTCATACGTT TCGTACGTAG AGTTAATCAG
8551  AGCAACCAGG TGTGGAAAGT CCCCAGGCTC CCCAGCAGGC AGAAGTATGC
      TCGTTGGTCC ACACCTTTCA GGGGTCCGAG GGGTCGTCCG TCTTCATACG
8601  AAAGCATGCA TCTCAATTAG TCAGCAACCA TAGTCCCGCC CCTAACTCCG
      TTTCGTACGT AGAGTTAATC AGTCGTTGGT ATCAGGGCGG GGATTGAGGC
8651  CCCATCCCGC CCCTAACTCC GCCCAGTTCC GCCCATTCTC CGCCCCATGG
      GGGTAGGGCG GGGATTGAGG CGGGTCAAGG CGGGTAAGAG GCGGGGTACC
8701  CTGACTAATT TTTTTTATTT ATGCAGAGGC CGAGGCCGCC TCGGCCTCTG
      GACTGATTAA AAAAAATAAA TACGTCTCCG GCTCCGGCGG AGCCGGAGAC
8751  AGCTATTCCA GAAGTAGTGA GGAGGCTTTT TTGGAGGCCT AGGCTTTTGC
      TCGATAAGGT CTTCATCACT CCTCCGAAAA AACCTCCGGA TCCGAAAACG
8801  AAAGATCGAT CAAGAGACAG GATGAGGATC GTTTCGCATG ATTGAACAAG
      TTTCTAGCTA GTTCTCTGTC CTACTCCTAG CAAAGCGTAC TAACTTGTTC
8851  ATGGATTGCA CGCAGGTTCT CCGGCCGCTT GGGTGGAGAG GCTATTCGGC
      TACCTAACGT GCGTCCAAGA GGCCGGCGAA CCCACCTCTC CGATAAGCCG
8901  TATGACTGGG CACAACAGAC AATCGGCTGC TCTGATGCCG CCGTGTTCCG
      ATACTGACCC GTGTTGTCTG TTAGCCGACG AGACTACGGC GGCACAAGGC
8951  GCTGTCAGCG CAGGGGCGCC CGGTTCTTTT TGTCAAGACC GACCTGTCCG
      CGACAGTCGC GTCCCCGCGG GCCAAGAAAA ACAGTTCTGG CTGGACAGGC
9001  GTGCCCTGAA TGAACTGCAA GACGAGGCAG CGCGGCTATC GTGGCTGGCC
      CACGGGACTT ACTTGACGTT CTGCTCCGTC GCGCCGATAG CACCGACCGG
9051  ACGACGGGCG TTCCTTGCGC AGCTGTGCTC GACGTTGTCA CTGAAGCGGG
      TGCTGCCCGC AAGGAACGCG TCGACACGAG CTGCAACAGT GACTTCGCCC
9101  AAGGGACTGG CTGCTATTGG GCGAAGTGCC GGGGCAGGAT CTCCTGTCAT
      TTCCCTGACC GACGATAACC CGCTTCACGG CCCCGTCCTA GAGGACAGTA
9151  CTCACCTTGC TCCTGCCGAG AAAGTATCCA TCATGGCTGA TGCAATGCGG
      GAGTGGAACG AGGACGGCTC TTTCATAGGT AGTACCGACT ACGTTACGCC
9201  CGGCTGCATA CGCTTGATCC GGCTACCTGC CCATTCGACC ACCAAGCGAA
      GCCGACGTAT GCGAACTAGG CCGATGGACG GGTAAGCTGG TGGTTCGCTT
9251  ACATCGCATC GAGCGAGCAC GTACTCGGAT GGAAGCCGGT CTTGTCGATC
      TGTAGCGTAG CTCGCTCGTG CATGAGCCTA CCTTCGGCCA GAACAGCTAG
9301  AGGATGATCA AGAGCATCAG GGGCTCGCGC CAGCCGAACT GTTCGCCAGG
      TCCTACTAGT TCTCGTAGTC CCCGAGCGCG GTCGGCTTGA CAAGCGGTCC
9351  CTCAAGGCGA GCATGCCCGA CGGCGAGGAT CTCGTCGTGA CCCATGGCGA
      GAGTTCCGCT CGTACGGGCT GCCGCTCCTA GAGCAGCACT GGGTACCGCT
9401  TGCCTGCTTG CCGAATATCA TGGTGGAAAA TGGCCGCTTT TCTGGATTCA
      ACGGACGAAC GGCTTATAGT ACCACCTTTT ACCGGCGAAA AGACCTAAGT
9451  TCGACTGTGG CCGGCTGGGT GTGGCGGACC GCTATCAGGA CATAGCGTTG
      AGCTGACACC GGCCGACCCA CACCGCCTGG CGATAGTCCT GTATCGCAAC
9501  GCTACCCGTG ATATTGCTGA AGAGCTTGGC GGCGAATGGG CTGACCGCTT
      CGATGGGCAC TATAACGACT TCTCGAACCG CCGCTTACCC GACTGGCGAA
9551  CCTCGTGCTT TACGGTATCG CCGCTCCCGA TTCGCAGCGC ATCGCCTTCT
      GGAGCACGAA ATGCCATAGC GGCGAGGGCT AAGCGTCGCG TAGCGGAAGA
9601  ATCGCCTTCT TGACGAGTTC TTCTGAGCGG GACTCTGGGG TTCGAAATGA
      TAGCGGAAGA ACTGCTCAAG AAGACTCGCC CTGAGACCCC AAGCTTTACT
9651  CCGACCAAGC GACGCCCAAC CTGCCATCAC GAGATTTCGA TTCCACCGCC
      GGCTGGTTCG CTGCGGGTTG GACGGTAGTG CTCTAAAGCT AAGGTGGCGG
9701  GCCTTCTATG AAAGGTTGGG CTTCGGAATC GTTTTCCGGG ACGCCGGCTG
      CGGAAGATAC TTTCCAACCC GAAGCCTTAG CAAAAGGCCC TGCGGCCGAC
9751  GATGATCCTC CAGCGCGGGG ATCTCATGCT GGAGTTCTTC GCCCACCCTA
      CTACTAGGAG GTCGCGCCCC TAGAGTACGA CCTCAAGAAG CGGGTGGGAT
```

Figure 27 cont.

```
9801   GGGGGAGGCT AACTGAAACA CGGAAGGAGA CAATACCGGA AGGAACCCGC
       CCCCCTCCGA TTGACTTTGT GCCTTCCTCT GTTATGGCCT TCCTTGGGCG
9851   GCTATGACGG CAATAAAAAG ACAGAATAAA ACGCACGGTG TTGGGTCGTT
       CGATACTGCC GTTATTTTTC TGTCTTATTT TGCGTGCCAC AACCCAGCAA
9901   TGTTCATAAA CGCGGGGTTC GGTCCCAGGG CTGGCACTCT GTCGATACCC
       ACAAGTATTT GCGCCCCAAG CCAGGGTCCC GACCGTGAGA CAGCTATGGG
9951   CACCGAGACC CCATTGGGGC CAATACGCCC GCGTTTCTTC CTTTTCCCCA
       GTGGCTCTGG GGTAACCCCG GTTATGCGGG CGCAAAGAAG GAAAAGGGGT
10001  CCCCACCCCC CAAGTTCGGG TGAAGGCCCA GGGCTCGCAG CCAACGTCGG
       GGGGTGGGGG GTTCAAGCCC ACTTCCGGGT CCCGAGCGTC GGTTGCAGCC
10051  GGCGGCAGGC CCTGCCATAG CCTCAAATTC CTTAGGCTCG AGGGCCGCCA
       CCGCCGTCCG GGACGGTATC GGAGTTTAAG GAATCCGAGC TCCCGGCGGT
10101  CCGCGGTGGA GCTCCAGCTT TTGTTCCCTT TAGTGAGGGT TAATTTCGAG
       GGCGCCACCT CGAGGTCGAA AACAAGGGAA ATCACTCCCA ATTAAAGCTC
10151  CTTGGCGTAA TCATGGTCAT AGCTGTTTCC TGTGTGAAAT TGTTATCCGC
       GAACCGCATT AGTACCAGTA TCGACAAAGG ACACACTTTA ACAATAGGCG
10201  TCACAATTCC ACACAACATA CGAGCCGGAA GCATAAAGTG TAAAGCCTGG
       AGTGTTAAGG TGTGTTGTAT GCTCGGCCTT CGTATTTCAC ATTTCGGACC
10251  GGTGCCTAAT GAGTGAGCTA ACTCACATTA ATTGCGTTGC GCTCACTGCC
       CCACGGATTA CTCACTCGAT TGAGTGTAAT TAACGCAACG CGAGTGACGG
10301  CGCTTTCCAG TCGGGAAACC TGTCGTGCCA GCATCGCGAG CACTTTTCGG
       GCGAAAGGTC AGCCCTTTGG ACAGCACGGT CGTAGCGCTC GTGAAAAGCC
10351  GGAAATGTGC GCGGAACCCC TATTTGTTTA TTTTTCTAAA TACATTCAAA
       CCTTTACACG CGCCTTGGGG ATAAACAAAT AAAAAGATTT ATGTAAGTTT
10401  TATGTATCCG CTCATGAGAC AATAACCCTG ATAAATGCTT CAATAATATT
       ATACATAGGC GAGTACTCTG TTATTGGGAC TATTTACGAA GTTATTATAA
10451  GAAAAAGGAA GAGTATGAGT ATTCAACATT TCCGTGTCGC CCTTATTCCC
       CTTTTTCCTT CTCATACTCA TAAGTTGTAA AGGCACAGCG GGAATAAGGG
10501  TTTTTTGCGG CATTTTGCCT TCCTGTTTTT GCTCACCCAG AAACGCTGGT
       AAAAAACGCC GTAAAACGGA AGGACAAAAA CGAGTGGGTC TTTGCGACCA
10551  GAAAGTAAAA GATGCTGAAG ATCAGTTGGG TGCACGAGTG GGTTACATCG
       CTTTCATTTT CTACGACTTC TAGTCAACCC ACGTGCTCAC CCAATGTAGC
10601  AACTGGATCT CAACAGCGGT AAGATCCTTG AGAGTTTTCG CCCCGAAGAA
       TTGACCTAGA GTTGTCGCCA TTCTAGGAAC TCTCAAAAGC GGGGCTTCTT
10651  CGTTTTCCAA TGATGAGCAC TTTTAAAGTT CTGCTATGTG GCGCGGTATT
       GCAAAAGGTT ACTACTCGTG AAAATTTCAA GACGATACAC CGCGCCATAA
10701  ATCCCGTATT GACGCCGGGC AAGAGCAACT CGGTCGCCGC ATACACTATT
       TAGGGCATAA CTGCGGCCCG TTCTCGTTGA GCCAGCGGCG TATGTGATAA
10751  CTCAGAATGA CTTGGTTGAG TACTCACCAG TCACAGAAAA GCATCTTACG
       GAGTCTTACT GAACCAACTC ATGAGTGGTC AGTGTCTTTT CGTAGAATGC
10801  GATGGCATGA CAGTAAGAGA ATTATGCAGT GCTGCCATAA CCATGAGTGA
       CTACCGTACT GTCATTCTCT TAATACGTCA CGACGGTATT GGTACTCACT
10851  TAACACTGCG GCCAACTTAC TTCTGACAAC GATCGGAGGA CCGAAGGAGC
       ATTGTGACGC CGGTTGAATG AAGACTGTTG CTAGCCTCCT GGCTTCCTCG
10901  TAACCGCTTT TTTGCACAAC ATGGGGGATC ATGTAACTCG CCTTGATCGT
       ATTGGCGAAA AAACGTGTTG TACCCCCTAG TACATTGAGC GGAACTAGCA
10951  TGGGAACCGG AGCTGAATGA AGCCATACCA AACGACGAGC GTGACACCAC
       ACCCTTGGCC TCGACTTACT TCGGTATGGT TTGCTGCTCG CACTGTGGTG
11001  GATGCCTGTA GCAATGGCAA CAACGTTGCG CAAACTATTA ACTGGCGAAC
       CTACGGACAT CGTTACCGTT GTTGCAACGC GTTTGATAAT TGACCGCTTG
11051  TACTTACTCT AGCTTCCCGG CAACAATTAA TAGACTGGAT GGAGGCGGAT
       ATGAATGAGA TCGAAGGGCC GTTGTTAATT ATCTGACCTA CCTCCGCCTA
11101  AAAGTTGCAG GACCACTTCT GCGCTCGGCC CTTCCGGCTG GCTGGTTTAT
       TTTCAACGTC CTGGTGAAGA CGCGAGCCGG GAAGGCCGAC CGACCAAATA
11151  TGCTGATAAA TCTGGAGCCG GTGAGCGTGG GTCTCGCGGT ATCATTGCAG
       ACGACTATTT AGACCTCGGC CACTCGCACC CAGAGCGCCA TAGTAACGTC
11201  CACTGGGGCC AGATGGTAAG CCCTCCCGTA TCGTAGTTAT CTACACGACG
       GTGACCCCGG TCTACCATTC GGGAGGGCAT AGCATCAATA GATGTGCTGC
11251  GGGAGTCAGG CAACTATGGA TGAACGAAAT AGACAGATCG CTGAGATAGG
       CCCTCAGTCC GTTGATACCT ACTTGCTTTA TCTGTCTAGC GACTCTATCC
11301  TGCCTCACTG ATTAAGCATT GGTAACTGTC AGACTCGCGA CACTGCATTA
       ACGGAGTGAC TAATTCGTAA CCATTGACAG TCTGAGCGCT GTGACGTAAT
11351  ATGAATCGGC CAACGCGCGG GGAGAGGCGG TTTGCGTATT GGGCGCTCTT
       TACTTAGCCG GTTGCGCGCC CCTCTCCGCC AAACGCATAA CCCGCGAGAA
11401  CCGCTTCCTC GCTCACTGAC TCGCTGCGCT CGGTCGTTCG GCTGCGGCGA
       GGCGAAGGAG CGAGTGACTG AGCGACGCGA GCCAGCAAGC CGACGCCGCT
```

Figure 27 cont.

```
11451   GCGGTATCAG CTCACTCAAA GGCGGTAATA CGGTTATCCA CAGAATCAGG
        CGCCATAGTC GAGTGAGTTT CCGCCATTAT GCCAATAGGT GTCTTAGTCC
11501   GGATAACGCA GGAAAGAACA TGTGAGCAAA AGGCCAGCAA AAGGCCAGGA
        CCTATTGCGT CCTTTCTTGT ACACTCGTTT TCCGGTCGTT TTCCGGTCCT
11551   ACCGTAAAAA GGCCGCGTTG CTGGCGTTTT TCCATAGGCT CCGCCCCCCT
        TGGCATTTTT CCGGCGCAAC GACCGCAAAA AGGTATCCGA GGCGGGGGGA
11601   GACGAGCATC ACAAAAATCG ACGCTCAAGT CAGAGGTGGC GAAACCCGAC
        CTGCTCGTAG TGTTTTTAGC TGCGAGTTCA GTCTCCACCG CTTTGGGCTG
11651   AGGACTATAA AGATACCAGG CGTTTCCCCC TGGAAGCTCC CTCGTGCGCT
        TCCTGATATT TCTATGGTCC GCAAAGGGGG ACCTTCGAGG GAGCACGCGA
11701   CTCCTGTTCC GACCCTGCCG CTTACCGGAT ACCTGTCCGC CTTTCTCCCT
        GAGGACAAGG CTGGGACGGC GAATGGCCTA TGGACAGGCG GAAAGAGGGA
11751   TCGGGAAGCG TGGCGCTTTC TCATAGCTCA CGCTGTAGGT ATCTCAGTTC
        AGCCCTTCGC ACCGCGAAAG AGTATCGAGT GCGACATCCA TAGAGTCAAG
11801   GGTGTAGGTC GTTCGCTCCA AGCTGGGCTG TGTGCACGAA CCCCCCGTTC
        CCACATCCAG CAAGCGAGGT TCGACCCGAC ACACGTGCTT GGGGGGCAAG
11851   AGCCCGACCG CTGCGCCTTA TCCGGTAACT ATCGTCTTGA GTCCAACCCG
        TCGGGCTGGC GACGCGGAAT AGGCCATTGA TAGCAGAACT CAGGTTGGGC
11901   GTAAGACACG ACTTATCGCC ACTGGCAGCA GCCACTGGTA ACAGGATTAG
        CATTCTGTGC TGAATAGCGG TGACCGTCGT CGGTGACCAT TGTCCTAATC
11951   CAGAGCGAGG TATGTAGGCG GTGCTACAGA GTTCTTGAAG TGGTGGCCTA
        GTCTCGCTCC ATACATCCGC CACGATGTCT CAAGAACTTC ACCACCGGAT
12001   ACTACGGCTA CACTAGAAGG ACAGTATTTG GTATCTGCGC TCTGCTGAAG
        TGATGCCGAT GTGATCTTCC TGTCATAAAC CATAGACGCG AGACGACTTC
12051   CCAGTTACCT TCGGAAAAAG AGTTGGTAGC TCTTGATCCG GCAAACAAAC
        GGTCAATGGA AGCCTTTTTC TCAACCATCG AGAACTAGGC CGTTTGTTTG
12101   CACCGCTGGT AGCGGTGGTT TTTTTGTTTG CAAGCAGCAG ATTACGCGCA
        GTGGCGACCA TCGCCACCAA AAAAACAAAC GTTCGTCGTC TAATGCGCGT
12151   GAAAAAAAGG ATCTCAAGAA GATCCTTTGA TCTTTTCTAC GGGGTCTGAC
        CTTTTTTTCC TAGAGTTCTT CTAGGAAACT AGAAAAGATG CCCCAGACTG
12201   GCTCAGTGGA ACGAAAACTC A
        CGAGTCACCT TGCTTTTGAG T
```

Figure 29 CET1120 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAAGCT
      TAACCCATGG CCCGGGGGGG AGCTTCAAAT TTGTAAATTT AGATCTTCGA
 101  TTTAACCCTC TATCCCTTTA AACTTCCTTG ATCCAGTGTA AGCACCTCCT
      AAATTGGGAG ATAGGGAAAT TTGAAGGAAC TAGGTCACAT TCGTGGAGGA
 151  AGAAAGTCAG TAGACAATAA AACAAAAGTT CTGCTTCACC GATTTACATT
      TCTTTCAGTC ATCTGTTATT TTGTTTTCAA GACGAAGTGG CTAAATGTAA
 201  TATAACCAAA TACCCTTCAC CAATACAATA AAAAAACAAA ACAACAAAAA
      ATATTGGTTT ATGGGAAGTG GTTATGTTAT TTTTTTGTTT TGTTGTTTTT
 251  ACCCCAACCA TCTGAGAAAT AATCTTCTCC TTTCCCAGCT TTATTCCCAG
      TGGGGTTGGT AGACTCTTTA TTAGAAGAGG AAAGGGTCGA AATAAGGGTC
 301  GATTCTACAT GACCAAATTA CCAGAGTCAC CACTCATTTT AATCACAACA
      CTAAGATGTA CTGGTTTAAT GGTCTCAGTG GTGAGTAAAA TTAGTGTTGT
 351  TAGTGTCAAA TAACTAGAAA ACATGAGACA ACAATGGAGA GCTGAGTAAC
      ATCACAGTTT ATTGATCTTT TGTACTCTGT TGTTACCTCT CGACTCATTG
 401  TATTAGTAGT AGTACTTTAC CAGAGAATGG CCTCTATAGG CTCACATGTA
      ATAATCATCA TCATGAAATG GTCTCTTACC GGAGATATCC GAGTGTACAT
 451  GGAATGGTTG GTCCCCAGGT GGTAGGTAGA GCTGTTTGAG GATTACGTGG
      CCTTACCAAC CAGGGGTCCA CCATCCATCT CGACAAACTC CTAATGCACC
 501  CCTTCTTGGA TGGGGGGTGG GGGTGGGGTG GGAGGGTTGG GTGGTGGGTA
      GGAAGAACCT ACCCCCCACC CCCACCCCAC CCTCCCAACC CACCACCCAT
 551  CTTAAGAGGT TTCAAAAGTC AATATTGTTT GCATTTAGCT CTTCCTTGTA
      GAATTCTCCA AAGTTTTCAG TTATAACAAA CGTAAATCGA GAAGGAACAT
 601  CTTGTGGATC AAACACAACC TGTCAGCTAC TGCTTCAAAT GTCATGCCTG
      GAACACCTAG TTTGTGTTGG ACAGTCGATG ACGAAGTTTA CAGTACGGAC
 651  CTGCCATCTT CTCAGCAGGA TGGTCATGGC CTCACCCTCT TCAACTGTAA
      GACGGTAGAA GAGTCGTCCT ACCAGTACCG GAGTGGGAGA AGTTGACATT
 701  ATCTTTCTTT CTTTTCTTCT TTTTCTTTTG GTTTCGAGAC AGGGTTTCTC
      TAGAAAGAAA GAAAAGAAGA AAAAGAAAAC CAAAGCTCTG TCCCAAAGAG
 751  TGTATAGTCC TGGCTGTCCT GGAACTCACT TTGTAGACCA GGCTGGCCTT
      ACATATCAGG ACCGACAGGA CCTTGAGTGA AACATCTGGT CCGACCGGAA
 801  GAACTCAGAA ATCCGCCTGC CTCTGCCTCC CTAGCACTGG GATTAAAGGC
      CTTGAGTCTT TAGGCGGACG GAGACGGAGG GATCGTGACC CTAATTTCCG
 851  GTGCGCCACC ACGCCCAGCT TTCAACTGGA AATCTTAATA AACTTTCCTA
      CACGCGGTGG TGCGGGTCGA AAGTTGACCT TTAGAATTAT TTGAAAGGAT
 901  GAAGTGGCCT TGGTTATGGG AGCTTATCAC AGCAATAGAA CAGCAATTAT
      CTTCACCGGA ACCAATACCC TCGAATAGTG TCGTTATCTT GTCGTTAATA
 951  GACTGGAGTA TGATAGTTAA AAACAAGCAA GCAAGCAAGC AAACACACAC
      CTGACCTCAT ACTATCAATT TTTGTTCGTT CGTTCGTTCG TTTGTGTGTG
1001  ACCAAAACAA CAAAACCCCA AGACAGAGTC ACATGTAGCC CAGGCTAGCC
      TGGTTTTGTT GTTTTGGGGT TCTGTCTCAG TGTACATCGG GTCCGATCGG
1051  TCCAAATTCA CTATATAACT GAAGAAGACC CCTAATTCCC ATTCCTCTAG
      AGGTTTAAGT GATATATTGA CTTCTTCTGG GGATTAAGGG TAAGGAGATC
1101  AATCTATACC TCAAGTACTG AATGGCTTGG TTCACAATAC CCCACTAAAT
      TTAGATATGG AGTTCATGAC TTACCGAACC AAGTGTTATG GGGTGATTTA
1151  GATTGGTCTT ACTAAGTGCA ACAAGGTAAA CCTAAAACTT CAGCCCTCAG
      CTAACCAGAA TGATTCACGT TGTTCCATTT GGATTTTGAA GTCGGGAGTC
1201  ACATCCCTTT TCCAGTATCA ATTTATAAAA TTAGATCCCA AGGATAAAAA
      TGTAGGGAAA AGGTCATAGT TAAATATTTT AATCTAGGGT TCCTATTTTT
1251  TTAATTGTAA AGTAAAATCA GAGTTCTAGC ATCAACTACA GGCTCAACCA
      AATTAACATT TCATTTTAGT CTCAAGATCG TAGTTGATGT CCGAGTTGGT
1301  TGGGGACCAC AAATAAACTA AAAGGGATAA GACTGGCTTC CCCATAATTA
      ACCCCTGGTG TTTATTTGAT TTTCCCTATT CTGACCGAAG GGGTATTAAT
1351  TTACATTTAG ATAATTTTCC TGACTACTCA ACAAAGCTAA AATATCACCA
      AATGTAAATC TATTAAAAGG ACTGATGAGT TGTTTCGATT TTATAGTGGT
1401  CTGGTTTATT TTCTCCTTCT AGGGTTTAAG CTCACTCTGA GGAGGGGCAT
      GACCAAATAA AAGAGGAAGA TCCCAAATTC GAGTGAGACT CCTCCCCGTA
1451  GCGGCACACA CTCATAGCAT CCAGGAAATA GAAATATGGT GACTATCATG
      CGCCGTGTGT GAGTATCGTA GGTCCTTTAT CTTTATACCA CTGATAGTAC
1501  GGTTCAGGGC CAACCTAGGC TTTAGAGAAA AACCTTGTCC CACAAACCAA
      CCAAGTCCCG GTTGGATCCG AAATCTCTTT TTGGAACAGG GTGTTTGGTT
```

Figure 29 cont.

```
1551  AAATGTCTCT TTTTTATTCT ATCAGGGGTG GATGGATTTG TTAAAGAAGT
      TTTACAGAGA AAAAATAAGA TAGTCCCCAC CTACCTAAAC AATTTCTTCA
1601  GCTTTTAAAA ACCTTGAGAT GGTTATTTAG AAGTCCCCAT GGGATACCAA
      CGAAAATTTT TGGAACTCTA CCAATAAATC TTCAGGGGTA CCCTATGGTT
1651  AATAACCCAC TATTTATATG CCCAAGCATT TCACCTCCAC AACAGTGCTA
      TTATTGGGTG ATAAATATAC GGGTTCGTAA AGTGGAGGTG TTGTCACGAT
1701  TGCACCCTTT AACATTTTTG AGACAGTAGC CCAGTCTAGT CTTTAACTTG
      ACGTGGGAAA TTGTAAAAAC TCTGTCATCG GGTCAGATCA GAAATTGAAC
1751  CAGTGATTTT TCCTGATTCA GCTTCTCCCA GTGCTGGAAT TATAGGTATG
      GTCACTAAAA AGGACTAAGT CGAAGAGGGT CACGACCTTA ATATCCATAC
1801  CACCACCATG TGTAACTACA GATGCTACTT AAAAATTTTT TAAAGGAATC
      GTGGTGGTAC ACATTGATGT CTACGATGAA TTTTTAAAAA ATTTCCTTAG
1851  ACAAAAATAA CCCCCTATCA AATGCCTAGT CCCTCTAACC ATCACCAAGT
      TGTTTTTATT GGGGGATAGT TTACGGATCA GGGAGATTGG TAGTGGTTCA
1901  GAAGGATCAC GCAGGAAAAA AAAAATCACC AGCAGCACCT CAGAACCAGG
      CTTCCTAGTG CGTCCTTTTT TTTTTAGTGG TCGTCGTGGA GTCTTGGTCC
1951  ATACTCAGTC CATCAGCATC CAGGGCCATA CCCACACTCA CAGCATCTCC
      TATGAGTCAG GTAGTCGTAG GTCCCGGTAT GGGTGTGAGT GTCGTAGAGG
2001  ACAGTTTACC AGATGATTCA TGCTTATCAC TGTATTGGGT CATCTAAGAG
      TGTCAAATGG TCTACTAAGT ACGAATAGTG ACATAACCCA GTAGATTCTC
2051  TGACCATCAG GGCTTCTGAT CACAGAATCT AGTCCACTTT GCAGACCAGT
      ACTGGTAGTC CCGAAGACTA GTGTCTTAGA TCAGGTGAAA CGTCTGGTCA
2101  TGAAGTCATG CACTATATGA GATAGAAATA CCCTCTTGCT CATTTTGGTC
      ACTTCAGTAC GTGATATACT CTATCTTTAT GGGAGAACGA GTAAAACCAG
2151  AGAAATTCAA GGATAAAAAC CCATGTTTTG TTAATGCACA CCTCCATATG
      TCTTTAAGTT CCTATTTTTG GGTACAAAAC AATTACGTGT GGAGGTATAC
2201  ATTGAGATCA ATGTGTCCTA ATTAATGTAG AAACCACAAC TGTAAATTTC
      TAACTCTAGT TACACAGGAT TAATTACATC TTTGGTGTTG ACATTTAAAG
2251  ACTCTTTTGA CATGAATCTT TTTCTAGACA GGGTCTTGGA TGCAGCCCCG
      TGAGAAAACT GTACTTAGAA AAAGATCTGT CCCAGAACCT ACGTCGGGGC
2301  ACTACCCAGA ATTTTGGAAT CCAGGCTAGC CTCAAACTCA AGGCAATCTG
      TGATGGGTCT TAAAACCTTA GGTCCGATCG GAGTTTGAGT TCCGTTAGAC
2351  CTTGCTTCAG CTTCTCACAG GCTGGATCAC AAACATACAC CTTCAGACCC
      GAACGAAGTC GAAGAGTGTC CGACCTAGTG TTTGTATGTG GAAGTCTGGG
2401  ATTTTTTTTT CCTCCCTCCG TTTTTGGTTT CTCTGTGTAG CCCTGGGTGT
      TAAAAAAAAA GGAGGGAGGC AAAAACCAAA GAGACACATC GGGACCCACA
2451  CCGTGGACTC GCTGTGTAGA TCTATCTACC AGCCTCTGTC TTGGAGTACT
      GGCACCTGAG CGACACATCT AGATAGATGG TCGGAGACAG AACCTCATGA
2501  GGGATTAAAG TTGTGGGCTA CCACTGCCTG GCTGACCCAG TTTTATTTAT
      CCCTAATTTC AACACCCGAT GGTGACGGAC CGACTGGGTC AAAATAAATA
2551  TTTAAATATA ACTTGACAAA AATAAATTTG TCTAACTTAC TAGAAATCCC
      AAATTTATAT TGAACTGTTT TTATTTAAAC AGATTGAATG ATCTTTAGGG
2601  AAGAAAACTA ACACTGGATT TAGCAACAGT CAGAAATCGC TGAAAAGAAA
      TTCTTTTGAT TGTGACCTAA ATCGTTGTCA GTCTTTAGCG ACTTTTCTTT
2651  CAGAATTGAT CTAACAGTCT TAGATCACTC CTAGACAGTT TGTAATTCTT
      GTCTTAACTA GATTGTCAGA ATCTAGTGAG GATCTGTCAA ACATTAAGAA
2701  GCTCATGGCA ACGTGAGCTC TATCTAACTC ACTCTCTGTG CACTAATGAA
      CGAGTACCGT TGCACTCGAG ATAGATTGAG TGAGAGACAC GTGATTACTT
2751  TGCTCAGTGT CTCCAGAACA GCACAGCTTC CAGGGTAATC ATGCCAACCC
      ACGAGTCACA GAGGTCTTGT CGTGTCGAAG GTCCCATTAG TACGGTTGGG
2801  ACAAGACTTT TATAGAGCTG TCCACGACTC TTCCCCCATT CAGCTCATTA
      TGTTCTGAAA ATATCTCGAC AGGTGCTGAG AAGGGGGTAA GTCGAGTAAT
2851  ACAATATGAT GGAGCTCCTG TGTGGAAATC AAGGCACACT CTGGTAGAAA
      TGTTATACTA CCTCGAGGAC ACACCTTTAG TTCCGTGTGA GACCATCTTT
2901  CTTGTTTTTT CTTTCCACTT TTCCTTGGGC TCTGAAGATT GAGCTGTTTT
      GAACAAAAAA GAAAGGTGAA AAGGAACCCG AGACTTCTAA CTCGACAAAA
2951  ATAACCCACA AACATGCATT TTTTACCTCA AAAGCATCCA GCAAAAACTG
      TATTGGGTGT TTGTACGTAA AAAATGGAGT TTTCGTAGGT CGTTTTTGAC
3001  TACAACGCTT TTTCAAAAAA ATGTATTGTG ATCCTCCTTA AGAAAAGCCT
      ATGTTGCGAA AAAGTTTTTT TACATAACAC TAGGAGGAAT TCTTTTCGGA
3051  TACTTAGTGT TAATTCCTTT TTCTTTAGAA TGCTGGTAAA TACAAGGACT
      ATGAATCACA ATTAAGGAAA AAGAAATCTT ACGACCATTT ATGTTCCTGA
3101  TAGGTAGGCT GGCTTCTAAC AGCAATTCAC CCACTTATGA TGGGATTAAA
      ATCCATCCGA CCGAAGATTG TCGTTAAGTG GGTGAATACT ACCCTAATTT
3151  GGAAGGCACA ACCATGTCCA CCACAGGTTC TAGCTCCCCC ACCCACACGC
      CCTTCCGTGT TGGTACAGGT GGTGTCCAAG ATCGAGGGGG TGGGTGTGCG
```

Figure 29 cont.

```
3201  CCAGAGAGGG TTTTTCTGTG TAGCTCTGAC TATTCTGGAA TTCACACTGC
      GGTCTCTCCC AAAAAGACAC ATCGAGACTG ATAAGACCTT AAGTGTGACG
3251  AGACCAGGCT GGTCTCGAAC TCAGAGATCC ACCACCACAT GGTTTCTTAA
      TCTGGTCCGA CCAGAGCTTG AGTCTCTAGG TGGTGGTGTA CCAAAGAATT
3301  TTGTAATTTT AAAGAAAAAA AAAAATCCTT CAGTTAAGAT TCTTATGTTC
      AACATTAAAA TTTCTTTTTT TTTTTAGGAA GTCAATTCTA AGAATACAAG
3351  TAGGTTTTCA CAAACTTACC AATGTAGTTT TATTGGAGGC CATTTTTTAA
      ATCCAAAAGT GTTTGAATGG TTACATCAAA ATAACCTCCG GTAAAAAATT
3401  ATTTAATCGG AGACTTGAAG AGCTATTGCA AGAAAAAAAA TGTAGGACAG
      TAAATTAGCC TCTGAACTTC TCGATAACGT TCTTTTTTTT ACATCCTGTC
3451  TTAAAATTTC ATGACACACA AAAGGCAGCT ACAAGTTTTG TGTGGATTTC
      AATTTTAAAG TACTGTGTGT TTTCCGTCGA TGTTCAAAAC ACACCTAAAG
3501  AACATGTAAA TTTCGGGTAA AAATGCAGGA AAACAGTTGA GTTCCCGTGT
      TTGTACATTT AAAGCCCATT TTTACGTCCT TTTGTCAACT CAAGGGCACA
3551  TATTAGTATG TTACTAATAA TTTCAGTATG TTAGTGAAAA TAATCTTACT
      ATAATCATAC AATGATTATT AAAGTCATAC AATCACTTTT ATTAGAATGA
3601  AAAACACTGG TACCTCAGAC AACTTTACAT GGTGAGGATT GTTACTTTCC
      TTTTGTGACC ATGGAGTCTG TTGAAATGTA CCACTCCTAA CAATGAAAGG
3651  CAATCCATAT AGAATTTTAA CAATTTTAGT GTTTATTTTG GATGAAAGGA
      GTTAGGTATA TCTTAAAATT GTTAAAATCA CAAATAAAAC CTACTTTCCT
3701  AATGACTATC TTTTGTTAGC AAATTACCAT AAGATCTTTT TCTTTAGATT
      TTACTGATAG AAAACAATCG TTTAATGGTA TTCTAGAAAA AGAAATCTAA
3751  TCTGAATACT CCAAGGAGCT CATATAATTC CATCCTTATT TTTTCAGAGG
      AGACTTATGA GGTTCCTCGA GTATATTAAG GTAGGAATAA AAAAGTCTCC
3801  CCCTCCCTGT TCAATCACGG TATAAAAAAA GGAACACATT AAGATGTCCC
      GGGAGGGACA AGTTAGTGCC ATATTTTTTT CCTTGTGTAA TTCTACAGGG
3851  AGTCCTATTT TCTGGCTTTT TTTTTCCGGG GGTGGTGGTG CGGTAATCAC
      TCAGGATAAA AGACCGAAAA AAAAAGGCCC CCACCACCAC GCCATTAGTG
3901  TCTCTATAGT CCAGTCTGGG CTTCAACGCC TGGCAATCCC CAGCCTCAAG
      AGAGATATCA GGTCAGACCC GAAGTTGCGG ACCGTTAGGG GTCGGAGTTC
3951  CTCCCAAGTA CTGTCCTGAT AAGGATAGAA GGAGTCGACC TCCTTCACGC
      GAGGGTTCAT GACAGGACTA TTCCTATCTT CCTCAGCTGG AGGAAGTGCG
4001  TCCCCTCCGA GGAGGGCTCC TTCCCAGCTC CATTCCCCGG TCGGGAGCCC
      AGGGGAGGCT CCTCCCGAGG AAGGGTCGAG GTAAGGGGCC AGCCCTCGGG
4051  GTCCCCCACC CGAGAGCGCG GGCCTCGTGG TCAGCGCCTC CGCGGGGAGA
      CAGGGGGTGG GCTCTCGCGC CCGGAGCACC AGTCGCGGAG GCGCCCCTCT
4101  AACAAAGGCG GCGGCGGGGG CTCAAGGGCA CTGCGCCACG GGCCCGCGCC
      TTGTTTCCGC CGCCGCCCCC GAGTTCCCGT GACGCGGTGC CCGGGCGCGG
4151  TCCCCCATCC GGCGGCGGCC ACGTAGCCGG GAGCGCGCCG CAGCCCGGAG
      AGGGGGTAGG CCGCCGCCGG TGCATCGGCC CTCGCGCGGC GTCGGGCCTC
4201  CCTCGGGCCT CGCAGCTGCA GAGCCTGAAC CGCTCTCTCC CTGCGGGCCT
      GGAGCCCGGA GCGTCGACGT CTCGGACTTG GCGAGAGAGG GACGCCCGGA
4251  GCGACGAGGC TGGGGGAGGG GAGGCCCGCG CTTTGTCTGG AGTCTCGGTA
      CGCTGCTCCG ACCCCCTCCC CTCCGGGCGC GAAACAGACC TCAGAGCCAT
4301  GCTGTCATCC GGCTCCCACC CTCATGCACA ATTGTCCCAT CTCCCCCACG
      CGACAGTAGG CCGAGGGTGG GAGTACGTGT TAACAGGGTA GAGGGGGTGC
4351  CACCGGCGCG GCGCCCGCCT CAGCGAGGCC CCAGCCGGTT TCCCGCAGCC
      GTGGCCGCGC CGCGGGCGGA GTCGCTCCGG GGTCGGCCAA AGGGCGTCGG
4401  CGCGGCCCAC GGGGCTCGCA GCCTCCCCGC AAGCTCGGAC GCACGGAGCA
      GCGCCGGGTG CCCCGAGCGT CGGAGGGGCG TTCGAGCCTG CGTGCCTCGT
4451  TCCTAAACCC CACCACACGC AAGATCGAAA AAAAGCAAAG GCACGAACTT
      AGGATTTGGG GTGGTGTGCG TTCTAGCTTT TTTTCGTTTC CGTGCTTGAA
4501  CACCGCTCCG ATGCTCAGGG CCGCGGATCC TGCAGAGTCT CCCGCCTGCG
      GTGGCGAGGC TACGAGTCCC GGCGCCTAGG ACGTCTCAGA GGGCGGACGC
4551  CGCTTCGGTT CAGCCACATC CGAGGGGAGG GGGCGCGGGC AGCTCCGCCG
      GCGAAGCCAA GTCGGTGTAG GCTCCCCTCC CCCGCGCCCG TCGAGGCGGC
4601  GGGGGGAGGG GGAGCACCGC CCACGCCCTG GCCGCGCGGG GCCCGCCGGG
      CCCCCCTCCC CCTCGTGGCG GGTGCGGGAC CGGCGCGCCC CGGGCGGCCC
4651  AACGCGTCCT GCGGGGGGCG GCGCGCGCAA TGCTCACCGT CCGCGGCGTG
      TTGCGCAGGA CGCCCCCCGC CGCGCGCGTT ACGAGTGGCA GGCGCCGCAC
4701  GCGCCCAGGG GGTCTCCTGG CTGGGGGGAG GGGGGGGAAG GCGGGCAGGA
      CGCGGGTCCC CCAGAGGACC GACCCCCCTC CCCCCCCTTC CGCCCGTCCT
4751  AGGACCGCGG AGGCCTCTCT GCGTCTCGGA GCGCGCCAAA GCGGGGCTCC
      TCCTGGCGCC TCCGGAGAGA CGCAGAGCCT CGCGCGGTTT CGCCCCGAGG
4801  ACCCACCTCC TTGCCCGGAT CTTGAAGGCC GGGGAGATAA ACAGCGGGGT
      TGGGTGGAGG AACGGGCCTA GAACTTCCGG CCCCTCTATT TGTCGCCCCA
```

Figure 29 cont.

```
4851  TCTTTAAGCA CCACCTCTCA CTAGGCGCGG GATCCCAAGG CTTGTGGCAT
      AGAAATTCGT GGTGGAGAGT GATCCGCGCC CTAGGGTTCC GAACACCGTA
4901  CCGGGGTGGT ACTTGGACTA AAAGTCCTTC TGGGAGGGAC CGAGTGAGAA
      GGCCCCACCA TGAACCTGAT TTTCAGGAAG ACCCTCCCTG GCTCACTCTT
4951  CCCCTTTGGG ACGTGTAGAA ATATTTGTGT GGTTCGAGAA TATTTGTGCG
      GGGGAAACCC TGCACATCTT TATAAACACA CCAAGCTCTT ATAAACACGC
5001  GACGGGCTTG GCAAAGGCGT AGCTGCAGAG AGCACGCTTG GGTGGAGAGG
      CTGCCCGAAC CGTTTCCGCA TCGACGTCTC TCGTGCGAAC CCACCTCTCC
5051  GCCGCACGCC CCAGCGCCGG CCTAAGCCCC TCCCGACGGC GTTATTTCAA
      CGGCGTGCGG GGTCGCGGCC GGATTCGGGG AGGGCTGCCG CAATAAAGTT
5101  ACTGCGCGAC CGTTTCTCCG CTCCCTACGC GGAGGTGGGG GCCGGACCTA
      TGACGCGCTG GCAAAGAGGC GAGGGATGCG CCTCCACCCC CGGCCTGGAT
5151  GTTCCGGACG TAGTAACACG CCGAGCGCGA GCCTTCCGCA ATTCACGGAA
      CAAGGCCTGC ATCATTGTGC GGCTCGCGCT CGGAAGGCGT TAAGTGCCTT
5201  CACAGTTGCG CAAGTGATGT AAAGCAGTCC CGCTGTACCT AAAGGGGGAG
      GTGTCAACGC GTTCACTACA TTTCGTCAGG GCGACATGGA TTTCCCCCTC
5251  TGTCACGTAC TTGGCGTAAG GAGAGTGTAG GCCCTTCCCG CCATTGGCGG
      ACAGTGCATG AACCGCATTC CTCTCACATC CGGGAAGGGC GGTAACCGCC
5301  CGGTTAGGGC GTTTACGTAA CGGCGTGACG TAAGCGGAGA CGCGTTAGTG
      GCCAATCCCG CAAATGCATT GCCGCACTGC ATTCGCCTCT GCGCAATCAC
5351  GGGGGAAGGT TCTAGAAAAG CGGCGGTCTC GGCTCCAGCG GCAGTAGCAG
      CCCCCTTCCA AGATCTTTTC GCCGCCAGAG CCGAGGTCGC CGTCATCGTC
5401  CGGCGCCGGT CCCGTGTGCA GGAGCTCCTT TGCGGCCCAG TTTCTTGGCC
      GCCGCGGCCA GGGCACACGT CCTCGAGGAA ACGCCGGGTC AAAGAACCGG
5451  ATCGCCTGCT CTCCCCACAG CGCCAGGACG AGTCCCGTGC GCGTCCGTCC
      TAGCGGACGA GAGGGGTGTC GCGGTCCTGC TCAGGGCACG CGCAGGCAGG
5501  GCGGAGGTCT TTCTCATCTC GCTCGGCTGC GGGAAATCGG GCTGAAGCGA
      CGCCTCCAGA AAGAGTAGAG CGAGCCGACG CCCTTTAGCC CGACTTCGCT
5551  CTGAGTCCGC GATGGAGGTA ACGGGTTTGA AATCAATGAG TTATTAAAAA
      GACTCAGGCG CTACCTCCAT TGCCCAAACT TTAGTTACTC AATAATTTTT
5601  TGGCATGGCG AGGCCGTAGG CACCGCAATG GAAACCGGCC ACCCGCCTCC
      ACCGTACCGC TCCGGCATCC GTGGCGTTAC CTTTGGCCGG TGGGCGGAGG
5651  GTGGTCCGGC GGAGGGGATG CGGCCACTCG AGTGGCGGTT GGCCTTGGCG
      CACCAGGCCG CCTCCCCTAC GCCGGTGAGC TCACCGCCAA CCGGAACCGC
5701  AGTTTCTGAG GGGTCGTTGG AGGAGGCCTC TGATTGTCCG ACCGCCTTCC
      TCAAAGACTC CCCAGCAACC TCCTCCGGAG ACTAACAGGC TGGCGGAAGG
5751  CCGCCCTCAG CCGCCCGGCG CCATTTCCCT CAGTTGGGGT GGGGGATGGG
      GGCGGGAGTC GGCGGGCCGC GGTAAAGGGA GTCAACCCCA CCCCCTACCC
5801  AAGTGCCCGC CGCGACCGGG CTGGACCGCT AAAGTAGCGC GTGAGCGGGC
      TTCACGGGCG GCGCTGGCCC GACCTGGCGA TTTCATCGCG CACTCGCCCG
5851  CATCGCTGGC CTTTCGATGT GCGCGGGCCT AGGGGCTCGG TTGTGTTCGC
      GTAGCGACCG GAAAGCTACA CGCGCCCGGA TCCCCGAGCC AACACAAGCG
5901  GGCGGAACGT TTCTGGGGCC CCCCCGGCTT CCCGGAGCGA GTCTGCGAAG
      CCGCCTTGCA AAGACCCCGG GGGGGCCGAA GGGCCTCGCT CAGACGCTTC
5951  CTAGCTTCCC CTCCCCCCTC TCCCGGGAAC CGGATTTGGC GGCCGCCATT
      GATCGAAGGG GAGGGGGGAG AGGGCCCTTG GCCTAAACCG CCGGCGGTAA
6001  TTCCCGTCTC CTTCCTCGCC ACGATTTTGC TTTCAACGCT TTAGGTTTAC
      AAGGGCAGAG GAAGGAGCGG TGCTAAAACG AAAGTTGCGA AATCCAAATG
6051  TAGTTTGGTT TTCTTTTTTC ACCACTGCGT AGACGTGTTT AGCGATTTTC
      ATCAAACCAA AAGAAAAAAG TGGTGACGCA TCTGCACAAA TCGCTAAAAG
6101  CTTTCTTTTG GAAGTCTTCA TACCGTTTCG AGGTGGATTT AGCGTTTTGA
      GAAAGAAAAC CTTCAGAAGT ATGGCAAAGC TCCACCTAAA TCGCAAAACT
6151  GCTTGGGTCT TCAGCGTCCT GCGCACCTCG CTAAAGGCTC TCTGCCTTCC
      CGAACCCAGA AGTCGCAGGA CGCGTGGAGC GATTTCCGAG AGACGGAAGG
6201  CCTCGACGAA ATGGCGCCAT TGCTTTCTGA AGCCACCGAG GCGCGGGGTG
      GGAGCTGCTT TACCGCGGTA ACGAAAGACT TCGGTGGCTC CGCGCCCCAC
6251  GGGGCGGGGT GGCGGCGCTC CACGAGCTTT ACTGGAACAG GCAGAGAGAA
      CCCCGCCCCA CCGCCGCGAG GTGCTCGAAA TGACCTTGTC CGTCTCTCTT
6301  CGTAGTACAA CCGAGGCCTG GGCGGGTGGC TGAAGGCAGC GTCGCTGCAA
      GCATCATGTT GGCTCCGGAC CCGCCCACCG ACTTCCGTCG CAGCGACGTT
6351  AGAGACCGTT TTATTTTTCA TAATACGTAA GATTACGGGT GCTGTAGTAA
      TCTCTGGCAA AATAAAAAGT ATTATGCATT CTAATGCCCA CGACATCATT
6401  AGCACTTGAG CATTAGTATA GTAGGAGGAA GTCAAAGTGG AAAAAATGGG
      TCGTGAACTC GTAATCATAT CATCCTCCTT CAGTTTCACC TTTTTTACCC
6451  AGCGCTCATC AGGAAGCTAG GGAGGCTATG TTGAGTGCAG GGTTACTTTC
      TCGCGAGTAG TCCTTCGATC CCTCCGATAC AACTCACGTC CCAATGAAAG
```

Figure 29 cont.

```
6501  CTTTTATTGC AGAACTTTTA TCTGCTTAAA GGATCCTCGG ATCGAAATAA
      GAAAATAACG TCTTGAAAAT AGACGAATTT CCTAGGAGCC TAGCTTTATT
6551  TTCAAATTAT AAGCATTTTT AAGGGAATCT TCGAATTTGT TGGTAAAGTC
      AAGTTTAATA TTCGTAAAAA TTCCCTTAGA AGCTTAAACA ACCATTTCAG
6601  AACGGATCCT TAGCACGTGG TGTTCACTTT AAGGAAGTGA AATAGCTGAC
      TTGCCTAGGA ATCGTGCACC ACAAGTGAAA TTCCTTCACT TTATCGACTG
6651  TTTTCATAGT TAGCCTTCGC TTAAAGCCTG GTTCAGTGGA CGAAAATCCA
      AAAAGTATCA ATCGGAAGCG AATTTCGGAC CAAGTCACCT GCTTTTAGGT
6701  CGTCCTGGCT ATATAAAAAC TTAGTTTGGG GTCACAGTGT TTGAGCGTGG
      GCAGGACCGA TATATTTTTG AATCAAACCC CAGTGTCACA AACTCGCACC
6751  TCATTCGGTT TTTTTATTTT TTATTTGTTT GAAATTATGA TGCATCATTA
      AGTAAGCCAA AAAAATAAAA AATAAACAAA CTTTAATACT ACGTAGTAAT
6801  CACTGATAAG CATTAGCTTT CGAATTGAAA GGGGTCTCCT TGGTTATTTT
      GTGACTATTC GTAATCGAAA GCTTAACTTT CCCCAGAGGA ACCAATAAAA
6851  CTTTGACTCT AAGCACACTT ATAAATAAAA TAACCTTGTT TATAATCGAT
      GAAACTGAGA TTCGTGTGAA TATTTATTTT ATTGGAACAA ATATTAGCTA
6901  AGTGGACGTC TGGTAAGTTT GGAAAAAACC CGAGGTAAGT AAAGAGCTTT
      TCACCTGCAG ACCATTCAAA CCTTTTTTGG GCTCCATTCA TTTCTCGAAA
6951  TGCTTTCGTT AGTGATATGA AAAAACAAGG TGTATTTAAT ACTTGCAACT
      ACGAAAGCAA TCACTATACT TTTTTGTTCC ACATAAATTA TGAACGTTGA
7001  TAGTTTAAGG AAAGCCAATT TACTGACATT TTAGTAGAGC TACCAGAAAC
      ATCAAATTCC TTTCGGTTAA ATGACTGTAA AATCATCTCG ATGGTCTTTG
7051  ACTATTTGGA GTCCTGATTA AGGCTTTTGT AACTATTTTG ACTATTTAAA
      TGATAAACCT CAGGACTAAT TCCGAAAACA TTGATAAAAC TGATAAATTT
7101  ACAATTTTGG TCGTTTTTAT TAAACATTTC AAAACCTAAA AATTGTAAAC
      TGTTAAAACC AGCAAAAATA ATTTGTAAAG TTTTGGATTT TTAACATTTG
7151  ATTGGCTTTT TGAGCACATT TTGGAGAAAC TTACAAATTT AGGCTATACA
      TAACCGAAAA ACTCGTGTAA AACCTCTTTG AATGTTTAAA TCCGATATGT
7201  GTAAAATAAC GGATTTGTTT TATAATTTTG CTTTTTCATT TCGTTGTGCA
      CATTTTATTG CCTAAACAAA ATATTAAAAC GAAAAAGTAA AGCAACACGT
7251  GTCATAGGTC CTGGATAGTA TGACCTAATT TATGAACATC TTGATAAGTT
      CAGTATCCAG GACCTATCAT ACTGGATTAA ATACTTGTAG AACTATTCAA
7301  TTTGTACTTA GCTATTGGAA AGCCAGTATT AAGTGCCTGA CAAAACCAGA
      AAACATGAAT CGATAACCTT TCGGTCATAA TTCACGGACT GTTTTGGTCT
7351  TTTAAGGTGA TATCTGGAGT TTCAGCATTC TTCATGGAGC TTGTTTCAGA
      AAATTCCACT ATAGACCTCA AAGTCGTAAG AAGTACCTCG AACAAAGTCT
7401  GTTGCAGGAT TTTTTTTTTT CATCTTGAGA TACTTACAAT TAACACCAGA
      CAACGTCCTA AAAAAAAAAA GTAGAACTCT ATGAATGTTA ATTGTGGTCT
7451  GGGGGCAGCT CAGGGAAAAG CAAATATGCC ACTTTTCAGA AACTGAATCT
      CCCCCGTCGA GTCCCTTTTC GTTTATACGG TGAAAAGTCT TTGACTTAGA
7501  TGGAAGTGGT GAATTTGGAA ACAGGTTTTT TAAATTTTTT TTAAATCTAA
      ACCTTCACCA CTTAAACCTT TGTCCAAAAA ATTTAAAAAA AATTTAGATT
7551  AAAGTAGTAA ATTTTGGACT TGGGTTGTAG AATTTAATGA ATTACAAAAG
      TTTCATCATT TAAAACCTGA ACCCAACATC TTAAATTACT TAATGTTTTC
7601  AATTCTTTAA TACCCTTTAA ATGACCTAAG AGCTGGGTAT GGTTTTTCTG
      TTAAGAAATT ATGGGAAATT TACTGGATTC TCGACCCATA CCAAAAAGAC
7651  AATTTTTTTG AAGAAAATCT AAGAAAGTTT ACGTGAATTA GAAGTTAGAT
      TTAAAAAAAC TTCTTTTAGA TTCTTTCAAA TGCACTTAAT CTTCAATCTA
7701  CGAATATTAG TGACTTTGAA ACTTGTATAG CTCAGGCAAT TTTTGGTGTA
      GCTTATAATC ACTGAAACTT TGAACATATC GAGTCCGTTA AAAACCACAT
7751  ACACAACTAA TATGCAGTTT AACATATGGT TTAAATTTGA TGTAAGTTTT
      TGTGTTGATT ATACGTCAAA TTGTATACCA AATTTAAACT ACATTCAAAA
7801  TTTTCTCCCC CCCAGAAAAC TTTAGAAACT GTTCCTTTGG AGAGGAAAAA
      AAAAGAGGGG GGGTCTTTTG AAATCTTTGA CAAGGAAACC TCTCCTTTTT
7851  GGTACTCTAC CAGCAGGTCA CCTCATATTT AAGAATTTAA TTTCCTGCAT
      CCATGAGATG GTCGTCCAGT GGAGTATAAA TTCTTAAATT AAAGGACGTA
7901  ACAAAGAAAG TGTAAATAAA AATTGAAATG GTATTTCCCT TTGCAGAGAG
      TGTTTCTTTC ACATTTATTT TTAACTTTAC CATAAAGGGA AACGTCTCTC
7951  AAAAGGAACA GTTCCGAAAG CTCTTTATTG GTGGCTTAAG CTTATCGATA
      TTTTCCTTGT CAAGGCTTTC GAGAAATAAC CACCGAATTC GAATAGCTAT
8001  CCGGTGGCGC GCCAATTGTT AATTAAGATC TGGCCCAATG GCCCGTACGA
      GGCCACCGCG CGGTTAACAA TTAATTCTAG ACCGGGTTAC CCGGCATGCT
8051  ATTTGAGGCG GAAAGAACCA GCTGTGGAAT GTGTGTCAGT TAGGGTGTGG
      TAAACTCCGC CTTTCTTGGT CGACACCTTA CACACAGTCA ATCCCACACC
8101  AAAGTCCCCA GGCTCCCCAG CAGGCAGAAG TATGCAAAGC ATGCATCTCA
      TTTCAGGGGT CCGAGGGGTC GTCCGTCTTC ATACGTTTCG TACGTAGAGT
```

Figure 29 cont.

```
8151  ATTAGTCAGC AACCAGGTGT GGAAAGTCCC CAGGCTCCCC AGCAGGCAGA
      TAATCAGTCG TTGGTCCACA CCTTTCAGGG GTCCGAGGGG TCGTCCGTCT
8201  AGTATGCAAA GCATGCATCT CAATTAGTCA GCAACCATAG TCCCGCCCCT
      TCATACGTTT CGTACGTAGA GTTAATCAGT CGTTGGTATC AGGGCGGGGA
8251  AACTCCGCCC ATCCCGCCCC TAACTCCGCC CAGTTCCGCC CATTCTCCGC
      TTGAGGCGGG TAGGGCGGGG ATTGAGGCGG GTCAAGGCGG GTAAGAGGCG
8301  CCCATGGCTG ACTAATTTTT TTTATTTATG CAGAGGCCGA GGCCGCCTCG
      GGGTACCGAC TGATTAAAAA AAATAAATAC GTCTCCGGCT CCGGCGGAGC
8351  GCCTCTGAGC TATTCCAGAA GTAGTGAGGA GGCTTTTTTG GAGGCCTAGG
      CGGAGACTCG ATAAGGTCTT CATCACTCCT CCGAAAAAAC CTCCGGATCC
8401  CTTTTGCAAA GATCGATCAA GAGACAGGAT GAGGATCGTT TCGCATGATT
      GAAAACGTTT CTAGCTAGTT CTCTGTCCTA CTCCTAGCAA AGCGTACTAA
8451  GAACAAGATG GATTGCACGC AGGTTCTCCG GCCGCTTGGG TGGAGAGGCT
      CTTGTTCTAC CTAACGTGCG TCCAAGAGGC CGGCGAACCC ACCTCTCCGA
8501  ATTCGGCTAT GACTGGGCAC AACAGACAAT CGGCTGCTCT GATGCCGCCG
      TAAGCCGATA CTGACCCGTG TTGTCTGTTA GCCGACGAGA CTACGGCGGC
8551  TGTTCCGGCT GTCAGCGCAG GGGCGCCCGG TTCTTTTTGT CAAGACCGAC
      ACAAGGCCGA CAGTCGCGTC CCCGCGGGCC AAGAAAAACA GTTCTGGCTG
8601  CTGTCCGGTG CCCTGAATGA ACTGCAAGAC GAGGCAGCGC GGCTATCGTG
      GACAGGCCAC GGGACTTACT TGACGTTCTG CTCCGTCGCG CCGATAGCAC
8651  GCTGGCCACG ACGGGCGTTC CTTGCGCAGC TGTGCTCGAC GTTGTCACTG
      CGACCGGTGC TGCCCGCAAG GAACGCGTCG ACACGAGCTG CAACAGTGAC
8701  AAGCGGGAAG GGACTGGCTG CTATTGGGCG AAGTGCCGGG GCAGGATCTC
      TTCGCCCTTC CCTGACCGAC GATAACCCGC TTCACGGCCC CGTCCTAGAG
8751  CTGTCATCTC ACCTTGCTCC TGCCGAGAAA GTATCCATCA TGGCTGATGC
      GACAGTAGAG TGGAACGAGG ACGGCTCTTT CATAGGTAGT ACCGACTACG
8801  AATGCGGCGG CTGCATACGC TTGATCCGGC TACCTGCCCA TTCGACCACC
      TTACGCCGCC GACGTATGCG AACTAGGCCG ATGGACGGGT AAGCTGGTGG
8851  AAGCGAAACA TCGCATCGAG CGAGCACGTA CTCGGATGGA AGCCGGTCTT
      TTCGCTTTGT AGCGTAGCTC GCTCGTGCAT GAGCCTACCT TCGGCCAGAA
8901  GTCGATCAGG ATGATCAAGA GCATCAGGGG CTCGCGCCAG CCGAACTGTT
      CAGCTAGTCC TACTAGTTCT CGTAGTCCCC GAGCGCGGTC GGCTTGACAA
8951  CGCCAGGCTC AAGGCGAGCA TGCCCGACGG CGAGGATCTC GTCGTGACCC
      GCGGTCCGAG TTCCGCTCGT ACGGGCTGCC GCTCCTAGAG CAGCACTGGG
9001  ATGGCGATGC CTGCTTGCCG AATATCATGG TGGAAAATGG CCGCTTTTCT
      TACCGCTACG GACGAACGGC TTATAGTACC ACCTTTTACC GGCGAAAAGA
9051  GGATTCATCG ACTGTGGCCG GCTGGGTGTG GCGGACCGCT ATCAGGACAT
      CCTAAGTAGC TGACACCGGC CGACCCACAC CGCCTGGCGA TAGTCCTGTA
9101  AGCGTTGGCT ACCCGTGATA TTGCTGAAGA GCTTGGCGGC GAATGGGCTG
      TCGCAACCGA TGGGCACTAT AACGACTTCT CGAACCGCCG CTTACCCGAC
9151  ACCGCTTCCT CGTGCTTTAC GGTATCGCCG CTCCCGATTC GCAGCGCATC
      TGGCGAAGGA GCACGAAATG CCATAGCGGC GAGGGCTAAG CGTCGCGTAG
9201  GCCTTCTATC GCCTTCTTGA CGAGTTCTTC TGAGCGGGAC TCTGGGGTTC
      CGGAAGATAG CGGAAGAACT GCTCAAGAAG ACTCGCCCTG AGACCCCAAG
9251  GAAATGACCG ACCAAGCGAC GCCCAACCTG CCATCACGAG ATTTCGATTC
      CTTTACTGGC TGGTTCGCTG CGGGTTGGAC GGTAGTGCTC TAAAGCTAAG
9301  CACCGCCGCC TTCTATGAAA GGTTGGGCTT CGGAATCGTT TTCCGGGACG
      GTGGCGGCGG AAGATACTTT CCAACCCGAA GCCTTAGCAA AAGGCCCTGC
9351  CCGGCTGGAT GATCCTCCAG CGCGGGGATC TCATGCTGGA GTTCTTCGCC
      GGCCGACCTA CTAGGAGGTC GCGCCCCTAG AGTACGACCT CAAGAAGCGG
9401  CACCCTAGGG GGAGGCTAAC TGAAACACGG AAGGAGACAA TACCGGAAGG
      GTGGGATCCC CCTCCGATTG ACTTTGTGCC TTCCTCTGTT ATGGCCTTCC
9451  AACCCGCGCT ATGACGGCAA TAAAAAGACA GAATAAAACG CACGGTGTTG
      TTGGGCGCGA TACTGCCGTT ATTTTTCTGT CTTATTTTGC GTGCCACAAC
9501  GGTCGTTTGT TCATAAACGC GGGGTTCGGT CCCAGGGCTG GCACTCTGTC
      CCAGCAAACA AGTATTTGCG CCCCAAGCCA GGGTCCCGAC CGTGAGACAG
9551  GATACCCCAC CGAGACCCCA TTGGGGCCAA TACGCCCGCG TTTCTTCCTT
      CTATGGGGTG GCTCTGGGGT AACCCCGGTT ATGCGGGCGC AAAGAAGGAA
9601  TTCCCCACCC CACCCCCCAA GTTCGGGTGA AGGCCCAGGG CTCGCAGCCA
      AAGGGGTGGG GTGGGGGGTT CAAGCCCACT TCCGGGTCCC GAGCGTCGGT
9651  ACGTCGGGGC GGCAGGCCCT GCCATAGCCT CAAATTCCTT AGGCTCGAGG
      TGCAGCCCCG CCGTCCGGGA CGGTATCGGA GTTTAAGGAA TCCGAGCTCC
9701  GCCGCCACCG CGGTGGAGCT CCAGCTTTTG TTCCCTTTAG TGAGGGTTAA
      CGGCGGTGGC GCCACCTCGA GGTCGAAAAC AAGGGAAATC ACTCCCAATT
9751  TTTCGAGCTT GGCGTAATCA TGGTCATAGC TGTTTCCTGT GTGAAATTGT
      AAAGCTCGAA CCGCATTAGT ACCAGTATCG ACAAAGGACA CACTTTAACA
```

Figure 29 cont.

```
9801   TATCCGCTCA CAATTCCACA CAACATACGA GCCGGAAGCA TAAAGTGTAA
       ATAGGCGAGT GTTAAGGTGT GTTGTATGCT CGGCCTTCGT ATTTCACATT
9851   AGCCTGGGGT GCCTAATGAG TGAGCTAACT CACATTAATT GCGTTGCGCT
       TCGGACCCCA CGGATTACTC ACTCGATTGA GTGTAATTAA CGCAACGCGA
9901   CACTGCCCGC TTTCCAGTCG GGAAACCTGT CGTGCCAGCA TCGCGAGCAC
       GTGACGGGCG AAAGGTCAGC CCTTTGGACA GCACGGTCGT AGCGCTCGTG
9951   TTTTCGGGGA AATGTGCGCG GAACCCCTAT TTGTTTATTT TTCTAAATAC
       AAAAGCCCCT TTACACGCGC CTTGGGGATA AACAAATAAA AAGATTTATG
10001  ATTCAAATAT GTATCCGCTC ATGAGACAAT AACCCTGATA AATGCTTCAA
       TAAGTTTATA CATAGGCGAG TACTCTGTTA TTGGGACTAT TTACGAAGTT
10051  TAATATTGAA AAAGGAAGAG TATGAGTATT CAACATTTCC GTGTCGCCCT
       ATTATAACTT TTTCCTTCTC ATACTCATAA GTTGTAAAGG CACAGCGGGA
10101  TATTCCCTTT TTTGCGGCAT TTTGCCTTCC TGTTTTTGCT CACCCAGAAA
       ATAAGGGAAA AAACGCCGTA AAACGGAAGG ACAAAAACGA GTGGGTCTTT
10151  CGCTGGTGAA AGTAAAAGAT GCTGAAGATC AGTTGGGTGC ACGAGTGGGT
       GCGACCACTT TCATTTTCTA CGACTTCTAG TCAACCCACG TGCTCACCCA
10201  TACATCGAAC TGGATCTCAA CAGCGGTAAG ATCCTTGAGA GTTTTCGCCC
       ATGTAGCTTG ACCTAGAGTT GTCGCCATTC TAGGAACTCT CAAAAGCGGG
10251  CGAAGAACGT TTTCCAATGA TGAGCACTTT TAAAGTTCTG CTATGTGGCG
       GCTTCTTGCA AAAGGTTACT ACTCGTGAAA ATTTCAAGAC GATACACCGC
10301  CGGTATTATC CCGTATTGAC GCCGGGCAAG AGCAACTCGG TCGCCGCATA
       GCCATAATAG GGCATAACTG CGGCCCGTTC TCGTTGAGCC AGCGGCGTAT
10351  CACTATTCTC AGAATGACTT GGTTGAGTAC TCACCAGTCA CAGAAAAGCA
       GTGATAAGAG TCTTACTGAA CCAACTCATG AGTGGTCAGT GTCTTTTCGT
10401  TCTTACGGAT GGCATGACAG TAAGAGAATT ATGCAGTGCT GCCATAACCA
       AGAATGCCTA CCGTACTGTC ATTCTCTTAA TACGTCACGA CGGTATTGGT
10451  TGAGTGATAA CACTGCGGCC AACTTACTTC TGACAACGAT CGGAGGACCG
       ACTCACTATT GTGACGCCGG TTGAATGAAG ACTGTTGCTA GCCTCCTGGC
10501  AAGGAGCTAA CCGCTTTTTT GCACAACATG GGGGATCATG TAACTCGCCT
       TTCCTCGATT GGCGAAAAAA CGTGTTGTAC CCCCTAGTAC ATTGAGCGGA
10551  TGATCGTTGG GAACCGGAGC TGAATGAAGC CATACCAAAC GACGAGCGTG
       ACTAGCAACC CTTGGCCTCG ACTTACTTCG GTATGGTTTG CTGCTCGCAC
10601  ACACCACGAT GCCTGTAGCA ATGGCAACAA CGTTGCGCAA ACTATTAACT
       TGTGGTGCTA CGGACATCGT TACCGTTGTT GCAACGCGTT TGATAATTGA
10651  GGCGAACTAC TTACTCTAGC TTCCCGGCAA CAATTAATAG ACTGGATGGA
       CCGCTTGATG AATGAGATCG AAGGGCCGTT GTTAATTATC TGACCTACCT
10701  GGCGGATAAA GTTGCAGGAC CACTTCTGCG CTCGGCCCTT CCGGCTGGCT
       CCGCCTATTT CAACGTCCTG GTGAAGACGC GAGCCGGGAA GGCCGACCGA
10751  GGTTTATTGC TGATAAATCT GGAGCCGGTG AGCGTGGGTC TCGCGGTATC
       CCAAATAACG ACTATTTAGA CCTCGGCCAC TCGCACCCAG AGCGCCATAG
10801  ATTGCAGCAC TGGGGCCAGA TGGTAAGCCC TCCCGTATCG TAGTTATCTA
       TAACGTCGTG ACCCCGGTCT ACCATTCGGG AGGGCATAGC ATCAATAGAT
10851  CACGACGGGG AGTCAGGCAA CTATGGATGA ACGAAATAGA CAGATCGCTG
       GTGCTGCCCC TCAGTCCGTT GATACCTACT TGCTTTATCT GTCTAGCGAC
10901  AGATAGGTGC CTCACTGATT AAGCATTGGT AACTGTCAGA CTCGCGACAC
       TCTATCCACG GAGTGACTAA TTCGTAACCA TTGACAGTCT GAGCGCTGTG
10951  TGCATTAATG AATCGGCCAA CGCGCGGGGA GAGGCGGTTT GCGTATTGGG
       ACGTAATTAC TTAGCCGGTT GCGCGCCCCT CTCCGCCAAA CGCATAACCC
11001  CGCTCTTCCG CTTCCTCGCT CACTGACTCG CTGCGCTCGG TCGTTCGGCT
       GCGAGAAGGC GAAGGAGCGA GTGACTGAGC GACGCGAGCC AGCAAGCCGA
11051  GCGGCGAGCG GTATCAGCTC ACTCAAAGGC GGTAATACGG TTATCCACAG
       CGCCGCTCGC CATAGTCGAG TGAGTTTCCG CCATTATGCC AATAGGTGTC
11101  AATCAGGGGA TAACGCAGGA AAGAACATGT GAGCAAAAGG CCAGCAAAAG
       TTAGTCCCCT ATTGCGTCCT TTCTTGTACA CTCGTTTTCC GGTCGTTTTC
11151  GCCAGGAACC GTAAAAAGGC CGCGTTGCTG GCGTTTTTCC ATAGGCTCCG
       CGGTCCTTGG CATTTTTCCG GCGCAACGAC CGCAAAAAGG TATCCGAGGC
11201  CCCCCCTGAC GAGCATCACA AAAATCGACG CTCAAGTCAG AGGTGGCGAA
       GGGGGGACTG CTCGTAGTGT TTTTAGCTGC GAGTTCAGTC TCCACCGCTT
11251  ACCCGACAGG ACTATAAAGA TACCAGGCGT TTCCCCCTGG AAGCTCCCTC
       TGGGCTGTCC TGATATTTCT ATGGTCCGCA AAGGGGGACC TTCGAGGGAG
11301  GTGCGCTCTC CTGTTCCGAC CCTGCCGCTT ACCGGATACC TGTCCGCCTT
       CACGCGAGAG GACAAGGCTG GGACGGCGAA TGGCCTATGG ACAGGCGGAA
11351  TCTCCCTTCG GGAAGCGTGG CGCTTTCTCA TAGCTCACGC TGTAGGTATC
       AGAGGGAAGC CCTTCGCACC GCGAAAGAGT ATCGAGTGCG ACATCCATAG
11401  TCAGTTCGGT GTAGGTCGTT CGCTCCAAGC TGGGCTGTGT GCACGAACCC
       AGTCAAGCCA CATCCAGCAA GCGAGGTTCG ACCCGACACA CGTGCTTGGG
```

Figure 29 cont.

```
11451  CCCGTTCAGC CCGACCGCTG CGCCTTATCC GGTAACTATC GTCTTGAGTC
       GGGCAAGTCG GGCTGGCGAC GCGGAATAGG CCATTGATAG CAGAACTCAG
11501  CAACCCGGTA AGACACGACT TATCGCCACT GGCAGCAGCC ACTGGTAACA
       GTTGGGCCAT TCTGTGCTGA ATAGCGGTGA CCGTCGTCGG TGACCATTGT
11551  GGATTAGCAG AGCGAGGTAT GTAGGCGGTG CTACAGAGTT CTTGAAGTGG
       CCTAATCGTC TCGCTCCATA CATCCGCCAC GATGTCTCAA GAACTTCACC
11601  TGGCCTAACT ACGGCTACAC TAGAAGGACA GTATTTGGTA TCTGCGCTCT
       ACCGGATTGA TGCCGATGTG ATCTTCCTGT CATAAACCAT AGACGCGAGA
11651  GCTGAAGCCA GTTACCTTCG GAAAAAGAGT TGGTAGCTCT TGATCCGGCA
       CGACTTCGGT CAATGGAAGC CTTTTTCTCA ACCATCGAGA ACTAGGCCGT
11701  AACAAACCAC CGCTGGTAGC GGTGGTTTTT TTGTTTGCAA GCAGCAGATT
       TTGTTTGGTG GCGACCATCG CCACCAAAAA AACAAACGTT CGTCGTCTAA
11751  ACGCGCAGAA AAAAAGGATC TCAAGAAGAT CCTTTGATCT TTTCTACGGG
       TGCGCGTCTT TTTTTCCTAG AGTTCTTCTA GGAAACTAGA AAAGATGCCC
11801  GTCTGACGCT CAGTGGAACG AAAACTCA
       CAGACTGCGA GTCACCTTGC TTTTGAGT
```

Figure 31 CET1130 nucleotide sequence

```
   1  CGTTGTAAAA CGACGGCCAG TGAATTGTAA TACGACTCAC TATAGGGCGA
      GCAACATTTT GCTGCCGGTC ACTTAACATT ATGCTGAGTG ATATCCCGCT
  51  ATTGGGTACC GGGCCCCCCC TCGAAGTTTA AACATTTAAA TCTAGAACTA
      TAACCCATGG CCCGGGGGGG AGCTTCAAAT TTGTAAATTT AGATCTTGAT
 101  GTGGATCCCC CGGGCTGCAG GAATTCGATA TCAAGCTCAT GGCACCTGTA
      CACCTAGGGG GCCCGACGTC CTTAAGCTAT AGTTCGAGTA CCGTGGACAT
 151  TTGTACTCTT ATCAGTCATT ATATGGACTT TAACTTCCCC AGATATTATT
      AACATGAGAA TAGTCAGTAA TATACCTGAA ATTGAAGGGG TCTATAATAA
 201  TGGGCTCCTC CATAAGACTG TGAGCATCTG ACCACTGGAG TGTTGCTTCC
      ACCCGAGGAG GTATTCTGAC ACTCGTAGAC TGGTGACCTC ACAACGAAGG
 251  CATTATATCC CTGTTATCAA GCACAAGGTC AGGCACAGAG TAAGACTCAA
      GTAATATAGG GACAATAGTT CGTGTTCCAG TCCGTGTCTC ATTCTGAGTT
 301  AACATGTTTT GGAATGTATG ACTGGTATGA ACTACAAACC AGTAAGCTGA
      TTGTACAAAA CCTTACATAC TGACCATACT TGATGTTTGG TCATTCGACT
 351  TGTTTTCATT TTGAGTCTAT AAATCTAATT TTGTGGTGGT TTTGTGTATG
      ACAAAAGTAA AACTCAGATA TTTAGATTAA AACACCACCA AAACACATAC
 401  GCTCAAGGCT CAAATTGTAA AATTTAATAT TATGTGACCA AAGAAAGTTA
      CGAGTTCCGA GTTTAACATT TTAAATTATA ATACACTGGT TTCTTTCAAT
 451  TACCCAGAAC CTCAATTTCC TCACCTTCAA AATGGGGCAG TTTCTCACTC
      ATGGGTCTTG GAGTTAAAGG AGTGGAAGTT TTACCCCGTC AAAGAGTGAG
 501  ATTGGTCTGC TGTCACGATT TTAATGAGCT CATGCACAAA CAGCCCTTTA
      TAACCAGACG ACAGTGCTAA AATTACTCGA GTACGTGTTT GTCGGGAAAT
 551  TATAAGGTAA GTGCTGGATA AATGTTGGCT ACTATAATAA AATAAGCCTC
      ATATTCCATT CACGACCTAT TTACAACCGA TGATATTATT TTATTCGGAG
 601  TAAGATACTT GGTCAGCACA AGTACTACCC AAGAGTATGC ACTGTAAGTA
      ATTCTATGAA CCAGTCGTGT TCATGATGGG TTCTCATACG TGACATTCAT
 651  AACTGACAAA ATTGTGTATC TAAAACTGGC CAGATGAAAG AGAAACTTTT
      TTGACTGTTT TAACACATAG ATTTTGACCG GTCTACTTTC TCTTTGAAAA
 701  AAGGGGCCCT TCTGCGTGCC CGACACTGTG CTAGGCACTC ACACTATCCC
      TTCCCCGGGA AGACGCACGG GCTGTGACAC GATCCGTGAG TGTGATAGGG
 751  GACCCGAGAA ACCGATCTGC GACCCAGAGG AACTTACCAA GCCTCCAGCA
      CTGGGCTCTT TGGCTAGACG CTGGGTCTCC TTGAATGGTT CGGAGGTCGT
 801  TCTTGTGCAG CCCTACTCAT GGGACCATCT GGATACCCAC CCTTGTCTTT
      AGAACACGTC GGGATGAGTA CCCTGGTAGA CCTATGGGTG GGAACAGAAA
 851  ACAGGGAGCA GAACACACCT CTTATGTGTC AGAAAACAAA GTCCAGGAAG
      TGTCCCTCGT CTTGTGTGGA GAATACACAG TCTTTTGTTT CAGGTCCTTC
 901  TATATTTTTA CCTGAGGCAA TATCTGAAAA TTGTATGCTA CAGCCTCCAA
      ATATAAAAAT GGACTCCGTT ATAGACTTTT AACATACGAT GTCGGAGGTT
 951  AGTGAGTCTT CCTCTCAGTA CCTCTCTTCT AGGCACATGG AGCCCTTTCT
      TCACTCAGAA GGAGAGTCAT GGAGAGAAGA TCCGTGTACC TCGGGAAAGA
1001  TCCAAGTATT ATGTTTAACC ACTTAATGAA TGAAGTCCTG AAACTGCTTA
      AGGTTCATAA TACAAATTGG TGAATTACTT ACTTCAGGAC TTTGACGAAT
1051  CCCATGCTCC CTATAATCTC TGAGTAATCT TCCTTTTCCA CAACCTCAGG
      GGGTACGAGG GATATTAGAG ACTCATTAGA AGGAAAAGGT GTTGGAGTCC
1101  CATAATCTCA TCTTCTGTTT CTATTACAAT TTCAAATTCT GGAAAAAGGA
      GTATTAGAGT AGAAGACAAA GATAATGTTA AAGTTTAAGA CCTTTTTCCT
1151  AGTTGTGGTC TGGAATTATA TGGTCCAGAT GATCTGAAAC AAAAAGGACA
      TCAACACCAG ACCTTAATAT ACCAGGTCTA CTAGACTTTG TTTTTCCTGT
1201  GCACTATTAG TAATCATTTA GTTTTGAAGA CAGTCTAATA ATTTGCTGTC
      CGTGATAATC ATTAGTAAAT CAAAACTTCT GTCAGATTAT TAAACGACAG
1251  TCTAAAGTAC TATATTCCCT ATAGTTCTGG CATTTTAGAT AAAGGGTCAT
      AGATTTCATG ATATAAGGGA TATCAAGACC GTAAAATCTA TTTCCCAGTA
1301  AAATTAAATG CCTATATGGT GACATTATTC AGTGATTCAG ACTTCACAGC
      TTTAATTTAC GGATATACCA CTGTAATAAG TCACTAAGTC TGAAGTGTCG
1351  CTTTTTTTTT TTTTTACAAA GGTGTTCCAG GCATGAAAAA TTTTAAAGTA
      GAAAAAAAAA AAAAATGTTT CCACAAGGTC CGTACTTTTT AAAATTTCAT
1401  CTATACCTTT CCTAATTTTA CCTTTAAAGT TGTCCTGGAA ATATCTGGGT
      GATATGGAAA GGATTAAAAT GGAAATTTCA ACAGGACCTT TATAGACCCA
1451  TGACAAAGGC GATGAAACTG AACTGAGACT TAAAAAAAAG ATTACCCACC
      ACTGTTTCCG CTACTTTGAC TTGACTCTGA ATTTTTTTTC TAATGGGTGG
1501  TGGTTGTGCA CAAGCCTGCT TATGTCCCAA TCTCCAGTCT AGGGTCTGAT
      ACCAACACGT GTTCGGACGA ATACAGGGTT AGAGGTCAGA TCCCAGACTA
```

Figure 31 cont.

```
1551  GCTCCTTGCT GCAGTAATAT GCTTTGTGGC ATCTGGAGCA CGTTTTGGGG
      CGAGGAACGA CGTCATTATA CGAAACACCG TAGACCTCGT GCAAAACCCC
1601  CCTAAACAGC CACAAACCCT GCAGAGATGA GCACCAGACT TAAGCTGGAG
      GGATTTGTCG GTGTTTGGGA CGTCTCTACT CGTGGTCTGA ATTCGACCTC
1651  ACACACTGAT TCTCCTGTTT CTGGGGGAGG ATTCTCAGAA GGTGGCTCAT
      TGTGTGACTA AGAGGACAAA GACCCCCTCC TAAGAGTCTT CCACCGAGTA
1701  ATGAGTAAAA ATCGTTTTTC CTGGGTAGTT GATTCCTAAA AACTAAAAAA
      TACTCATTTT TAGCAAAAAG GACCCATCAA CTAAGGATTT TTGATTTTTT
1751  GAATACAGAG AAAAGTTTTA TCTTCAAACA AAACAGCAAT TCACATATTT
      CTTATGTCTC TTTTCAAAAT AGAAGTTTGT TTTGTCGTTA AGTGTATAAA
1801  TATCCTCTGC ACGTAAAACT GAAAATAACA ACAACAAAAA AGAAATGAAA
      ATAGGAGACG TGCATTTTGA CTTTTATTGT TGTTGTTTTT TCTTTACTTT
1851  GTTTTTGCTT TCAGGAATAA GCTTTTAAAA TCCAGAAACT AGATTTCGTC
      CAAAAACGAA AGTCCTTATT CGAAAATTTT AGGTCTTTGA TCTAAAGCAG
1901  CGGTACACGC AACTGAGTTG CCTCCTAGAG GTGGTTTGAG TTAATCAAAT
      GCCATGTGCG TTGACTCAAC GGAGGATCTC CACCAAACTC AATTAGTTTA
1951  TAATAAGACT GATCGTTAAG AACGACTGCC AAAAATACGA AAAAGCTACT
      ATTATTCTGA CTAGCAATTC TTGCTGACGG TTTTTATGCT TTTTCGATGA
2001  GGGATCCATC TTTCCAAGAC AATTTCTATT ATCTGAATTA ACACCATACC
      CCCTAGGTAG AAAGGTTCTG TTAAAGATAA TAGACTTAAT TGTGGTATGG
2051  TGGTACCCAC TGATTAAAAG CTGGGGGTTA CCAATGCGCG TGGGCACAGT
      ACCATGGGTG ACTAATTTTC GACCCCCAAT GGTTACGCGC ACCCGTGTCA
2101  TAGAAGCTTA TGTAGCAAAA ATGAGCACAT CCTGGAAGGG CCCGGGAGAA
      ATCTTCGAAT ACATCGTTTT TACTCGTGTA GGACCTTCCC GGGCCCTCTT
2151  GGTGCTCCTG GGGCAGCGCG GAGAGGGAGC TCTGAGGCTG GGGCGGCAGC
      CCACGAGGAC CCCGTCGCGC CTCTCCCTCG AGACTCCGAC CCCGCCGTCG
2201  GGTGCTTGCC GCCGTCCCCC TGGTCGCTCC CGGAATTAAC GCCGCGCACG
      CCACGAACGG CGGCAGGGGG ACCAGCGAGG GCCTTAATTG CGGCGCGTGC
2251  CGTCGGAGGC ATGGCCCCGT CCCGACCCCG TTTGGCGGCT CACCTCGCAG
      GCAGCCTCCG TACCGGGGCA GGGCTGGGGC AAACCGCCGA GTGGAGCGTC
2301  GCCGGCACAG CACGGCTGCT CGCGGCAGCA GAAGAGGAAG ATGCAGCGGT
      CGGCCGTGTC GTGCCGACGA GCGCCGTCGT CTTCTCCTTC TACGTCGCCA
2351  GGAAGGCGTC CGGGCGGCCA GGCAGCGGCG CATACACCTG CAGCAGGAAG
      CCTTCCGCAG GCCCGCCGGT CCGTCGCCGC GTATGTGGAC GTCGTCCTTC
2401  GAGAGCGGGC GGCCGCACAG CTCGCAGGCC AGGGCCTGGG GCCCCGGCAG
      CTCTCGCCCG CCGGCGTGTC GAGCGTCCGG TCCCGGACCC CGGGGCCGTC
2451  CCCGGCCGCG CCCAGCCATG CCGGCCGCCC GCCCACCTTG CTGGGGAACT
      GGGCCGGCGC GGGTCGGTAC GGCCGGCGGG CGGGTGGAAC GACCCCTTGA
2501  GCTCGCTGCG CAGTCGCCAC GCCGGCGCCG ACTCGGCGAA GCCCAGCTCC
      CGAGCGACGC GTCAGCGGTG CGGCCGCGGC TGAGCCGCTT CGGGTCGAGG
2551  ACAGGCCTGG CCCCGGCGGC AGCCATGCGG GGCGCGGGCT GGCGTGGGGC
      TGTCCGGACC GGGGCCGCCG TCGGTACGCC CCGCGCCCGA CCGCACCCCG
2601  GCAGCCCACA GCTGGGTCGG AAGGCGGAAA TCGGGCGCCG GGCCGGAAGG
      CGTCGGGTGT CGACCCAGCC TTCCGCCTTT AGCCCGCGGC CCGGCCTTCC
2651  CAAGAGGCGG GCACCTTTCC GGAGGACAGG AGGCGGAAAC GCGTCTGACG
      GTTCTCCGCC CGTGGAAAGG CCTCCTGTCC TCCGCCTTTG CGCAGACTGC
2701  GGAGCGGTTG CAGGACCAAT GCGAGGGAAC GGGGCAGAGG AAACCTCTCG
      CCTCGCCAAC GTCCTGGTTA CGCTCCCTTG CCCCGTCTCC TTTGGAGAGC
2751  GCATCAGCCC CGCCCCTGGC GCCTCTGCCT CCGAGCCGCT TTCCTGGTGC
      CGTAGTCGGG GCGGGGACCG CGGAGACGGA GGCTCGGCGA AAGGACCACG
2801  CTCCGGGTGC TCTGGGATGG TTCTGGTCTT TGGGAGAGTG GCAGCTGGTG
      GAGGCCCACG AGACCCTACC AAGACCAGAA ACCCTCTCAC CGTCGACCAC
2851  ACGGCGCTCC GCTCACCTCT GCACATGTCT TGCTGTGGGC CTGCGGGTGG
      TGCCGCGAGG CGAGTGGAGA CGTGTACAGA ACGACACCCG GACGCCCACC
2901  CCGCCAGGGA GGCAGAGCCC TCCCGCAAAC CTTCCCTGCT GGTGTCCACC
      GGCGGTCCCT CCGTCTCGGG AGGGCGTTTG GAAGGGACGA CCACAGGTGG
2951  TCAGGGTGTG GGAAACCTGT GCGCTGGCCG AGTGCTAACC AAGAGTAGGC
      AGTCCCACAC CCTTTGGACA CGCGACCGGC TCACGATTGG TTCTCATCCG
3001  AGTGAAAGAC AAATGAAGGT TGAACAGGTA AAGTGAGGAC CCTACAGCGG
      TCACTTTCTG TTTACTTCCA ACTTGTCCAT TTCACTCCTG GGATGTCGCC
3051  AAACCAAGAA TCCTGTGTGC CTGAGAGTAA TGAAGAAGCC TCTGCAGAAG
      TTTGGTTCTT AGGACACACG GACTCTCATT ACTTCTTCGG AGACGTCTTC
3101  AGTCTTTTCT GTCAGTCTTA AGGTCTCTGT TTTAATGTTA GTGCTGGCTT
      TCAGAAAAGA CAGTCAGAAT TCCAGAGACA AAATTACAAT CACGACCGAA
3151  GCTGTACCTG AATTCCAAGG GAGGAGTGTA TAATGAGGCA TGGCCAACCC
      CGACATGGAC TTAAGGTTCC CTCCTCACAT ATTACTCCGT ACCGGTTGGG
```

Figure 31cont.

```
3201  CCACTTCCCA TCATTGCCTG AACTAGTTTT TCAGGTTAAC TTCAGAATGC
      GGTGAAGGGT AGTAACGGAC TTGATCAAAA AGTCCAATTG AAGTCTTACG
3251  CCTTGGTACC GCGGGCCCCC TCTGTGGTCC CACGCCACTG ATCGCTGCAT
      GGAACCATGG CGCCCGGGGG AGACACCAGG GTGCGGTGAC TAGCGACGTA
3301  GCCCACCACC TGGGTACACA CAGTCTGTGA TTCCCGGAGC AGAACGGACC
      CGGGTGGTGG ACCCATGTGT GTCAGACACT AAGGGCCTCG TCTTGCCTGG
3351  CTGCCCACCC GGTCTTGTGT GCTACTCAGT GGACAGACCC AAGGCAAGAA
      GACGGGTGGG CCAGAACACA CGATGAGTCA CCTGTCTGGG TTCCGTTCTT
3401  AGGGTGACAA GGACAGGGTC TTCCCAGGCT GGCTTTGAGT TCCTAGCACC
      TCCCACTGTT CCTGTCCCAG AAGGGTCCGA CCGAAACTCA AGGATCGTGG
3451  GCCCCGCCCC CAATCCTCTG TGGCACATGG AGTCTTGGTC CCCAGAGTCC
      CGGGGCGGGG GTTAGGAGAC ACCGTGTACC TCAGAACCAG GGGTCTCAGG
3501  CCCAGCGGCC TCCAGATGGT CTGGGAGGGC AGTTCAGCTG TGGCTGCGCA
      GGGTCGCCGG AGGTCTACCA GACCCTCCCG TCAAGTCGAC ACCGACGCGT
3551  TAGCAGACAT ACAACGGACG GTGGGCCCAG ACCCAGGCTG TGTAGACCCA
      ATCGTCTGTA TGTTGCCTGC CACCCGGGTC TGGGTCCGAC ACATCTGGGT
3601  GCCCCCCCGC CCCGCAGTGC CTAGGTCACC CACTAACGCC CCAGGCCTGG
      CGGGGGGGCG GGGCGTCACG GATCCAGTGG GTGATTGCGG GGTCCGGACC
3651  TCTTGGCTGG GCGTGACTGT TACCCTCAAA AGCAGGCAGC TCCAGGGTAA
      AGAACCGACC CGCACTGACA ATGGGAGTTT TCGTCCGTCG AGGTCCCATT
3701  AAGGTGCCCT GCCCTGTAGA GCCCACTTCC TTCCCAGGGC TGCGGCTGGG
      TTCCACGGGA CGGGACATCT CGGGTGAAGG AAGGGTCCCG ACGCCGACCC
3751  TAGGTTTGTA GCCTTCATCA CGGGCCACCT CCAGCCACTG GACCGCTGGC
      ATCCAAACAT CGGAAGTAGT GCCCGGTGGA GGTCGGTGAC CTGGCGACCG
3801  CCCTGCCCTG TCCTGGGGAG TGTGGTCCTG CGACTCTAAT GGCCGCAAGC
      GGGACGGGAC AGGACCCCTC ACACCAGGAC GCTGAGATTA CCGGCGTTCG
3851  CACCTGACTC CCCCAACACC ACACTCTACC TCTCAAGCCC AGGTCTCTCC
      GTGGACTGAG GGGGTTGTGG TGTGAGATGG AGAGTTCGGG TCCAGAGAGG
3901  CTAGTGACCC ACCCAGCACA TTTAGCTAGC TGAGCCCCAC AGCCAGAGGT
      GATCACTGGG TGGGTCGTGT AAATCGATCG ACTCGGGGTG TCGGTCTCCA
3951  CCTCAGGCCC TGCTTTCAGG GCAGTTGCTC TGAAGTCGGC AAGGGGGAGT
      GGAGTCCGGG ACGAAAGTCC CGTCAACGAG ACTTCAGCCG TTCCCCCTCA
4001  GACTGCCTGG CCACTCCATG CCCTCCAAGA GCTCCTTCTG CAGGAGCGTA
      CTGACGGACC GGTGAGGTAC GGGAGGTTCT CGAGGAAGAC GTCCTCGCAT
4051  CAGAACCCAG GGCCCTGGCA CCCGTGCAGA CCCTGGCCCA CCCCACCTGG
      GTCTTGGGTC CCGGGACCGT GGGCACGTCT GGGACCGGGT GGGGTGGACC
4101  GCGCTCAGTG CCCAAGAGAT GTCCACACCT AGGATGTCCC GCGGTGGGTG
      CGCGAGTCAC GGGTTCTCTA CAGGTGTGGA TCCTACAGGG CGCCACCCAC
4151  GGGGGCCCGA GAGACGGGCA GGCCGGGGGC AGGCCTGGCC ATGCGGGGCC
      CCCCCGGGCT CTCTGCCCGT CCGGCCCCCG TCCGGACCGG TACGCCCCGG
4201  GAACCGGGCA CTGCCCAGCG TGGGGCGCGG GGGCCACGGC GCGCGCCCCC
      CTTGGCCCGT GACGGGTCGC ACCCCGCGCC CCCGGTGCCG CGCGCGGGGG
4251  AGCCCCCGGG CCCAGCACCC CAAGGCGGCC AACGCCAAAA CTCTCCCTCC
      TCGGGGGCCC GGGTCGTGGG GTTCCGCCGG TTGCGGTTTT GAGAGGGAGG
4301  TCCTCTTCCT CAATCTCGCT CTCGCTCTTT TTTTTTTTCG CAAAAGGAGG
      AGGAGAAGGA GTTAGAGCGA GAGCGAGAAA AAAAAAAAGC GTTTTCCTCC
4351  GGAGAGGGGG TAAAAAAATG CTGCACTGTG CGGCGAAGCC GGTGAGTGAG
      CCTCTCCCCC ATTTTTTTAC GACGTGACAC GCCGCTTCGG CCACTCACTC
4401  CGGCGCGGGG CCAATCAGCG TGCGCCGTTC CGAAAGTTGC CTTTTATGGC
      GCCGCGCCCC GGTTAGTCGC ACGCGGCAAG GCTTTCAACG GAAAATACCG
4451  TCGAGCGGCC GCGGCGGCGC CCTATAAAAC CCAGCGGCGC GACGCGCCAC
      AGCTCGCCGG CGCCGCCGCG GGATATTTTG GGTCGCCGCG CTGCGCGGTG
4501  CACCGCCGAG ACCGCGTCCG CCCGCGAGCA CAGAGCCTCG CCTTTGCCGA
      GTGGCGGCTC TGGCGCAGGC GGGCGCTCGT GTCTCGGAGC GGAAACGGCT
4551  TCCGCCGCCC GTCCACACCC GCCGCCAGGT AAGCCCGGCC AGCCGACCGG
      AGGCGGCGGG CAGGTGTGGG CGGCGGTCCA TTCGGGCCGG TCGGCTGGCC
4601  GGCATGCGGC CGCGGCCCTT CGCCCGTGCA GAGCCGCCGT CTGGGCCGCA
      CCGTACGCCG GCGCCGGGAA GCGGGCACGT CTCGGCGGCA GACCCGGCGT
4651  GCGGGGGGCG CATGGGGCGG AACCGGACCG CCGTGGGGGG CGCGGGAGAA
      CGCCCCCCGC GTACCCCGCC TTGGCCTGGC GGCACCCCCC GCGCCCTCTT
4701  GCCCCTGGGC CTCCGGAGAT GGGGGACACC CCACGCCAGT TCGCAGGCGC
      CGGGGACCCG GAGGCCTCTA CCCCCTGTGG GGTGCGGTCA AGCGTCCGCG
4751  GAGGCCGCGC TCGGGCGGGC GCGCTCCGGG GGTGCCGCTC TCGGGGCGGG
      CTCCGGCGCG AGCCCGCCCG CGCGAGGCCC CCACGGCGAG AGCCCCGCCC
4801  GGCAACCGGC GGGGTCTTTG TCTGAGCCGG GCTCTTGCCA ATGGGGATCG
      CCGTTGGCCG CCCCAGAAAC AGACTCGGCC CGAGAACGGT TACCCCTAGC
```

Figure 31 cont.

```
4851   CACGGTGGGC GCGGCGTAGC CCCCGTCAGG CCCGGTGGGG GCTGGGGCGC
       GTGCCACCCG CGCCGCATCG GGGGCAGTCC GGGCCACCCC CGACCCCGCG
4901   CATGCGCGTG CGCGCTGGTC CTTTGGGCGC TAACTGCGTG CGCGCTGGGA
       GTACGCGCAC GCGCGACCAG GAAACCCGCG ATTGACGCAC GCGCGACCCT
4951   ATTGGCGCTA ATTGCGCGTG CGCGCTGGGA CTCAATGGCG CTAATCGCGC
       TAACCGCGAT TAACGCGCAC GCGCGACCCT GAGTTACCGC GATTAGCGCG
5001   GTGCGTTCTG GGGCCCGGGC GCTTGCGCCA CTTCCTGCCC GAGCCGCTGG
       CACGCAAGAC CCCGGGCCCG CGAACGCGGT GAAGGACGGG CTCGGCGACC
5051   CGCCCGAGGG TGTGGCCGCT GCGTGCGCGC GCGCGACCCG GTCGCTGTTT
       GCGGGCTCCC ACACCGGCGA CGCACGCGCG CGCGCTGGGC CAGCGACAAA
5101   GAACCGGGCG GAGGCGGGGC TGGCGCCCGG TTGGGAGGGG GTTGGGGCCT
       CTTGGCCCGC CTCCGCCCCG ACCGCGGGCC AACCCTCCCC CAACCCCGGA
5151   GGCTTCCTGC CGCGCGCCGC GGGGACGCCT CCGACCAGTG TTTGCCTTTT
       CCGAAGGACG GCGCGCGGCG CCCCTGCGGA GGCTGGTCAC AAACGGAAAA
5201   ATGGTAATAA CGCGGCCGGC CCGGCTTCCT TTGTCCCCAA TCTGGGCGCG
       TACCATTATT GCGCCGGCCG GGCCGAAGGA AACAGGGGTT AGACCCGCGC
5251   CGCCGGCGCC CCCTGGCGGC CTAAGGACTC GGCGCGCCGG AAGTGGCCAG
       GCGGCCGCGG GGGACCGCCG GATTCCTGAG CCGCGCGGCC TTCACCGGTC
5301   GGCGGGGGCG ACTTCGGCTC ACAGCGCGCC CGGCTATTCT CGCAGCTCAC
       CCGCCCCCGC TGAAGCCGAG TGTCGCGCGG GCCGATAAGA GCGTCGAGTG
5351   CATGCCGGTC GCCACCATGA GCTTATCGAT ACCGGTGGCG CGCCAATTGT
       GTACGGCCAG CGGTGGTACT CGAATAGCTA TGGCCACCGC GCGGTTAACA
5401   TAATTAAGAT CTGGCCCAAT GGGCCGTACG AATTTGAGGC GGAAAGAACC
       ATTAATTCTA GACCGGGTTA CCCGGCATGC TTAAACTCCG CCTTTCTTGG
5451   AGCTGTGGAA TGTGTGTCAG TTAGGGTGTG GAAAGTCCCC AGGCTCCCCA
       TCGACACCTT ACACACAGTC AATCCCACAC CTTTCAGGGG TCCGAGGGGT
5501   GCAGGCAGAA GTATGCAAAG CATGCATCTC AATTAGTCAG CAACCAGGTG
       CGTCCGTCTT CATACGTTTC GTACGTAGAG TTAATCAGTC GTTGGTCCAC
5551   TGGAAAGTCC CCAGGCTCCC CAGCAGGCAG AAGTATGCAA AGCATGCATC
       ACCTTTCAGG GGTCCGAGGG GTCGTCCGTC TTCATACGTT TCGTACGTAG
5601   TCAATTAGTC AGCAACCATA GTCCCGCCCC TAACTCCGCC CATCCCGCCC
       AGTTAATCAG TCGTTGGTAT CAGGGCGGGG ATTGAGGCGG GTAGGGCGGG
5651   CTAACTCCGC CCAGTTCCGC CCATTCTCCG CCCCATGGCT GACTAATTTT
       GATTGAGGCG GGTCAAGGCG GGTAAGAGGC GGGGTACCGA CTGATTAAAA
5701   TTTTATTTAT GCAGAGGCCG AGGCCGCCTC GGCCTCTGAG CTATTCCAGA
       AAAATAAATA CGTCTCCGGC TCCGGCGGAG CCGGAGACTC GATAAGGTCT
5751   AGTAGTGAGG AGGCTTTTTT GGAGGCCTAG GCTTTTGCAA AGATCGATCA
       TCATCACTCC TCCGAAAAAA CCTCCGGATC CGAAAACGTT TCTAGCTAGT
5801   AGAGACAGGA TGAGGATCGT TTCGCATGAT TGAACAAGAT GGATTGCACG
       TCTCTGTCCT ACTCCTAGCA AAGCGTACTA ACTTGTTCTA CCTAACGTGC
5851   CAGGTTCTCC GGCCGCTTGG GTGGAGAGGC TATTCGGCTA TGACTGGGCA
       GTCCAAGAGG CCGGCGAACC CACCTCTCCG ATAAGCCGAT ACTGACCCGT
5901   CAACAGACAA TCGGCTGCTC TGATGCCGCC GTGTTCCGGC TGTCAGCGCA
       GTTGTCTGTT AGCCGACGAG ACTACGGCGG CACAAGGCCG ACAGTCGCGT
5951   GGGGCGCCCG GTTCTTTTTG TCAAGACCGA CCTGTCCGGT GCCCTGAATG
       CCCCGCGGGC CAAGAAAAAC AGTTCTGGCT GGACAGGCCA CGGGACTTAC
6001   AACTGCAAGA CGAGGCAGCG CGGCTATCGT GGCTGGCCAC GACGGGCGTT
       TTGACGTTCT GCTCCGTCGC GCCGATAGCA CCGACCGGTG CTGCCCGCAA
6051   CCTTGCGCAG CTGTGCTCGA CGTTGTCACT GAAGCGGGAA GGGACTGGCT
       GGAACGCGTC GACACGAGCT GCAACAGTGA CTTCGCCCTT CCCTGACCGA
6101   GCTATTGGGC GAAGTGCCGG GGCAGGATCT CCTGTCATCT CACCTTGCTC
       CGATAACCCG CTTCACGGCC CCGTCCTAGA GGACAGTAGA GTGGAACGAG
6151   CTGCCGAGAA AGTATCCATC ATGGCTGATG CAATGCGGCG GCTGCATACG
       GACGGCTCTT TCATAGGTAG TACCGACTAC GTTACGCCGC CGACGTATGC
6201   CTTGATCCGG CTACCTGCCC ATTCGACCAC CAAGCGAAAC ATCGCATCGA
       GAACTAGGCC GATGGACGGG TAAGCTGGTG GTTCGCTTTG TAGCGTAGCT
6251   GCGAGCACGT ACTCGGATGG AAGCCGGTCT TGTCGATCAG GATGATCAAG
       CGCTCGTGCA TGAGCCTACC TTCGGCCAGA ACAGCTAGTC CTACTAGTTC
6301   AGCATCAGGG GCTCGCGCCA GCCGAACTGT TCGCCAGGCT CAAGGCGAGC
       TCGTAGTCCC CGAGCGCGGT CGGCTTGACA AGCGGTCCGA GTTCCGCTCG
6351   ATGCCCGACG GCGAGGATCT CGTCGTGACC CATGGCGATG CCTGCTTGCC
       TACGGGCTGC CGCTCCTAGA GCAGCACTGG GTACCGCTAC GGACGAACGG
6401   GAATATCATG GTGGAAAATG GCCGCTTTTC TGGATTCATC GACTGTGGCC
       CTTATAGTAC CACCTTTTAC CGGCGAAAAG ACCTAAGTAG CTGACACCGG
6451   GGCTGGGTGT GGCGGACCGC TATCAGGACA TAGCGTTGGC TACCCGTGAT
       CCGACCCACA CCGCCTGGCG ATAGTCCTGT ATCGCAACCG ATGGGCACTA
```

Figure 31 cont.

```
6501  ATTGCTGAAG AGCTTGGCGG CGAATGGGCT GACCGCTTCC TCGTGCTTTA
      TAACGACTTC TCGAACCGCC GCTTACCCGA CTGGCGAAGG AGCACGAAAT
6551  CGGTATCGCC GCTCCCGATT CGCAGCGCAT CGCCTTCTAT CGCCTTCTTG
      GCCATAGCGG CGAGGGCTAA GCGTCGCGTA GCGGAAGATA GCGGAAGAAC
6601  ACGAGTTCTT CTGAGCGGGA CTCTGGGGTT CGAAATGACC GACCAAGCGA
      TGCTCAAGAA GACTCGCCCT GAGACCCCAA GCTTTACTGG CTGGTTCGCT
6651  CGCCCAACCT GCCATCACGA GATTTCGATT CCACCGCCGC CTTCTATGAA
      GCGGGTTGGA CGGTAGTGCT CTAAAGCTAA GGTGGCGGCG GAAGATACTT
6701  AGGTTGGGCT TCGGAATCGT TTTCCGGGAC GCCGGCTGGA TGATCCTCCA
      TCCAACCCGA AGCCTTAGCA AAAGGCCCTG CGGCCGACCT ACTAGGAGGT
6751  GCGCGGGGAT CTCATGCTGG AGTTCTTCGC CCACCCTAGG GGGAGGCTAA
      CGCGCCCCTA GAGTACGACC TCAAGAAGCG GGTGGGATCC CCCTCCGATT
6801  CTGAAACACG GAAGGAGACA ATACCGGAAG GAACCCGCGC TATGACGGCA
      GACTTTGTGC CTTCCTCTGT TATGGCCTTC CTTGGGCGCG ATACTGCCGT
6851  ATAAAAAGAC AGAATAAAAC GCACGGTGTT GGGTCGTTTG TTCATAAACG
      TATTTTTCTG TCTTATTTTG CGTGCCACAA CCCAGCAAAC AAGTATTTGC
6901  CGGGGTTCGG TCCCAGGGCT GGCACTCTGT CGATACCCCA CCGAGACCCC
      GCCCCAAGCC AGGGTCCCGA CCGTGAGACA GCTATGGGGT GGCTCTGGGG
6951  ATTGGGGCCA ATACGCCCGC GTTTCTTCCT TTTCCCCACC CCACCCCCCA
      TAACCCCGGT TATGCGGGCG CAAAGAAGGA AAAGGGGTGG GGTGGGGGGT
7001  AGTTCGGGTG AAGGCCCAGG GCTCGCAGCC AACGTCGGGG CGGCAGGCCC
      TCAAGCCCAC TTCCGGGTCC CGAGCGTCGG TTGCAGCCCC GCCGTCCGGG
7051  TGCCATAGCC TCAAATTCCT TAGGCTCGAG GGCCGCCACC GCGGTGGAGC
      ACGGTATCGG AGTTTAAGGA ATCCGAGCTC CCGGCGGTGG CGCCACCTCG
7101  TCCAGCTTTT GTTCCCTTTA GTGAGGGTTA ATTTCGAGCT TGGCGTAATC
      AGGTCGAAAA CAAGGGAAAT CACTCCCAAT TAAAGCTCGA ACCGCATTAG
7151  ATGGTCATAG CTGTTTCCTG TGTGAAATTG TTATCCGCTC ACAATTCCAC
      TACCAGTATC GACAAAGGAC ACACTTTAAC AATAGGCGAG TGTTAAGGTG
7201  ACAACATACG AGCCGGAAGC ATAAAGTGTA AAGCCTGGGG TGCCTAATGA
      TGTTGTATGC TCGGCCTTCG TATTTCACAT TTCGGACCCC ACGGATTACT
7251  GTGAGCTAAC TCACATTAAT TGCGTTGCGC TCACTGCCCG CTTTCCAGTC
      CACTCGATTG AGTGTAATTA ACGCAACGCG AGTGACGGGC GAAAGGTCAG
7301  GGGAAACCTG TCGTGCCAGC ATCGCGAGCA CTTTTCGGGG AAATGTGCGC
      CCCTTTGGAC AGCACGGTCG TAGCGCTCGT GAAAAGCCCC TTTACACGCG
7351  GGAACCCCTA TTTGTTTATT TTTCTAAATA CATTCAAATA TGTATCCGCT
      CCTTGGGGAT AAACAAATAA AAAGATTTAT GTAAGTTTAT ACATAGGCGA
7401  CATGAGACAA TAACCCTGAT AAATGCTTCA ATAATATTGA AAAAGGAAGA
      GTACTCTGTT ATTGGGACTA TTTACGAAGT TATTATAACT TTTTCCTTCT
7451  GTATGAGTAT TCAACATTTC CGTGTCGCCC TTATTCCCTT TTTTGCGGCA
      CATACTCATA AGTTGTAAAG GCACAGCGGG AATAAGGGAA AAAACGCCGT
7501  TTTTGCCTTC CTGTTTTTGC TCACCCAGAA ACGCTGGTGA AAGTAAAAGA
      AAAACGGAAG GACAAAAACG AGTGGGTCTT TGCGACCACT TTCATTTTCT
7551  TGCTGAAGAT CAGTTGGGTG CACGAGTGGG TTACATCGAA CTGGATCTCA
      ACGACTTCTA GTCAACCCAC GTGCTCACCC AATGTAGCTT GACCTAGAGT
7601  ACAGCGGTAA GATCCTTGAG AGTTTTCGCC CCGAAGAACG TTTTCCAATG
      TGTCGCCATT CTAGGAACTC TCAAAAGCGG GGCTTCTTGC AAAAGGTTAC
7651  ATGAGCACTT TTAAAGTTCT GCTATGTGGC GCGGTATTAT CCCGTATTGA
      TACTCGTGAA AATTTCAAGA CGATACACCG CGCCATAATA GGGCATAACT
7701  CGCCGGGCAA GAGCAACTCG GTCGCCGCAT ACACTATTCT CAGAATGACT
      GCGGCCCGTT CTCGTTGAGC CAGCGGCGTA TGTGATAAGA GTCTTACTGA
7751  TGGTTGAGTA CTCACCAGTC ACAGAAAAGC ATCTTACGGA TGGCATGACA
      ACCAACTCAT GAGTGGTCAG TGTCTTTTCG TAGAATGCCT ACCGTACTGT
7801  GTAAGAGAAT TATGCAGTGC TGCCATAACC ATGAGTGATA ACACTGCGGC
      CATTCTCTTA ATACGTCACG ACGGTATTGG TACTCACTAT TGTGACGCCG
7851  CAACTTACTT CTGACAACGA TCGGAGGACC GAAGGAGCTA ACCGCTTTTT
      GTTGAATGAA GACTGTTGCT AGCCTCCTGG CTTCCTCGAT TGGCGAAAAA
7901  TGCACAACAT GGGGGATCAT GTAACTCGCC TTGATCGTTG GGAACCGGAG
      ACGTGTTGTA CCCCCTAGTA CATTGAGCGG AACTAGCAAC CCTTGGCCTC
7951  CTGAATGAAG CCATACCAAA CGACGAGCGT GACACCACGA TGCCTGTAGC
      GACTTACTTC GGTATGGTTT GCTGCTCGCA CTGTGGTGCT ACGGACATCG
8001  AATGGCAACA ACGTTGCGCA AACTATTAAC TGGCGAACTA CTTACTCTAG
      TTACCGTTGT TGCAACGCGT TTGATAATTG ACCGCTTGAT GAATGAGATC
8051  CTTCCCGGCA ACAATTAATA GACTGGATGG AGGCGGATAA AGTTGCAGGA
      GAAGGGCCGT TGTTAATTAT CTGACCTACC TCCGCCTATT TCAACGTCCT
8101  CCACTTCTGC GCTCGGCCCT TCCGGCTGGC TGGTTTATTG CTGATAAATC
      GGTGAAGACG CGAGCCGGGA AGGCCGACCG ACCAAATAAC GACTATTTAG
```

Figure 31 cont.

```
8151  TGGAGCCGGT GAGCGTGGGT CTCGCGGTAT CATTGCAGCA CTGGGGCCAG
      ACCTCGGCCA CTCGCACCCA GAGCGCCATA GTAACGTCGT GACCCCGGTC
8201  ATGGTAAGCC CTCCCGTATC GTAGTTATCT ACACGACGGG GAGTCAGGCA
      TACCATTCGG GAGGGCATAG CATCAATAGA TGTGCTGCCC CTCAGTCCGT
8251  ACTATGGATG AACGAAATAG ACAGATCGCT GAGATAGGTG CCTCACTGAT
      TGATACCTAC TTGCTTTATC TGTCTAGCGA CTCTATCCAC GGAGTGACTA
8301  TAAGCATTGG TAACTGTCAG ACTCGCGACA CTGCATTAAT GAATCGGCCA
      ATTCGTAACC ATTGACAGTC TGAGCGCTGT GACGTAATTA CTTAGCCGGT
8351  ACGCGCGGGG AGAGGCGGTT TGCGTATTGG GCGCTCTTCC GCTTCCTCGC
      TGCGCGCCCC TCTCCGCCAA ACGCATAACC CGCGAGAAGG CGAAGGAGCG
8401  TCACTGACTC GCTGCGCTCG GTCGTTCGGC TGCGGCGAGC GGTATCAGCT
      AGTGACTGAG CGACGCGAGC CAGCAAGCCG ACGCCGCTCG CCATAGTCGA
8451  CACTCAAAGG CGGTAATACG GTTATCCACA GAATCAGGGG ATAACGCAGG
      GTGAGTTTCC GCCATTATGC CAATAGGTGT CTTAGTCCCC TATTGCGTCC
8501  AAAGAACATG TGAGCAAAAG GCCAGCAAAA GGCCAGGAAC CGTAAAAAGG
      TTTCTTGTAC ACTCGTTTTC CGGTCGTTTT CCGGTCCTTG GCATTTTTCC
8551  CCGCGTTGCT GGCGTTTTTC CATAGGCTCC GCCCCCCTGA CGAGCATCAC
      GGCGCAACGA CCGCAAAAAG GTATCCGAGG CGGGGGGACT GCTCGTAGTG
8601  AAAAATCGAC GCTCAAGTCA GAGGTGGCGA AACCCGACAG GACTATAAAG
      TTTTTAGCTG CGAGTTCAGT CTCCACCGCT TTGGGCTGTC CTGATATTTC
8651  ATACCAGGCG TTTCCCCCTG GAAGCTCCCT CGTGCGCTCT CCTGTTCCGA
      TATGGTCCGC AAAGGGGGAC CTTCGAGGGA GCACGCGAGA GGACAAGGCT
8701  CCCTGCCGCT TACCGGATAC CTGTCCGCCT TTCTCCCTTC GGGAAGCGTG
      GGGACGGCGA ATGGCCTATG GACAGGCGGA AAGAGGGAAG CCCTTCGCAC
8751  GCGCTTTCTC ATAGCTCACG CTGTAGGTAT CTCAGTTCGG TGTAGGTCGT
      CGCGAAAGAG TATCGAGTGC GACATCCATA GAGTCAAGCC ACATCCAGCA
8801  TCGCTCCAAG CTGGGCTGTG TGCACGAACC CCCCGTTCAG CCCGACCGCT
      AGCGAGGTTC GACCCGACAC ACGTGCTTGG GGGGCAAGTC GGGCTGGCGA
8851  GCGCCTTATC CGGTAACTAT CGTCTTGAGT CCAACCCGGT AAGACACGAC
      CGCGGAATAG GCCATTGATA GCAGAACTCA GGTTGGGCCA TTCTGTGCTG
8901  TTATCGCCAC TGGCAGCAGC CACTGGTAAC AGGATTAGCA GAGCGAGGTA
      AATAGCGGTG ACCGTCGTCG GTGACCATTG TCCTAATCGT CTCGCTCCAT
8951  TGTAGGCGGT GCTACAGAGT TCTTGAAGTG GTGGCCTAAC TACGGCTACA
      ACATCCGCCA CGATGTCTCA AGAACTTCAC CACCGGATTG ATGCCGATGT
9001  CTAGAAGGAC AGTATTTGGT ATCTGCGCTC TGCTGAAGCC AGTTACCTTC
      GATCTTCCTG TCATAAACCA TAGACGCGAG ACGACTTCGG TCAATGGAAG
9051  GGAAAAAGAG TTGGTAGCTC TTGATCCGGC AAACAAACCA CCGCTGGTAG
      CCTTTTTCTC AACCATCGAG AACTAGGCCG TTTGTTTGGT GGCGACCATC
9101  CGGTGGTTTT TTTGTTTGCA AGCAGCAGAT TACGCGCAGA AAAAAAGGAT
      GCCACCAAAA AAACAAACGT TCGTCGTCTA ATGCGCGTCT TTTTTTCCTA
9151  CTCAAGAAGA TCCTTTGATC TTTTCTACGG GGTCTGACGC TCAGTGGAAC
      GAGTTCTTCT AGGAAACTAG AAAAGATGCC CCAGACTGCG AGTCACCTTG
9201  GAAAACTCA
      CTTTTGAGT
```

VECTORS COMPRISING CPG ISLANDS WITHOUT POSITION EFFECT VARIGATION AND HAVING INCREASED EXPRESSION

CROSS-REFERENCE TO RELATED APPLICATIONS

This application claims priority under 35 U.S.C. §119(a) to U.K. Application No. GB0109335.0, filed Apr. 17, 2001, and claims priority under 35 U.S.C. §119(e) to U.S. Provisional Application Ser. No. 60/281,605, filed Apr. 5, 2001 and to U.S. Provisional Application Ser. No. 60/298,675, filed Jun. 15, 2001. All applications are hereby incorporated by reference in their entireties.

FIELD OF THE INVENTION

The present invention relates to a polynucleotide comprising a ubiquitous chromatin-opening element (UCOE) together with a selectable marker element. When operably linked to, and flanking, an expressible nucleic acid sequence, the combination of elements provides high and reproducible levels of gene expression. The present invention also relates to a vector comprising the polynucleotide sequence, a host cell comprising the vector and use of the polynucleotide, vector or host cell in therapy, or for applications involving protein expression in cell culture.

BACKGROUND OF THE INVENTION

The current model of chromatin structure in higher eukaryotes postulates that genes are organised in "domains" (Dillon, N. & Grosveld, F. Chromatin domains as potential units of eukaryotic gene function. *Curr. Opin. Genet. Dev.* 4, 260-264 (1994); Higgs, D. R. Do LCRs open chromatin domains? *Cell* 95, 299-302 (1998), each of which is incorporated herein by reference). Chromatin domains are envisaged to exist in either a condensed, "closed", transcriptionally silent state, or in a de-condensed, "open" and transcriptionally competent configuration. The establishment of an open chromatin structure characterized by increased DNaseI sensitivity, DNA hypomethylation and histone hyperacetylation, is considered a pre-requisite to the commencement of gene expression.

The open and closed nature of chromatin regions is reflected in the behaviour of transgenes that are randomly integrated into the host cell genome. Identical constructs give different patterns of tissue-specific and development stage-specific expression when integrated at different locations in the mouse genome (Palmiter, R. D. & Brinster, R. L. *Ann. Ref. Genet.* 20, 465-499 (1986); Allen, N. D. et al. *Nature* 333, 852-855 (1988); Bonnerot, C., Grimber, G., Briand, P. & Nicolas, J. F. *Proc. Natl. Acad. Sci. USA* 87:6331-6335 (1990), each of which is incorporated herein by reference).

A variegated expression pattern within a given transgenic mouse tissue, known as position effect variegation (PEV), is also frequently observed (Kioussis, D. & Festenstein, R. *Curr. Opin. Genet. Dev.* 7, 614-619 (1997), which is incorporated herein by reference). When exogenous genes are integrated into the chromosome of mammalian cells cultures in vitro, many of the integration events result in rapid silencing of the transgene and the remainder give large variability in expression levels (Pikaart, M. J., Recillas-Targa, F. & Felsenfield, G. *Genes Dev.* 12, 2852-2862 (1998); Fussenegger, M., Bailey, J. E., Hauser, H. & Mueller, P. P *Trends Biotech.* 17, 35-42 (1999), each of which is incorporated herein by reference). These position effects render transgene expression inefficient, with implication for both basic research and biotechnology applications.

The chromatin domain model of gene organization suggests that genetic control elements that are able to establish and maintain a transcriptionally competent open chromatin structure should be associated with active regions of the genome.

Locus Control Regions (LCRs) are a class of transcriptional regulatory elements with long-range chromatin remodelling capability. LCRs are functionally defined in transgenic mice by their ability to confer site-of-integration independent, transgene copy number-dependent, physiological levels of expression on a gene linked in cis, especially single copy transgenes (Fraser, P. & Grosveld, F., *Curr. Opin. Cell Biol.* 10, 361-365 (1998); Li, Q., Harju, S. & Peterson, K. R., *Trends Genet.* 15: 403-408 (1999), each of which is incorporated herein by reference). Crucially, such expression is tissue-specific. LCRs are able to obstruct the spread of heterochromatin, prevent PEV (Kioussis, D. & Festenstein, R. *Curr. Opin. Genet. Dev.* 7, 614-619 (1997), which is incorporated herein by reference) and consist of a series of DNase I hypersensitive (HS) sites which can be located either 5' or 3' of the genes that they regulate (Li, Q., Harju, S. & Peterson, K. R. *Trends Genet.* 15: 403-408 (1999), which is incorporated herein by reference).

LCRs appear to be comprised of two separate, although not necessarily independent components. First, the establishment of an 'open chromatin domain', and second a dominant transcriptional activation capacity to confer transgene copy number dependent expression (Fraser, P. & Grosveld, F. *Curr. Opin. Cell Biol.* 10, 361-365 (1998), which is incorporated herein by reference). The molecular mechanisms by which LCRs exert their function remain a point of contention (Higgs, D. R. *Cell* 95, 299-302 (1998); Bulger, M. & Groudine, M. *Genes Dev.* 13, 2465-2477 (1999); Grosveld, F. *Curr. Opin. Genet. Dev.* 9 152-157 (1999); Bender, M. A., Bulger, M., Close, J. & Groudine, M., *Mol. Cell* 5, 387-393 (2000), each of which is incorporated herein by reference).

The generation of cultured mammalian cell lines producing high levels of a therapeutic protein product is a major developing industry. Chromatin position effects make it a difficult, time consuming and expensive process. The most commonly used approach to the production of such mammalian "cell factories" relies on gene amplification induced by a combination of a drug resistance gene (e.g., DHFR, glutamine synthetase (Kaufman R J. *Methods Enzymol* 185, 537-566 (1990), which is incorporated herein by reference), and the maintenance of stringent selective pressure. The use of vectors containing LCRs from highly expressed gene domains, using cells derived from the appropriate tissue, greatly simplifies the procedure, giving a large proportion of clonal cell lines showing stable high levels of expression (Needham M, Gooding C, Hudson K, Antoniou M, Grosfeld F and Hollis M. *Nucleic Acids Res* 20, 997-1003 (1992); Needham M, Egerton M, Millest A, Evans S, Popplewell M, Cerillo G, McPheat J, Monk A, Jack A, Johnstone D & Hollis M. *Protein Expr Purif* 6, 124-131 (1995), each of which is incorporated herein by reference).

However, the tissue-specificity of LCRs, although useful in some circumstances, is also a major limitation for many applications, for instance where no LCR is known for the tissue in which expression is required, or where expression in many, or all, tissues is required.

Our co-pending patent applications PCT/GB99/02357 (WO 00/05393), U.S. Ser. No. 09/358,082, GB 0022995.5 and U.S. 60/252,048, each of which is incorporated herein by reference, describe elements that are responsible, in their natural chromosomal context, for establishing an open chromatin structure across a locus that consists exclusively of ubiquitously expressed, housekeeping genes. These elements are not derived from an LCR and comprise extended methylation-free CpG islands. We have used the term Ubiquitous Chromatin Opening Element (UCOE) to describe such elements.

In mammalian DNA, the dinucleotide CpG is recognised by a DNA methyltransferase enzyme that methylates cytosine to 5-methylcytosine. However, 5-methylcytosine is unstable and is converted to thymine. As a result, CpG dinucleotides occur far less frequently than one would expect by chance. Some sections of genomic DNA nevertheless do have a frequency of CpG that is closer to that expected, and these sequences are known as "CpG islands". As used herein a "CpG island" is defined as a sequence of DNA, of at least 200 bp, that has a GC content of at least 50% and an observed/expected CpG content ratio of at least 0.6 (i.e., a CpG dinucleotide content of at least 60% of that which would be expected by chance) (Gardiner-Green M and Frommer M. *J Mol Biol* 196, 261-282 (1987); Rice P, Longden I and Bleasby A *Trends Genet* 16, 276-277 (2000), each of which is incorporated herein by reference).

Methylation-free CpG islands are well-known in the art (Bird et al. (1985) Cell 40: 91-99; Tazi & Bird (1990) Cell 60: 909-920, each of which is incorporated herein by reference) and may be defined as CpG islands where a substantial proportion of the cytosine residues are not methylated and which usually extend over the 5' ends of two closely spaced (0.1-3 kb) divergently transcribed genes. These regions of DNA are reported to remain hypomethylated in all tissues throughout development (Wise and Pravtcheva (1999) Genomics 60: 258-271, which is incorporated herein by reference). They are often associated with the 5' ends of ubiquitously expressed genes, as well as an estimated 40% of genes showing a tissue-restricted expression profile (Antequera, F. & Bird, A. *Proc. Natl. Acad. Sci. USA* 90, 1195-11999 (1993); Cross, S. H. & Bird, A. P. *Curr. Opin, Genet. Dev.* 5, 309-314 (1995), each of which is incorporated herein by reference), and are known to be localized regions of active chromatin (Tazi, J. & Bird, A. *Cell* 60, 909-920 (1990), which is incorporated herein by reference).

An 'extended' methylation-free CpG island is a methylation-free CpG island that extends across a region encompassing more than one transcriptional start site and/or extends for more than 300 bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognises and digests at the site CCGG, which is commonly found within CpG islands, but only if the central CG residues are not methylated. Therefore, PCR conducted with HpaII-digested DNA and over a region harboring HpaII sites, does not give an amplification product due to HpaII digestion if the DNA is unmethylated. The PCR will only give an amplified product if the DNA is methylated. Therefore, beyond the methylation-free region HpaII will not digest the DNA a PCR amplified product will be observed thereby defining the boundaries of the "extended methylation-free CpG island".

We have demonstrated (WO 00/05393, which is incorporated herein by reference) that regions spanning methylation-free CpG islands encompassing dual, divergently transcribed promoters from the human TATA binding protein (TBP)/proteosome component-B1 (PSMBI) and heterogeneous nuclear ribonucleoprotein A2/B1 (hnRNPA2)/heterochromatin protein 1Hsγ ($HP1^{Hs\gamma}$) gene loci give reproducible, physiological levels of gene expression and that they are able to prevent a variegated expression pattern and silencing that normally occurs with transgene integration within centromeric heterochromatin.

As used herein, the term "reproducible expression" means that the polynucleotide of the invention will direct expression of the expressible gene at substantially the same level of expression irrespective of its chromatin environment and preferably irrespective of the cell type or tissue type in which the polynucleotide of the invention may be. Those of skill in the art will recognize that substantially the same level of expression of the operably-linked expressible gene is achieved, irrespective of the chromatin environment of the claimed polynucleotide, and preferably irrespective of the cell type, assuming that the cell is capable of active gene expression.

We have shown (WO 00/05393, incorporated herein by reference) that methylation-free CpG islands associated with actively transcribing promoters possess the ability to remodel chromatin and are thus thought to be a prime determinant in establishing and maintaining an open domain at housekeeping gene loci.

UCOEs confer an increased proportion of productive gene delivery events with improvements in the level and stability of transgene expression. This has important research and biotechnological applications including the generation of transgenic animals and recombinant protein products in cultured cells. We have shown (WO 00/05393, incorporated herein by reference) beneficial effects of UCOEs on expression of the CMV-EGFP reporter construct and with the secreted, pharmaceutically valuable protein erythropoietin. The properties of UCOEs also suggest utility in gene therapy, the effectiveness of which is often limited by a low frequency of productive gene delivery events and an inadequate level and duration of expression (Verma, I. M. & Somia, N. *Nature* 389: 239-242 (1997), which is incorporated herein by reference).

Given these significant implications and wide ranging applications, there is a desire to further optimize transgene expression levels. There is a need to further increase the levels of expression obtainable by the use of a UCOE alone, particularly in the fields of in vivo gene therapy and for in vitro production of recombinant proteins.

The expression of a nucleic acid operably linked to a 5' UCOE may surprisingly be further increased by the presence of a selectable element 3' to the expressed nucleic acid, so that the expressible nucleic acid sequence is flanked by a 5' UCOE and a 3' selectable marker.

A selectable element that performs more than one function in a vector, such as providing a selectable marker as well as increasing expression of an operably linked gene, allows construction of more compact and efficient expression vectors.

Mei, Kothary and Wall (Mei, Q, Kothary, R. & Wall, L. *Exp Cell Research* 260, 304-312 (2000), which is incorporated herein by reference) disclose constructs comprising an expressible gene (β-globin) operably linked to an LCR and a pgk/puromycin resistance element. However, this work teaches that it is the combination of an expressible gene, and LCR and a tk/neomycin resistance element that is important in imposing position effects on gene expression, with the pgk/puromycin resistance element being used as a negative control. This paper teaches away from any beneficial effect being gained from the use of a pgk/puromycin resistance element. The paper does not disclose constructs comprising an extended unmethylated CpG island (or UCOE), an expressible gene and a pgk/puromycin resistance element, since the constructs comprise LCRs. Similarly, the paper does not disclose an expressible gene operably linked to a promoter with which it is not naturally linked, also operably linked to a pgk/puromycin resistance element, since in each case the β-globin gene is expressed under control of its endogenous promoter.

Artelt et al. compare the influence of neomycin and puromycin resistance genes on cis-linked genes in eukaryotic expression vectors (Artelt P, Grannemann R, Stocking C, Friel J, Bartsch J and Hauser H *Gene* 99, 249-254 (1991), which is incorporated herein by reference). They conclude that neomycin resistance genes may have a silencing effect on linked genes, but that "the gene conferring resistance to puromycin from *Streptomyces alboniger* does not influence adjacent promoters." Accordingly, there is nothing in Artelt et al. that discloses or suggests the importance of the position or spacing use of resistance genes as disclosed in the present application.

Our co-pending patent applications PCT/GB99/02357 (WO 00/05393), U.S. Ser. No. 09/358,082, GB 0022995.5 and U.S. 60/252,048 (each of which is incorporated herein by reference) disclose polynucleotides and vectors comprising extended, methylation-free CpG islands operably linked to expressible nucleic acids with antibiotic resistance genes. However, in the examples disclosed, the antibiotic gene is not adjacent and 3' to the expressible nucleic acid. The surprising contribution of such an adjacent selectable marker is likewise not disclosed or implied.

SUMMARY OF THE INVENTION

The present invention provides isolated polynucleotides comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order, in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker. The selectable marker can be an antibiotic resistance gene.

The present invention also provides vectors comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides vectors constructed such that, when linearized and integrated into a chromosome, they will deliver a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides vectors comprising (a) an extended methylation-free CpG island, (b) a multiple cloning site, and (c) an antibiotic resistance gene from a *Streptomyces* species, wherein both the CpG island and the antibiotic resistance gene are operably-linked to the expressible nucleic acid, and the components are positioned in the following order, in the 5' to 3' orientation with respect to the sense strand of the expressible nucleic acid: extended methylation-free CpG island, multiple cloning site, selectable marker, and wherein the multiple cloning site is within 2000 bp of the proximal end of the antibiotic resistance gene.

The present invention also provides host cells transfected with a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order, in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides methods for obtaining the expression of an expressible nucleic acid comprising expressing, in a host cell, a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides methods for obtaining the expression of an expressible nucleic acid comprising expressing, in a host cell, a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides a method for obtaining a desired gene product comprising expressing, in a host cell, a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker, and recovering the desired gene product.

The present invention also provides a method for obtaining a desired gene product comprising expressing, in a host cell, a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker, and recovering the desired gene product.

The present invention also provides methods of therapy or treatment comprising administering to a patient a pharmaceutically effective amount of a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides methods of therapy or treatment comprising administering to a patient a pharmaceutically effective amount of a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides a method of therapy or treatment comprising administering to a patient a pharmaceutically effective amount of a host cell comprising a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker.

The present invention also provides pharmaceutical compositions comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker, in combination with a pharmaceutically acceptable excipient.

The present invention also provides pharmaceutical compositions comprising a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker, in combination with a pharmaceutically acceptable excipient.

The present invention also provides pharmaceutical compositions comprising a host cell comprising a vector comprising a polynucleotide comprising (a) an extended methylation-free CpG island, (b) an expressible nucleic acid terminated by a polyadenylation signal, and (c) a selectable marker operably linked to a promoter, wherein both the CpG island and the selectable marker are operably-linked to the expressible nucleic acid, and wherein the components are positioned in the following order in the 5' to 3' orientation with respect to the sense strand of the expressible nucleic acid: extended methylation-free CpG island, expressible nucleic acid, selectable marker, and wherein the polyadenylation signal at the 3' end of the expressible nucleic acid is within 2000 bp of the proximal end of the selectable marker, in combination with a pharmaceutically acceptable excipient.

The present invention also provides a non-human transgenic animal comprising an artificially introduced extended methylation-free CpG island element and an artificially introduced selectable marker, wherein both the CpG island and the selectable marker are operably-linked to the expressible nucleic acid, and the components are positioned in the following order: extended methylation-free CpG island, expressible nucleic acid, selectable marker, in the 5' to 3' orientation with respect to the sense strand of the expressible nucleic acid, and wherein the polyadenylation signal at the 3' end of the expressible nucleic acid is within 2000 bp of the proximal end of the selectable marker.

BRIEF DESCRIPTION OF THE DRAWINGS

FIG. 1 shows maps of 'empty' vectors CET200.1, CET210, CET710, and CET720. Insertion of the Enhanced Green Fluorescent Protein (EGFP) gene into the multi-cloning site (MCS) of CET200.1, CET210, CET710, and CET720 results in CET220, CET230, CET711, and CET721, respectively. All vectors contain a cytomegalovirus (CMV) promoter from which inserted genes are expressed. However, in the case of CET210 (and its EGFP-expressing derivative, CET230) although such an inserted gene would be flanked by a UCOE and a pgk/puromycin resistance element in the plasmid, the latter is not immediately adjacent. More importantly, it is separated by a PvuI site used to linearize the plasmid before transfection. After integration into the host cell chromosome, this results in the gene no longer being flanked, since both the UCOE and the pgk/puromycin resistance element will integrate in the same side of the gene. In the case of CET710 (and its EGFP-expressing derivative, CET711) and CET720 (and its EGFP-expressing derivative, CET721), PvuI linearization results in the integration of the gene closely flanked by the UCOE on one side and the pgk/puromycin resistance element on the other. CET210 (and CET230) and CET720 (and CET721) carry hnRNP-derived UCOEs, while CET710 (and CET711) carry an 'artificial' β-actin/PDCD2-derived UCOE.

FIG. 10 shows the entire double stranded nucleotide sequence of plasmid CET710 (SEQ ID NO: 1).

FIG. 12 shows the entire double stranded nucleotide sequence of plasmid CET720 (SEQ ID NO: 2).

FIG. 13 shows the double stranded nucleotide sequence of the wild-type *S. alboniger* puromycin N-acetyl transferase gene (SEQ ID NO: 5).

FIG. 14 shows the double stranded nucleotide sequence of the modified *S. alboniger* puromycin N-acetyl transferase gene (SEQ ID NO: 3).

FIG. 15 shows the double stranded nucleotide sequence of the *S. fradiae* aminoglycoside phosphotransferase gene (SEQ ID NO: 4).

FIG. 16 shows the double stranded nucleotide sequence of the *S. hygroscopicus* hygromycin phosphotransferase gene (SEQ ID NO: 6).

FIG. 17 shows the double stranded nucleotide sequence of the *E. coli* aminocyclitol phosphotransferase (hygro$^r$) gene (SEQ ID NO: 7).

FIG. 18 shows the double stranded nucleotide sequence of the transposon Tn5 (*Klebsiella pneumoniae*) neomycin phosphotransferase gene (SEQ ID NO: 8).

FIG. 19 shows the nucleotide sequence of the mouse hnRNP A2 HindIII fragment (SEQ ID NO: 15).

FIG. 21 shows the entire double stranded nucleotide sequence of plasmid CET1010 (SEQ ID NO: 9).

FIG. 23 shows the entire double stranded nucleotide sequence of plasmid CET1020 (SEQ ID NO: 10).

FIG. 25 shows the entire double stranded nucleotide sequence of CET1030 (SEQ ID NO: 11).

FIG. 27 shows the entire double stranded nucleotide sequence of plasmid CET1110 (SEQ ID NO: 12).

FIG. 29 shows the entire double stranded nucleotide sequence of plasmid CET1120 (SEQ ID NO: 13).

FIG. 31 shows the entire double stranded nucleotide sequence of plasmid CET1130 (SEQ ID NO: 14).

DETAILED DESCRIPTION OF THE INVENTION

Figure 2:
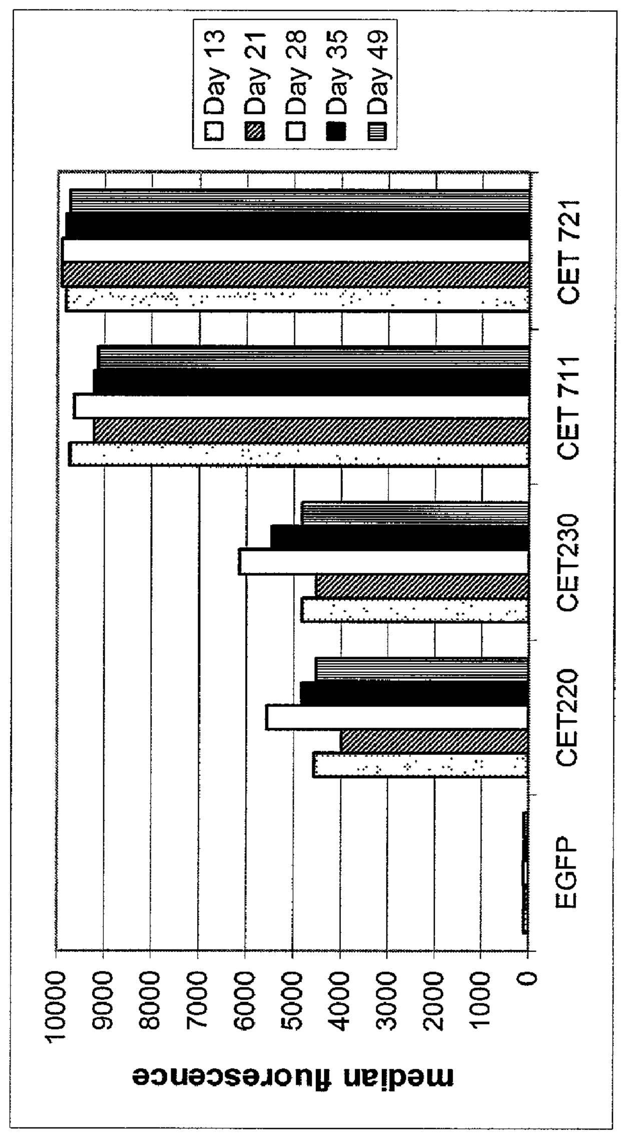
FIG. 2 shows expression of EGFP from various vectors transfected into CHO-K1 cells as measured by median fluorescence by fluorescence activated cell sorting (FACS) analysis measured on the indicated days post-transfection. 'EGFP' depicts cells transfected with a control (pEGFP) non-UCOE containing plasmid. 'CET220' depicts cells transfected with a plasmid where the EGFP expression unit is operably linked to a hnRNP-derived UCOE but not to a pgk/puromycin resistance element. Instead a SV40/neomycin resistance element is used (see FIG. 1 for CET220 structure). The remaining cells are transfected with CET230, CET711, or CET721, the structures of which are also shown in FIG. 1.

The present invention discloses that the influence of extended, unmethylated CpG islands (UCOEs) to upregulate expression of operably linked nucleic acid sequences may be further increased by the presence of a selectable element providing that said selectable marker is situated 3' of the expressible nucleic acid sequence and adjacent to it.

The terms 5' and 3' are herein used with respect to the sense strand of the expressible nucleic acid sequence. Hence the 5' end of said sequence corresponds to the start of transcription, which proceeds in a 3' direction.

As used herein, the term "operably linked" refers to a relationship of operability between elements in the polynucleotides of the invention. "Operably linked" is a term, well known to those of skill in the art, that describes a functional relationship between cis-acting DNA sequences. The exact structural relationship may or may not be relevant and differs for different types of elements. For a promoter, it implies an essentially adjacent (usually within less than 100 bp) position 5' to the open reading frame that it drives. In the case of extended methylation-free CpG islands, it appears that a regional effect on chromatin structure is responsible for increasing the level and consistency of gene expression. By way of example, the element comprising an extended methylation-free CpG-island is positioned immediately 5' of the expressible gene. However, "operably-linked" embraces the possibility of being positioned elsewhere, as long as a clear functional effect can be demonstrated.

In particular, the flanking of an expressible gene with a UCOE at the 5' end and a selectable element at the other results in an increase in expression of approximately two-fold. In some cases the increase is greater than five-fold over that obtained with a single UCOE alone.

According to the present invention, there is provided an isolated polynucleotide that enables increased levels of expression of an operably linked gene to be obtained as compared to those obtainable using an operably-linked UCOE or extended methylation-free CpG island alone.

The isolated polynucleotide comprises: an extended methylation-free CpG island, an expressible nucleic acid terminated by a polyadenylation signal and a selectable marker operably linked to a promoter, wherein both the CpG island and the selectable marker are operably-linked to the expressible nucleic acid, and the components are positioned in the order: extended methylation-free CpG island, expressible nucleic acid, selectable marker, in the 5' to 3' orientation with respect to the sense strand of the expressible nucleic acid, and the polyadenylation signal at the 3' end of the expressible nucleic acid is within 2000 bp of the proximal end of the selectable marker.

As used herein, "proximal end" means the end of the selectable marker gene (including its promoter) that is closest to the 3' end of the expressible nucleic acid, as marked by its polyadenylation signal. It is envisaged that the selectable marker might be in either orientation, so that the proximal end relative to the expressible nucleic acid might be at either the 5' promoter end of the selectable marker or the 3', termination of transcription end, taking 5' and 3' as being according to the sense strand of the selectable marker.

Preferably, the transcriptional start of the selectable marker is within 1500 bp of the 3' end of the expressible nucleic acid sequence, as marked by its polyadenylation signal of the latter. More preferably, it is within 1000 bp. Most preferably it is within 500 bp.

In one aspect of the invention, the selectable element is an antibiotic resistance gene. Preferably it is an antibiotic resistance gene obtained from a *Streptomyces* species. More preferably, said antibiotic resistance gene is operably linked to a promoter of the phosphoglycerate kinase (pgk) gene. Most preferably, it is the promoter of the murine pgk gene (Adra, C N, Boer P H and McBurney, M W. *Gene* 60, 65-74 (1987). Alternatively, it may be another mammalian pgk promoter.

In a preferred embodiment, the antibiotic resistance gene is the puromycin resistance gene from a *Streptomyces* species. Most preferably, it is the puromycin N-acetyl transferase gene from *Streptomyces alboniger* (Vara J A, Portela A, Ortin J, Jimenez A. *Nucleic Acids Res* 14, 4617-4624 (1986), which is incorporated herein by reference).

Alternatively, the antibiotic resistance gene is a modified form of the puromycin N-acetyl transferase gene from *Streptomyces alboniger*. Preferably this gene has been modified by manipulation of its codon usage, in a manner commonly done to adapt bacterial genes for expression in mammalian host cells. Such codon modification leaves the encoded amino acid sequence unchanged, with the result that the expressed enzyme is unchanged from the wild-type puromycin N-acetyl transferase. Most preferably, the modified gene has the sequence shown in FIG. 15.

Alternatively, the antibiotic resistance gene is a neomycin resistance gene derived from a *Streptomyces* species. Preferably it is the aminoglycoside phosphotransferase gene from *Streptomyces fradiae* (Thompson C J and Gray G S. *Proc Natl Acad Sci USA* 80, 51905194 (1983), which is incorporated herein by reference).

In an alternative embodiment, the antibiotic resistance gene is a hygromycin resistance gene. Preferably, it is the hygromycin phosphotransferase gene from *Streptomyces hygroscopicus*.

In a further alternative embodiment, the antibiotic resistance gene is a bleomycin resistance gene. Preferably, it is the bleomycin binding protein from *Streptomyces verticillus*. Alternatively, it is the bleomycin N-acetyltransferase from *Streptomyces verticillus*.

In another embodiment, the antibiotic resistance gene is a blasticidin resistance gene. Preferably, it is the blasticidin S-acetyltransferase gene from *Streptomyces verticillum*.

In another aspect of the invention, the antibiotic resistance gene is not obtained from a *Streptomyces* species. In one preferred embodiment it is the hygromycin resistance gene encoding aminocyclitol phosphotransferase from *Escherichia coli*.

In another preferred embodiment, it is the neomycin phosphotransferase gene from transposon Tn5, originally derived from *Klebsiella pneumoniae*.

In an alternative aspect of the invention, the selectable marker is not an antibiotic resistance gene. Alternative selection mechanisms involve using genes encoding thymidylate synthase, thymidine kinase or dihydrofolate reductase. Such selection mechanisms are well-known to those of appropriate skill in the art. In a medium lacking methionine, a gene encoding glutamine synthetase may be used as a means of selection either in cells lacking an endogenous glutamine synthetase, or where use of an inhibitor, such as methionine sulphoxamine, has rendered it inactive (Kaufman R J. Selection and coamplification of heterologous genes in mammalian cells. *Methods Enzymol* 185, 537-566 (1990), which is incorporated herein by reference).

In a further aspect, a screenable marker can be used. For instance, a gene encoding a fluorescent protein, such as the *Aequoria victoria* green fluorescent protein (GFP), or enhanced variants of it (EGFP), may be used as a selectable marker. Transfectants containing a polynucleotide according to the current invention, wherein the selectable marker encodes GFP, may be sorted by brightness of fluorescence on a FACS, by a process well-known in the art. Using the polynucleotide of the invention, and comparing with expressible constructs with the selectable marker situated either 5' to the UCOE, or 3' but remotely from the transgene (expressible nucleic acid), higher levels of expression of the transgene will be found for comparable levels of brightness. Selection of the brightest cells will, therefore, allow selection of cells with the highest level of transgene expression.

In one aspect of the invention, the extended methylation-free CpG island comprises a 16 kb DNA fragment spanning the human hnRNP A2 gene with 5 kb 5' and 1.5 kb 3' flanking sequence. Preferably, the extended methylation-free CpG island comprises an 8 kb DNA fragment spanning the human hnRNP A2 gene (WO 00/05393).

Alternatively, the extended methylation-free CpG island of the disclosed polynucleotide is an 'artificial UCOE' as disclosed in our co-pending applications GB 0022995.5 and U.S. 60/252,048, comprising the human β-actin CpG island/promoter region or a fragment thereof. Preferably this fragment is within the size range of 100 bp to 3.0 kb and spans the human β-actin CpG island/promoter region or a fragment thereof. Preferably the artificial UCOE also comprises the human PDCD2 CpG island/promoter region or a fragment thereof. More preferably the human PDCD2 CpG island/promoter region comprises a fragment within the size range of 100 bp to 3.0 kb. Further preferably, the extended methylation-free CpG island comprises a DNA fragment within the size range of 100 bp to 3.0 kb spanning the human β-actin CpG island/promoter region and a DNA fragment within the size range of 100 bp to 3.0 kb spanning the human PDCD2 CpG island/promoter region.

Most preferably the claimed polynucleotide of this embodiment of the invention comprises an artificial UCOE comprising a 2.0 kb DNA fragment spanning the human β-actin CpG island/promoter region and a 1.8 kb DNA fragment spanning the human PDCD2 CpG island/promoter region.

Also provided is a vector comprising the polynucleotide of any one of the previous embodiments. This vector may alternatively be either an episomal or an integrating vector. Depending on the intended use, episomal vectors may be desirable since they are self-replicating and so persist without the need for integration. Episomal vectors of this type are described in WO98/07876, which is incorporated herein by reference. Also preferred are non-replicating, non-integrating vectors.

Also provided is a vector so constructed as to deliver, when linearized and integrated into a chromosome, a polynucleotide comprising an extended methylation-free CpG island, an expressible nucleic acid terminated by a polyadenylation signal and a selectable marker operably linked to a promoter, wherein both the CpG island and the selectable marker are operably-linked to the expressible nucleic acid, and the components are positioned in the order: extended methylation-free CpG island, expressible nucleic acid, selectable marker, in the 5' to 3' orientation with respect to the sense strand of the expressible nucleic acid, and the polyadenylation signal at the 3' end of the expressible nucleic acid is within 2000 bp of the proximal end of the selectable marker.

Preferably the vector is a plasmid. Alternatively, the vector may be a virus, such as an adenovirus, adeno-associated virus, a herpesvirus, vaccinia virus, lentivirus or other retrovirus.

Preferably said vector is an expression vector adapted for eukaryotic gene expression. Typically said adaptation includes, by example and not by way of limitation, the provision of transcription control sequences (promoter sequences) that mediate cell/tissue specific expression. Promoter and enhancer are terms well-known in the art and include the following features which are provided by example only, and not by way of limitation. Promoters are 5', cis-acting regulatory sequences directly linked to the initiation of transcription. Promoter elements include so-called TATA box and RNA polymerase initiation selection (RIS) sequences that function to select a site of transcription initiation. These sequences also bind polypeptides that function, inter alia, to facilitate transcription initiation selection by RNA polymerase.

Enhancer elements are cis acting nucleic acid sequences often found 5' to the transcription initiation site of a gene (enhancers can also be found 3' to a gene sequence or even located in intronic sequences and are therefore position independent). Enhancers function to increase the rate of transcription of the gene to which the enhancer is linked. Enhancer activity is responsive to trans acting transcription factors (polypeptides) that have been shown to bind specifically to enhancer elements. The binding/activity of transcription factors is responsive to a number of environmental cues which include, by way of example and not by way of limitation, intermediary metabolites (e.g., glucose), environmental effectors (e.g., heat) (see Eukaryotic Transcription Factors, by David S Latchman, Academic Press Ltd, San Diego, which is incorporated herein by reference).

Adaptations also include the provision of selectable markers and autonomous replication sequences which both facilitate the maintenance of said vector in either the eukaryotic cell or prokaryotic host. Vectors that are maintained autonomously in eukaryotic cells are referred to as episomal vectors. Other adaptations which facilitate the expression of vector encoded genes include the provision of transcription termination/polyadenylation sequences. This also includes the provision of internal ribosome entry sites (IRES) that function to maximize expression of vector encoded genes arranged in bicistronic or multi-cistronic expression cassettes. These adaptations are well-known in the art. There is a significant amount of published literature with respect to expression vector construction and recombinant DNA techniques in general. Please see, Sambrook et al. (1989) Molecular Cloning: A Laboratory Manual, Cold Spring Harbour Laboratory, Cold Spring Harbor, N.Y. and references therein; Marston, F (1987) DNA Cloning Techniques: A Practical Approach Vol. III IRL Press, Oxford UK; DNA Cloning: F M Ausubel et al., Current Protocols in Molecular Biology, John Wiley & Sons, Inc. (1994), each of which is incorporated herein by reference.

In a preferred method of the invention said vector encodes, and thus said polypeptide is provided with, a secretion signal to facilitate purification of said polypeptide.

Alternatively, other preferred embodiments may include further refinements to facilitate purification of expressed recombinant protein, such as affinity tags or epitopes, or enzymatic cleavage sites.

Preferably the expressible nucleic acid is a therapeutic nucleic acid.

Alternatively, the expressible nucleic acid encodes a recombinant protein for expression in an in vitro cell culture system.

Alternatively, the expressible gene encodes a non-polypeptide product, such as RNA. Such RNA may be an antisense RNA capable of inhibiting expression of a particular gene at a post-transcriptional level, or may have an enzymatic (ribozyme) or other function, such as a ribosomal RNA.

One preferred embodiment is a vector comprising: an extended methylation-free CpG island, an expressible nucleic acid terminated by a polyadenylation signal and a selectable marker operably linked to a promoter, wherein both the CpG island and the selectable marker are operably-linked to the expressible nucleic acid, and the components are positioned in the order: extended methylation-free CpG island, expressible nucleic acid, selectable marker, in the 5' to 3' orientation with respect to the sense strand of the expressible nucleic acid, and the polyadenylation signal at the 3' end of the expressible nucleic acid is within 2000 bp of the proximal end of the selectable marker. Preferably, the the polyadenylation signal at the 3' end of the expressible nucleic acid is within 1500 bp of the proximal end of the selectable marker. More preferably it is within 1000 bp, most preferably, 500 bp.

A preferred embodiment is a vector comprising: an extended methylation-free CpG island, a multiple cloning site, an antibiotic resistance gene obtained from a *Streptomyces* species, wherein both the CpG island and the selectable marker are operably-linked to the multiple cloning site, and the components are positioned in the order: extended methylation-free CpG island, multiple cloning site, selectable marker, in the 5' to 3' orientation with respect to the sense strand of the expressible nucleic acid, and the multiple cloning site is within 2000 bp of the proximal end of the selectable marker.

More preferably, the multiple cloning site is further operably linked to a promoter. Further preferably the promoter is selected from CMV, EF-1α, RSV LTR or HIV2 LTR, or combinations of sequences derived therefrom. More preferably the promoter is a CMV immediate/early promoter. Most preferably it is the mouse CMV immediate/early promoter. In a preferred embodiment, the vector comprises a CMV promoter, a multiple cloning site, a polyadenylation sequence and genes encoding selectable markers under suitable control elements.

Figure 9:
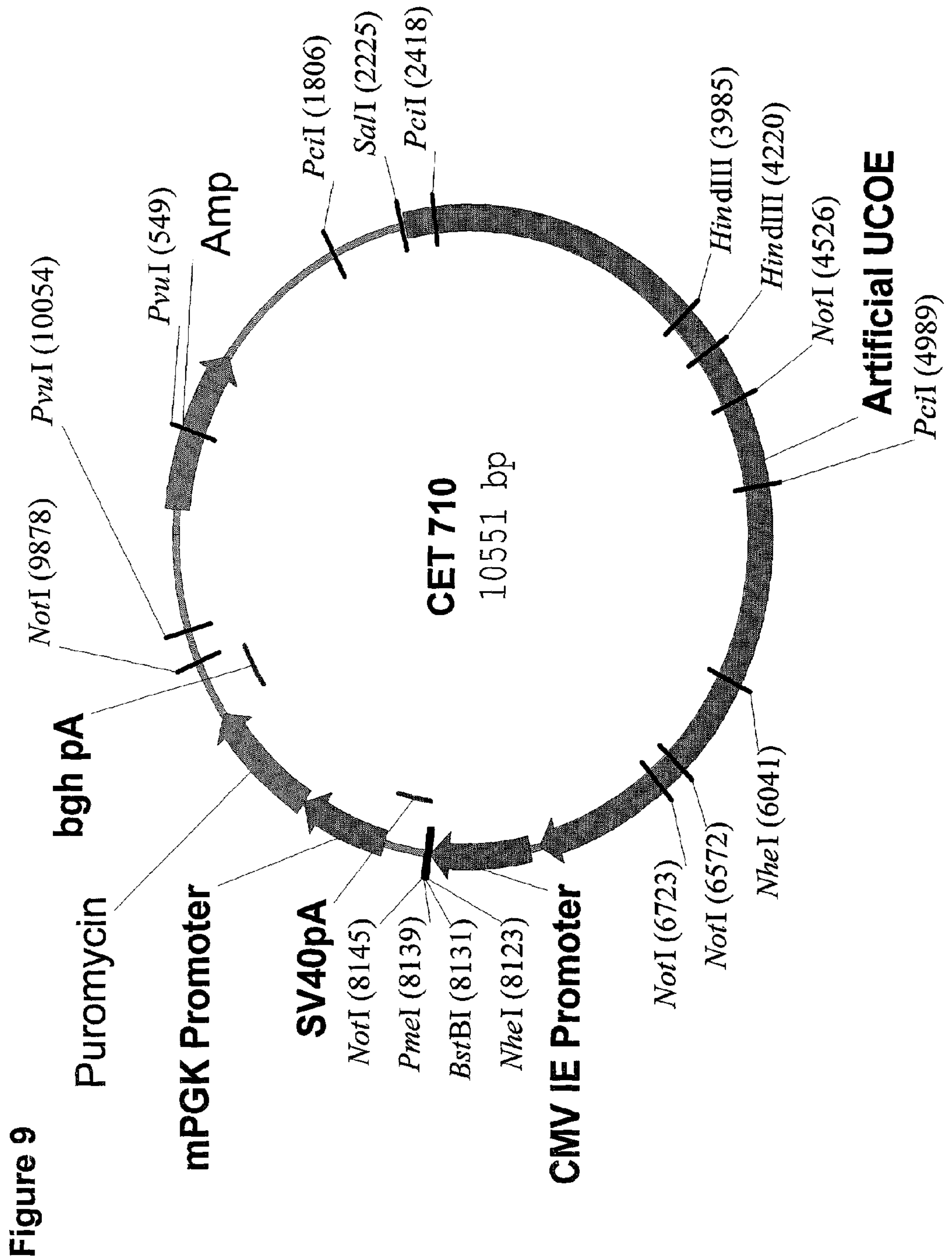
FIG. 9 shows a map of plasmid CET710.
Figure 11:
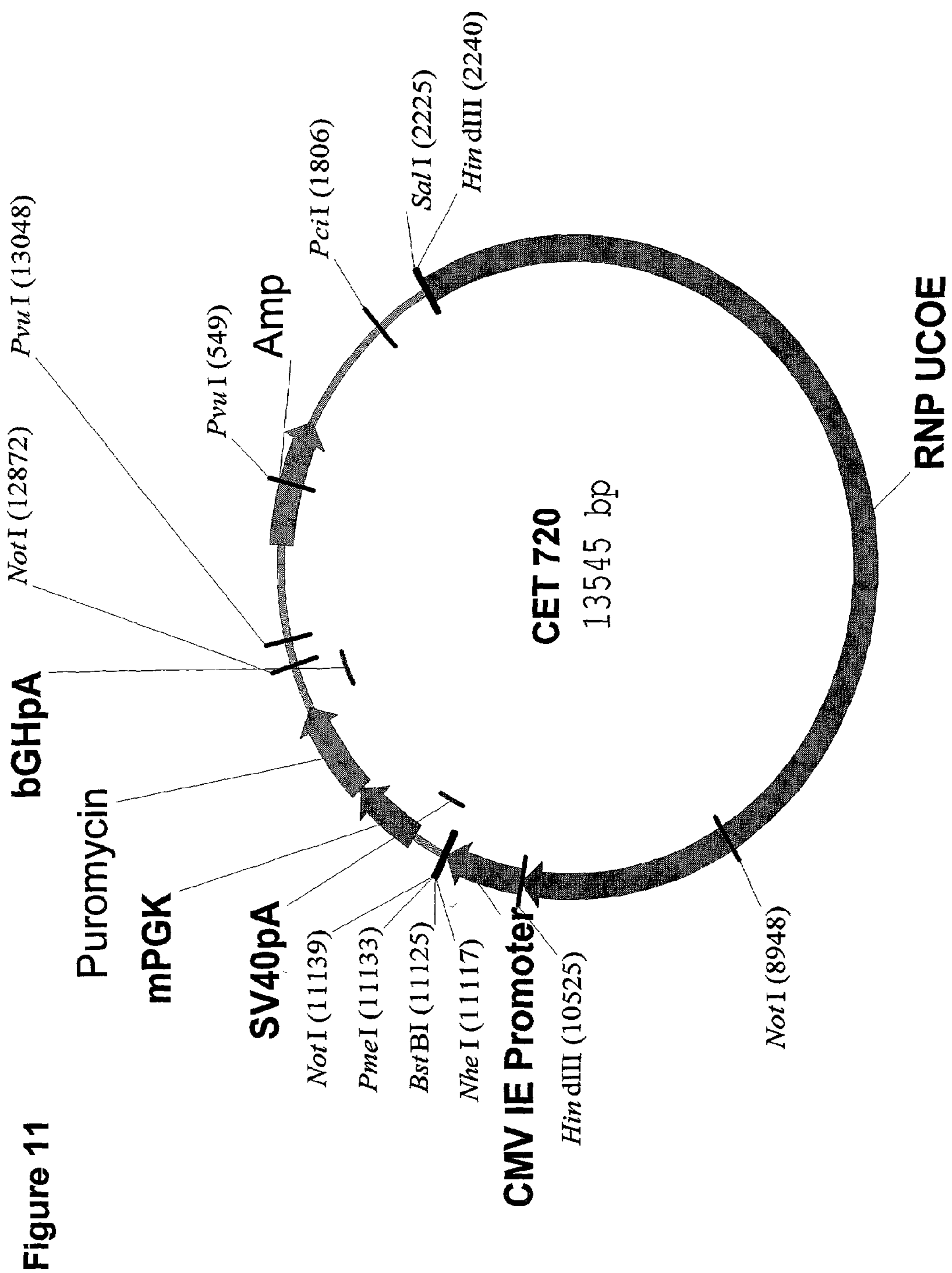
FIG. 11 shows a map of plasmid CET720.
Figure 20:
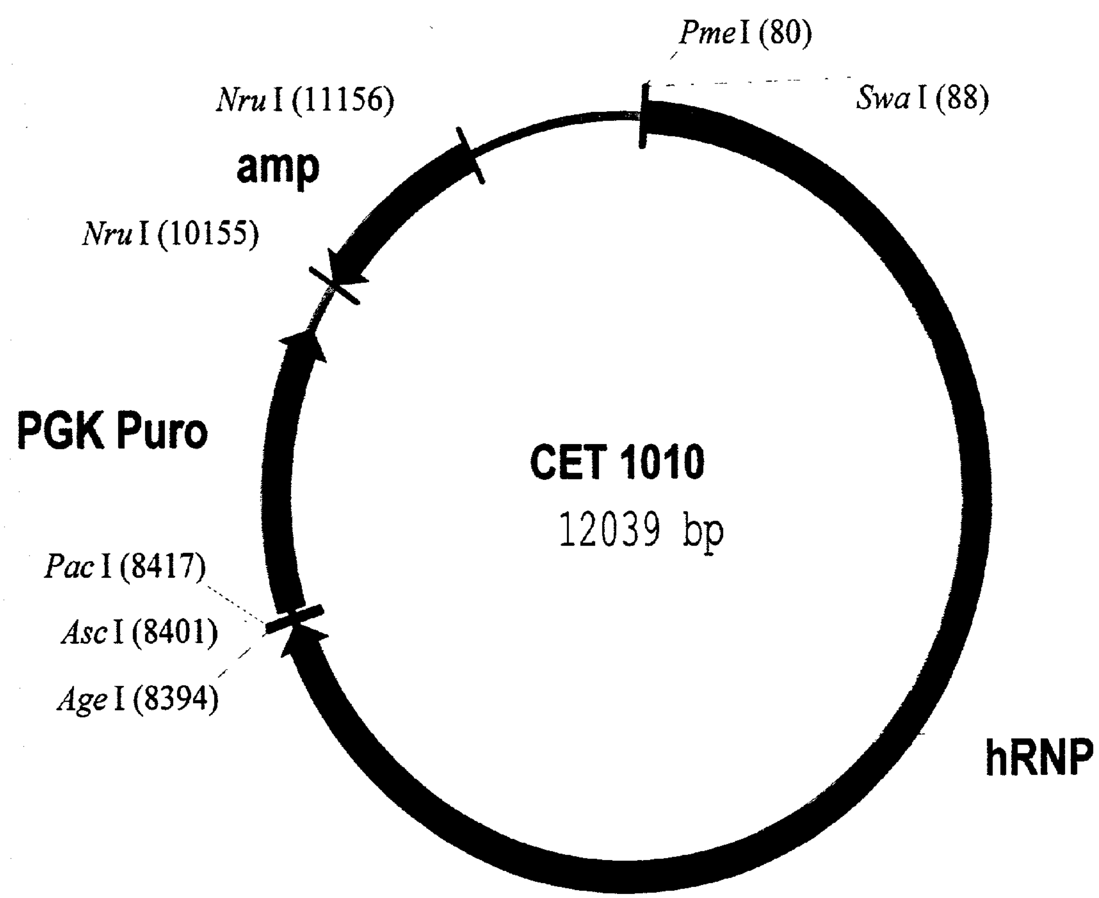
FIG. 20 shows a map of plasmid CET1010.
Figure 22:
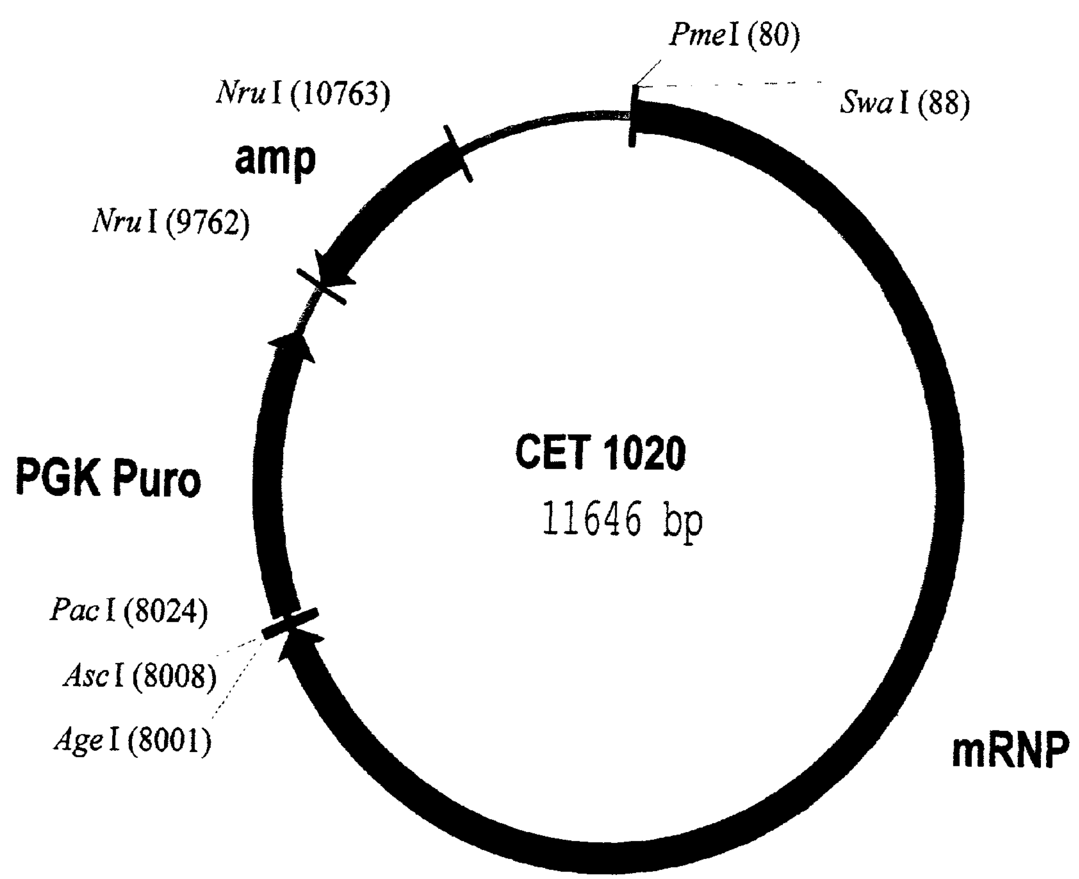
FIG. 22 shows a map of plasmid CET1020.
Figure 24:
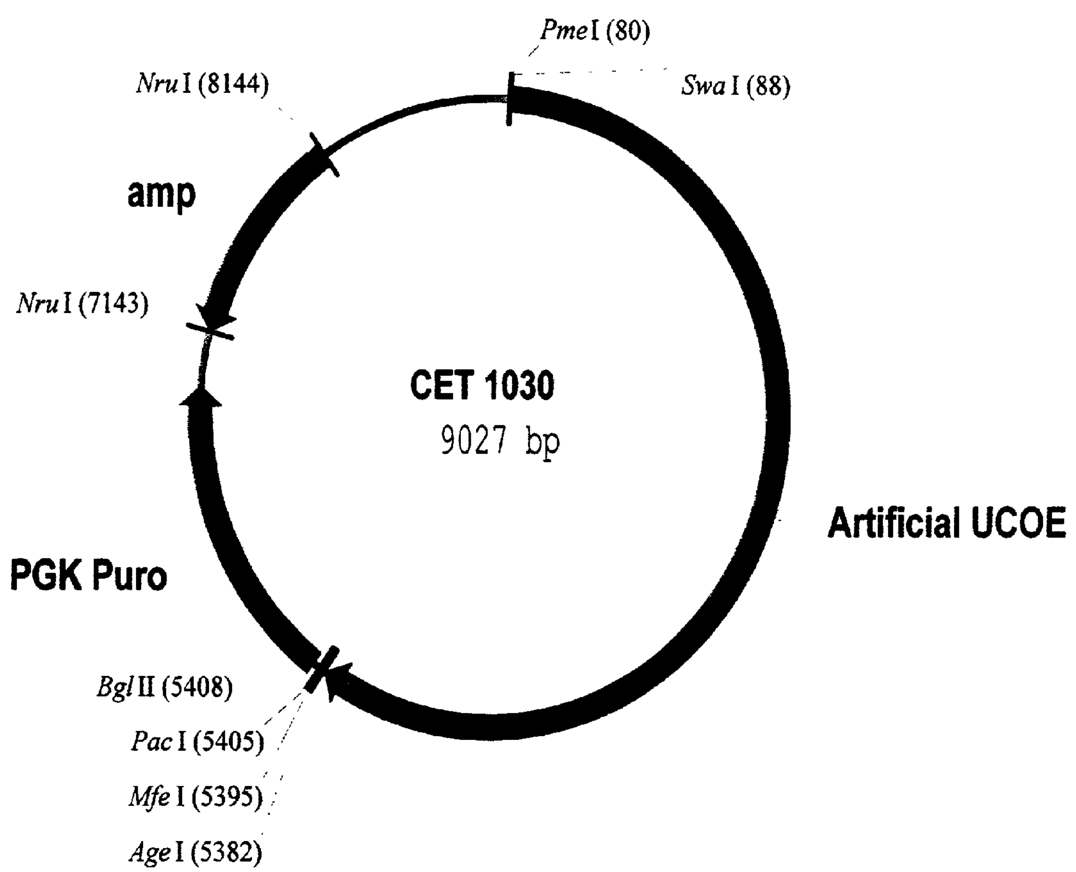
FIG. 24 shows a map of plasmid CET1030.
Figure 26:
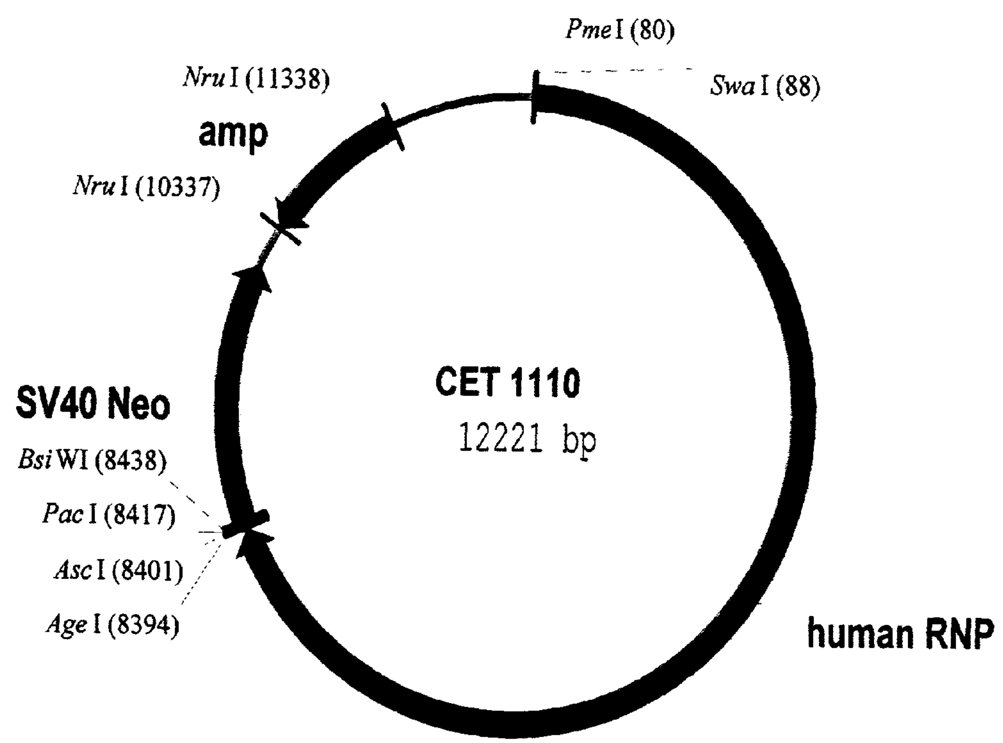
FIG. 26 shows a map of plasmid CET1110.
Figure 28:
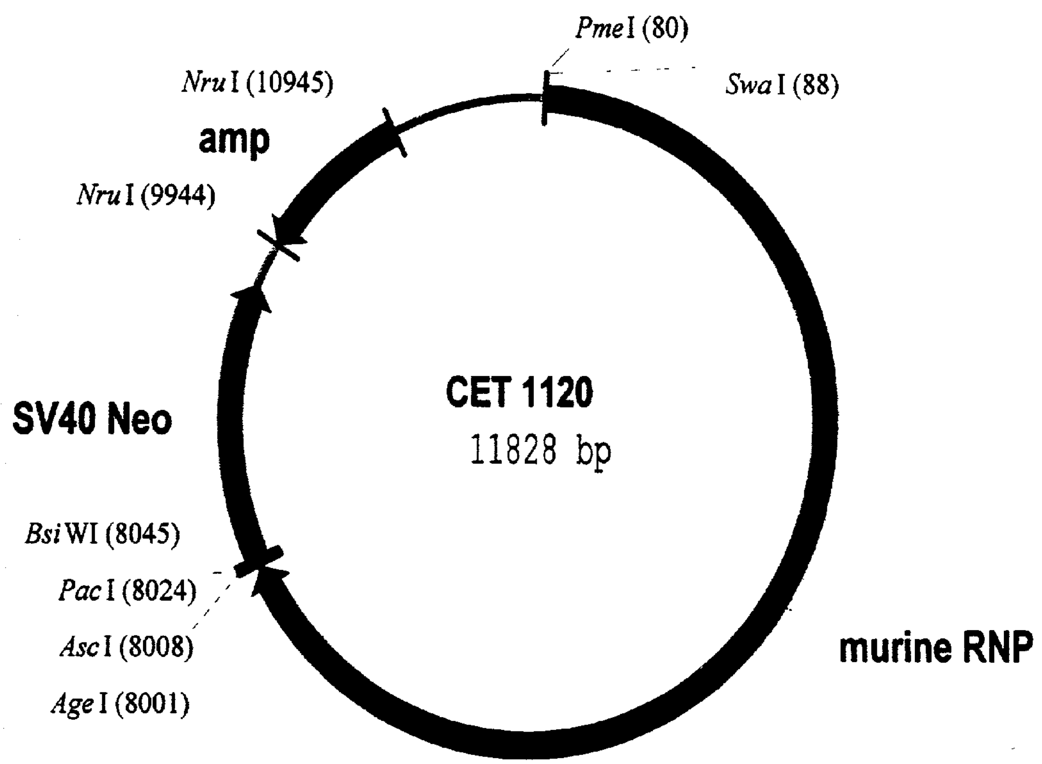
FIG. 28 shows a map of plasmid CET1120.
Figure 30:
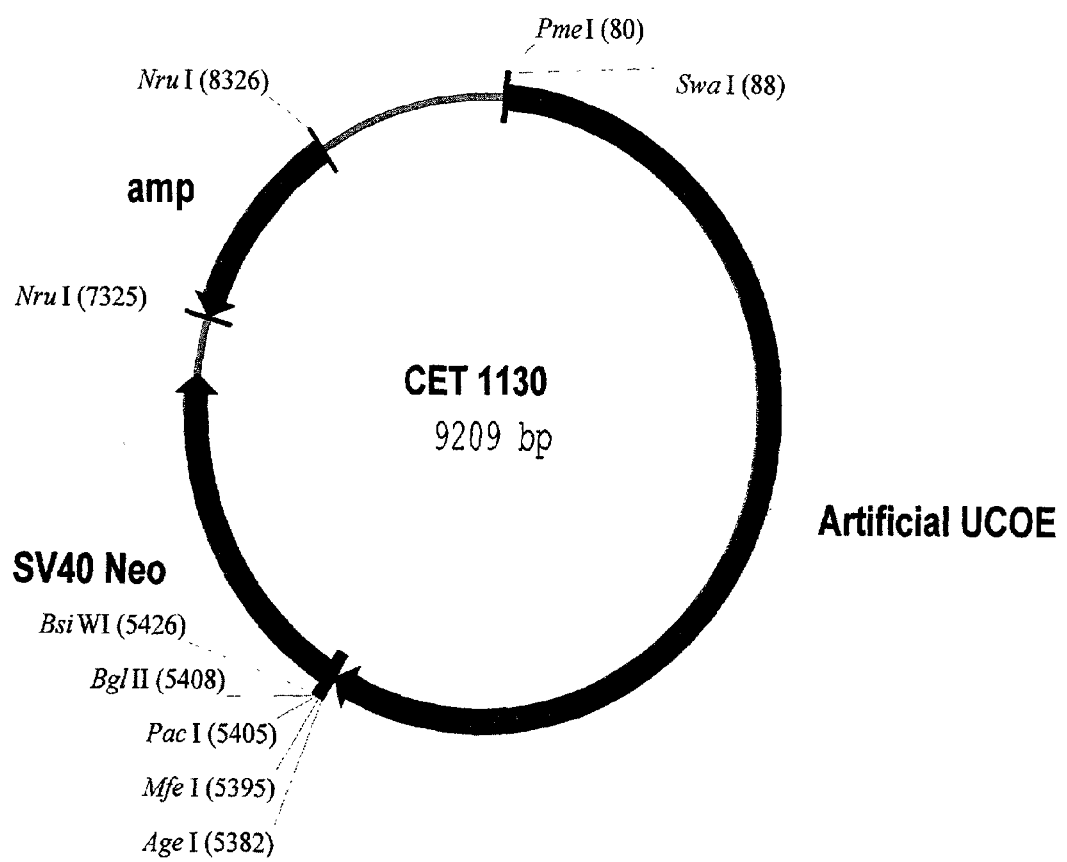
FIG. 30 shows a map of plasmid CET1130.

A preferred embodiment of the vector comprises nucleotides 1-10551 of the sequence of FIG. 9. A most preferred embodiment is vector CET710.

Alternatively, the vector comprises nucleotides 1-13545 of the sequence of FIG. 10, and is preferably vector CET720.

Further preferred embodiment of vectors are:

CET740 in which the puromycin resistance gene of CET720 is replaced with the aminoglycoside phosphotransferase gene from *Streptomyces fradiae* (as listed in FIG. 15) Also preferred are vectors having expressible nucleic acid sequences inserted into the multiple cloning site of CET740, such as CET741.

CET760 in which the puromycin resistance gene of CET720 is replaced with the aminocyclitol phosphotransferase from *Escherichia coli* (as listed in FIG. 17). Also preferred are vectors having expressible nucleic acid sequences inserted into the multiple cloning site of CET760, such as CET761.

CET780 in which the puromycin resistance gene of CET720 is replaced with the modified form of the puromycin N-acetyl transferase gene from *Streptomyces alboniger* (as listed in FIG. 14). Also preferred are vectors having expressible nucleic acid sequences inserted into the multiple cloning site of CET780, such as CET781.

CET820 in which the human IE CMV promoter, operably linked to the multicloning site in order to drive expression of expressible nucleic acid sequences inserted there, has been replaced with the murine IE CMV promoter. Also preferred are vectors having expressible nucleic acid sequences inserted into the multiple cloning site of CET820, such as CET821.

CET823 in which the extended methylation-free CpG island comprising an 8 kb DNA fragment spanning the human hnRNP A2 gene is replaced with the extended methylation-free CpG island comprising an 8 kb fragment spanning the murine hnRNP A2 gene (as shown in the sequence of FIG. 19). Also preferred are vectors having expressible nucleic acid sequences inserted into the multiple cloning site of CET823, such as CET824.

Also provided is host cell transfected with any of the embodiments of the disclosed vectors.

Alternatively said polynucleotide, vector or the host cell may be used in a cell culture system to obtain expression of a desired gene product. Suitable cell culture systems are well known in the art and are fully described in the body of literature known to those skilled in the art. There is provided a method for the production of a polypeptide according to the invention comprising:

i) providing a cell transformed/transfected with a nucleic acid molecule according to the invention;

ii) growing said cell in conditions conducive to the manufacture of said polypeptide; and iii) purifying said polypeptide from said cell, or its growth environment.

In a preferred embodiment of the invention said nucleic acid molecule is the vector according to the invention.

The present invention also provides the polynucleotide, vector or the host cell for use in therapy.

The present invention also provides use of the polynucleotide, vector or host cell in the manufacture of a composition for use in gene therapy.

The present invention also provides a method of treatment, comprising administering to a patient in need of such treatment a pharmaceutically effective amount of the polynucleotide, vector or host cell of the present invention. Preferably the patient is suffering from a disease treatable by gene therapy.

The present invention also provides a pharmaceutical composition comprising the polynucleotide and/or the vector and/or host cell, optionally in admixture with a pharmaceutically acceptable carrier or diluent, for therapy to treat a disease or provide the cells of a particular tissue with an advantageous protein or function.

The polynucleotide, vector or host cell of the invention or the pharmaceutical composition may be administered via a route which includes systemic intramuscular, intravenous, aerosol, oral (solid or liquid form), topical, ocular, rectal, intraperitoneal and/or intrathecal and local direct injection.

The exact dosage regime will, of course, need to be determined by individual clinicians for individual patients and this, in turn, will be controlled by the exact nature of the protein expressed by the gene of interest and the type of tissue that is being targeted for treatment.

The dosage also will depend upon the disease indication and the route of administration. The number of doses will depend upon the disease, and the efficacy data from clinical trials.

The amount of polynucleotide or vector DNA delivered for effective gene therapy according to the invention will preferably be in the range of between 50 ng-1000 μg of vector DNA/kg body weight; and more preferably in the range of between about 1-100 μg vector DNA/kg.

Although it is preferred according to the invention to administer the polynucleotide, vector or host cell to a mammal for in vivo cell uptake, an ex vivo approach may be utilised whereby cells are removed from an animal, transduced with the polynucleotide or vector, and then re-implanted into the animal. The liver, for example, can be accessed by an ex vivo approach by removing hepatocytes from an animal, transducing the hepatocytes in vitro and re-implanting the transduced hepatocytes into the animal (e.g., as described for rabbits by Chowdhury et al., *Science* 254:1802-1805, 1991, or in humans by Wilson, *Hum. Gene Ther.* 3:179-222 (1992), each of which is incorporated herein by reference). Such methods also may be effective for delivery to various populations of cells in the circulatory or lymphatic systems, such as erythrocytes, T cells, B cells and haematopoietic stem cells.

Another aspect of the invention provides an isolated polynucleotide comprising a first promoter operably linked to an expressible gene to which it is not naturally operably linked and a selectable element, also operably linked and 3' to the expressible gene, comprising a pgk promoter and a puromycin resistance gene. The use of such a polynucleotide to obtain reproducible expression of said expressible gene in at least two tissue or cell types is also provided.

In another embodiment of the invention there is provided a non-human transgenic animal comprising an artificially introduced extended methylation-free CpG island element and an artificially introduced selectable marker element wherein both elements are operably-linked to an expressible gene situated between them and wherein reproducible expression of said expressible gene occurs in at least two tissue or cell types. Methods of making transgenic mice (Gordon et al., *Proc. Natl. Acad. Sci. USA* 77:7380 (1980); Harbers et al., *Nature* 293:540 (1981); Wagner et al., *Proc. Natl. Acad. Sci. USA* 78:5016 (1981); and Wagner et al., *Proc. Natl. Acad. Sci. USA* 78:6376 (1981), each of which is incorporated herein by reference), sheep pigs, chickens (see Hammer et al., *Nature* 315:680 (1985), which is incorporated herein by reference), etc., are well-known in the art and are contemplated for use according to the invention.

Such transgenic animals containing the polynucleotide of the invention also may be used for long-term production of a protein of interest.

There is also provided a mammalian model for determining the efficacy of gene therapy using the polynucleotide, vector or host cell of the invention. The mammalian model comprises a transgenic animal whose cells contain the vector of the present invention. Such animals permit testing prior to clinical trials in humans.

The present invention also provides the use of the polynucleotide of the present invention in producing transgenic plants.

The generation of transgenic plants that have increased yield, or increased resistance to disease, pests, drought or salt are well known to those skilled in the art. The present invention also provides for transgenic plant containing cells that contain the polynucleotide of the present invention. Some or all of the cells comprising the artificial UCOE may originate from plants.

The present invention also relates to the use of polynucleotide of the present invention in functional genomics applications. Functional genomics relates principally to the identification of genes specifically expressed in particular cell types or disease states and now provides thousands of novel gene sequences of potential interest for drug discovery or gene therapy purposes. The major problem in using this information for the development of novel therapies lies in how to determine the functions of these genes. The polypeptides of the invention can be used in a number of functional genomic applications in order to determine the function of gene sequences. The functional genomic applications of the present invention include, but are not limited to:

(1) Using the polynucleotide of the present invention to achieve sustained expression of anti-sense versions of the gene sequences or ribozyme knockdown libraries, thereby determining the effects of inactivating the gene on cell phenotype.

(2) Using the polynucleotide of the present invention to prepare expression libraries for the gene sequences, such that delivery into cells will result in reliable, reproducible, sustained expression of the gene sequences. The resulting cells, expressing the gene sequences can be used in a variety of approaches to function determination and drug discovery. For example, raising neutralising antibodies to the gene product; rapid purification of the protein product of the gene itself for use in structural, functional or drug screening studies; or in cell-based drug screening.

(3) Using the polynucleotide of the present invention in approaches involving mouse embryonic stem (ES) cells and transgenic mice. One of the most powerful functional genomics approaches involves random insertion into genes in mouse ES cells of constructs which only allow drug selection following insertion into expressed genes, and which can readily be rescued for sequencing (G. Hicks et al., 1997, Nature Genet., 16, 338-344, which is incorporated herein by reference). Transgenic mice with knockout mutations in genes with novel sequences can then readily be made to probe their function. At present this technology works well for the 10% of mouse genes which are well expressed in mouse ES cells. Incorporation of the polynucleotides of the present invention into the integrating constructs will enable this technique to be extended to identify all genes expressed in mice.

The invention is further illustrated by way of the following examples, which are intended to elaborate several embodiments of the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Flanking of an Expressible Gene with UCOEs and Selectable Elements

Materials and Methods

Construction of PGK-Puro CET Expression Vectors

CET700: The CMV-MCS-SV40pA cassette was removed from CET31 (A CMV MCS pA SV40Neo based plasmid) as an AseI/AflI fragment, blunt end filled with T4 DNA polymerase and ligated into pPGK-Puro (mPGK promoter, Puromycin resistance gene, bGHpA in pBluescript®) that had been digested with EcoRV.

CET720: CET20 (8.3 kb hnRNPA2 fragment in pBluescript®) was digested with HindIII to obtain the 8 kb RNP UCOE and this was then ligated into CET700 that had also been cut with HindIII.

CET710: The Artificial UCOE was removed from CET21 (Artificial UCOE in pBluescript®) as an XbaI/ClaI fragment, blunt end filled with T4 DNA polymerase and ligated into CET700 that had been digested with HindIII and again blunt end filled with T4 DNA polymerase.

CET230: This vector was constructed by digesting pUC19 with NarI an EcoRI to remove approximately 160 bp, followed by blunting and religation. This removed one of the two PvuI and PvuII sites in the vector backbone. The CMV-EGFP-SV40pA cassette (with its MCS deleted) was excised from pEGFPN-1 (Clontech, Palo Alto, Calif.), as an AseI/AflII digest followed by blunt end filling, and then inserted into the pUC19 vector backbone that had been digested with NdeI and Eco109 I and again blunt end filled.

The PGK-Puro-bGpA cassette was then removed from pPGK-Puro as an EcoRI/XhoI blunt end filled fragment and inserted into the unique PvuII site of the above vector. Finally the 8.3 kb hnRNPA2 fragment was inserted into the unique HindIII site of this vector as a HindIII fragment derived from CET20.

For clarity:

CET230 is the EGFP-expressing version of the 'empty' vector CET210.

CET711 is the EGFP-expressing version of the 'empty' vector CET710.

CET721 is the EGFP-expressing version of the 'empty' vector CET720.

Vectors based on CET720 with different antibiotic resistant genes and with alternative promoters or UCOEs can be constructed in the following manner.

The PGK promoter (bp11384-11894) and the bghpA (bp 12567-12893) can be removed from CET720 by restriction digestion. These elements can be inserted into the pBluescript® backbone such that restriction sites are available for the insertion of any resistance gene sequences (derived by PCR or restriction digestion) between the PGK promoter and the bghpA in such a manner as to allow expression of that gene. The CMV-MCS-SV40pA expression cassette can also be removed from CET720 (bp 10533-11380) and inserted 5' to the PGK promoter in the above vector; alternatively the mCMV-MCS-SV40pA expression cassette can be placed in the same position (CET801, CET821, CET824-EGFP expression versions). The hnRNPA2 UCOE can be removed from CET720 (bp 2240-10525) by restriction digestion and inserted 5' to the CMV expression cassette in the above vectors, alternatively other UCOEs (e.g., murine hnRNPA2) can be inserted into the same position (CET824-EGFP expression version).

For clarity:

CET741 is the EGFP-expressing version of the 'empty' vector CET740 and comprises a 5' human RNP UCOE and a 3' *S fradiae* $neo^r$ gene.

CET761 is the EGFP-expressing version of the 'empty' vector CET760 and comprises a 5' human RNP UCOE and a 3' *E. coli* aminocyclitol phosphotransferase ($hygro^r$) gene.

CET781 is the EGFP-expressing version of the 'empty' vector CET780 and comprises a 5' human RNP UCOE and a 3' modified *S. alboniger* puromycin N-acetyl transferase gene.

CET821 is the EGFP-expressing version of the 'empty' vector CET820 and comprises a 5' human RNP UCOE and a 3' wild-type *S. alboniger* puromycin N-acetyl transferase gene. Expression of the EGFP transgene is driven by the murine (rather than human) CMV IE promoter.

CET824 is the EGFP-expressing version of the 'empty' vector CET823 and comprises a 5' murine (rather than human) RNP UCOE and a 3' wild-type *S. alboniger* puromycin N-acetyl transferase gene.

pCIA Vectors

This is a series of vectors that easily allow the construction of UCOE expression vectors with the final optimal configuration (UCOE-expression cassette-resistance cassette) when integrated into the chromosome.

CET900 is an empty cloning vector in which pairs of rare restriction sites flank the MCS. CET901 and CET902 contain the hCMV and mCMV promoters respectively, an MCS and the SV40pA. The same pairs of rare restriction sites also flank these cassettes.

The CET1000 series of vectors contain various combinations of UCOEs and resistance expression cassettes. They also contain the same rare restriction sites as the CET900 series at a position 3' to the UCOE and 5' to the resistance cassette. The vectors also contain linearization sites 5' to the UCOE and 3' to the resistance cassette.

Expression cassettes for any transgene can therefore be constructed in the CET900 series and then easily be transferred into the CET1000 series such that the ultimate configuration when integrated into the chromosome is the desired UCOE-expression cassette-resistance cassette.

As described above the antibiotic gene can be exchanged within the CET1000 series by restriction digestion or PCR.

Transfection

CHO K1 cells were transfected and selected according to standard methods and as described in the co-pending applications incorporated by reference.

Results

With particular reference to FIG. 2, comparison of cells transfected with CET721 and CET230 shows a consistently higher level of expression obtained with CET721. These two vectors are similar in that both carry an 8 kb hnRNP-derived UCOE operably-linked to the CMV promoter driven EGFP gene and both carry the pgk/puromycin resistance gene element. However, following linearization with Pvu I, integration of CET230 into the host cell chromosome results in the elements being positioned in the order: pgk/Puro, hnRNP UCOE, EGFP gene. The same process with CET721 results in the EGFP gene being flanked by the UCOE and the pgk/Puro. The levels of expression obtained with CET230 are not significantly higher than those obtained with CET220, a vector carrying no pgk/Puro element but with the same UCOE and promoter driving EGFP expression.

All UCOE carrying vectors show greatly increased expression compared with the basic EGFP expression plasmid.

Figure 3:
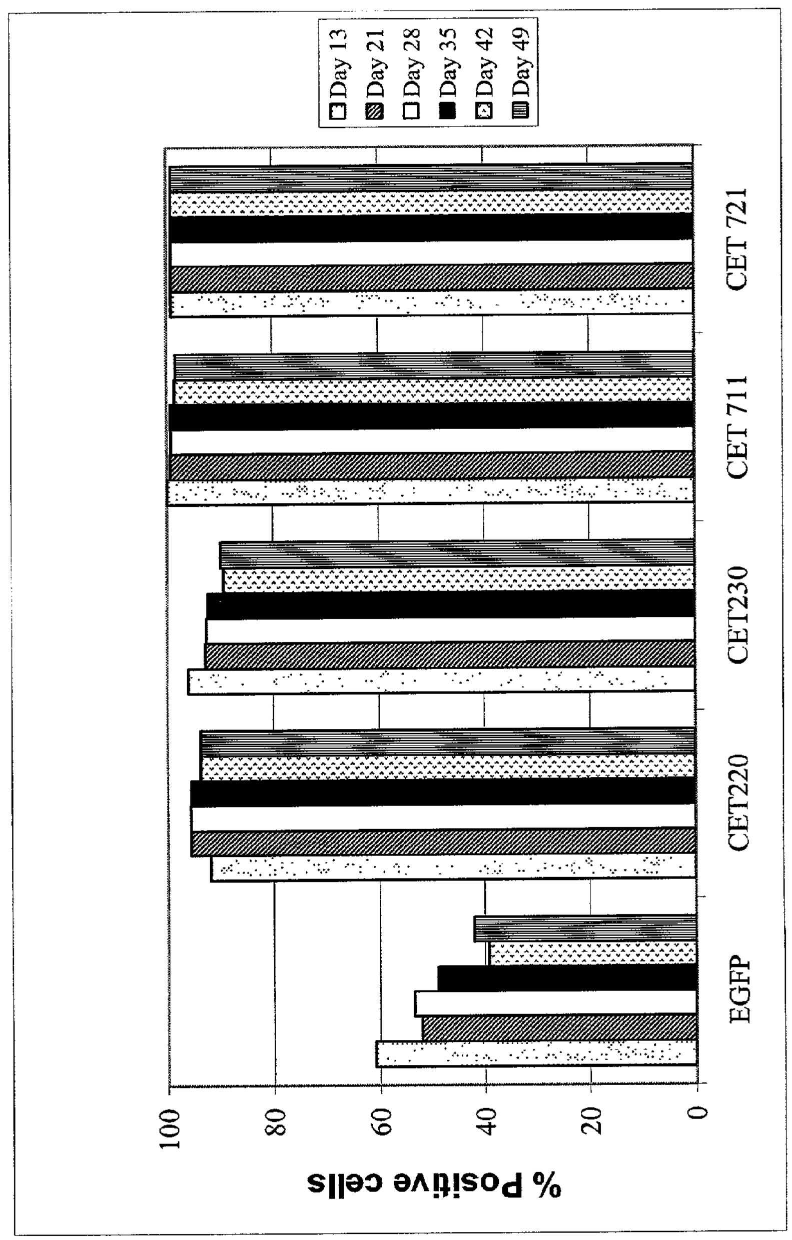
FIG. 3 shows the proportion of the populations of cells shown in FIG. 2 judged to be positive for expression on the indicated days post-transfection.

FIG. 3 shows that increased expression as expressed by median fluorescence is also reflected in an increased proportion of cells within the transfected population judged to be positive, in terms of expression, at all time points following transfection. This is a measure of the lack of position effects, since random integration of the construct would normally result in a range of expression levels within the (non-clonal) population of transfected cells. This is overcome by the combination of 5' UCOE and 3' selectable element, resulting in a homogenous, highly-expressing population.

The levels of expression in some of the pools of cells in FIG. 2 are so high that the fluorescence produced has exceeded the capacity of the detector.

Figure 4:
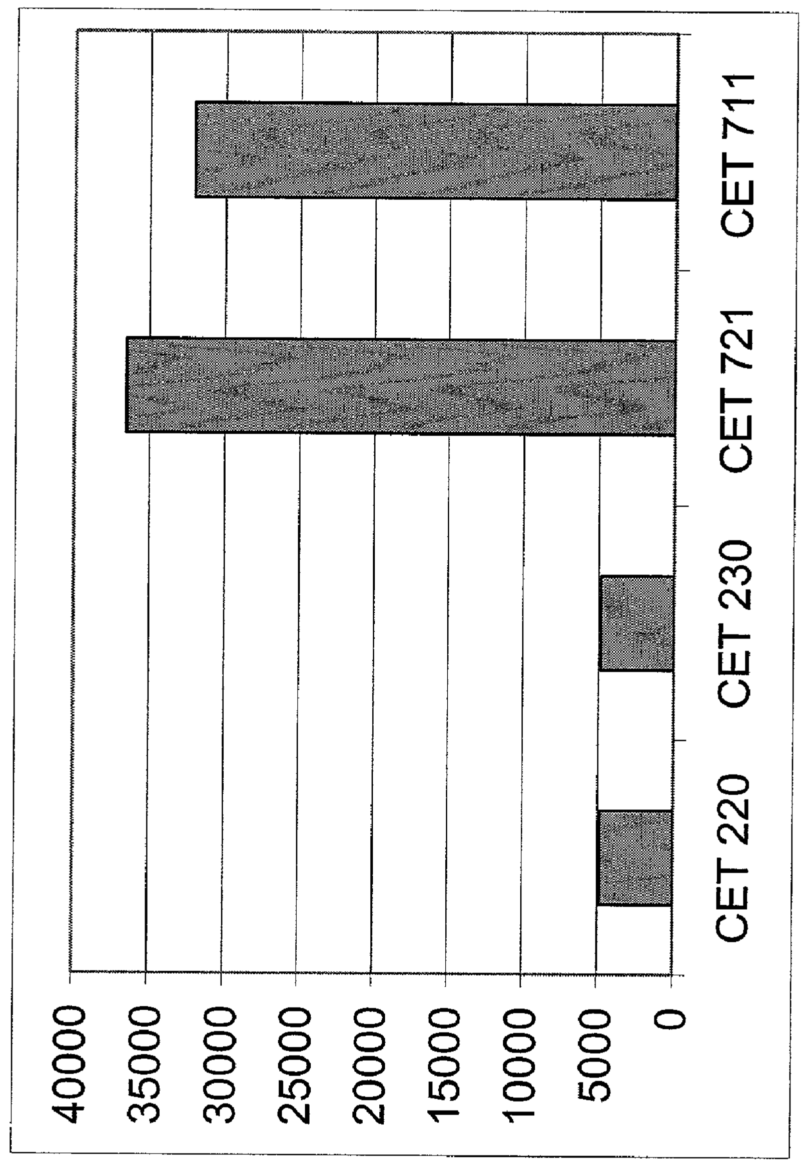
FIG. 4 shows the expression of EGFP in CHO-K1 cells transfected with vectors CET220, CET230, CET721 and CET711 as measured by median fluorescence corrected to allow comparison without exceeding the detection capacity of the FACScan. This clearly shows the comparative effect of placing the selectable marker (puro$^r$) either 5' (CET230) or 3' (CET721) to the expressible transgene (EGFP).

In FIG. 4, measurements have been corrected to the linear region of the detector's response to allow comparison between constructs. This shows that the combination of UCOE and 3' flanking selectable element used in CET721 has produced an approximately 7-fold increase in levels of expression of EGFP as compared with that obtained with the UCOE alone (CET220) or that obtained with the selectable element ($puro^r$) placed 5' to the UCOE. It is clear that flanking the expressed transgene with the UCOE and selectable marker is required to obtain the boost in expression.

Figure 7:
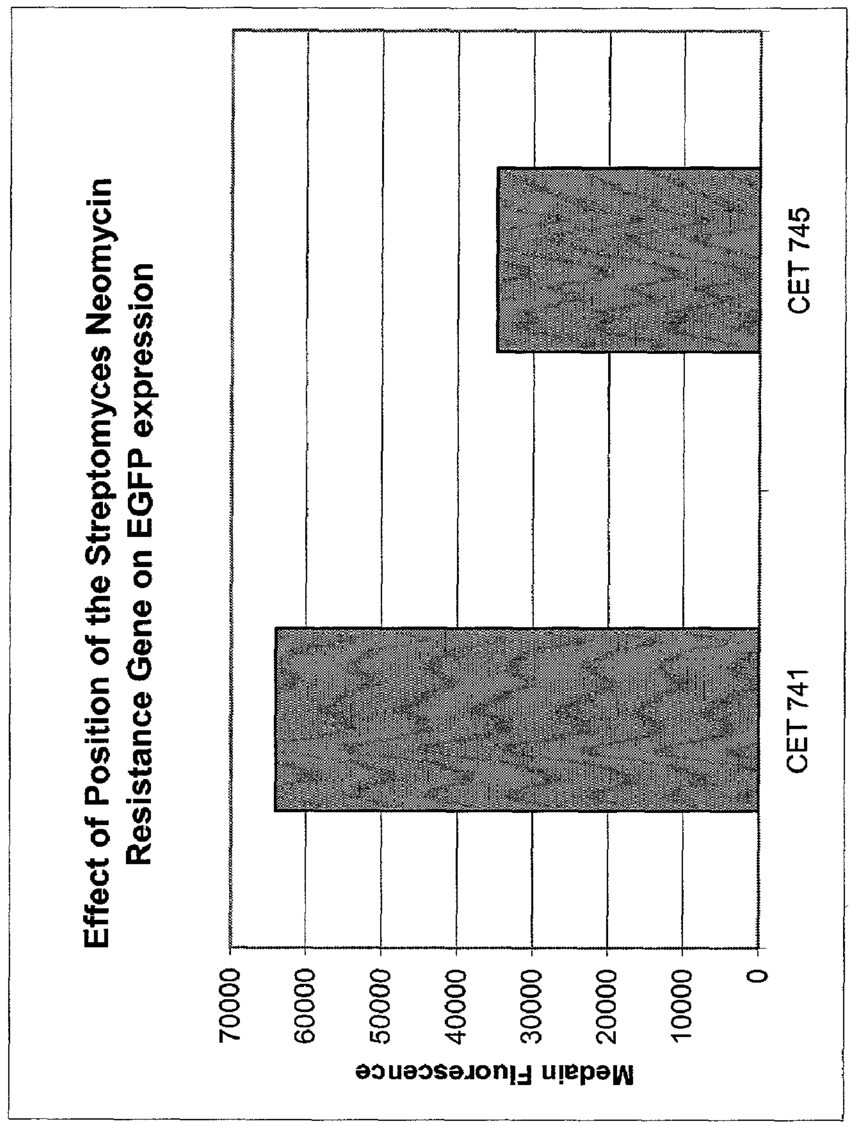
FIG. 7 shows the effect of position of the *Streptomyces* neomycin resistance gene on EGFP expression. CET741 has the selectable marker 3' of the transgene, CET745 has the marker 5' of the transgene and UCOE. The UCOE is the human RNP UCOE in both cases.
Figure 8:
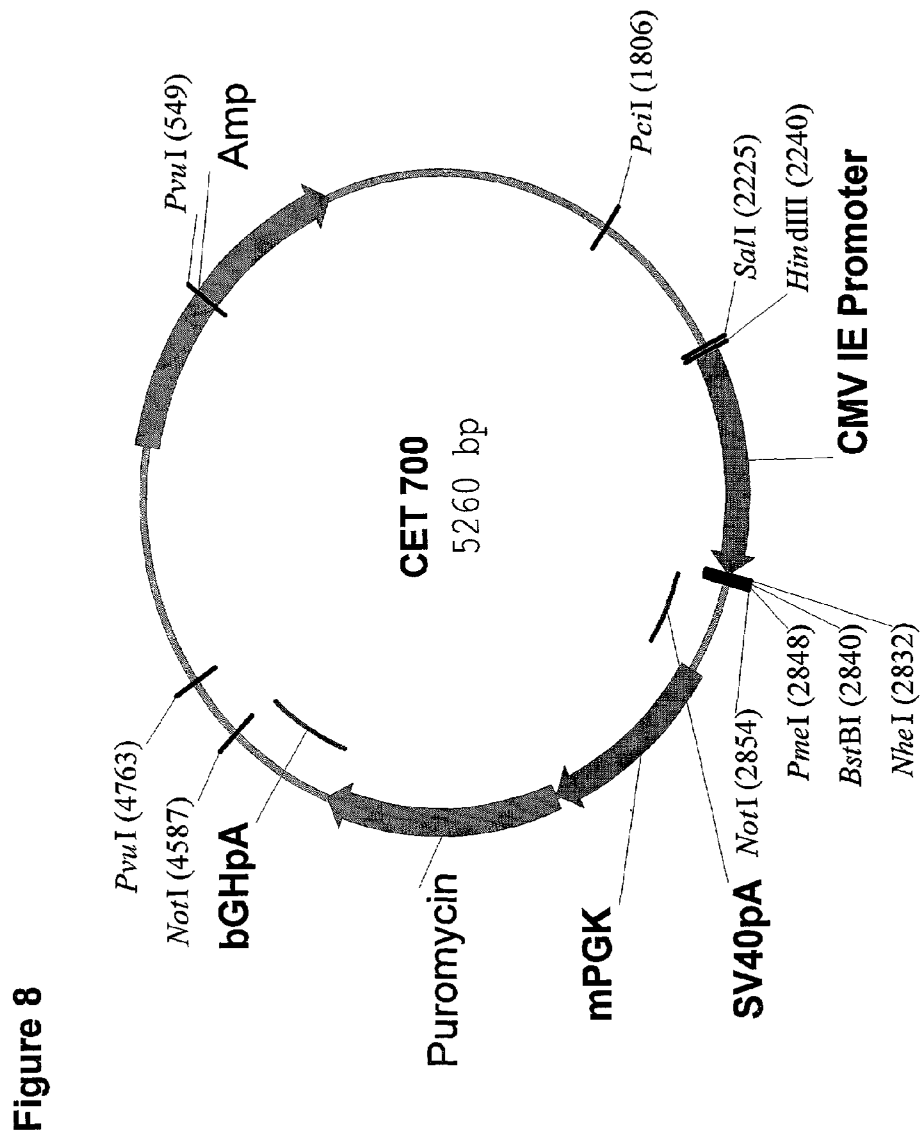
FIG. 8 shows a map of plasmid CET700.

This effect is not restricted to a particular selectable marker. FIG. 7 compares expression of EGFP operable linked to a 5' human RNP UCOE and either a 5' (CET745) or 3' (CET741) placed *S. fradiae* neomycin resistance gene. There is almost a doubling of the already high expression level.

Example 2

Effectiveness of Other 3' Flanking Selectable Markers

Results

Figure 5:
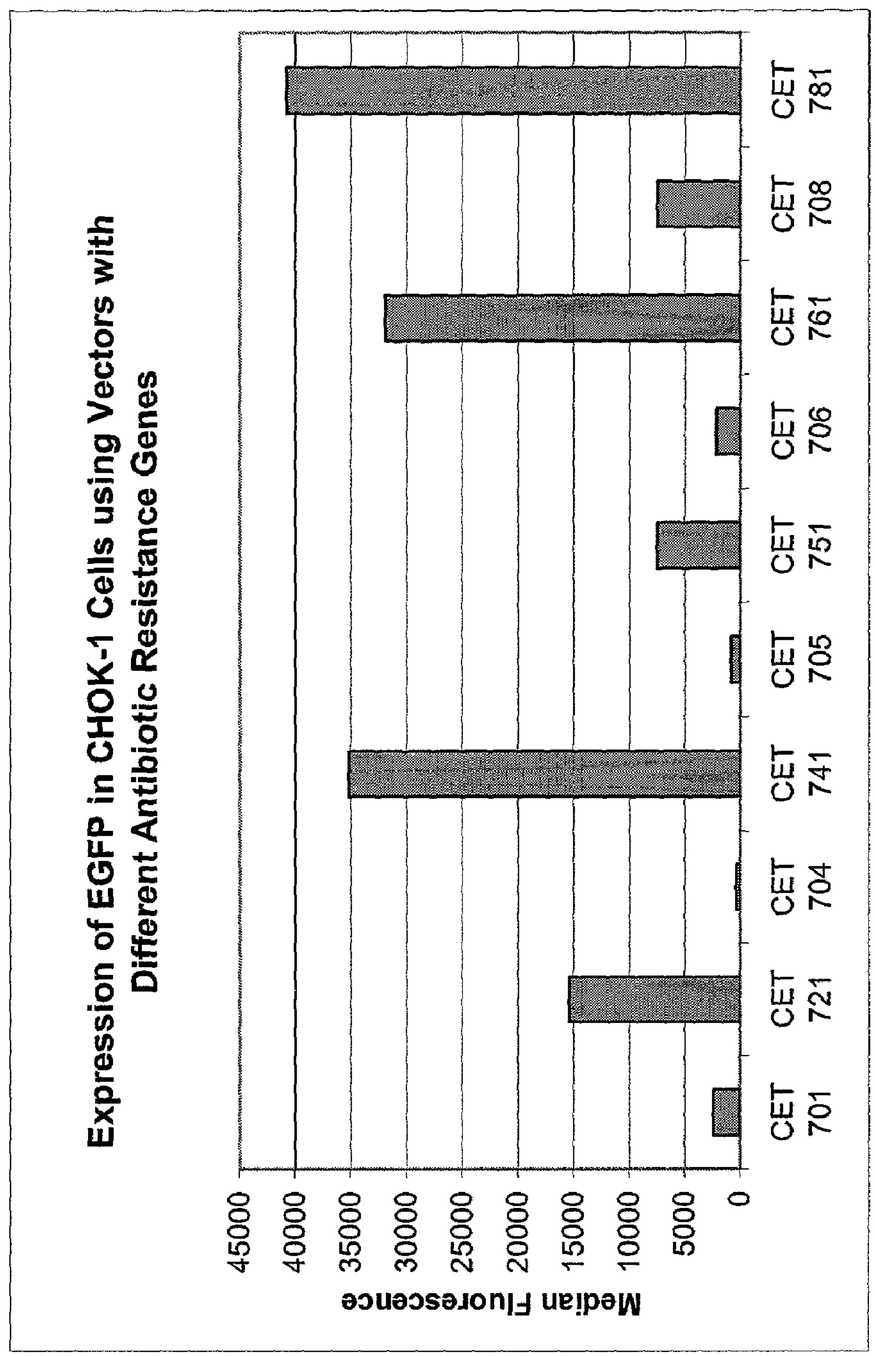
FIG. 5 shows the expression of EGFP in CHO-K1 cells transfected with vectors CET701, CET721, CET704, CET741, CET705, CET751, CET706, CET761, CET708 and CET781 as measured by median fluorescence corrected to allow comparison without exceeding the detection capacity of the FACScan.

FIG. 5 shows the effect of flanking the EGFP transgene with a 5' human RNP UCOE and various 3' flanking antibiotic resistance genes. CET701 is a control containing no UCOE, but with the wild-type *S alboniger* $puro^r$. CET721 has both the 5' UCOE and 3' $puro^r$. CET704 contains the *S fradiae* $neo^r$ but no UCOE, CET741 has both. CET705 contains the *S hygroscopicus* $hygro^r$ but no UCOE, CET751 has both. CET706 has the *E coli* $hygro^r$ but no UCOE, CET761 has both. CET708 has the codon-modified $puro^r$ but no UCOE, CET781 has both. In all cases the boosting effect of the 3' flanking resistance gene is evident.

Example 3

Combination of an Artificial UCOE and pgk/Puro Selectable Element

Results

As shown in FIGS. 2 and 3, expression from a comparable plasmid carrying an artificially constructed UCOE (CET711) was comparable to that obtained with the RNP UCOE both in terms of median fluorescence and proportion of positive cells. This demonstrates that the phenomenon of amplification of the effect of a UCOE by a second flanking CpG-rich element is a general one, not confined to a particular combination of the RNP UCOE and the pgk/Puro element. The comparison of CET711 and CET721 expression in FIG. 4 indicates a slightly lower level of expression was obtained with CET711, but this was still at least 6-fold higher than that obtained with a UCOE alone.

Figure 6:
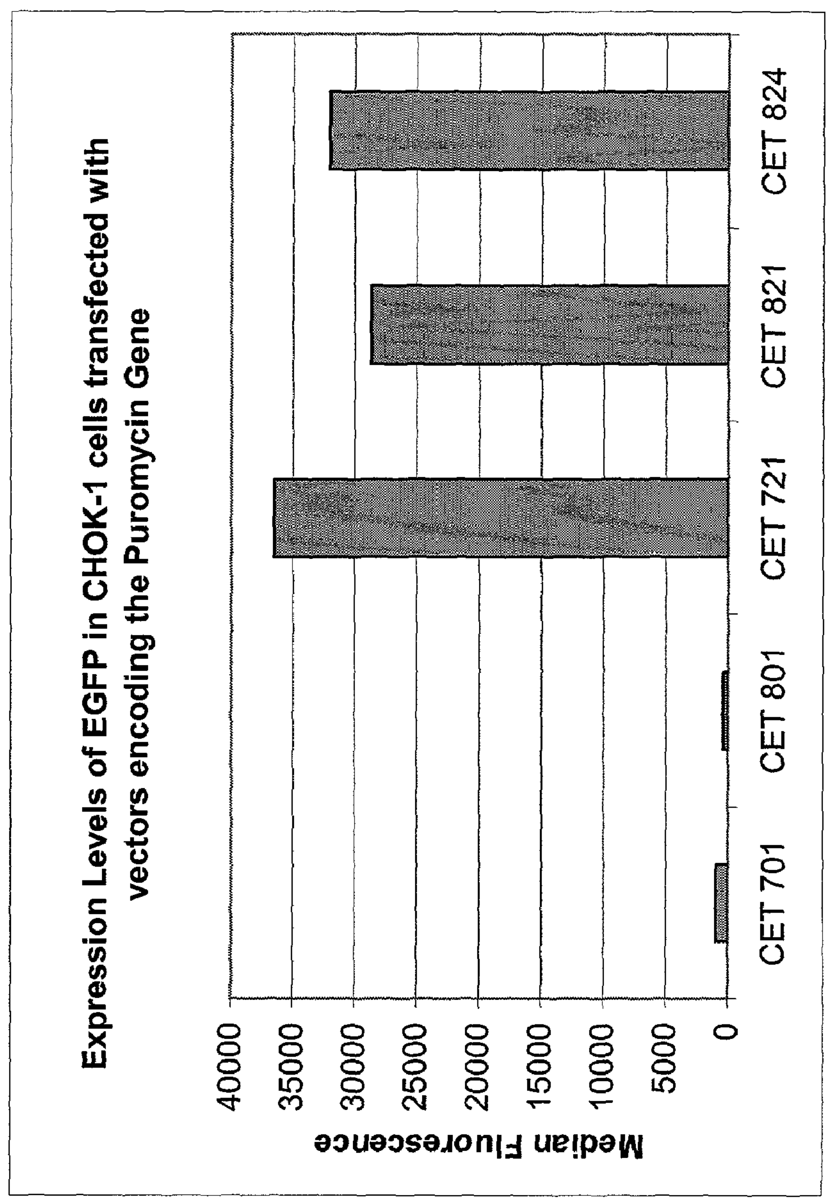
FIG. 6 shows the expression levels of EGFP in CHO-K1 cells transfected with vectors comparing 5' human and murine hnRNP UCOEs with a 3' puromycin resistance gene.

FIG. 6 shows the comparable effect obtained with either a human hnRNP UCOE using the murine CMV promoter to drive expression (CET821) and the murine equivalent (CET824). CET721 comprises the human hnRNP UCOE and uses the human CMV promoter.

The foregoing examples are meant to illustrate the invention and are not to be construed to limit the invention in any way. Those skilled in the art will recognize modifications that are within the spirit and scope of the invention. All references cited herein are hereby incorporated by reference in their entirety.

What is claimed is:

1. An isolated vector comprising polynucleotide, wherein the polynucleotide comprises:

a. an extended methylation-free CpG island encompassing dual, divergently transcribed promoters, wherein the CpG island
   1. comprises a DNA sequence associated with the 5' end of ubiquitously expressed genes; and/or
   2. extends across a region encompassing more than one transcriptional start site; and/or
   3. extends more than 500 bp;

b. an expressible nucleic acid terminated by a polyadenylation signal, and c. a selectable marker gene operably linked to a promoter, wherein the selectable marker gene is an antibiotic resistance gene, wherein when the vector is linearized and integrated into a chromosome, both the extended methylation-free CpG island and the selectable marker gene are operably linked to the expressible nucleic acid, and the components are positioned in the order: extended methylation-free island, expressible nucleic acid, selectable marker gene, in the 5' to 3' orientation with respect to the sense strand of the expressible nucleic acid, and wherein the polyadenylation signal at the 3' end of the expressible nucleic acid is within 2000 by of the proximal end of the selectable marker gene, and wherein the expression of the expressible nucleic acid is increased relative to the expression in the presence of the extended methylation-free CpG island alone or when the selectable marker is 5' of the expressible nucleic acid.

2. An isolated vector comprising polynucleotide, wherein the polynucleotide comprises:

a. an extended methylation-free CpG island encompassing dual, divergently transcribed promoters, wherein the CpG island
   1. comprises a DNA sequence associated with the 5' end of ubiquitously expressed genes; and/or
   2. extends across a region encompassing more than one transcriptional start site; and/or
   3. extends more than 500 bp;

b. an expressible nucleic acid terminated by a polyadenylation signal, and c. a selectable marker gene operably linked to a promoter, wherein the selectable marker gene is an antibiotic resistance gene, wherein when the vector is linearized and integrated into a chromosome, both the extended methylation-free CpG island and the selectable marker gene are operably linked to the expressible nucleic acid, and the components are positioned in the order: extended methylation-free island, expressible nucleic acid, selectable marker gene, in the 5' to 3' orientation with respect to the sense strand of the expressible nucleic acid, and wherein the polyadenylation signal at the 3' end of the expressible nucleic acid is within 1500 by of the proximal end of the selectable marker gene, and wherein the expression of the expressible nucleic acid is increased relative to the expression in the presence of the extended methylation-free CpG island alone or when the selectable marker is 5' of the expressible nucleic acid.

3. An isolated vector comprising polynucleotide, wherein the polynucleotide comprises:

a. an extended methylation-free CpG island encompassing dual, divergently transcribed promoters, wherein the CpG island
   1. comprises a DNA sequence associated with the 5' end of ubiquitously expressed genes; and/or
   2. extends across a region encompassing more than one transcriptional start site; and/or
   3. extends more than 500 bp;

b. an expressible nucleic acid terminated by a polyadenylation signal, and c. a selectable marker gene operably linked to a promoter, wherein the selectable marker gene is an antibiotic resistance gene, wherein when the vector is linearized and integrated into a chromosome, both the extended methylation-free CpG island and the selectable marker gene are operably linked to the expressible nucleic acid, and the components are positioned in the order: extended methylation-free island, expressible nucleic acid, selectable marker gene, in the 5' to 3' orientation with respect to the sense strand of the expressible nucleic acid, and wherein the polyadenylation signal at the 3' end of the expressible nucleic acid is within 1000 by of the proximal end of the selectable marker gene, and wherein the expression of the expressible nucleic acid is increased relative to the expression in the presence of the extended methylation-free CpG island alone or when the selectable marker is 5' of the expressible nucleic acid.

4. An isolated vector comprising polynucleotide, wherein the polynucleotide comprises:

a. an extended methylation-free CpG island encompassing dual, divergently transcribed promoters, wherein the CpG island
   1. comprises a DNA sequence associated with the 5' end of ubiquitously expressed genes; and/or
   2. extends across a region encompassing more than one transcriptional start site; and/or
   3. extends more than 500 bp;

b. an expressible nucleic acid terminated by a polyadenylation signal, and c. a selectable marker gene operably linked to a promoter, wherein the selectable marker gene is an antibiotic resistance gene, wherein when the vector is linearized and integrated into a chromosome, both the extended methylation-free CpG island and the selectable marker gene are operably linked to the expressible nucleic acid, and the components are positioned in the order: extended methylation-free island, expressible nucleic acid, selectable marker gene, in the 5' to 3' orientation with respect to the sense strand of the expressible nucleic acid, and wherein the polyadenylation signal at the 3' end of the expressible nucleic acid is within 500 by of the proximal end of the selectable marker gene, and wherein the expression of the expressible nucleic acid is increased relative to the expression in the presence of the extended methylation-free CpG island alone or when the selectable marker is 5' of the expressible nucleic acid.

5. The isolated vector of any one of claims 1-4, wherein the antibiotic resistance gene is from a *Streptomyces* species.

6. The isolated vector of claim 5, wherein the antibiotic resistance gene is a puromycin resistance gene.

7. The isolated vector of claim 6, wherein the puromycin resistance gene is the puromycin N-acetyl transferase gene from *Streptomyces alboniger.*

8. The isolated vector of claim 7, wherein the puromycin resistance gene is a modified puromycin N-acetyl transferase gene from *Streptomyces alboniger.*

9. The isolated vector of claim 8, comprising SEQ ID NO: 3.

10. The isolated vector of claim 5, wherein the antibiotic resistance gene is a neomycin resistance gene.

11. The isolated vector of claim 10, wherein the neomycin resistance gene is the aminoglycoside phosphotransferase gene from *Streptomyces fradiae.*

12. The isolated vector of claim 5, wherein the antibiotic resistance gene is a hygromycin resistance gene.

13. The isolated vector of claim 12, wherein the antibiotic resistance gene is the hygromycin phosphotransferase gene from *Streptomyces hygroscopicus.*

14. The isolated vector of claim 5, wherein the antibiotic resistance gene is a bleomycin resistance gene.

15. The isolated vector of claim 14, wherein the bleomycin resistance gene is the bleomycin binding protein from *Streptomyces verticillus.*

16. The isolated vector of claim 14, wherein the bleomycin resistance gene is the bleomycin N-acetyltransferase gene from *Streptomyces verticillus.*

17. The isolated vector of claim 5, wherein the antibiotic resistance gene is a blasticidin resistance gene.

18. The isolated vector of claim 17, wherein the blasticidin resistance gene is the blasticidin S-acetyltransferase gene from *Streptomyces verticillum.*

19. The isolated vector of any one of claims 1-4, wherein the antibiotic resistance gene is the aminocyclitol phosphotransferase from *Escherichia coli.*

20. The isolated vector of any one of claims 1-4, wherein the antibiotic resistance gene is the neomycin phosphotransferase gene from transposon Tn5.

21. The isolated vector of any one of claims 1-4, wherein the vector is a plasmid.

22. The isolated vector of any one of claims 1-4, wherein the expressible nucleic acid encodes a recombinant protein for expression in an in vitro cell culture system.

23. The isolated vector of any one of claims 1-4 comprising nucleotides 1-10551 of SEQ ID NO: 1.

24. The isolated vector of any one of claims 1-4 comprising nucleotides 1-13547 of SEQ ID NO: 2.

25. A method for obtaining expression of an expressible nucleic acid comprising transfecting the isolated vector of any one of claims 1-4 into a host cell.

26. A method for obtaining a desired gene product comprising expressing the expressible nucleic acid from the isolated vector of any one of claims 1-4 in a host cell, wherein the expressible nucleic acid encodes the desired gene product and recovering the desired gene product.

27. The isolated vector of any one of claims 1-4, wherein the expressible nucleic acid is operably linked to a cytomegalovirus immediate/early promoter.

28. The isolated vector of any one of claims 1-4, wherein the expressible nucleic acid is contained within a multiple cloning site and the multiple cloning site is further operably linked to a promoter.

29. The isolated vector of claim 28, wherein said promoter is a cytomegalovirus immediate/early promoter.

30. The vector CET710.

31. The vector CET720.

32. A vector comprising nucleotides 1-12041 of SEQ ID NO:9.

33. The vector CET1010.

34. A vector comprising nucleotides 1-11646 of SEQ ID NO:10.

35. The vector CET1020.

36. A vector comprising nucleotides 1-9027 of SEQ ID NO:11.

37. The vector CET1030.

38. A vector comprising nucleotides 1-12221 of SEQ ID NO:12.

39. The vector CET1110.

40. A vector comprising nucleotides 1-11828 of SEQ ID NO:13.

41. The vector CET1120.

42. A vector comprising nucleotides 1-9209 of SEQ ID NO:14.

43. The vector CET1130.

44. An isolated vector comprising polynucleotide comprising:

a. an extended methylation-free CpG island selected from the group consisting of: an extended methylation-free CpG island comprising an 8 Kb DNA fragment spanning the human hnRNPA2 gene; an extended methylation-free CpG island comprising an 8 Kb fragment spanning the murine hnRNPA2 gene; an extended methylation-free CpG island comprising nucleotides 1-7898 of SEQ ID NO: 15; and an extended methylation free island comprising a 2.0 kb DNA fragment spanning the human β-actin CpG island/promoter region and a 1.8 kb DNA fragment spanning the human PDCD2 CpG island/promoter region; and combinations thereof;

b. an expressible nucleic acid terminated by a polyadenylation signal; and c. a selectable marker gene operably linked to a promoter, wherein the selectable marker gene is an antibiotic resistance gene and wherein when the vector is linearized and integrated into a chromosome, both the CpG island and the selectable marker gene are operably-linked to the expressible nucleic acid, and the components are positioned in the order: extended methylation-free CpG island, expressible nucleic acid, selectable marker gene, in the 5' to 3' orientation with respect to the sense strand of the expressible nucleic acid, and wherein the polyadenylation signal at the 3' end of the expressible nucleic acid is within 2000 bp of the proximal end of the selectable marker gene, and wherein the expression of the expressible nucleic acid is increased relative to the expression in the presence of the extended methylation-free CpG island alone or when the selectable marker is 5' of the expressible nucleic acid.

45. An isolated vector comprising a polynucleotide comprising:

a. an extended methylation-free CpG island selected from the group consisting of: an extended methylation-free CpG island comprising an 8 Kb DNA fragment spanning the human hnRNPA2 gene; an extended methylation-free CpG island comprising an 8 Kb fragment spanning the murine hnRNPA2 gene; an extended methylation-free CpG island comprising nucleotides 1-7898 of SEQ ID NO: 15; and an extended methylation free island comprising a 2.0 kb DNA fragment spanning the human β-actin CpG island/promoter region and a 1.8 kb DNA fragment spanning the human PDCD2 CpG island/promoter region; and combinations thereof;

b. an expressible nucleic acid terminated by a polyadenylation signal; and c. a selectable marker gene operably linked to a promoter, wherein the selectable marker gene is an antibiotic resistance gene and wherein when the vector is linearized and integrated into a chromosome, both the CpG island and the selectable marker gene are operably-linked to the expressible nucleic acid, and the components are positioned in the order: extended methylation-free CpG island, expressible nucleic acid, selectable marker gene, in the 5' to 3' orientation with respect to the sense strand of the expressible nucleic acid, and wherein the polyadenylation signal at the 3' end of the expressible nucleic acid is within 1500 by of the proximal end of the selectable marker gene, and wherein the expression of the expressible nucleic acid is increased relative to the expression in the presence of the extended methylation-free CpG island alone or when the selectable marker is 5' of the expressible nucleic acid.

46. An isolated vector comprising a polynucleotide comprising:

a. an extended methylation-free CpG island selected from the group consisting of: an extended methylation-free CpG island comprising an 8 Kb DNA fragment spanning the human hnRNPA2 gene; an extended methylation-free CpG island comprising an 8 Kb fragment spanning the murine hnRNPA2 gene; an extended methylation-free CpG island comprising nucleotides 1-7898 of SEQ ID NO: 15; and an extended methylation free island comprising a 2.0 kb DNA fragment spanning the human β-actin CpG island/promoter region and a 1.8 kb DNA fragment spanning the human PDCD2 CpG island/promoter region; and combinations thereof;

b. an expressible nucleic acid terminated by a polyadenylation signal; and c. a selectable marker gene operably linked to a promoter, wherein the selectable marker gene is an antibiotic resistance gene and wherein when the vector is linearized and integrated into a chromosome, both the CpG island and the selectable marker gene are operably-linked to the expressible nucleic acid, and the components are positioned in the order: extended methylation-free CpG island, expressible nucleic acid, selectable marker gene, in the 5' to 3' orientation with respect to the sense strand of the expressible nucleic acid, and wherein the polyadenylation signal at the 3' end of the expressible nucleic acid is within 1000 by of the proximal end of the selectable marker gene, and wherein the expression of the expressible nucleic acid is increased relative to the expression in the presence of the extended methylation-free CpG island alone or when the selectable marker is 5' of the expressible nucleic acid.

47. An isolated vector comprising a polynucleotide comprising:

a. an extended methylation-free CpG island selected from the group consisting of: an extended methylation-free CpG island comprising an 8 Kb DNA fragment spanning the human hnRNPA2 gene; an extended methylation-free CpG island comprising an 8 Kb fragment spanning the murine hnRNPA2 gene; an extended methylation-free CpG island comprising nucleotides 1-7898 of SEQ ID NO: 15; and an extended methylation free island comprising a 2.0 kb DNA fragment spanning the human β-actin CpG island/promoter region and a 1.8 kb DNA fragment spanning the human PDCD2 CpG island/promoter region; and combinations thereof;

b. an expressible nucleic acid terminated by a polyadenylation signal; and c. a selectable marker gene operably linked to a promoter, wherein the selectable marker gene is an antibiotic resistance gene and wherein when the vector is linearized and integrated into a chromosome, both the CpG island and the selectable marker gene are operably-linked to the expressible nucleic acid, and the components are positioned in the order: extended methylation-free CpG island, expressible nucleic acid, selectable marker gene, in the 5' to 3' orientation with respect to the sense strand of the expressible nucleic acid, and wherein the polyadenylation signal at the 3' end of the expressible nucleic acid is within 500 by of the proximal end of the selectable marker gene, and wherein the expression of the expressible nucleic acid is increased relative to the expression in the presence of the extended methylation-free CpG island alone or when the selectable marker is 5' of the expressible nucleic acid.

* * * * *

UNITED STATES PATENT AND TRADEMARK OFFICE

CERTIFICATE OF CORRECTION

PATENT NO. : 7,812,148 B2
APPLICATION NO. : 10/117960
DATED : October 12, 2010
INVENTOR(S) : Crombie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 529 days.

Signed and Sealed this
Seventeenth Day of May, 2011

David J. Kappos
*Director of the United States Patent and Trademark Office*

SEQUENCE LISTING

```
<160> NUMBER OF SEQ ID NOS: 15

<210> SEQ ID NO 1
<211> LENGTH: 10551
<212> TYPE: DNA
<213> ORGANISM: Artificial Sequence
<220> FEATURE:
<223> OTHER INFORMATION: Plasmid

<400> SEQUENCE: 1

ggtggcactt ttcggggaaa tgtgcgcgga acccctattt gtttattttt ctaaatacat      60

tcaaatatgt atccgctcat gagacaataa ccctgataaa tgcttcaata atattgaaaa     120

aggaagagta tgagtattca acatttccgt gtcgccctta ttcccttttt tgcggcattt     180

tgccttcctg tttttgctca cccagaaacg ctggtgaaag taaaagatgc tgaagatcag     240

ttgggtgcac gagtgggtta catcgaactg gatctcaaca gcggtaagat ccttgagagt     300

tttcgccccg aagaacgttt tccaatgatg agcactttta aagttctgct atgtggcgcg     360

gtattatccc gtattgacgc cgggcaagag caactcggtc gccgcataca ctattctcag     420

aatgacttgg ttgagtactc accagtcaca gaaaagcatc ttacggatgg catgacagta     480

agagaattat gcagtgctgc cataaccatg agtgataaca ctgcggccaa cttacttctg     540

acaacgatcg gaggaccgaa ggagctaacc gcttttttgc acaacatggg ggatcatgta     600

actcgccttg atcgttggga accggagctg aatgaagcca taccaaacga cgagcgtgac     660

accacgatgc ctgtagcaat ggcaacaacg ttgcgcaaac tattaactgg cgaactactt     720

actctagctt cccggcaaca attaatagac tggatggagg cggataaagt tgcaggacca     780

cttctgcgct cggcccttcc ggctggctgg tttattgctg ataaatctgg agccggtgag     840

cgtgggtctc gcggtatcat tgcagcactg gggccagatg gtaagccctc ccgtatcgta     900

gttatctaca cgacggggag tcaggcaact atggatgaac gaaatagaca gatcgctgag     960

ataggtgcct cactgattaa gcattggtaa ctgtcagacc aagtttactc atatatactt    1020

tagattgatt taaaacttca tttttaattt aaaaggatct aggtgaagat cctttttgat    1080

aatctcatga ccaaaatccc ttaacgtgag ttttcgttcc actgagcgtc agaccccgta    1140

gaaaagatca aaggatcttc ttgagatcct ttttttctgc gcgtaatctg ctgcttgcaa    1200

acaaaaaaac caccgctacc agcggtggtt tgtttgccgg atcaagagct accaactctt    1260

tttccgaagg taactggctt cagcagagcg cagataccaa atactgtcct tctagtgtag    1320

ccgtagttag gccaccactt caagaactct gtagcaccgc ctacatacct cgctctgcta    1380

atcctgttac cagtggctgc tgccagtggc gataagtcgt gtcttaccgg gttggactca    1440

agacgatagt taccggataa ggcgcagcgg tcgggctgaa cggggggttc gtgcacacag    1500

cccagcttgg agcgaacgac ctacaccgaa ctgagatacc tacagcgtga gctatgagaa    1560

agcgccacgc ttcccgaagg gagaaaggcg gacaggtatc cggtaagcgg cagggtcgga    1620
```

-continued

```
acaggagagc gcacgaggga gcttccaggg ggaaacgcct ggtatcttta tagtcctgtc   1680

gggtttcgcc acctctgact tgagcgtcga tttttgtgat gctcgtcagg ggggcggagc   1740

ctatggaaaa acgccagcaa cgcggccttt ttacggttcc tggccttttg ctggcctttt   1800

gctcacatgt tctttcctgc gttatcccct gattctgtgg ataaccgtat taccgccttt   1860

gagtgagctg ataccgctcg ccgcagccga acgaccgagc gcagcgagtc agtgagcgag   1920

gaagcggaag agcgcccaat acgcaaaccg cctctccccg cgcgttggcc gattcattaa   1980

tgcagctggc acgacaggtt tcccgactgg aaagcgggca gtgagcgcaa cgcaattaat   2040

gtgagttagc tcactcatta ggcaccccag gctttacact ttatgcttcc ggctcgtatg   2100

ttgtgtggaa ttgtgagcgg ataacaattt cacacaggaa acagctatga ccatgattac   2160

gccaagcgcg caattaaccc tcactaaagg gaacaaaagc tgggtaccgg gccccccctc   2220

gaggtcgacg gtatcgataa gctcgataag ctcatggcac ctgtattgta ctcttatcag   2280

tcattatatg gactttaact tccccagata ttatttgggc tcctccataa gactgtgagc   2340

atctgaccac tggagtgttg cttcccatta tatccctgtt atcaagcaca aggtcaggca   2400

cagagtaaga ctcaaaacat gttttggaat gtatgactgg tatgaactac aaaccagtaa   2460

gctgatgttt tcattttgag tctataaatc taattttgtg gtggttttgt gtatggctca   2520

aggctcaaat tgtaaaattt aatattatgt gaccaaagaa agttataccc agaacctcaa   2580

tttcctcacc ttcaaaatgg ggcagtttct cactcattgg tctgctgtca cgattttaat   2640

gagctcatgc acaaacagcc ctttatataa ggtaagtgct ggataaatgt tggctactat   2700

aataaaataa gcctctaaga tacttggtca gcacaagtac tacccaagag tatgcactgt   2760

aagtaaactg acaaaattgt gtatctaaaa ctggccagat gaaagagaaa cttttaaggg   2820

gcccttctgc gtgcccgaca ctgtgctagg cactcacact atcccgaccc gagaaaccga   2880

tctgcgaccc agaggaactt accaagcctc cagcatcttg tgcagcccta ctcatgggac   2940

catctggata cccacccttg tctttacagg gagcagaaca cacctcttat gtgtcagaaa   3000

acaaagtcca ggaagtatat ttttacctga ggcaatatct gaaaattgta tgctacagcc   3060

tccaaagtga gtcttcctct cagtacctct cttctaggca catggagccc tttcttccaa   3120

gtattatgtt taaccactta atgaatgaag tcctgaaact gcttacccat gctccctata   3180

atctctgagt aatcttcctt ttccacaacc tcaggcataa tctcatcttc tgtttctatt   3240

acaatttcaa attctggaaa aaggaagttg tggtctggaa ttatatggtc cagatgatct   3300

gaaacaaaaa ggacagcact attagtaatc atttagtttt gaagacagtc taataatttg   3360

ctgtctctaa agtactatat tccctatagt tctggcattt tagataaagg gtcataaatt   3420

aaatgcctat atggtgacat tattcagtga ttcagacttc acagcctttt tttttttttt   3480

acaaaggtgt tccaggcatg aaaaatttta aagtactata cctttcctaa ttttaccttt   3540

aaagttgtcc tggaaatatc tgggttgaca aaggcgatga aactgaactg agacttaaaa   3600

aaaagattac ccacctggtt gtgcacaagc ctgcttatgt cccaatctcc agtctagggt   3660

ctgatgctcc ttgctgcagt aatatgcttt gtggcatctg gagcacgttt tggggcctaa   3720

acagccacaa accctgcaga gatgagcacc agacttaagc tggagacaca ctgattctcc   3780

tgtttctggg ggaggattct cagaaggtgg ctcatatgag taaaaatcgt tttcctggg    3840

tagttgattc ctaaaaacta aaaaagaata cagagaaaag ttttatcttc aaacaaaaca   3900

gcaattcaca tattttatcc tctgcacgta aaactgaaaa taacaacaac aaaaaagaaa   3960

tgaaagtttt tgctttcagg aataagcttt taaaatccag aaactagatt tcgtccggta   4020
```

-continued

```
cacgcaactg agttgcctcc tagaggtggt ttgagttaat caaattaata agactgatcg   4080
ttaagaacga ctgccaaaaa tacgaaaaag ctactgggat ccatctttcc aagacaattt   4140
ctattatctg aattaacacc atacctggta cccactgatt aaaagctggg ggttaccaat   4200
gcgcgtgggc acagttagaa gcttatgtag caaaaatgag cacatcctgg aagggcccgg   4260
gagaaggtgc tcctggggca gcgcggagag ggagctctga ggctggggcg gcagcggtgc   4320
ttgccgccgt ccccctggtc gctcccggaa ttaacgccgc gcacgcgtcg gaggcatggc   4380
cccgtcccga ccccgtttgg cggctcacct cgcaggccgg cacagcacgg ctgctcgcgg   4440
cagcagaaga ggaagatgca gcggtggaag gcgtccgggc ggccaggcag cggcgcatac   4500
acctgcagca ggaaggagag cgggcggccg cacagctcgc aggccagggc ctggggcccc   4560
ggcagcccgg ccgcgcccag ccatgccggc cgcccgccca ccttgctggg gaactgctcg   4620
ctgcgcagtc gccacgccgg cgccgactcg gcgaagccca gctccacagg cctggccccg   4680
gcggcagcca tgcggggcgc gggctggcgt ggggcgcagc ccacagctgg gtcggaaggc   4740
ggaaatcggg cgccgggccg gaaggcaaga ggcgggcacc tttccggagg acaggaggcg   4800
gaaacgcgtc tgacgggagc ggttgcagga ccaatgcgag ggaacggggc agaggaaacc   4860
tctcggcatc agccccgccc ctggcgcctc tgcctccgag ccgctttcct ggtgcctccg   4920
ggtgctctgg gatggttctg gtctttggga gagtggcagc tggtgacggc gctccgctca   4980
cctctgcaca tgtcttgctg tgggcctgcg ggtggccgcc agggaggcag agccctcccg   5040
caaaccttcc ctgctggtgt ccacctcagg gtgtgggaaa cctgtgcgct ggccgagtgc   5100
taaccaagag taggcagtga aagacaaatg aaggttgaac aggtaaagtg aggaccctac   5160
agcggaaacc aagaatcctg tgtgcctgag agtaatgaag aagcctctgc agaagagtct   5220
tttctgtcag tcttaaggtc tctgttttaa tgttagtgct ggcttgctgt acctgaattc   5280
caagggagga gtgtataatg aggcatggcc aaccccccact tcccatcatt gcctgaacta   5340
gtttttcagg ttaacttcag aatgcccttg gtaccgcggg cccccctctgt ggtcccacgc   5400
cactgatcgc tgcatgccca ccacctgggt acacacagtc tgtgattccc ggagcagaac   5460
ggaccctgcc cacccggtct tgtgtgctac tcagtggaca gacccaaggc aagaaagggt   5520
gacaaggaca gggtcttccc aggctggctt tgagttccta gcaccgcccc gcccccaatc   5580
ctctgtggca catggagtct tggtccccag agtcccccag cggcctccag atggtctggg   5640
agggcagttc agctgtggct gcgcatagca gacatacaac ggacggtggg cccagaccca   5700
ggctgtgtag acccagcccc cccgccccgc agtgcctagg tcacccacta acgccccagg   5760
cctggtcttg gctgggcgtg actgttaccc tcaaaagcag gcagctccag ggtaaaaggt   5820
gccctgccct gtagagccca cttccttccc agggctgcgg ctgggtaggt ttgtagcctt   5880
catcacgggc cacctccagc cactggaccg ctggcccctg ccctgtcctg gggagtgtgg   5940
tcctgcgact ctaatggccg caagccacct gactccccca acaccacact ctacctctca   6000
agcccaggtc tctccctagt gacccaccca gcacatttag ctagctgagc cccacagcca   6060
gaggtcctca ggccctgctt tcagggcagt tgctctgaag tcggcaaggg ggagtgactg   6120
cctggccact ccatgccctc caagagctcc ttctgcagga gcgtacagaa cccagggccc   6180
tggcacccgt gcagaccctg gcccacccca cctgggcgct cagtgcccaa gagatgtcca   6240
cacctaggat gtcccgcggt gggtgggggg cccgagagac gggcaggccg ggggcaggcc   6300
tggccatgcg gggccgaacc gggcactgcc cagcgtgggg cgcgggggcc acggcgcgcg   6360
```

-continued

```
cccccagccc ccgggcccag caccccaagg cggccaacgc caaaactctc cctcctcctc   6420
ttcctcaatc tcgctctcgc tctttttttt tttcgcaaaa ggaggggaga gggggtaaaa   6480
aaatgctgca ctgtgcggcg aagccggtga gtgagcggcg cggggccaat cagcgtgcgc   6540
cgttccgaaa gttgcctttt atggctcgag cggccgcggc ggcgccctat aaaacccagc   6600
ggcgcgacgc gccaccaccg ccgagaccgc gtccgcccgc gagcacagag cctcgccttt   6660
gccgatccgc cgcccgtcca cacccgccgc caggtaagcc cggccagccg accggggcat   6720
gcggccgcgg cccttcgccc gtgcagagcc gccgtctggg ccgcagcggg gggcgcatgg   6780
ggcggaaccg gaccgccgtg gggggcgcgg gagaagcccc tgggcctccg gagatggggg   6840
acaccccacg ccagttcgca ggcgcgaggc cgcgctcggg cgggcgcgct ccgggggtgc   6900
cgctctcggg gcgggggcaa ccggcggggt ctttgtctga gccgggctct tgccaatggg   6960
gatcgcacgg tgggcgcggc gtagcccccg tcaggcccgg tgggggctgg ggcgccatgc   7020
gcgtgcgcgc tggtcctttg ggcgctaact gcgtgcgcgc tgggaattgg cgctaattgc   7080
gcgtgcgcgc tgggactcaa tggcgctaat cgcgcgtgcg ttctggggcc cgggcgcttg   7140
cgccacttcc tgcccgagcc gctggcgccc gagggtgtgg ccgctgcgtg cgcgcgcgcg   7200
acccggtcgc tgtttgaacc gggcggaggc ggggctggcg cccggttggg agggggttgg   7260
ggcctggctt cctgccgcgc gccgcgggga cgcctccgac cagtgtttgc cttttatggt   7320
aataacgcgg ccggcccggc ttcctttgtc cccaatctgg gcgcgcgccg gcgccccctg   7380
gcggcctaag gactcggcgc gccggaagtg gccagggcgg gggcgacttc ggctcacagc   7440
gcgcccggct attctcgcag ctcaccatgc cggtcgccac catgagcttg atatcgaatt   7500
cctgcagccc gggggatcca ctagttctag agcttgatta atagtaatca attacggggt   7560
cattagttca tagcccatat atggagttcc gcgttacata acttacggta aatggcccgc   7620
ctggctgacc gcccaacgac ccccgcccat tgacgtcaat aatgacgtat gttcccatag   7680
taacgccaat agggactttc cattgacgtc aatgggtgga gtatttacgg taaactgccc   7740
acttggcagt acatcaagtg tatcatatgc caagtacgcc ccctattgac gtcaatgacg   7800
gtaaatggcc cgcctggcat tatgcccagt acatgacctt atgggacttt cctacttggc   7860
agtacatcta cgtattagtc atcgctatta ccatggtgat gcggttttgg cagtacatca   7920
atgggcgtgg atagcggttt gactcacggg gatttccaag tctccacccc attgacgtca   7980
atgggagttt gttttggcac caaaatcaac gggactttcc aaaatgtcgt aacaactccg   8040
ccccattgac gcaaatgggc ggtaggcgtg tacggtggga ggtctatata agcagagctg   8100
gtttagtgaa ccgtcagatc cgctagcgtt cgaagtttaa acgcggccgc gactctagat   8160
cataatcagc cataccacat ttgtagaggt tttacttgct ttaaaaaacc tcccacacct   8220
ccccctgaac ctgaaacata aaatgaatgc aattgttgtt gttaacttgt ttattgcagc   8280
ttataatggt tacaaataaa gcaatagcat cacaaatttc acaaataaag cattttttc   8340
actgcattct agttgtggtt tgtccaaact catcaatgta tcttaaatcg aattctaccg   8400
ggtaggggag gcgcttttcc caaggcagtc tggagcatgc gctttagcag ccccgctggg   8460
cacttggcgc tacacaagtg gcctctggcc tcgcacacat tccacatcca ccggtaggcg   8520
ccaaccggct ccgttctttg gtggcccctt cgcgccacct tctactcctc ccctagtcag   8580
gaagttcccc cccgccccgc agctcgcgtc gtgcaggacg tgacaaatgg aagtagcacg   8640
tctcactagt ctcgtgcaga tggacagcac cgctgagcaa tggaagcggg taggcctttg   8700
gggcagcggc caatagcagc tttgctcctt cgctttctgg gctcagaggc tgggaagggg   8760
```

```
tgggtccggg ggcgggctca ggggcgggct caggggcggg gcgggcgccc gaaggtcctc    8820

cggaggcccg gcattctgca cgcttcaaaa gcgcacgtct gccgcgctgt tctcctcttc    8880

ctcatctccg ggcctttcga ccagcttacc atgaccgagt acaagcccac ggtgcgcctc    8940

gccacccgcg acgacgtccc cagggccgta cgcaccctcg ccgccgcgtt cgccgactac    9000

cccgccacgc gccacaccgt cgatccggac cgccacatcg agcgggtcac cgagctgcaa    9060

gaactcttcc tcacgcgcgt cgggctcgac atcggcaagg tgtgggtcgc ggacgacggc    9120

gccgcggtgg cggtctggac cacgccggag agcgtcgaag cgggggcggt gttcgccgag    9180

atcggcccgc gcatggccga gttgagcggt tcccggctgg ccgcgcagaa cagatggaag    9240

gcctcctggc gccgcaccgg cccaaggagc ccgcgtggtt cctggccacc gtcgcgtctc    9300

gcccgaccac cagggcaagg gtctgggcag cgccgtcgtg ctccccggag tggaggcggc    9360

cgagcgcgcc ggggtgcccg ccttcctgga gacctccgcg ccccgcaacc tccccttcta    9420

cgagcggctc ggcttcaccg tcaccgccga cgtcgaggtg cccgaaggac cgcgcacctg    9480

gtgcatgacc cgcaagcccg gtgcctgacg cccgccccac gacccgcagc gcccgaccga    9540

aaggagcgca cgaccccatg catcgtagag ctcgctgatc agcctcgact gtgccttcta    9600

gttgccagcc atctgttgtt tgcccctccc ccgtgccttc cttgaccctg gaaggtgcca    9660

ctcccactgt cctttcctaa taaaatgagg aaattgcatc gcattgtctg agtaggtgtc    9720

attctattct ggggggtggg gtggggcagg acagcaaggg ggaggattgg gragacaata    9780

gcaggcatgc tggggggggcg gtgggggcta tggcttctga ggcggaaaga accagctggg    9840

gctcgagatc cactagttct agcctcgagg ctagagcggc cgccaccgcg gtggagctcc    9900

aattcgccct atagtgagtc gtattacgcg cgctcactgg ccgtcgtttt acaacgtcgt    9960

gactgggaaa accctggcgt tacccaactt aatcgccttg cagcacatcc ccctttcgcc   10020

agctggcgta atagcgaaga ggcccgcacc gatcgccctt cccaacagtt gcgcagcctg   10080

aatggcgaat ggaaattgta agcgttaata ttttgttaaa attcgcgtta aatttttgtt   10140

aaatcagctc attttttaac caataggccg aaatcggcaa aatcccttat aaatcaaaag   10200

aatagaccga gatagggttg agtgttgttc cagtttggaa caagagtcca ctattaaaga   10260

acgtggactc caacgtcaaa gggcgaaaaa ccgtctatca gggcgatggc ccactacgtg   10320

aaccatcacc ctaatcaagt tttttggggt cgaggtgccg taaagcacta aatcggaacc   10380

ctaaagggag cccccgattt agagcttgac ggggaaagcc ggcgaacgtg gcgagaaagg   10440

aagggaagaa agcgaaagga gcgggcgcta gggcgctggc aagtgtagcg gtcacgctgc   10500

gcgtaaccac cacacccgcc gcgcttaatg cgccgctaca gggcgcgtca g             10551
```

<210> SEQ ID NO 2
<211> LENGTH: 13547
<212> TYPE: DNA
<213> ORGANISM: Artificial Sequence
<220> FEATURE:
<223> OTHER INFORMATION: Plasmid

<400> SEQUENCE: 2

```
ggtggcactt ttcggggaaa tgtgcgcgga acccctattt gtttattttt ctaaatacat      60

tcaaatatgt atccgctcat gagacaataa ccctgataaa tgcttcaata atattgaaaa     120

aggaagagta tgagtattca acatttccgt gtcgccctta ttcccttttt tgcggcattt     180

tgccttcctg tttttgctca cccagaaacg ctggtgaaag taaaagatgc tgaagatcag     240
```

-continued

```
ttgggtgcac gagtgggtta catcgaactg gatctcaaca gcggtaagat ccttgagagt    300

tttcgccccg aagaacgttt tccaatgatg agcactttta aagttctgct atgtggcgcg    360

gtattatccc gtattgacgc cgggcaagag caactcggtc gccgcataca ctattctcag    420

aatgacttgg ttgagtactc accagtcaca gaaaagcatc ttacggatgg catgacagta    480

agagaattat gcagtgctgc cataaccatg agtgataaca ctgcggccaa cttacttctg    540

acaacgatcg gaggaccgaa ggagctaacc gcttttttgc acaacatggg ggatcatgta    600

actcgccttg atcgttggga accggagctg aatgaagcca taccaaacga cgagcgtgac    660

accacgatgc ctgtagcaat ggcaacaacg ttgcgcaaac tattaactgg cgaactactt    720

actctagctt cccggcaaca attaatagac tggatggagg cggataaagt tgcaggacca    780

cttctgcgct cggcccttcc ggctggctgg tttattgctg ataaatctgg agccggtgag    840

cgtgggtctc gcggtatcat tgcagcactg gggccagatg gtaagccctc ccgtatcgta    900

gttatctaca cgacggggag tcaggcaact atggatgaac gaaatagaca gatcgctgag    960

ataggtgcct cactgattaa gcattggtaa ctgtcagacc aagtttactc atatatactt   1020

tagattgatt taaaacttca tttttaattt aaaaggatct aggtgaagat cctttttgat   1080

aatctcatga ccaaaatccc ttaacgtgag ttttcgttcc actgagcgtc agaccccgta   1140

gaaaagatca aaggatcttc ttgagatcct ttttttctgc gcgtaatctg ctgcttgcaa   1200

acaaaaaaac caccgctacc agcggtggtt tgtttgccgg atcaagagct accaactctt   1260

tttccgaagg taactggctt cagcagagcg cagataccaa atactgtcct tctagtgtag   1320

ccgtagttag gccaccactt caagaactct gtagcaccgc ctacatacct cgctctgcta   1380

atcctgttac cagtggctgc tgccagtggc gataagtcgt gtcttaccgg gttggactca   1440

agacgatagt taccggataa ggcgcagcgg tcgggctgaa cggggggttc gtgcacacag   1500

cccagcttgg agcgaacgac ctacaccgaa ctgagatacc tacagcgtga gctatgagaa   1560

agcgccacgc ttcccgaagg gagaaaggcg gacaggtatc cggtaagcgg cagggtcgga   1620

acaggagagc gcacgaggga gcttccaggg ggaaacgcct ggtatcttta tagtcctgtc   1680

gggtttcgcc acctctgact tgagcgtcga tttttgtgat gctcgtcagg ggggcggagc   1740

ctatggaaaa acgccagcaa cgcggccttt ttacggttcc tggccttttg ctggcctttt   1800

gctcacatgt tctttcctgc gttatcccct gattctgtgg ataaccgtat taccgccttt   1860

gagtgagctg ataccgctcg ccgcagccga acgaccgagc gcagcgagtc agtgagcgag   1920

gaagcggaag agcgcccaat acgcaaaccg cctctccccg cgcgttggcc gattcattaa   1980

tgcagctggc acgacaggtt tcccgactgg aaagcgggca gtgagcgcaa cgcaattaat   2040

gtgagttagc tcactcatta ggcaccccag gctttacact ttatgcttcc ggctcgtatg   2100

ttgtgtggaa ttgtgagcgg ataacaattt cacacaggaa acagctatga ccatgattac   2160

gccaagcgcg caattaaccc tcactaaagg gaacaaaagc tgggtaccgg gccccccctc   2220

gaggtcgacg gtatcgataa gcttcaatgt ttttagcacc ctctgtgtgg aggaaaataa   2280

tgcagattat tctaattagt gtaatatcta accacattaa aatatattac atagtaaact   2340

acactccata attttataaa tttgactccc cagggtaata aactagtctc tagtctgctc   2400

accttcaact gtacaataaa gtcttggttc ttttgaaata gacctcaaat gagacaccta   2460

aaattcaaag tgtctttaca tttaaagaca cctacaggaa agcaggtaaa agagccaggt   2520

taaaaacaaa ttctaaaacc acttagctgc agttaaacat atagtaaaga tgcactaaag   2580

tttcttactc tgtaaatccc ttccacttca ggaaatattc cactttccca ttcactacac   2640
```

-continued

```
gtcgatctag tactttttcc acgacaaatt cttcaggctc tgcctcttca acttttttac   2700
tctttccatt ctgttttttt cccatttttt gctaaaataa aacaaaagag aaattaagaa   2760
atattcctct tgaattttga gcacattttc aaggctcaat tgcttatatt attatcacat   2820
tcgacataaa tttttacttc tatatcccag ggcagacacc ttctggaaag attaaaagtc   2880
aacagacaat aaaataaaag aatgctttat cttgttcatt tagttcaaac ttacaaccca   2940
ccaccaaaat aatacaataa aaaaacacta tctggaaaca gttatttttt tccagtcttt   3000
tttttgaga cagggtctca cactcttgtc gcccaggctg gagtgcagtg gcgtgatctc   3060
agctcactgc aacctccgcc tccccaggtt caagcagttc tcatgcctca gcctccagag   3120
tagctgggat tataggcgga tgccaccatg ccgggctaat tttttttgtg tttttattag   3180
aaacagggtt tcaccatgtt gaccaggctg gtctcaaact cctgacctga agtgattcac   3240
cagcctgggc ctcccaaagt gctggcatta caggcgtgag ccactgcgcc cggccctgta   3300
gtcttaaaag accaagttta ctaattttca ctcattttaa caacactgca acaaacaact   3360
atgcaggaag tacctaaagg gtgatccaga gaagcaagta gtagtgacag gtcttaggtg   3420
aacctatgac agaccttgta tccaccccca gatggtaaaa gccccagccc ccttctcaat   3480
tcaaatatta atgtcaaaag catcaatgat acagagaaaa gataaatgca gaatgaaaac   3540
atggttcaaa atcctgatac caactgcagg gtcaactata gagaccacta ggaggttcaa   3600
ttaaaggaca agattatttt tccataatct ctgtagataa tatttcctac cacttagaac   3660
aaaactataa agctatcact tcaagagacc aacattacaa atttatttta attccctaag   3720
gtgaaaaaaa tccttccttc ctggtttctc aagagaaagt ctatactggt aaccaaattc   3780
actttaaaca ggcattttct ttggtatgac actatttaag agaagcagga aaccaacgtg   3840
aaccagctct ttccaatggc tcaagatttc ctatgagagg actaaaaatg gggaaaattt   3900
ttatgagagg attaaaaatg gggggaaaaaa aaccctgaaa tggttaatca gaagatccta   3960
tgggctgaga aggaatccat cttaacattt catcttaaag caaatgctat tgccgggggc   4020
agtggctcat gcctgtaatc ccagcacttt gggaggccga ggtgggcaga tcatctgagg   4080
tcaggagttt gagaccagcc tgaccaacat ggagaaaccc cgtttctact aaaaatacaa   4140
aattagccag gcatagtggt gcatgcctgt aatcccagct acttgggagg ctgaggcagg   4200
agaactgctt gaacccagga ggcttaagtt gcggtgagcc aagatcacgc cattgcactc   4260
tagcctggac aacaagagaa aaactctgtc tcaaaaaaac acaaaaacaa aaaacccaaa   4320
tactatttaa aaaagataaa ccttaattgc tcaatcatta aagccatccc acaagtaaag   4380
cagcaagcag aaaaaagtta agaacacctc aaggctacag aaggacattt caagctatgc   4440
aggcatatga agtgtgcaga cagatatgta agaaaggcct caagactgca aaagggcatt   4500
tcaagctatg caagcatata ggtaacacat acacacacac aaaataaaat ccccctgaaat   4560
acaaaaacat gcagcaaaca cctgacgttt ttggatacca tttctaagtc aggtgttatg   4620
attctcatta gtcaagatac ttgagtactg ggcccaaaca gctttctgcc actgtacagt   4680
acaagaaggt aggaataatg gtgggaggag caaagacaaa ctgtaataga cagaagtgta   4740
tcagatacct atactacatg aaaaacaaaa cagctactgc cacaaaggga gaaggctaac   4800
aaaataaagt caacaataaa tacagaaaat gaaaaggata cacactaagg tttacaaaaa   4860
aaaaaaggca gacaaaatgc catacagtat tcattcacta ctatggcatt cataagctag   4920
tttcaaatgc tcactatttt cttttatagt atatatttgc cttaacccag cacttttttc   4980
```

-continued

```
caaaagtgga tgagtcaaaa taaatttccc attatttaag tgaaattaac agcacacata   5040
tctcacaaca ctaatgaatt tttaaaatgg aaagttaaga acttttaaag tggccaacct   5100
gtgatccttc acaaaataaa ctaaatacaa taacagaccc caaaggctat caattgcgtg   5160
caaaaacaac ttctgttttc cagggtaaac agaatctaat gcagaatcta atgcagggta   5220
aacagactta atgcagaatc taatgatggc acaaattaaa aatcactaac gtgccctttt   5280
tagtgtgaaa cccagagaga gcacatacaa gccaaaaaca aatgctttat tttacctagg   5340
agacattaac attcaccttt acgtgtttaa gattaatgca atgttaaata ttgtgaaaac   5400
tgtaactttg aatttcatga tttttatgtg aatattccag ggtttaaaaa aacttgtaac   5460
atgacatggc tgaataagat aaaaaaaaaa tctagccttt tctcccttct ggctcatatt   5520
tgcgatttcg atcattttgt ttaaaaaaca aaacactgca atgaattaaa cttaatattc   5580
ttctatgttt tagagtaagt taaaacaaga taaagtgacc aaagtaattt gaaagattca   5640
atgacttttg ctccaaccta ggtgcacaag gtaccttgtt ctttaaattg ggctttaatg   5700
aaaatacttc tccagaattc tggggattta agaaaaatta tgccaaccaa caagggcttt   5760
accattttat gtaacatttt tcaacgctgc aaaaatgtgt gtatttctat ttgaagataa   5820
aaatcctcag caaaatccac attgcactgt ccttcaaaga ttagccttct ttgaactagt   5880
taagacacta ttaagccaag ccagtatctc cctgtaatga attcgttttt ctcttaattt   5940
tcccctgtaa tttacactgg gagagctggg aaatatgtgg atgtaaattt ctcagccaca   6000
gagatgcaaa gttatactgt ggggaaaaaa aacttgagtt aaatccttac atattttagg   6060
ttttcattaa cttaccaatg tagttttgtt ggaggccatt ttttttattg cagacttgaa   6120
gagctattac tagaaaaatg catgacagtt aaggtaagtt tgcatgacac aaaaaaggta   6180
actaaataca aattctgttt ggattccaac ccccaagtag agagcgcaca ctttcaaacg   6240
tgaatacaaa tccagagtag atctgcgctc ctacctacat tgcttatgat gtacttaagt   6300
acgtgtccta accatgtgag tctagaaaga ctttactggg gatcctggta cctaaaacag   6360
cttcacatgg cttaaaatag gggaccaatg tcttttccaa tctaagtccc atttataata   6420
aagtccatgt tccattttta aaggacaatc ctttcggttt aaaaccaggc acgattaccc   6480
aaacaactca caacggtaaa gcactgtgaa tcttctctgt tctgcaatcc caacttggtt   6540
tctgctcaga aaccctccct ctttccaatc ggtaattaaa taacaaaagg aaaaaactta   6600
agatgcttca accccgtttc gtgacacttt gaaaaaagaa tcacctcttg caaacacccg   6660
ctcccgaccc ccgccgctga agcccggcgt ccagaggcct aagcgcgggt gcccgccccc   6720
acccgggagc gcgggcctcg tggtcagcgc atccgcgggg agaaacaaag gccgcggcac   6780
gggggctcaa gggcactgcg ccacaccgca cgcgcctacc cccgcgcggc cacgttaact   6840
ggcggtcgcc gcagcctcgg gacagccggc cgcgcgccgc caggctcgcg gacgcgggac   6900
cacgcgccgc cctccgggag gcccaagtct cgacccagcc ccgcgtggcg ctgggggagg   6960
gggcgcctcc gccggaacgc gggtggggga ggggaggggg aaatgcgctt tgtctcgaaa   7020
tggggcaacc gtcgccacag ctccctaccc cctcgagggc agagcagtcc ccccactaac   7080
taccgggctg gccgcgcgcc aggccagccg cgaggccacc gcccgaccct ccactccttc   7140
ccgcagctcc cggcgcgggg tccggcgaga aggggagggg aggggagcgg agaaccgggc   7200
ccccgggacg cgtgtggcat ctgaagcacc accagcgagc gagagctaga gagaaggaaa   7260
gccaccgact tcaccgcctc cgagctgctc cgggtcgcgg gtctgcagcg tctccggccc   7320
tccgcgccta cagctcaagc cacatccgaa gggggaggga gccgggagct gcgcgcgggg   7380
```

-continued

```
ccgccggggg gaggggtggc accgcccacg ccgggcggcc acgaagggcg gggcagcggg   7440
cgcgcgcgcg gcggggggag gggccggcgc cgcgcccgct gggaattggg gccctagggg   7500
gagggcggag gcgccgacga ccgcggcact taccgttcgc ggcgtggcgc ccggtggtcc   7560
ccaaggggag ggaaggggga ggcggggcga ggacagtgac cggagtctcc tcagcggtgg   7620
cttttctgct tggcagcctc agcggctggc gccaaaaccg gactccgccc acttcctcgc   7680
ccgccggtgc gagggtgtgg aatcctccag acgctggggg agggggagtt gggagcttaa   7740
aaactagtac ccctttggga ccactttcag cagcgaactc tcctgtacac caggggtcag   7800
ttccacagac gcgggccagg ggtgggtcat tgcggcgtga acaataattt gactagaagt   7860
tgattcgggt gtttccggaa ggggccgagt caatccgccg agttggggca cggaaaacaa   7920
aaagggaagg ctactaagat ttttctggcg gggttatca ttggcgtaac tgcagggacc   7980
acctcccggg ttgagggggc tggatctcca ggctgcggat taagcccctc ccgtcggcgt   8040
taatttcaaa ctgcgcgacg tttctcacct gccttcgcca aggcaggggc cgggacccta   8100
ttccaagagg tagtaactag caggactcta gccttccgca attcattgag cgcatttacg   8160
gaagtaacgt cgggtactgt ctctggccgc aagggtggga ggagtacgca tttggcgtaa   8220
ggtggggcgt agagccttcc cgccattggc ggcggatagg gcgtttacgc gacggcctga   8280
cgtagcggaa gacgcgttag tgggggggaa ggttctagaa aagcggcggc agcggctcta   8340
gcggcagtag cagcagcgcc gggtcccgtg cggaggtgct cctcgcagag ttgtttctcg   8400
agcagcggca gttctcacta cagcgccagg acgagtccgg ttcgtgttcg tccgcggaga   8460
tctctctcat ctcgctcggc tgcgggaaat cgggctgaag cgactgagtc cgcgatggag   8520
gtaacgggtt tgaaatcaat gagttattga aaagggcatg gcgaggccgt tggcgcctca   8580
gtggaagtcg gccagccgcc tccgtgggag agaggcagga aatcggacca attcagtagc   8640
agtggggctt aaggtttatg aacggggtct tgagcggagg cctgagcgta caaacagctt   8700
ccccaccctc agcctcccgg cgccatttcc cttcactggg ggtgggggat ggggagcttt   8760
cacatggcgg acgctgcccc gctggggtga aagtggggcg cggaggcggg aattcttatt   8820
ccctttctaa agcacgctgc ttcgggggcc acggcgtctc ctcggcgagc gtttcggcgg   8880
gcagcaggtc ctcgtgagcg aggctgcgga gcttcccctc cccctctctc ccgggaaccg   8940
atttggcggc cgccattttc atggctcgcc ttcctctcag cgttttcctt ataactcttt   9000
tattttctta gtgtgctttc tctatcaaga agtagaagtg gttaactatt tttttttct   9060
tctcgggctg ttttcatatc gtttcgaggt ggatttggag tgttttgtga gcttggatct   9120
ttagagtcct gcgcacctca ttaaaggcgc tcagccttcc cctcgatgaa atggcgccat   9180
tgcgttcgga agccacaccg aagagcgggg agggggggtg ctccgggttt gcgggcccgg   9240
tttcagagaa gatatcacca cccagggcgt cgggccgggt tcaatgcgag ccgtaggaca   9300
aagaaaccat tttatgtttt tcctgtcttt tttttccttt gagtaacggt tttatctggg   9360
tctgcagtca gtaaaacgac agatgaaccg cggcaaaata aacataaatt ggaagccatc   9420
ggccacgagg ggcagggacg aaggtggttt tctgggcggg ggagggatat tcgcgtcaga   9480
atcctttact gttcttaagg attccgttta agttgtagag ctgactcatt ttaagtaatg   9540
ttgttactga gaagtttaac ccttacggga cagatccatg gacctttata gatgattacg   9600
aggaaagtga aataacgatt ttgtccttag ttatacttcg attaaaacat ggcttcagag   9660
gctccttcct gtaatgcgta tggattgatg tgcaaaactg ttttgggcct gggccgctct   9720
```

-continued

```
gtatttgaac tttgttactt ttctcatttt gtttgcaatc ttggttgaac attacattga   9780
taagcataag gtctcaagcg aagggggtct acctggttat ttttctttga ccctaagcac   9840
gtttataaaa taacattgtt taaaatcgat agtggacatc gggtaagttt ggataaattg   9900
tgaggtaagt aatgagtttt tgctttttgt tagtgatttg taaaacttgt tataaatgta   9960
cattatccgt aatttcagtt tagagataac ctatgtgctg acgacaatta agaataaaaa  10020
ctagctgaaa aaatgaaaat aactatcgtg acaagtaacc atttcaaaag actgctttgt  10080
gtctcatagg agctagtttg atcatttcag ttaatttttt ctttaatttt tacgagtcat  10140
gaaaactaca ggaaaaaaaa tctgaactgg gttttaccac tactttttag gagttgggag  10200
catgcgaatg gagggagagc tccgtagaac tgggatgaga gcagcaatta atgctgcttg  10260
ctaggaacaa aaaataattg attgaaaatt acgtgtgact tttagtttg cattatgcgt  10320
ttgtagcagt tggtcctgga tatcactttc tctcgtttga ggttttttaa cctagttaac  10380
ttttaagaca ggtttcctta acattcataa gtgcccagaa tacagctgtg tagtacagca  10440
tataaagatt tcagctctga ggtttttcct attgacttgg aaaattgttt tgtgcctgtc  10500
gcttgccaca tggccaatca agtaagcttg attaatagta atcaattacg gggtcattag  10560
ttcatagccc atatatggag ttccgcgtta cataacttac ggtaaatggc ccgcctggct  10620
gaccgcccaa cgacccccgc ccattgacgt caataatgac gtatgttccc atagtaacgc  10680
caatagggac tttccattga cgtcaatggg tggagtattt acggtaaact gcccacttgg  10740
cagtacatca agtgtatcat atgccaagta cgccccctat tgacgtcaat gacggtaaat  10800
ggcccgcctg gcattatgcc cagtacatga ccttatggga ctttcctact tggcagtaca  10860
tctacgtatt agtcatcgct attaccatgg tgatgcggtt ttggcagtac atcaatgggc  10920
gtggatagcg gtttgactca cggggatttc caagtctcca ccccattgac gtcaatggga  10980
gtttgttttg gcaccaaaat caacgggact ttccaaaatg tcgtaacaac tccgccccat  11040
tgacgcaaat gggcggtagg cgtgtacggt gggaggtcta tataagcaga gctggtttag  11100
tgaaccgtca gatccgctag cgttcgaagt ttaaacgcgg ccgcgactct agatcataat  11160
cagccatacc acatttgtag aggttttact tgctttaaaa aacctcccac acctccccct  11220
gaacctgaaa cataaaatga atgcaattgt tgttgttaac ttgtttattg cagcttataa  11280
tggttacaaa taaagcaata gcatcacaaa tttcacaaat aaagcatttt tttcactgca  11340
ttctagttgt ggtttgtcca aactcatcaa tgtatcttaa atcgaattct accgggtagg  11400
ggaggcgctt ttcccaaggc agtctggagc atgcgcttta gcagccccgc tgggcacttg  11460
gcgctacaca agtggcctct ggcctcgcac acattccaca tccaccggta ggcgccaacc  11520
ggctccgttc tttggtggcc ccttcgcgcc accttctact cctcccctag tcaggaagtt  11580
cccccccgcc ccgcagctcg cgtcgtgcag gacgtgacaa atggaagtag cacgtctcac  11640
tagtctcgtg cagatggaca gcaccgctga gcaatggaag cgggtaggcc tttggggcag  11700
cggccaatag cagctttgct ccttcgcttt ctgggctcag aggctgggaa ggggtgggtc  11760
cgggggcggg ctcaggggcg ggctcagggg cggggcgggc gcccgaaggt cctccggagg  11820
cccggcattc tgcacgcttc aaaagcgcac gtctgccgcg ctgttctcct cttcctcatc  11880
tccgggcctt tcgaccagct taccatgacc gagtacaagc ccacggtgcg cctcgccacc  11940
cgcgacgacg tccccagggc cgtacgcacc ctcgccgccg cgttcgccga ctaccccgcc  12000
acgcgccaca ccgtcgatcc ggaccgccac atcgagcggg tcaccgagct gcaagaactc  12060
ttcctcacgc gcgtcgggct cgacatcggc aaggtgtggg tcgcggacga cggcgccgcg  12120
```

```
gtggcggtct ggaccacgcc ggagagcgtc gaagcggggg cggtgttcgc cgagatcggc  12180

ccgcgcatgg ccgagttgag cggttcccgg ctggccgcgc agcaacagat ggaaggcctc  12240

ctggcgccgc accggcccaa ggagcccgcg tggttcctgg ccaccgtcgg cgtctcgccc  12300

gaccaccagg gcaagggtct gggcagcgcc gtcgtgctcc ccggagtgga ggcggccgag  12360

cgcgccgggg tgcccgcctt cctggagacc tccgcgcccc gcaacctccc cttctacgag  12420

cggctcggct tcaccgtcac cgccgacgtc gaggtgcccg aaggaccgcg cacctggtgc  12480

atgacccgca agcccggtgc ctgacgcccg ccccacgacc cgcagcgccc gaccgaaagg  12540

agcgcacgac cccatgcatc gtagagctcg ctgatcagcc tcgactgtgc cttctagttg  12600

ccagccatct gttgtttgcc cctcccccgt gccttccttg accctggaag gtgccactcc  12660

cactgtcctt tcctaataaa atgaggaaat tgcatcgcat tgtctgagta ggtgtcattc  12720

tattctgggg ggtggggtgg ggcaggacag caaggggggg gattgggrag acaatagcag  12780

gcatgctggg ggggcggtgg gggctatggc ttctgaggcg gaaagaacca gctggggctc  12840

gagatccact agttctagcc tcgaggctag agcggccgcc accgcggtgg agctccaatt  12900

cgccctatag tgagtcgtat tacgcgcgct cactggccgt cgttttacaa cgtcgtgact  12960

gggaaaaccc tggcgttacc caacttaatc gccttgcagc acatccccct ttcgccagct  13020

ggcgtaatag cgaagaggcc cgcaccgatc gcccttccca acagttgcgc agcctgaatg  13080

gcgaatggaa attgtaagcg ttaatatttt gttaaaattc gcgttaaatt tttgttaaat  13140

cagctcattt tttaaccaat aggccgaaat cggcaaaatc ccttataaat caaaagaata  13200

gaccgagata gggttgagtg ttgttccagt ttggaacaag agtccactat taaagaacgt  13260

ggactccaac gtcaaagggc gaaaaaccgt ctatcagggc gatggcccac tacgtgaacc  13320

atcaccctaa tcaagttttt tggggtcgag gtgccgtaaa gcactaaatc ggaaccctaa  13380

agggagcccc cgatttagag cttgacgggg aaagccggcg aacgtggcga gaaaggaagg  13440

gaagaaagcg aaaggagcgg gcgctagggc gctggcaagt gtagcggtca cgctgcgcgt  13500

aaccaccaca cccgccgcgc ttaatgcgcc gctacagggc gcgtcag                13547
```

<210> SEQ ID NO 3
<211> LENGTH: 600
<212> TYPE: DNA
<213> ORGANISM: Artificial Sequence
<220> FEATURE:
<223> OTHER INFORMATION: S. albongier puro

<400> SEQUENCE: 3

```
atgactgaat acaaaccaac tgttcgcctg gcaactcgtg atgatgttcc acgtgcagtt     60

cgcaccctgg ctgctgcatt tgctgactac cctgcaaccc gtcacactgt ggacccagac    120

cgccacattg aacgtgtgac tgaactgcag gagctgttcc tgacccgtgt gggcctggac    180

attggcaaag tgtgggtggc agatgatggt gctgctgtgg cagtgtggac cacccctgaa    240

tctgttgaag ctggtgcagt gtttgctgag attggcccac gcatggcaga actgtctggc    300

agccgcctgg cagcacaaca gcagatggaa ggtctgctgg caccacaccg cccaaaagaa    360

cctgcttggt tcctggcaac tgtgggtgtg agccctgacc accagggtaa gggcctgggc    420

tctgcagtgg tgctgcctgg tgtggaagca gctgaacgtg caggtgtgcc tgctttcctg    480

gagacctcag ctccacgcaa cctgcctttc tatgaacgcc tgggcttcac tgtgactgct    540

gatgtggaag tgccagaagg cccacgcact tggtgcatga ctcgcaaacc aggtgcttaa    600
```

<210> SEQ ID NO 4
<211> LENGTH: 807
<212> TYPE: DNA
<213> ORGANISM: Artificial Sequence
<220> FEATURE:
<223> OTHER INFORMATION: S. fradiae Neo

<400> SEQUENCE: 4

```
atggacgaca gcacgttgcg ccggaagtac ccgcaccacg agtggcacgc agtgaacgaa      60

ggagactcgg gcgccttcgt ctaccagctc accggcggcc ccgagcccca gcccgagctc     120

tacgcgaaga tcgccccccg cgcccccgag aactccgcct tcgacctgtc cggcgaggcc     180

gaccggctgg agtggctcca ccgccacggg atccccgtcc cccgcgtcgt cgagcgcggt     240

gccgacgaca ccgccgcgtg gctcgtcacg gaggccgtcc ccggcgtcgc ggcggccgag     300

gagtggcccg agcaccagcg gttcgccgtg gtcgaggcga tggcggagct ggcccgcgcc     360

ctccacgagc tgcccgtgga ggactgcccc tccgaccggc gcctcgacgc ggcggtcgcc     420

gaggcccggc ggaacgtcgc cgagggcttg gtggacctcg acgacctgca ggaggagcgg     480

gccgggtgga ccggcgacca gctcctggcg gagctcgacc gcacccgtcc cgagaaggag     540

gacctggtcg tctgccatgg cgacctgtgc cccaacaacg tcctgctcga ccccgggacc     600

tgccgggtca ccggcgtgat cgacgtcggc cgcctcgggg tcgccgaccg ccacgccgac     660

atcgccttgg ccgccccgcga gctggagatc gacgaggacc cctggttcgg ccccgcctac     720

gccgagcggt tcctggagcg gtacggcgcc caccgcgtcg acaaggagaa gctggccttc     780

taccagcttc tcgacgagtt cttctag                                          807
```

<210> SEQ ID NO 5
<211> LENGTH: 600
<212> TYPE: DNA
<213> ORGANISM: Artificial Sequence
<220> FEATURE:
<223> OTHER INFORMATION: S. alboniger puro

<400> SEQUENCE: 5

```
atgaccgagt acaagcccac ggtgcgcctc gccacccgcg acgacgtccc cagggccgta      60

cgcaccctcg ccgccgcgtt cgccgactac cccgccacgc gccacaccgt cgatccggac     120

cgccacatcg agcgggtcac cgagctgcaa gaactcttcc tcacgcgcgt cgggctcgac     180

atcggcaagg tgtgggtcgc ggacgacggc gccgcggtgg cggtctggac cacgccggag     240

agcgtcgaag cgggggcggt gttcgccgag atcggcccgc gcatggccga gttgagcggt     300

tcccggctgg ccgcgcagca acagatggaa ggcctcctgg cgccgcaccg gcccaaggag     360

cccgcgtggt tcctggccac cgtcggcgtc tcgcccgacc accagggcaa gggtctgggc     420

agcgccgtcg tgctccccgg agtggaggcg gccgagcgcg ccggggtgcc cgccttcctg     480

gagacctccg cgccccgcaa cctccccttc tacgagcggc tcggcttcac cgtcaccgcc     540

gacgtcgagg tgcccgaagg accgcgcacc tggtgcatga cccgcaagcc cggtgcctga     600
```

<210> SEQ ID NO 6
<211> LENGTH: 999
<212> TYPE: DNA
<213> ORGANISM: Artificial Sequence
<220> FEATURE:
<223> OTHER INFORMATION: S. hygroscopicus hygro

<400> SEQUENCE: 6

```
atgacacaag aatccctgtt acttctcgac cgtattgatt cggatgattc ctacgcgagc      60
```

-continued ctgcggaacg accaggaatt ctgggagccg ctggcccgcc gagccctgga ggagctcggg 120
ctgccggtgc cgccggtgct gcgggtgccc ggcgagagca ccaaccccgt actggtcggc 180
gagcccgacc cggtgatcaa gctgttcggc gagcactggt gcggtccgga gagcctcgcg 240
tcggagtcgg aggcgtacgc ggtcctggcg gacgccccgg tgccggtgcc ccgcctcctc 300
ggccgcggcg agctgcggcc cggcaccgga gcctggccgt ggccctacct ggtgatgagc 360
cggatgaccg gcaccacctg gcggtccgcg atggacggca cgaccgaccg gaacgcgctg 420
ctcgccctgg cccgcgaact cggccgggtg ctcggccggc tgcacagggt gccgctgacc 480
gggaacaccg tgctcacccc ccattccgag gtcttcccgg aactgctgcg ggaacgccgc 540
gcggcgaccg tcgaggacca ccgcgggtgg ggctacctct cgccccggct gctggaccgc 600
ctggaggact ggctgccgga cgtggacacg ctgctggccg gccgcgaacc ccggttcgtc 660
cacggcgacc tgcacgggac caacatcttc gtggacctgg ccgcgaccga ggtcaccggg 720
atcgtcgact tcaccgacgt ctatgcggga gactcccgct acagcctggt gcaactgcat 780
ctcaacgcct tccggggcga ccgcgagatc ctggccgcgc tgctcgacgg ggcgcagtgg 840
aagcggaccg aggacttcgc ccgcgaactg ctcgccttca ccttcctgca cgacttcgag 900
gtgttcgagg agaccccgct ggatctctcc ggcttcaccg atccggagga actggcgcag 960
ttcctctggg ggccgccgga caccgccccc ggcgcctga 999

<210> SEQ ID NO 7
<211> LENGTH: 1026
<212> TYPE: DNA
<213> ORGANISM: Artificial Sequence
<220> FEATURE:
<223> OTHER INFORMATION: E. coli hygro

<400> SEQUENCE: 7
atgaaaaagc ctgaactcac cgcgacgtct gtcgcgaagt ttctgatcga aaagttcgac 60
agcgtctccg acctgatgca gctctcggag ggcgaagaat ctcgtgcttt cagcttcgat 120
gtaggagggc gtggatatgt cctgcgggta aatagctgcg ccgatggttt ctacaaagat 180
cgttatgttt atcggcactt tgcatcggcc gcgctcccga ttccggaagt gcttgacatt 240
ggggaattca gcgagagcct gacctattgc atctcccgcc gtgcacaggg tgtcacgttg 300
caagacctgc ctgaaaccga actgcccgct gttctgcaac ccgtcgcgga gctcatggat 360
gcgatcgctg cggccgatct tagccagacg agcgggttcg gcccattcgg accgcaagga 420
atcggtcaat acactacatg gcgtgatttc atatgcgcga ttgctgatcc ccatgtgtat 480
cactggcaaa ctgtgatgga cgacaccgtc agtgcgtccg tcgcgcaggc tctcgatgag 540
ctgatgcttt gggccgagga ctgccccgaa gtccggcacc tcgtgcacgc ggatttcggc 600
tccaacaatg tcctgacgga caatggccgc ataacagcgg tcattgactg gagcgaggcg 660
atgttcgggg attcccaata cgaggtcgcc aacatcttct tctggaggcc gtggttggct 720
tgtatggagc agcagacgcg ctacttcgag cggaggcatc cggagcttgc aggatcgccg 780
cggctccggg cgtatatgct ccgcattggt cttgaccaac tctatcagag cttggttgac 840
ggcaatttcg atgatgcagc ttgggcgcag ggtcgatgcg acgcaatcgt ccgatccgga 900
gccgggactg tcgggcgtac acaaatcgcc cgcagaagcg cggccgtctg gaccgatggc 960
tgtgtagaag tactcgccga tagtggaaac cgacgcccca gcactcgtcc gagggcaaag 1020
gaatga 1026

-continued

<210> SEQ ID NO 8
<211> LENGTH: 795
<212> TYPE: DNA
<213> ORGANISM: Artificial Sequence
<220> FEATURE:
<223> OTHER INFORMATION: Tn5 Neo

<400> SEQUENCE: 8

```
atgattgaac aagatggatt gcacgcaggt tctccggccg cttgggtgga gaggctattc     60

ggctatgact gggcacaaca gacaatcggc tgctctgatg ccgccgtgtt ccggctgtca    120

gcgcaggggc gcccggttct ttttgtcaag accgacctgt ccggtgccct gaatgaactg    180

caagacgagg cagcgcggct atcgtggctg gccacgacgg gcgttccttg cgcagctgtg    240

ctcgacgttg tcactgaagc gggaagggac tggctgctat tgggcgaagt gccggggcag    300

gatctcctgt catctcacct tgctcctgcc gagaaagtat ccatcatggc tgatgcaatg    360

cggcggctgc atacgcttga tccggctacc tgcccattcg accaccaagc gaaacatcgc    420

atcgagcgag cacgtactcg gatggaagcc ggtcttgtcg atcaggatga tctggacgaa    480

gagcatcagg ggctcgcgcc agccgaactg ttcgccaggc tcaaggcgag catgcccgac    540

ggcgaggatc tcgtcgtgac ccatggcgat gcctgcttgc cgaatatcat ggtggaaaat    600

ggccgctttt ctggattcat cgactgtggc cggctgggtg tggcggaccg ctatcaggac    660

atagcgttgg ctacccgtga tattgctgaa gagcttggcg gcgaatgggc tgaccgcttc    720

ctcgtgcttt acggtatcgc cgctcccgat tcgcagcgca tcgccttcta tcgccttctt    780

gacgagttct tctga                                                     795
```

<210> SEQ ID NO 9
<211> LENGTH: 12041
<212> TYPE: DNA
<213> ORGANISM: Artificial Sequence
<220> FEATURE:
<223> OTHER INFORMATION: Plasmid

<400> SEQUENCE: 9

```
cgttgtaaaa cgacggccag tgaattgtaa tacgactcac tatagggcga attgggtacc     60

gggccccccc tcgaagttta aacatttaaa tctagaagct tcaatgtttt tagcaccctc    120

tgtgtggagg aaaataatgc agattattct aattagtgta atatctaacc acattaaaat    180

atattacata gtaaactaca ctccataatt ttataaattt gactccccag ggtaataaac    240

tagtctctag tctgctcacc ttcaactgta caataaagtc ttggttcttt tgaaatagac    300

ctcaaatgag acacctaaaa ttcaaagtgt ctttacattt aaagacacct acaggaaagc    360

aggtaaaaga gccaggttaa aaacaaattc taaaaccact tagctgcagt taaacatata    420

gtaaagatgc actaaagttt cttactctgt aaatcccttc cacttcagga aatattccac    480

tttcccattc actacacgtc gatctagtac tttttccacg acaaattctt caggctctgc    540

ctcttcaact tttttactct ttccattctg tttttttccc attttttgct aaaataaaac    600

aaaagagaaa ttaagaaata ttcctcttga attttgagca cattttcaag gctcaattgc    660

ttatattatt atcacattcg acataaattt ttacttctat atcccagggc agacaccttc    720

tggaaagatt aaaagtcaac agacaataaa ataaaagaat gctttatctt gttcatttag    780

ttcaaactta caacccacca ccaaaataat acaataaaaa aacactatct ggaaacagtt    840

atttttttcc agtctttttt tttgagacag ggtctcacac tcttgtcgcc caggctggag    900

tgcagtggcg tgatctcagc tcactgcaac ctccgcctcc ccaggttcaa gcagttctca    960
```

```
tgcctcagcc tccagagtag ctgggattat aggcggatgc caccatgccg ggctaatttt   1020
ttttgtgttt ttattagaaa cagggtttca ccatgttgac caggctggtc tcaaactcct   1080
gacctgaagt gattcaccag cctgggcctc ccaaagtgct ggcattacag gcgtgagcca   1140
ctgcgcccgg ccctgtagtc ttaaaagacc aagtttacta attttcactc attttaacaa   1200
cactgcaaca aacaactatg caggaagtac ctaaagggtg atccagagaa gcaagtagta   1260
gtgacaggtc ttaggtgaac ctatgacaga ccttgtatcc acccccagat ggtaaaagcc   1320
ccagccccct tctcaattca aatattaatg tcaaaagcat caatgataca gagaaaagat   1380
aaatgcagaa tgaaaacatg gttcaaaatc ctgataccaa ctgcagggtc aactatagag   1440
accactagga ggttcaatta aaggacaaga ttatttttcc ataatctctg tagataatat   1500
ttcctaccac ttagaacaaa actataaagc tatcacttca agagaccaac attacaaatt   1560
tattttaatt ccctaaggtg aaaaaaatcc ttccttcctg gtttctcaag agaaagtcta   1620
tactggtaac caaattcact ttaaacaggc attttctttg gtatgacact atttaagaga   1680
agcaggaaac caacgtgaac cagctctttc caatggctca agatttccta tgagaggact   1740
aaaaatgggg aaaattttta tgagaggatt aaaaatgggg gaaaaaaaac cctgaaatgg   1800
ttaatcagaa gatcctatgg gctgagaagg aatccatctt aacatttcat cttaaagcaa   1860
atgctattgc cgggggcagt ggctcatgcc tgtaatccca gcactttggg aggccgaggt   1920
gggcagatca tctgaggtca ggagtttgag accagcctga ccaacatgga gaaaccccgt   1980
ttctactaaa aatacaaaat tagccaggca tagtggtgca tgcctgtaat cccagctact   2040
tgggaggctg aggcaggaga actgcttgaa cccaggaggc ttaagttgcg gtgagccaag   2100
atcacgccat tgcactctag cctggacaac aagagaaaaa ctctgtctca aaaaaacaca   2160
aaaacaaaaa acccaaatac tatttaaaaa agataaacct taattgctca atcattaaag   2220
ccatcccaca agtaaagcag caagcagaaa aaagttaaga acacctcaag gctacagaag   2280
gacatttcaa gctatgcagg catatgaagt gtgcagacag atatgtaaga aaggcctcaa   2340
gactgcaaaa gggcatttca agctatgcaa gcatataggt aacacataca cacacacaaa   2400
ataaaatccc ctgaaataca aaaacatgca gcaaacacct gacgtttttg gataccattt   2460
ctaagtcagg tgttatgatt ctcattagtc aagatacttg agtactgggc ccaaacagct   2520
ttctgccact gtacagtaca agaaggtagg aataatggtg ggaggagcaa agacaaactg   2580
taatagacag aagtgtatca gatacctata ctacatgaaa aacaaaacag ctactgccac   2640
aaagggagaa ggctaacaaa ataaagtcaa caataaatac agaaaatgaa aaggatacac   2700
actaaggttt acaaaaaaaa aaaggcagac aaaatgccat acagtattca ttcactacta   2760
tggcattcat aagctagttt caaatgctca ctattttctt ttatagtata tatttgcctt   2820
aacccagcac ttttttccaa aagtggatga gtcaaaataa atttcccatt atttaagtga   2880
aattaacagc acacatatct cacaacacta atgaattttt aaaatggaaa gttaagaact   2940
tttaaagtgg ccaacctgtg atccttcaca aaataaacta aatacaataa cagaccccaa   3000
aggctatcaa ttgcgtgcaa aaacaacttc tgttttccag ggtaaacaga atctaatgca   3060
gaatctaatg cagggtaaac agacttaatg cagaatctaa tgatggcaca aattaaaaat   3120
cactaacgtg cccttttag tgtgaaaccc agagagagca catacaagcc aaaaacaaat   3180
gctttatttt acctaggaga cattaacatt cacctttacg tgtttaagat taatgcaatg   3240
ttaaatattg tgaaaactgt aactttgaat ttcatgattt ttatgtgaat attccagggt   3300
```

-continued

```
ttaaaaaaac ttgtaacatg acatggctga ataagataaa aaaaaaatct agccttttct   3360
cccttctggc tcatatttgc gatttcgatc attttgttta aaaaacaaaa cactgcaatg   3420
aattaaactt aatattcttc tatgttttag agtaagttaa aacaagataa agtgaccaaa   3480
gtaatttgaa agattcaatg acttttgctc caacctaggt gcacaaggta ccttgttctt   3540
taaattgggc tttaatgaaa atacttctcc agaattctgg ggatttaaga aaaattatgc   3600
caaccaacaa gggctttacc attttatgta acatttttca acgctgcaaa aatgtgtgta   3660
tttctatttg aagataaaaa tcctcagcaa aatccacatt gcactgtcct tcaaagatta   3720
gccttctttg aactagttaa gacactatta agccaagcca gtatctccct gtaatgaatt   3780
cgtttttctc ttaatttcc cctgtaattt acactgggag agctgggaaa tatgtggatg   3840
taaatttctc agccacagag atgcaaagtt atactgtggg gaaaaaaaac ttgagttaaa   3900
tccttacata ttttaggttt tcattaactt accaatgtag ttttgttgga ggccattttt   3960
tttattgcag acttgaagag ctattactag aaaaatgcat gacagttaag gtaagtttgc   4020
atgacacaaa aaaggtaact aaatacaaat tctgtttgga ttccaacccc caagtagaga   4080
gcgcacactt tcaaacgtga atacaaatcc agagtagatc tgcgctccta cctacattgc   4140
ttatgatgta cttaagtacg tgtcctaacc atgtgagtct agaaagactt tactggggat   4200
cctggtacct aaaacagctt cacatggctt aaaatagggg accaatgtct tttccaatct   4260
aagtcccatt tataataaag tccatgttcc atttttaaag gacaatcctt tcggtttaaa   4320
accaggcacg attacccaaa caactcacaa cggtaaagca ctgtgaatct tctctgttct   4380
gcaatcccaa cttggtttct gctcagaaac cctccctctt tccaatcggt aattaaataa   4440
caaaaggaaa aaacttaaga tgcttcaacc ccgtttcgtg acactttgaa aaaagaatca   4500
cctcttgcaa acacccgctc ccgacccccg ccgctgaagc ccggcgtcca gaggcctaag   4560
cgcgggtgcc cgcccccacc cgggagcgcg ggcctcgtgg tcagcgcatc cgcggggaga   4620
aacaaaggcc gcggcacggg ggctcaaggg cactgcgcca caccgcacgc gcctaccccc   4680
gcgcggccac gttaactggc ggtcgccgca gcctcgggac agccggccgc gcgccgccag   4740
gctcgcggac gcgggaccac gcgccgccct ccgggaggcc caagtctcga cccagccccg   4800
cgtggcgctg gggggagggg cgcctccgcc ggaacgcggg tgggggaggg gagggggaaa   4860
tgcgctttgt ctcgaaatgg ggcaaccgtc gccacagctc cctacccct cgagggcaga   4920
gcagtccccc cactaactac cgggctggcc gcgcgccagg ccagccgcga ggccaccgcc   4980
cgaccctcca ctccttcccg cagctcccgg cgcggggtcc ggcgagaagg ggaggggagg   5040
ggagcggaga accgggcccc cgggacgcgt gtggcatctg aagcaccacc agcgagcgag   5100
agctagagag aaggaaagcc accgacttca ccgcctccga gctgctccgg gtcgcgggtc   5160
tgcagcgtct ccggccctcc gcgcctacag ctcaagccac atccgaaggg ggagggagcc   5220
gggagctgcg cgcggggccg ccggggggag gggtggcacc gcccacgccg ggcggccacg   5280
aagggcgggg cagcgggcgc gcgcgcggcg gggggagggg ccggcgccgc gcccgctggg   5340
aattggggcc ctagggggag ggcggaggcg ccgacgaccg cggcacttac cgttcgcggc   5400
gtggcgcccg gtggtcccca aggggaggga agggggaggc ggggcgagga cagtgaccgg   5460
agtctcctca gcggtggctt ttctgcttgg cagcctcagc ggctggcgcc aaaaccggac   5520
tccgcccact tcctcgcccg ccggtgcgag ggtgtggaat cctccagacg ctgggggagg   5580
gggagttggg agcttaaaaa ctagtacccc tttgggacca ctttcagcag cgaactctcc   5640
tgtacaccag gggtcagttc cacagacgcg ggccaggggt gggtcattgc ggcgtgaaca   5700
```

-continued

```
ataatttgac tagaagttga ttcgggtgtt tccggaaggg gccgagtcaa tccgccgagt   5760
tggggcacgg aaaacaaaaa gggaaggcta ctaagatttt tctggcgggg gttatcattg   5820
gcgtaactgc agggaccacc tcccgggttg agggggctgg atctccaggc tgcggattaa   5880
gcccctcccg tcggcgttaa tttcaaactg cgcgacgttt ctcacctgcc ttcgccaagg   5940
caggggccgg gaccctattc caagaggtag taactagcag gactctagcc ttccgcaatt   6000
cattgagcgc atttacggaa gtaacgtcgg gtactgtctc tggccgcaag ggtgggagga   6060
gtacgcattt ggcgtaaggt ggggcgtaga gccttcccgc cattggcggc ggatagggcg   6120
tttacgcgac ggcctgacgt agcggaagac gcgttagtgg gggggaaggt tctagaaaag   6180
cggcggcagc ggctctagcg gcagtagcag cagcgccggg tcccgtgcgg aggtgctcct   6240
cgcagagttg tttctcgagc agcggcagtt ctcactacag cgccaggacg agtccggttc   6300
gtgttcgtcc gcggagatct ctctcatctc gctcggctgc gggaaatcgg gctgaagcga   6360
ctgagtccgc gatggaggta acgggtttga aatcaatgag ttattgaaaa gggcatggcg   6420
aggccgttgg cgcctcagtg gaagtcggcc agccgcctcc gtgggagaga ggcaggaaat   6480
cggaccaatt cagtagcagt ggggcttaag gtttatgaac ggggtcttga gcggaggcct   6540
gagcgtacaa acagcttccc caccctcagc ctcccggcgc catttccctt cactgggggt   6600
gggggatggg gagctttcac atggcggacg ctgccccgct ggggtgaaag tggggcgcgg   6660
aggcgggaat tcttattccc tttctaaagc acgctgcttc gggggccacg gcgtctcctc   6720
ggcgagcgtt tcggcgggca gcaggtcctc gtgagcgagg ctgcggagct tcccctcccc   6780
ctctctcccg ggaaccgatt tggcggccgc cattttcatg gctcgccttc ctctcagcgt   6840
tttccttata actcttttat tttcttagtg tgctttctct atcaagaagt agaagtggtt   6900
aactattttt tttttcttct cgggctgttt tcatatcgtt tcgaggtgga tttggagtgt   6960
tttgtgagct tggatcttta gagtcctgcg cacctcatta aaggcgctca gccttcccct   7020
cgatgaaatg gcgccattgc gttcggaagc cacaccgaag agcggggagg gggggtgctc   7080
cgggtttgcg ggcccggttt cagagaagat atcaccaccc agggcgtcgg gccgggttca   7140
atgcgagccg taggacaaag aaaccatttt atgtttttcc tgtctttttt ttcctttgag   7200
taacggtttt atctgggtct gcagtcagta aaacgacaga tgaaccgcgg caaaataaac   7260
ataaattgga agccatcggc cacgaggggc agggacgaag gtggttttct gggcggggga   7320
gggatattcg cgtcagaatc ctttactgtt cttaaggatt ccgtttaagt tgtagagctg   7380
actcatttta agtaatgttg ttactgagaa gtttaaccct tacgggacag atccatggac   7440
ctttatagat gattacgagg aaagtgaaat aacgattttg tccttagtta tacttcgatt   7500
aaaacatggc ttcagaggct ccttcctgta atgcgtatgg attgatgtgc aaaactgttt   7560
tgggcctggg ccgctctgta tttgaacttt gttacttttc tcattttgtt tgcaatcttg   7620
gttgaacatt acattgataa gcataaggtc tcaagcgaag gggtctacc tggttatttt   7680
tctttgaccc taagcacgtt tataaaataa cattgtttaa aatcgatagt ggacatcggg   7740
taagtttgga taaattgtga ggtaagtaat gagtttttgc tttttgttag tgatttgtaa   7800
aacttgttat aaatgtacat tatccgtaat ttcagtttag agataaccta tgtgctgacg   7860
acaattaaga ataaaaacta gctgaaaaaa tgaaaataac tatcgtgaca agtaaccatt   7920
tcaaaagact gctttgtgtc tcataggagc tagtttgatc atttcagtta attttttctt   7980
taatttttac gagtcatgaa aactacagga aaaaaaatct gaactgggtt ttaccactac   8040
```

-continued

```
tttttaggag ttgggagcat gcgaatggag ggagagctcc gtagaactgg gatgagagca   8100
gcaattaatg ctgcttgcta ggaacaaaaa ataattgatt gaaaattacg tgtgactttt   8160
tagtttgcat tatgcgtttg tagcagttgg tcctggatat cactttctct cgtttgaggt   8220
tttttaacct agttaacttt taagacaggt ttccttaaca ttcataagtg cccagaatac   8280
agctgtgtag tacagcatat aaagatttca gctctgaggt tttcctatt gacttggaaa   8340
attgttttgt gcctgtcgct tgccacatgg ccaatcaagt aagcttatcg ataccggtgg   8400
cgcgccaatt gttaattaag atctggccca atgggccgta cgaattcctt aggctaccgg   8460
gtaggggagg cgcttttccc aaggcagtct ggagcatgcg ctttagcagc cccgctgggc   8520
acttggcgct acacaagtgg cctctggcct cgcacacatt ccacatccac cggccggtag   8580
gcgccaaccg gctccgttct ttggtggccc cttcgcgcca ccttctactc ctcccctagt   8640
caggaagttc ccccccgccc cgcagctcgc gtcgtgcagg acgtgacaaa tggaagtagc   8700
acgtctcact agtctcgtgc agatggacag caccgctgag caatggaagc gggtaggcct   8760
ttggggcagc ggccaatagc agctttgctc cttcgctttc tgggctcaga ggctgggaag   8820
gggtgggtcc gggggcgggc tcaggggcgg gctcaggggc ggggcgggcg cccgaaggtc   8880
ctccggaggc ccggcattct gcacgcttca aaagcgcacg tctgccgcgc tgttctcctc   8940
ttcctcatct ccgggccttt cgaccagctt accatgaccg agtacaagcc cacggtgcgc   9000
ctcgccaccc gcgacgacgt ccccagggcc gtacgcaccc tcgccgccgc gttcgccgac   9060
taccccgcca cgcgccacac cgtcgatccg gaccgccaca tcgagcgggt caccgagctg   9120
caagaactct tcctcacgcg cgtcgggctc gacatcggca aggtgtgggt cgcggacgac   9180
ggcgccgcgg tggcggtctg gaccacgccg gagagcgtcg aagcgggggc ggtgttcgcc   9240
gagatcggcc cgcgcatggc cgagttgagc ggttcccggc tggccgcgca gcaacagatg   9300
gaaggcctcc tggcgccgca ccggcccaag gagcccgcgt ggttcctggc caccgtcggc   9360
gtctcgcccg accaccaggg caagggtctg ggcagcgccg tcgtgctccc cggagtggag   9420
gcggccgagc gcgccggggt gcccgccttc ctggagacct ccgcgccccg caacctcccc   9480
ttctacgagc ggctcggctt caccgtcacc gccgacgtcg aggtgcccga aggaccgcgc   9540
acctggtgca tgacccgcaa gcccggtgcc tgacgcccgc cccacgaccc gcagcgcccg   9600
accgaaagga gcgcacgacc ccatgcatcg tagagctcgc tgatcagcct cgactgtgcc   9660
ttctagttgc cagccatctg ttgtttgccc ctcccccgtg ccttccttga ccctggaagg   9720
tgccactccc actgtccttt cctaataaaa tgaggaaatt gcatcgcatt gtctgagtag   9780
gtgtcattct attctggggg gtggggtggg gcaggacagc aagggggggg attgggraga   9840
caatagcagg catgctgggg gggcggtggg ggctatggct tctgaggcgg aaagaaccag   9900
ctggggctcg agggccgcca ccgcggtgga gctccagctt ttgttccctt tagtgagggt   9960
taatttcgag cttggcgtaa tcatggtcat agctgtttcc tgtgtgaaat tgttatccgc  10020
tcacaattcc acacaacata cgagccggaa gcataaagtg taaagcctgg ggtgcctaat  10080
gagtgagcta actcacatta attgcgttgc gctcactgcc cgctttccag tcgggaaacc  10140
tgtcgtgcca gcatcgcgag cacttttcgg ggaaatgtgc gcggaacccc tatttgttta  10200
tttttctaaa tacattcaaa tatgtatccg ctcatgagac aataaccctg ataaatgctt  10260
caataatatt gaaaaaggaa gagtatgagt attcaacatt tccgtgtcgc ccttattccc  10320
ttttttgcgg cattttgcct tcctgttttt gctcacccag aaacgctggt gaaagtaaaa  10380
gatgctgaag atcagttggg tgcacgagtg ggttacatcg aactggatct caacagcggt  10440
```

```
aagatccttg agagttttcg ccccgaagaa cgttttccaa tgatgagcac ttttaaagtt  10500

ctgctatgtg gcgcggtatt atcccgtatt gacgccgggc aagagcaact cggtcgccgc  10560

atacactatt ctcagaatga cttggttgag tactcaccag tcacagaaaa gcatcttacg  10620

gatggcatga cagtaagaga attatgcagt gctgccataa ccatgagtga taacactgcg  10680

gccaacttac ttctgacaac gatcggagga ccgaaggagc taaccgcttt tttgcacaac  10740

atgggggatc atgtaactcg ccttgatcgt tgggaaccgg agctgaatga agccatacca  10800

aacgacgagc gtgacaccac gatgcctgta gcaatggcaa caacgttgcg caaactatta  10860

actggcgaac tacttactct agcttcccgg caacaattaa tagactggat ggaggcggat  10920

aaagttgcag gaccacttct gcgctcggcc cttccggctg gctggtttat tgctgataaa  10980

tctggagccg gtgagcgtgg gtctcgcggt atcattgcag cactggggcc agatggtaag  11040

ccctcccgta tcgtagttat ctacacgacg gggagtcagg caactatgga tgaacgaaat  11100

agacagatcg ctgagatagg tgcctcactg attaagcatt ggtaactgtc agactcgcga  11160

cactgcatta atgaatcggc caacgcgcgg ggagaggcgg tttgcgtatt gggcgctctt  11220

ccgcttcctc gctcactgac tcgctgcgct cggtcgttcg gctgcggcga gcggtatcag  11280

ctcactcaaa ggcggtaata cggttatcca cagaatcagg ggataacgca ggaaagaaca  11340

tgtgagcaaa aggccagcaa aaggccagga accgtaaaaa ggccgcgttg ctggcgtttt  11400

tccataggct ccgcccccct gacgagcatc acaaaaatcg acgctcaagt cagaggtggc  11460

gaaacccgac aggactataa agataccagg cgtttccccc tggaagctcc ctcgtgcgct  11520

ctcctgttcc gaccctgccg cttaccggat acctgtccgc ctttctccct tcgggaagcg  11580

tggcgctttc tcatagctca cgctgtaggt atctcagttc ggtgtaggtc gttcgctcca  11640

agctgggctg tgtgcacgaa ccccccgttc agcccgaccg ctgcgcctta tccggtaact  11700

atcgtcttga gtccaacccg gtaagacacg acttatcgcc actggcagca gccactggta  11760

acaggattag cagagcgagg tatgtaggcg gtgctacaga gttcttgaag tggtggccta  11820

actacggcta cactagaagg acagtatttg gtatctgcgc tctgctgaag ccagttacct  11880

tcggaaaaag agttggtagc tcttgatccg gcaaacaaac caccgctggt agcggtggtt  11940

tttttgtttg caagcagcag attacgcgca gaaaaaaagg atctcaagaa gatcctttga  12000

tcttttctac ggggtctgac gctcagtgga acgaaaactc a                      12041
```

<210> SEQ ID NO 10
<211> LENGTH: 11646
<212> TYPE: DNA
<213> ORGANISM: Artificial Sequence
<220> FEATURE:
<223> OTHER INFORMATION: Plasmid

<400> SEQUENCE: 10

```
cgttgtaaaa cgacggccag tgaattgtaa tacgactcac tatagggcga attgggtacc     60

gggccccccc tcgaagttta aacatttaaa tctagaagct tttaaccctc tatcccttta    120

aacttccttg atccagtgta agcacctcct agaaagtcag tagacaataa aacaaaagtt    180

ctgcttcacc gatttacatt tataaccaaa tacccttcac caatacaata aaaaaacaaa    240

acaacaaaaa accccaacca tctgagaaat aatcttctcc tttcccagct ttattcccag    300

gattctacat gaccaaatta ccagagtcac cactcatttt aatcacaaca tagtgtcaaa    360

taactagaaa acatgagaca acaatggaga gctgagtaac tattagtagt agtactttac    420
```

-continued

```
cagagaatgg cctctatagg ctcacatgta ggaatggttg gtccccaggt ggtaggtaga    480
gctgtttgag gattacgtgg ccttcttgga tggggggtgg gggtggggtg ggagggttgg    540
gtggtgggta cttaagaggt ttcaaaagtc aatattgttt gcatttagct cttccttgta    600
cttgtggatc aaacacaacc tgtcagctac tgcttcaaat gtcatgcctg ctgccatctt    660
ctcagcagga tggtcatggc ctcaccctct tcaactgtaa atctttcttt cttttcttct    720
ttttcttttg gtttcgagac agggtttctc tgtatagtcc tggctgtcct ggaactcact    780
ttgtagacca ggctggcctt gaactcagaa atccgcctgc ctctgcctcc ctagcactgg    840
gattaaaggc gtgcgccacc acgcccagct ttcaactgga aatcttaata aactttccta    900
gaagtggcct tggttatggg agcttatcac agcaatagaa cagcaattat gactggagta    960
tgatagttaa aaacaagcaa gcaagcaagc aaacacacac accaaaacaa caaaacccca   1020
agacagagtc acatgtagcc caggctagcc tccaaattca ctatataact gaagaagacc   1080
cctaattccc attcctctag aatctatacc tcaagtactg aatggcttgg ttcacaatac   1140
cccactaaat gattggtctt actaagtgca acaaggtaaa cctaaaactt cagccctcag   1200
acatcccttt tccagtatca atttataaaa ttagatccca aggataaaaa ttaattgtaa   1260
agtaaaatca gagttctagc atcaactaca ggctcaacca tggggaccac aaataaacta   1320
aaagggataa gactggcttc cccataatta ttacatttag ataattttcc tgactactca   1380
acaaagctaa aatatcacca ctggtttatt ttctccttct agggtttaag ctcactctga   1440
ggaggggcat gcggcacaca ctcatagcat ccaggaaata gaaatatggt gactatcatg   1500
ggttcagggc caacctaggc tttagagaaa aaccttgtcc cacaaaccaa aaatgtctct   1560
tttttattct atcaggggtg gatggatttg ttaaagaagt gcttttaaaa accttgagat   1620
ggttatttag aagtccccat gggataccaa aataacccac tatttatatg cccaagcatt   1680
tcacctccac aacagtgcta tgcacccttt aacatttttg agacagtagc ccagtctagt   1740
ctttaacttg cagtgatttt tcctgattca gcttctccca gtgctggaat tataggtatg   1800
caccaccatg tgtaactaca gatgctactt aaaaattttt taaaggaatc acaaaaataa   1860
ccccctatca aatgcctagt ccctctaacc atcaccaagt gaaggatcac gcaggaaaaa   1920
aaaaatcacc agcagcacct cagaaccagg atactcagtc catcagcatc cagggccata   1980
cccacactca cagcatctcc acagtttacc agatgattca tgcttatcac tgtattgggt   2040
catctaagag tgaccatcag ggcttctgat cacagaatct agtccacttt gcagaccagt   2100
tgaagtcatg cactatatga gatagaaata ccctcttgct cattttggtc agaaattcaa   2160
ggataaaaac ccatgttttg ttaatgcaca cctccatatg attgagatca atgtgtccta   2220
attaatgtag aaaccacaac tgtaaatttc actcttttga catgaatctt tttctagaca   2280
gggtcttgga tgcagccccg actacccaga attttggaat ccaggctagc ctcaaactca   2340
aggcaatctg cttgcttcag cttctcacag gctggatcac aaacatacac cttcagaccc   2400
attttttttt cctccctccg tttttggttt ctctgtgtag ccctgggtgt ccgtggactc   2460
gctgtgtaga tctatctacc agcctctgtc ttggagtact gggattaaag ttgtgggcta   2520
ccactgcctg gctgacccag ttttatttat tttaaatata acttgacaaa aataaatttg   2580
tctaacttac tagaaatccc aagaaaacta acactggatt tagcaacagt cagaaatcgc   2640
tgaaaagaaa cagaattgat ctaacagtct tagatcactc ctagacagtt tgtaattctt   2700
gctcatggca acgtgagctc tatctaactc actctctgtg cactaatgaa tgctcagtgt   2760
ctccagaaca gcacagcttc cagggtaatc atgccaaccc acaagacttt tatagagctg   2820
```

-continued tccacgactc ttcccccatt cagctcatta acaatatgat ggagctcctg tgtggaaatc 2880
aaggcacact ctggtagaaa cttgtttttt ctttccactt ttccttgggc tctgaagatt 2940
gagctgtttt ataacccaca aacatgcatt ttttacctca aaagcatcca gcaaaaactg 3000
tacaacgctt tttcaaaaaa atgtattgtg atcctcctta agaaaagcct tacttagtgt 3060
taattccttt ttctttagaa tgctggtaaa tacaaggact taggtaggct ggcttctaac 3120
agcaattcac ccacttatga tgggattaaa ggaaggcaca accatgtcca ccacaggttc 3180
tagctccccc acccacacgc ccagagaggg tttttctgtg tagctctgac tattctggaa 3240
ttcacactgc agaccaggct ggtctcgaac tcagagatcc accaccacat ggtttcttaa 3300
ttgtaatttt aaagaaaaaa aaaaatcctt cagttaagat tcttatgttc taggttttca 3360
caaacttacc aatgtagttt tattggaggc catttttttaa atttaatcgg agacttgaag 3420
agctattgca agaaaaaaaa tgtaggacag ttaaaatttc atgacacaca aaaggcagct 3480
acaagttttg tgtggatttc aacatgtaaa tttcgggtaa aaatgcagga aaacagttga 3540
gttcccgtgt tattagtatg ttactaataa tttcagtatg ttagtgaaaa taatcttact 3600
aaaacactgg tacctcagac aactttacat ggtgaggatt gttactttcc caatccatat 3660
agaattttaa caattttagt gtttattttg gatgaaagga aatgactatc ttttgttagc 3720
aaattaccat aagatctttt tctttagatt tctgaatact ccaaggagct catataattc 3780
catccttatt ttttcagagg ccctccctgt tcaatcacgg tataaaaaaa ggaacacatt 3840
aagatgtccc agtcctattt tctggctttt tttttccggg ggtggtggtg cggtaatcac 3900
tctctatagt ccagtctggg cttcaacgcc tggcaatccc cagcctcaag ctcccaagta 3960
ctgtcctgat aaggatagaa ggagtcgacc tccttcacgc tcccctccga ggagggctcc 4020
ttcccagctc cattccccgg tcgggagccc gtcccccacc cgagagcgcg ggcctcgtgg 4080
tcagcgcctc cgcggggaga aacaaaggcg gcggcggggg ctcaagggca ctgcgccacg 4140
ggcccgcgcc tcccccatcc ggcggcggcc acgtagccgg gagcgcgccg cagcccggag 4200
cctcgggcct cgcagctgca gagcctgaac cgctctctcc ctgcgggcct gcgacgaggc 4260
tgggggaggg gaggcccgcg ctttgtctgg agtctcggta gctgtcatcc ggctcccacc 4320
ctcatgcaca attgtcccat ctcccccacg caccggcgcg gcgcccgcct cagcgaggcc 4380
ccagccggtt tcccgcagcc cgcggcccac ggggctcgca gcctccccgc aagctcggac 4440
gcacggagca tcctaaaccc caccacacgc aagatcgaaa aaaagcaaag gcacgaactt 4500
caccgctccg atgctcaggg ccgcggatcc tgcagagtct cccgcctgcg cgcttcggtt 4560
cagccacatc cgaggggagg gggcgcgggc agctccgccg ggggggaggg ggagcaccgc 4620
ccacgccctg gccgcgcggg gcccgccggg aacgcgtcct gcggggggcg gcgcgcgcaa 4680
tgctcaccgt ccgcggcgtg gcgcccaggg ggtctcctgg ctggggggag gggggggaag 4740
gcgggcagga aggaccgcgg aggcctctct gcgtctcgga gcgcgccaaa gcggggctcc 4800
acccacctcc ttgcccggat cttgaaggcc ggggagataa acagcggggt tctttaagca 4860
ccacctctca ctaggcgcgg gatcccaagg cttgtggcat ccggggtggt acttggacta 4920
aaagtccttc tgggagggac cgagtgagaa ccccttttggg acgtgtagaa atatttgtgt 4980
ggttcgagaa tatttgtgcg gacgggcttg gcaaaggcgt agctgcagag agcacgcttg 5040
ggtggagagg gccgcacgcc ccagcgccgg cctaagcccc tcccgacggc gttatttcaa 5100
actgcgcgac cgtttctccg ctccctacgc ggaggtgggg gccggaccta gttccggacg 5160

-continued

```
tagtaacacg ccgagcgcga gccttccgca attcacggaa cacagttgcg caagtgatgt   5220
aaagcagtcc cgctgtacct aaagggggag tgtcacgtac ttggcgtaag gagagtgtag   5280
gcccttcccg ccattggcgg cggttagggc gtttacgtaa cggcgtgacg taagcggaga   5340
cgcgttagtg gggggaaggt tctagaaaag cggcggtctc ggctccagcg gcagtagcag   5400
cggcgccggt cccgtgtgca ggagctcctt tgcggcccag tttcttggcc atcgcctgct   5460
ctccccacag cgccaggacg agtcccgtgc gcgtccgtcc gcggaggtct ttctcatctc   5520
gctcggctgc gggaaatcgg gctgaagcga ctgagtccgc gatggaggta acgggtttga   5580
aatcaatgag ttattaaaaa tggcatggcg aggccgtagg caccgcaatg gaaaccggcc   5640
acccgcctcc gtggtccggc ggaggggatg cggccactcg agtggcggtt ggccttggcg   5700
agtttctgag ggtcgttgg aggaggcctc tgattgtccg accgccttcc ccgccctcag   5760
ccgcccggcg ccatttccct cagttggggt gggggatggg aagtgcccgc cgcgaccggg   5820
ctggaccgct aaagtagcgc gtgagcgggc catcgctggc ctttcgatgt gcgcgggcct   5880
aggggctcgg ttgtgttcgc ggcggaacgt ttctggggcc cccccggctt cccggagcga   5940
gtctgcgaag ctagcttccc ctcccccctc tcccgggaac cggatttggc ggccgccatt   6000
ttcccgtctc cttcctcgcc acgattttgc tttcaacgct ttaggtttac tagtttggtt   6060
ttcttttttc accactgcgt agacgtgttt agcgattttc ctttcttttg gaagtcttca   6120
taccgtttcg aggtggattt agcgttttga gcttgggtct tcagcgtcct gcgcacctcg   6180
ctaaaggctc tctgccttcc cctcgacgaa atggcgccat tgctttctga agccaccgag   6240
gcgcggggtg ggggcggggt ggcggcgctc cacgagcttt actggaacag gcagagagaa   6300
cgtagtacaa ccgaggcctg ggcgggtggc tgaaggcagc gtcgctgcaa agagaccgtt   6360
ttatttttca taatacgtaa gattacgggt gctgtagtaa agcacttgag cattagtata   6420
gtaggaggaa gtcaaagtgg aaaaaatggg agcgctcatc aggaagctag ggaggctatg   6480
ttgagtgcag ggttactttc cttttattgc agaactttta tctgcttaaa ggatcctcgg   6540
atcgaaataa ttcaaattat aagcattttt aagggaatct tcgaatttgt tggtaaagtc   6600
aacggatcct tagcacgtgg tgttcacttt aaggaagtga aatagctgac ttttcatagt   6660
tagccttcgc ttaaagcctg gttcagtgga cgaaaatcca cgtcctggct atataaaaac   6720
ttagtttggg gtcacagtgt ttgagcgtgg tcattcggtt tttttatttt ttatttgttt   6780
gaaattatga tgcatcatta cactgataag cattagcttt cgaattgaaa ggggtctcct   6840
tggttatttt ctttgactct aagcacactt ataaataaaa taaccttgtt tataatcgat   6900
agtggacgtc tggtaagttt ggaaaaaacc cgaggtaagt aaagagcttt tgctttcgtt   6960
agtgatatga aaaaacaagg tgtatttaat acttgcaact tagtttaagg aaagccaatt   7020
tactgacatt ttagtagagc taccagaaac actatttgga gtcctgatta aggcttttgt   7080
aactattttg actatttaaa acaattttgg tcgtttttat taaacatttc aaaacctaaa   7140
aattgtaaac attggctttt tgagcacatt ttggagaaac ttacaaattt aggctataca   7200
gtaaaataac ggatttgttt tataattttg ctttttcatt tcgttgtgca gtcataggtc   7260
ctggatagta tgacctaatt tatgaacatc ttgataagtt tttgtactta gctattggaa   7320
agccagtatt aagtgcctga caaaaccaga tttaaggtga tatctggagt ttcagcattc   7380
ttcatggagc ttgtttcaga gttgcaggat tttttttttt catcttgaga tacttacaat   7440
taacaccaga gggggcagct cagggaaaag caaatatgcc acttttcaga aactgaatct   7500
tggaagtggt gaatttggaa acaggttttt taaatttttt ttaaatctaa aaagtagtaa   7560
```

-continued

```
attttggact tgggttgtag aatttaatga attacaaaag aattctttaa taccctttaa   7620
atgacctaag agctgggtat ggtttttctg aatttttttg aagaaaatct aagaaagttt   7680
acgtgaatta gaagttagat cgaatattag tgactttgaa acttgtatag ctcaggcaat   7740
ttttggtgta acacaactaa tatgcagttt aacatatggt ttaaatttga tgtaagtttt   7800
ttttctcccc cccagaaaac tttagaaact gttcctttgg agaggaaaaa ggtactctac   7860
cagcaggtca cctcatattt aagaatttaa tttcctgcat acaaagaaag tgtaaataaa   7920
aattgaaatg gtatttccct ttgcagagag aaaaggaaca gttccgaaag ctctttattg   7980
gtggcttaag cttatcgata ccggtggcgc gccaattgtt aattaagatc tggcccaatg   8040
ggccgtacga attccttagg ctaccgggta ggggaggcgc ttttcccaag gcagtctgga   8100
gcatgcgctt tagcagcccc gctgggcact tggcgctaca caagtggcct ctggcctcgc   8160
acacattcca catccaccgg ccggtaggcg ccaaccggct ccgttctttg gtggcccctt   8220
cgcgccacct tctactcctc ccctagtcag gaagttcccc cccgccccgc agctcgcgtc   8280
gtgcaggacg tgacaaatgg aagtagcacg tctcactagt ctcgtgcaga tggacagcac   8340
cgctgagcaa tggaagcggg taggcctttg gggcagcggc caatagcagc tttgctcctt   8400
cgctttctgg gctcagaggc tgggaagggg tgggtccggg ggcgggctca ggggcgggct   8460
caggggcggg gcgggcgccc gaaggtcctc cggaggcccg gcattctgca cgcttcaaaa   8520
gcgcacgtct gccgcgctgt tctcctcttc ctcatctccg ggcctttcga ccagcttacc   8580
atgaccgagt acaagcccac ggtgcgcctc gccacccgcg acgacgtccc cagggccgta   8640
cgcaccctcg ccgccgcgtt cgccgactac cccgccacgc gccacaccgt cgatccggac   8700
cgccacatcg agcgggtcac cgagctgcaa gaactcttcc tcacgcgcgt cgggctcgac   8760
atcggcaagg tgtgggtcgc ggacgacggc gccgcggtgg cggtctggac cacgccggag   8820
agcgtcgaag cgggggcggt gttcgccgag atcggcccgc gcatggccga gttgagcggt   8880
tcccggctgg ccgcgcagaa cagatggaag gcctcctggc gccgcaccgg cccaaggagc   8940
ccgcgtggtt cctggccacc gtcgcgtctc gcccgaccac cagggcaagg gtctgggcag   9000
cgccgtcgtg ctccccggag tggaggcggc cgagcgcgcc ggggtgcccg ccttcctgga   9060
gacctccgcg ccccgcaacc tccccttcta cgagcggctc ggcttcaccg tcaccgccga   9120
cgtcgaggtg cccgaaggac cgcgcacctg gtgcatgacc cgcaagcccg gtgcctgacg   9180
cccgccccac gacccgcagc gcccgaccga aaggagcgca cgaccccatg catcgtagag   9240
ctcgctgatc agcctcgact gtgccttcta gttgccagcc atctgttgtt tgcccctccc   9300
ccgtgccttc cttgaccctg gaaggtgcca ctcccactgt cctttcctaa taaaatgagg   9360
aaattgcatc gcattgtctg agtaggtgtc attctattct ggggggtggg gtggggcagg   9420
acagcaaggg ggggattggg gragacaata gcaggcatgc tggggggggcg gtgggggcta   9480
tggcttctga ggcggaaaga accagctggg gctcgagggc cgccaccgcg gtggagctcc   9540
agcttttgtt ccctttagtg agggttaatt tcgagcttgg cgtaatcatg gtcatagctg   9600
tttcctgtgt gaaattgtta tccgctcaca attccacaca acatacgagc cggaagcata   9660
aagtgtaaag cctggggtgc ctaatgagtg agctaactca cattaattgc gttgcgctca   9720
ctgcccgctt tccagtcggg aaacctgtcg tgccagcatc gcgagcactt ttcggggaaa   9780
tgtgcgcgga acccctattt gtttattttt ctaaatacat tcaaatatgt atccgctcat   9840
gagacaataa ccctgataaa tgcttcaata atattgaaaa aggaagagta tgagtattca   9900
```

-continued

```
acatttccgt gtcgccctta ttcccttttt tgcggcattt tgccttcctg tttttgctca   9960

cccagaaacg ctggtgaaag taaaagatgc tgaagatcag ttgggtgcac gagtgggtta  10020

catcgaactg gatctcaaca gcggtaagat ccttgagagt tttcgccccg aagaacgttt  10080

tccaatgatg agcactttta aagttctgct atgtggcgcg gtattatccc gtattgacgc  10140

cgggcaagag caactcggtc gccgcataca ctattctcag aatgacttgg ttgagtactc  10200

accagtcaca gaaaagcatc ttacggatgg catgacagta agagaattat gcagtgctgc  10260

cataaccatg agtgataaca ctgcggccaa cttacttctg acaacgatcg gaggaccgaa  10320

ggagctaacc gcttttttgc acaacatggg ggatcatgta actcgccttg atcgttggga  10380

accggagctg aatgaagcca taccaaacga cgagcgtgac accacgatgc ctgtagcaat  10440

ggcaacaacg ttgcgcaaac tattaactgg cgaactactt actctagctt cccggcaaca  10500

attaatagac tggatggagg cggataaagt tgcaggacca cttctgcgct cggcccttcc  10560

ggctggctgg tttattgctg ataaatctgg agccggtgag cgtgggtctc gcggtatcat  10620

tgcagcactg gggccagatg gtaagccctc ccgtatcgta gttatctaca cgacggggag  10680

tcaggcaact atggatgaac gaaatagaca gatcgctgag ataggtgcct cactgattaa  10740

gcattggtaa ctgtcagact cgcgacactg cattaatgaa tcggccaacg cgcggggaga  10800

ggcggtttgc gtattgggcg ctcttccgct tcctcgctca ctgactcgct gcgctcggtc  10860

gttcggctgc ggcgagcggt atcagctcac tcaaaggcgg taatacggtt atccacagaa  10920

tcaggggata acgcaggaaa gaacatgtga gcaaaaggcc agcaaaaggc caggaaccgt  10980

aaaaaggccg cgttgctggc gtttttccat aggctccgcc cccctgacga gcatcacaaa  11040

aatcgacgct caagtcagag gtggcgaaac ccgacaggac tataaagata ccaggcgttt  11100

ccccctggaa gctccctcgt gcgctctcct gttccgaccc tgccgcttac cggatacctg  11160

tccgcctttc tcccttcggg aagcgtggcg ctttctcata gctcacgctg taggtatctc  11220

agttcggtgt aggtcgttcg ctccaagctg ggctgtgtgc acgaaccccc cgttcagccc  11280

gaccgctgcg ccttatccgg taactatcgt cttgagtcca acccggtaag acacgactta  11340

tcgccactgg cagcagccac tggtaacagg attagcagag cgaggtatgt aggcggtgct  11400

acagagttct tgaagtggtg gcctaactac ggctacacta gaaggacagt atttggtatc  11460

tgcgctctgc tgaagccagt taccttcgga aaaagagttg gtagctcttg atccggcaaa  11520

caaaccaccg ctggtagcgg tggttttttt gtttgcaagc agcagattac gcgcagaaaa  11580

aaaggatctc aagaagatcc tttgatcttt tctacggggt ctgacgctca gtggaacgaa  11640

aactca                                                             11646
```

```
<210> SEQ ID NO 11
<211> LENGTH: 9027
<212> TYPE: DNA
<213> ORGANISM: Artificial Sequence
<220> FEATURE:
<223> OTHER INFORMATION: Plasmid

<400> SEQUENCE: 11

cgttgtaaaa cgacggccag tgaattgtaa tacgactcac tatagggcga attgggtacc     60

gggccccccc tcgaagttta aacatttaaa tctagaacta gtggatcccc cgggctgcag    120

gaattcgata tcaagctcat ggcacctgta ttgtactctt atcagtcatt atatggactt    180

taacttcccc agatattatt tgggctcctc cataagactg tgagcatctg accactggag    240

tgttgcttcc cattatatcc ctgttatcaa gcacaaggtc aggcacagag taagactcaa    300
```

-continued

```
aacatgtttt ggaatgtatg actggtatga actacaaacc agtaagctga tgttttcatt    360
ttgagtctat aaatctaatt ttgtggtggt tttgtgtatg gctcaaggct caaattgtaa    420
aatttaatat tatgtgacca aagaaagtta tacccagaac ctcaatttcc tcaccttcaa    480
aatggggcag tttctcactc attggtctgc tgtcacgatt ttaatgagct catgcacaaa    540
cagcccttta tataaggtaa gtgctggata aatgttggct actataataa aataagcctc    600
taagatactt ggtcagcaca agtactaccc aagagtatgc actgtaagta aactgacaaa    660
attgtgtatc taaaactggc cagatgaaag agaaactttt aaggggccct tctgcgtgcc    720
cgacactgtg ctaggcactc acactatccc gacccgagaa accgatctgc gacccagagg    780
aacttaccaa gcctccagca tcttgtgcag ccctactcat gggaccatct ggatacccac    840
ccttgtcttt acagggagca gaacacacct cttatgtgtc agaaaacaaa gtccaggaag    900
tatattttta cctgaggcaa tatctgaaaa ttgtatgcta cagcctccaa agtgagtctt    960
cctctcagta cctctcttct aggcacatgg agccctttct tccaagtatt atgtttaacc   1020
acttaatgaa tgaagtcctg aaactgctta cccatgctcc ctataatctc tgagtaatct   1080
tccttttcca caacctcagg cataatctca tcttctgttt ctattacaat ttcaaattct   1140
ggaaaaagga agttgtggtc tggaattata tggtccagat gatctgaaac aaaaaggaca   1200
gcactattag taatcattta gttttgaaga cagtctaata atttgctgtc tctaaagtac   1260
tatattccct atagttctgg cattttagat aaagggtcat aaattaaatg cctatatggt   1320
gacattattc agtgattcag acttcacagc cttttttttt tttttacaaa ggtgttccag   1380
gcatgaaaaa ttttaaagta ctataccttt cctaatttta cctttaaagt tgtcctggaa   1440
atatctgggt tgacaaaggc gatgaaactg aactgagact taaaaaaaag attacccacc   1500
tggttgtgca caagcctgct tatgtcccaa tctccagtct agggtctgat gctccttgct   1560
gcagtaatat gctttgtggc atctggagca cgttttgggg cctaaacagc cacaaaccct   1620
gcagagatga gcaccagact taagctggag acacactgat tctcctgttt ctgggggagg   1680
attctcagaa ggtggctcat atgagtaaaa atcgtttttc ctgggtagtt gattcctaaa   1740
aactaaaaaa gaatacagag aaaagtttta tcttcaaaca aaacagcaat tcacatattt   1800
tatcctctgc acgtaaaact gaaaataaca acaacaaaaa agaaatgaaa gtttttgctt   1860
tcaggaataa gcttttaaaa tccagaaact agatttcgtc cggtacacgc aactgagttg   1920
cctcctagag gtggtttgag ttaatcaaat taataagact gatcgttaag aacgactgcc   1980
aaaaatacga aaaagctact gggatccatc tttccaagac aatttctatt atctgaatta   2040
acaccatacc tggtacccac tgattaaaag ctgggggtta ccaatgcgcg tgggcacagt   2100
tagaagctta tgtagcaaaa atgagcacat cctggaaggg cccgggagaa ggtgctcctg   2160
gggcagcgcg gagagggagc tctgaggctg gggcggcagc ggtgcttgcc gccgtccccc   2220
tggtcgctcc cggaattaac gccgcgcacg cgtcggaggc atggccccgt cccgaccccg   2280
tttggcggct cacctcgcag gccggcacag cacggctgct cgcggcagca gaagaggaag   2340
atgcagcggt ggaaggcgtc cgggcggcca ggcagcggcg catacacctg cagcaggaag   2400
gagagcgggc ggccgcacag ctcgcaggcc agggcctggg gccccggcag cccggccgcg   2460
cccagccatg ccggccgccc gcccaccttg ctggggaact gctcgctgcg cagtcgccac   2520
gccggcgccg actcggcgaa gcccagctcc acaggcctgg ccccggcggc agccatgcgg   2580
ggcgcgggct ggcgtggggc gcagcccaca gctgggtcgg aaggcggaaa tcgggcgccg   2640
```

-continued

```
ggccggaagg caagaggcgg gcacctttcc ggaggacagg aggcggaaac gcgtctgacg   2700
ggagcggttg caggaccaat gcgagggaac ggggcagagg aaacctctcg gcatcagccc   2760
cgcccctggc gcctctgcct ccgagccgct ttcctggtgc ctccgggtgc tctgggatgg   2820
ttctggtctt tgggagagtg gcagctggtg acggcgctcc gctcacctct gcacatgtct   2880
tgctgtgggc ctgcgggtgg ccgccaggga ggcagagccc tcccgcaaac cttccctgct   2940
ggtgtccacc tcagggtgtg ggaaacctgt gcgctggccg agtgctaacc aagagtaggc   3000
agtgaaagac aaatgaaggt tgaacaggta aagtgaggac cctacagcgg aaaccaagaa   3060
tcctgtgtgc ctgagagtaa tgaagaagcc tctgcagaag agtcttttct gtcagtctta   3120
aggtctctgt tttaatgtta gtgctggctt gctgtacctg aattccaagg gaggagtgta   3180
taatgaggca tggccaaccc ccacttccca tcattgcctg aactagtttt tcaggttaac   3240
ttcagaatgc ccttggtacc gcgggccccc tctgtggtcc cacgccactg atcgctgcat   3300
gcccaccacc tgggtacaca cagtctgtga ttcccggagc agaacggacc ctgcccaccc   3360
ggtcttgtgt gctactcagt ggacagaccc aaggcaagaa agggtgacaa ggacagggtc   3420
ttcccaggct ggctttgagt tcctagcacc gccccgcccc caatcctctg tggcacatgg   3480
agtcttggtc cccagagtcc cccagcggcc tccagatggt ctgggagggc agttcagctg   3540
tggctgcgca tagcagacat acaacggacg gtgggcccag acccaggctg tgtagaccca   3600
gcccccccgc cccgcagtgc ctaggtcacc cactaacgcc ccaggcctgg tcttggctgg   3660
gcgtgactgt taccctcaaa agcaggcagc tccagggtaa aaggtgccct gccctgtaga   3720
gcccacttcc ttcccagggc tgcggctggg taggtttgta gccttcatca cgggccacct   3780
ccagccactg gaccgctggc ccctgccctg tcctggggag tgtggtcctg cgactctaat   3840
ggccgcaagc cacctgactc ccccaacacc acactctacc tctcaagccc aggtctctcc   3900
ctagtgaccc acccagcaca tttagctagc tgagccccac agccagaggt cctcaggccc   3960
tgctttcagg gcagttgctc tgaagtcggc aagggggagt gactgcctgg ccactccatg   4020
ccctccaaga gctccttctg caggagcgta cagaacccag ggccctggca cccgtgcaga   4080
ccctggccca ccccacctgg gcgctcagtg cccaagagat gtccacacct aggatgtccc   4140
gcggtgggtg gggggcccga gagacgggca ggccgggggc aggcctggcc atgcggggcc   4200
gaaccgggca ctgcccagcg tggggcgcgg gggccacggc gcgcgccccc agcccccggg   4260
cccagcaccc caaggcggcc aacgccaaaa ctctccctcc tcctcttcct caatctcgct   4320
ctcgctcttt tttttttcg caaaaggagg ggagaggggg taaaaaaatg ctgcactgtg   4380
cggcgaagcc ggtgagtgag cggcgcgggg ccaatcagcg tgcgccgttc cgaaagttgc   4440
cttttatggc tcgagcggcc gcggcggcgc cctataaaac ccagcggcgc gacgcgccac   4500
caccgccgag accgcgtccg cccgcgagca cagagcctcg cctttgccga tccgccgccc   4560
gtccacaccc gccgccaggt aagcccggcc agccgaccgg ggcatgcggc cgcggccctt   4620
cgcccgtgca gagccgccgt ctgggccgca gcgggggcg catggggcgg aaccggaccg   4680
ccgtgggggg cgcgggagaa gcccctgggc ctccggagat gggggacacc ccacgccagt   4740
tcgcaggcgc gaggccgcgc tcgggcgggc gcgctccggg ggtgccgctc tcggggcggg   4800
ggcaaccggc ggggtctttg tctgagccgg gctcttgcca atggggatcg cacggtgggc   4860
gcggcgtagc ccccgtcagg cccggtgggg gctggggcgc catgcgcgtg cgcgctggtc   4920
ctttgggcgc taactgcgtg cgcgctggga attggcgcta attgcgcgtg cgcgctggga   4980
ctcaatggcg ctaatcgcgc gtgcgttctg ggcccgggc gcttgcgcca cttcctgccc   5040
```

-continued

```
gagccgctgg cgcccgaggg tgtggccgct gcgtgcgcgc gcgcgacccg gtcgctgttt   5100
gaaccgggcg gaggcggggc tggcgcccgg ttgggagggg gttggggcct ggcttcctgc   5160
cgcgcgccgc ggggacgcct ccgaccagtg tttgcctttt atggtaataa cgcggccggc   5220
ccggcttcct ttgtccccaa tctgggcgcg cgccggcgcc ccctggcggc ctaaggactc   5280
ggcgcgccgg aagtggccag ggcgggggcg acttcggctc acagcgcgcc cggctattct   5340
cgcagctcac catgccggtc gccaccatga gcttatcgat accggtggcg cgccaattgt   5400
taattaagat ctggcccaat gggccgtacg aattccttag gctaccgggt aggggaggcg   5460
cttttcccaa ggcagtctgg agcatgcgct ttagcagccc cgctgggcac ttggcgctac   5520
acaagtggcc tctggcctcg cacacattcc acatccaccg gccggtaggc gccaaccggc   5580
tccgttcttt ggtggcccct tcgcgccacc ttctactcct cccctagtca ggaagttccc   5640
ccccgccccg cagctcgcgt cgtgcaggac gtgacaaatg gaagtagcac gtctcactag   5700
tctcgtgcag atggacagca ccgctgagca atggaagcgg gtaggccttt ggggcagcgg   5760
ccaatagcag ctttgctcct tcgctttctg ggctcagagg ctgggaaggg gtgggtccgg   5820
gggcgggctc aggggcgggc tcaggggcgg ggcgggcgcc cgaaggtcct ccggaggccc   5880
ggcattctgc acgcttcaaa agcgcacgtc tgccgcgctg ttctcctctt cctcatctcc   5940
gggcctttcg accagcttac catgaccgag tacaagccca cggtgcgcct cgccacccgc   6000
gacgacgtcc ccagggccgt acgcaccctc gccgccgcgt tcgccgacta ccccgccacg   6060
cgccacaccg tcgatccgga ccgccacatc gagcgggtca ccgagctgca agaactcttc   6120
ctcacgcgcg tcgggctcga catcggcaag gtgtgggtcg cggacgacgg cgccgcggtg   6180
gcggtctgga ccacgccgga gagcgtcgaa gcgggggcgg tgttcgccga gatcggcccg   6240
cgcatggccg agttgagcgg ttcccggctg gccgcgcaga acagatggaa ggcctcctgg   6300
cgccgcaccg gcccaaggag cccgcgtggt tcctggccac cgtcgcgtct cgcccgacca   6360
ccagggcaag ggtctgggca gcgccgtcgt gctccccgga gtggaggcgg ccgagcgcgc   6420
cggggtgccc gccttcctgg agacctccgc gccccgcaac ctccccttct acgagcggct   6480
cggcttcacc gtcaccgccg acgtcgaggt gcccgaagga ccgcgcacct ggtgcatgac   6540
ccgcaagccc ggtgcctgac gcccgcccca cgacccgcag cgcccgaccg aaaggagcgc   6600
acgaccccat gcatcgtaga gctcgctgat cagcctcgac tgtgccttct agttgccagc   6660
catctgttgt ttgcccctcc cccgtgcctt ccttgaccct ggaaggtgcc actcccactg   6720
tcctttccta ataaaatgag gaaattgcat cgcattgtct gagtaggtgt cattctattc   6780
tggggggtgg ggtggggcag gacagcaagg gggaggattg ggragacaat agcaggcatg   6840
ctggggggc ggtgggggct atggcttctg aggcggaaag aaccagctgg ggctcgaggg   6900
ccgccaccgc ggtggagctc cagcttttgt tccctttagt gagggttaat ttcgagcttg   6960
gcgtaatcat ggtcatagct gtttcctgtg tgaaattgtt atccgctcac aattccacac   7020
aacatacgag ccggaagcat aaagtgtaaa gcctggggtg cctaatgagt gagctaactc   7080
acattaattg cgttgcgctc actgcccgct ttccagtcgg gaaacctgtc gtgccagcat   7140
cgcgagcact tttcggggaa atgtgcgcgg aacccctatt tgtttatttt tctaaataca   7200
ttcaaatatg tatccgctca tgagacaata accctgataa atgcttcaat aatattgaaa   7260
aaggaagagt atgagtattc aacatttccg tgtcgccctt attccctttt ttgcggcatt   7320
ttgccttcct gtttttgctc acccagaaac gctggtgaaa gtaaaagatg ctgaagatca   7380
```

-continued

```
gttgggtgca cgagtgggtt acatcgaact ggatctcaac agcggtaaga tccttgagag   7440

ttttcgcccc gaagaacgtt ttccaatgat gagcactttt aaagttctgc tatgtggcgc   7500

ggtattatcc cgtattgacg ccgggcaaga gcaactcggt cgccgcatac actattctca   7560

gaatgacttg gttgagtact caccagtcac agaaaagcat cttacggatg gcatgacagt   7620

aagagaatta tgcagtgctg ccataaccat gagtgataac actgcggcca acttacttct   7680

gacaacgatc ggaggaccga aggagctaac cgcttttttg cacaacatgg gggatcatgt   7740

aactcgcctt gatcgttggg aaccggagct gaatgaagcc ataccaaacg acgagcgtga   7800

caccacgatg cctgtagcaa tggcaacaac gttgcgcaaa ctattaactg gcgaactact   7860

tactctagct tcccggcaac aattaataga ctggatggag gcggataaag ttgcaggacc   7920

acttctgcgc tcggcccttc cggctggctg gtttattgct gataaatctg gagccggtga   7980

gcgtgggtct cgcggtatca ttgcagcact ggggccagat ggtaagccct cccgtatcgt   8040

agttatctac acgacgggga gtcaggcaac tatggatgaa cgaaatagac agatcgctga   8100

gataggtgcc tcactgatta agcattggta actgtcagac tcgcgacact gcattaatga   8160

atcggccaac gcgcggggag aggcggtttg cgtattgggc gctcttccgc ttcctcgctc   8220

actgactcgc tgcgctcggt cgttcggctg cggcgagcgg tatcagctca ctcaaaggcg   8280

gtaatacggt tatccacaga atcaggggat aacgcaggaa agaacatgtg agcaaaaggc   8340

cagcaaaagg ccaggaaccg taaaaaggcc gcgttgctgg cgtttttcca taggctccgc   8400

ccccctgacg agcatcacaa aaatcgacgc tcaagtcaga ggtggcgaaa cccgacagga   8460

ctataaagat accaggcgtt tccccctgga agctccctcg tgcgctctcc tgttccgacc   8520

ctgccgctta ccggatacct gtccgccttt ctcccttcgg gaagcgtggc gctttctcat   8580

agctcacgct gtaggtatct cagttcggtg taggtcgttc gctccaagct gggctgtgtg   8640

cacgaacccc ccgttcagcc cgaccgctgc gccttatccg gtaactatcg tcttgagtcc   8700

aacccggtaa gacacgactt atcgccactg gcagcagcca ctggtaacag gattagcaga   8760

gcgaggtatg taggcggtgc tacagagttc ttgaagtggt ggcctaacta cggctacact   8820

agaaggacag tatttggtat ctgcgctctg ctgaagccag ttaccttcgg aaaaagagtt   8880

ggtagctctt gatccggcaa acaaaccacc gctggtagcg gtggtttttt tgtttgcaag   8940

cagcagatta cgcgcagaaa aaaaggatct caagaagatc ctttgatctt ttctacgggg   9000

tctgacgctc agtggaacga aaactca                                       9027
```

```
<210> SEQ ID NO 12
<211> LENGTH: 12221
<212> TYPE: DNA
<213> ORGANISM: Artificial Sequence
<220> FEATURE:
<223> OTHER INFORMATION: Plasmid

<400> SEQUENCE: 12

cgttgtaaaa cgacggccag tgaattgtaa tacgactcac tatagggcga attgggtacc     60

gggccccccc tcgaagttta aacatttaaa tctagaagct tcaatgtttt tagcaccctc    120

tgtgtggagg aaaataatgc agattattct aattagtgta atatctaacc acattaaaat    180

atattacata gtaaactaca ctccataatt ttataaattt gactccccag ggtaataaac    240

tagtctctag tctgctcacc ttcaactgta caataaagtc ttggttcttt tgaaatagac    300

ctcaaatgag acacctaaaa ttcaaagtgt ctttacattt aaagacacct acaggaaagc    360

aggtaaaaga gccaggttaa aaacaaattc taaaaccact tagctgcagt taaacatata    420
```

-continued

```
gtaaagatgc actaaagttt cttactctgt aaatcccttc cacttcagga aatattccac    480
tttcccattc actacacgtc gatctagtac tttttccacg acaaattctt caggctctgc    540
ctcttcaact tttttactct ttccattctg tttttttccc attttttgct aaaataaaac    600
aaaagagaaa ttaagaaata ttcctcttga attttgagca cattttcaag gctcaattgc    660
ttatattatt atcacattcg acataaattt ttacttctat atcccagggc agacaccttc    720
tggaaagatt aaaagtcaac agacaataaa ataaaagaat gctttatctt gttcatttag    780
ttcaaactta caacccacca ccaaaataat acaataaaaa aacactatct ggaaacagtt    840
atttttttcc agtctttttt tttgagacag ggtctcacac tcttgtcgcc caggctggag    900
tgcagtggcg tgatctcagc tcactgcaac ctccgcctcc ccaggttcaa gcagttctca    960
tgcctcagcc tccagagtag ctgggattat aggcggatgc caccatgccg ggctaatttt   1020
ttttgtgttt ttattagaaa cagggtttca ccatgttgac caggctggtc tcaaactcct   1080
gacctgaagt gattcaccag cctgggcctc ccaaagtgct ggcattacag gcgtgagcca   1140
ctgcgcccgg ccctgtagtc ttaaaagacc aagtttacta attttcactc attttaacaa   1200
cactgcaaca aacaactatg caggaagtac ctaaagggtg atccagagaa gcaagtagta   1260
gtgacaggtc ttaggtgaac ctatgacaga ccttgtatcc acccccagat ggtaaaagcc   1320
ccagccccct tctcaattca aatattaatg tcaaaagcat caatgataca gagaaaagat   1380
aaatgcagaa tgaaaacatg gttcaaaatc ctgataccaa ctgcagggtc aactatagag   1440
accactagga ggttcaatta aaggacaaga ttatttttcc ataatctctg tagataatat   1500
ttcctaccac ttagaacaaa actataaagc tatcacttca agagaccaac attacaaatt   1560
tattttaatt ccctaaggtg aaaaaaatcc ttccttcctg gtttctcaag agaaagtcta   1620
tactggtaac caaattcact ttaaacaggc attttctttg gtatgacact atttaagaga   1680
agcaggaaac caacgtgaac cagctctttc caatggctca agatttccta tgagaggact   1740
aaaaatgggg aaaattttta tgagaggatt aaaaatgggg gaaaaaaaac cctgaaatgg   1800
ttaatcagaa gatcctatgg gctgagaagg aatccatctt aacatttcat cttaaagcaa   1860
atgctattgc cgggggcagt ggctcatgcc tgtaatccca gcactttggg aggccgaggt   1920
gggcagatca tctgaggtca ggagtttgag accagcctga ccaacatgga gaaaccccgt   1980
ttctactaaa aatacaaaat tagccaggca tagtggtgca tgcctgtaat cccagctact   2040
tgggaggctg aggcaggaga actgcttgaa cccaggaggc ttaagttgcg gtgagccaag   2100
atcacgccat tgcactctag cctggacaac aagagaaaaa ctctgtctca aaaaaacaca   2160
aaaacaaaaa acccaaatac tatttaaaaa agataaacct taattgctca atcattaaag   2220
ccatcccaca agtaaagcag caagcagaaa aaagttaaga acacctcaag gctacagaag   2280
gacatttcaa gctatgcagg catatgaagt gtgcagacag atatgtaaga aaggcctcaa   2340
gactgcaaaa gggcatttca agctatgcaa gcatataggt aacacataca cacacacaaa   2400
ataaaatccc ctgaaataca aaaacatgca gcaaacacct gacgtttttg gataccattt   2460
ctaagtcagg tgttatgatt ctcattagtc aagatacttg agtactgggc ccaaacagct   2520
ttctgccact gtacagtaca agaaggtagg aataatggtg ggaggagcaa agacaaactg   2580
taatagacag aagtgtatca gatacctata ctacatgaaa aacaaaacag ctactgccac   2640
aaagggagaa ggctaacaaa ataaagtcaa caataaatac agaaaatgaa aaggatacac   2700
actaaggttt acaaaaaaaa aaaggcagac aaaatgccat acagtattca ttcactacta   2760
```

-continued

```
tggcattcat aagctagttt caaatgctca ctattttctt ttatagtata tatttgcctt   2820
aacccagcac tttttttccaa aagtggatga gtcaaaataa atttcccatt atttaagtga   2880
aattaacagc acacatatct cacaacacta atgaattttt aaaatggaaa gttaagaact   2940
tttaaagtgg ccaacctgtg atccttcaca aaataaacta aatacaataa cagaccccaa   3000
aggctatcaa ttgcgtgcaa aaacaacttc tgttttccag ggtaaacaga atctaatgca   3060
gaatctaatg cagggtaaac agacttaatg cagaatctaa tgatggcaca aattaaaaat   3120
cactaacgtg ccctttttag tgtgaaaccc agagagagca catacaagcc aaaaacaaat   3180
gctttatttt acctaggaga cattaacatt cacctttacg tgtttaagat taatgcaatg   3240
ttaaatattg tgaaaactgt aactttgaat ttcatgattt ttatgtgaat attccagggt   3300
ttaaaaaaac ttgtaacatg acatggctga ataagataaa aaaaaaatct agccttttct   3360
cccttctggc tcatatttgc gatttcgatc attttgttta aaaaacaaaa cactgcaatg   3420
aattaaactt aatattcttc tatgttttag agtaagttaa aacaagataa agtgaccaaa   3480
gtaatttgaa agattcaatg acttttgctc caacctaggt gcacaaggta ccttgttctt   3540
taaattgggc tttaatgaaa atacttctcc agaattctgg ggatttaaga aaaattatgc   3600
caaccaacaa gggctttacc attttatgta acatttttca acgctgcaaa aatgtgtgta   3660
tttctatttg aagataaaaa tcctcagcaa aatccacatt gcactgtcct tcaaagatta   3720
gccttctttg aactagttaa gacactatta agccaagcca gtatctccct gtaatgaatt   3780
cgtttttctc ttaattttcc cctgtaattt acactgggag agctgggaaa tatgtggatg   3840
taaatttctc agccacagag atgcaaagtt atactgtggg gaaaaaaaac ttgagttaaa   3900
tccttacata ttttaggttt tcattaactt accaatgtag ttttgttgga ggccattttt   3960
tttattgcag acttgaagag ctattactag aaaaatgcat gacagttaag gtaagtttgc   4020
atgacacaaa aaaggtaact aaatacaaat tctgtttgga ttccaacccc caagtagaga   4080
gcgcacactt tcaaacgtga atacaaatcc agagtagatc tgcgctccta cctacattgc   4140
ttatgatgta cttaagtacg tgtcctaacc atgtgagtct agaaagactt tactggggat   4200
cctggtacct aaaacagctt cacatggctt aaaatagggg accaatgtct tttccaatct   4260
aagtcccatt tataataaag tccatgttcc atttttaaag gacaatcctt tcggtttaaa   4320
accaggcacg attacccaaa caactcacaa cggtaaagca ctgtgaatct tctctgttct   4380
gcaatcccaa cttggtttct gctcagaaac cctccctctt tccaatcggt aattaaataa   4440
caaaaggaaa aaacttaaga tgcttcaacc ccgtttcgtg acactttgaa aaaagaatca   4500
cctcttgcaa acacccgctc ccgacccccg ccgctgaagc ccggcgtcca gaggcctaag   4560
cgcgggtgcc cgcccccacc cgggagcgcg ggcctcgtgg tcagcgcatc cgcggggaga   4620
aacaaaggcc gcggcacggg ggctcaaggg cactgcgcca caccgcacgc gcctaccccc   4680
gcgcggccac gttaactggc ggtcgccgca gcctcgggac agccggccgc gcgccgccag   4740
gctcgcggac gcgggaccac gcgccgccct ccgggaggcc caagtctcga cccagccccg   4800
cgtggcgctg gggggagggg cgcctccgcc ggaacgcggg tgggggaggg gaggggggaaa   4860
tgcgctttgt ctcgaaatgg ggcaaccgtc gccacagctc cctacccccct cgagggcaga   4920
gcagtccccc cactaactac cgggctggcc gcgcgccagg ccagccgcga ggccaccgcc   4980
cgaccctcca ctccttcccg cagctcccgg cgcggggtcc ggcgagaagg ggaggggagg   5040
ggagcggaga accgggcccc cgggacgcgt gtggcatctg aagcaccacc agcgagcgag   5100
agctagagag aaggaaagcc accgacttca ccgcctccga gctgctccgg gtcgcgggtc   5160
```

-continued

```
tgcagcgtct ccggccctcc gcgcctacag ctcaagccac atccgaaggg ggagggagcc   5220
gggagctgcg cgcggggccg ccggggggag gggtggcacc gcccacgccg ggcggccacg   5280
aagggcgggg cagcgggcgc gcgcgcggcg gggggagggg ccggcgccgc gcccgctggg   5340
aattggggcc ctagggggag ggcggaggcg ccgacgaccg cggcacttac cgttcgcggc   5400
gtggcgcccg gtggtcccca aggggaggga agggggaggc ggggcgagga cagtgaccgg   5460
agtctcctca gcggtggctt ttctgcttgg cagcctcagc ggctggcgcc aaaaccggac   5520
tccgcccact tcctcgcccg ccggtgcgag ggtgtggaat cctccagacg ctgggggagg   5580
gggagttggg agcttaaaaa ctagtacccc tttgggacca ctttcagcag cgaactctcc   5640
tgtacaccag gggtcagttc cacagacgcg ggccaggggt gggtcattgc ggcgtgaaca   5700
ataatttgac tagaagttga ttcgggtgtt tccggaaggg gccgagtcaa tccgccgagt   5760
tggggcacgg aaaacaaaaa gggaaggcta ctaagatttt tctggcgggg gttatcattg   5820
gcgtaactgc agggaccacc tcccgggttg agggggctgg atctccaggc tgcggattaa   5880
gcccctcccg tcggcgttaa tttcaaactg cgcgacgttt ctcacctgcc ttcgccaagg   5940
caggggccgg gaccctattc caagaggtag taactagcag gactctagcc ttccgcaatt   6000
cattgagcgc atttacggaa gtaacgtcgg gtactgtctc tggccgcaag ggtgggagga   6060
gtacgcattt ggcgtaaggt ggggcgtaga gccttcccgc cattggcggc ggatagggcg   6120
tttacgcgac ggcctgacgt agcggaagac gcgttagtgg gggggaaggt tctagaaaag   6180
cggcggcagc ggctctagcg gcagtagcag cagcgccggg tcccgtgcgg aggtgctcct   6240
cgcagagttg tttctcgagc agcggcagtt ctcactacag cgccaggacg agtccggttc   6300
gtgttcgtcc gcggagatct ctctcatctc gctcggctgc gggaaatcgg gctgaagcga   6360
ctgagtccgc gatggaggta acgggtttga aatcaatgag ttattgaaaa gggcatggcg   6420
aggccgttgg cgcctcagtg gaagtcggcc agccgcctcc gtgggagaga ggcaggaaat   6480
cggaccaatt cagtagcagt ggggcttaag gtttatgaac ggggtcttga gcggaggcct   6540
gagcgtacaa acagcttccc caccctcagc ctcccggcgc catttccctt cactgggggt   6600
gggggatggg gagctttcac atggcggacg ctgccccgct ggggtgaaag tggggcgcgg   6660
aggcgggaat tcttattccc tttctaaagc acgctgcttc gggggccacg gcgtctcctc   6720
ggcgagcgtt tcggcgggca gcaggtcctc gtgagcgagg ctgcggagct tcccctcccc   6780
ctctctcccg ggaaccgatt tggcggccgc cattttcatg gctcgccttc ctctcagcgt   6840
tttccttata actcttttat tttcttagtg tgctttctct atcaagaagt agaagtggtt   6900
aactattttt tttttcttct cggctgttt tcatatcgtt tcgaggtgga tttggagtgt   6960
tttgtgagct tggatcttta gagtcctgcg cacctcatta aaggcgctca gccttcccct   7020
cgatgaaatg gcgccattgc gttcggaagc cacaccgaag agcggggagg gggggtgctc   7080
cgggtttgcg ggcccggttt cagagaagat atcaccaccc agggcgtcgg gccgggttca   7140
atgcgagccg taggacaaag aaaccatttt atgtttttcc tgtctttttt ttcctttgag   7200
taacggtttt atctgggtct gcagtcagta aaacgacaga tgaaccgcgg caaaataaac   7260
ataaattgga agccatcggc cacgaggggc agggacgaag gtggttttct gggcggggga   7320
gggatattcg cgtcagaatc ctttactgtt cttaaggatt ccgtttaagt tgtagagctg   7380
actcatttta agtaatgttg ttactgagaa gtttaaccct tacgggacag atccatggac   7440
ctttatagat gattacgagg aaagtgaaat aacgattttg tccttagtta tacttcgatt   7500
```

-continued

```
aaaacatggc ttcagaggct ccttcctgta atgcgtatgg attgatgtgc aaaactgttt   7560
tgggcctggg ccgctctgta tttgaacttt gttacttttc tcattttgtt tgcaatcttg   7620
gttgaacatt acattgataa gcataaggtc tcaagcgaag gggtctacc tggttatttt   7680
tctttgaccc taagcacgtt tataaaataa cattgtttaa aatcgatagt ggacatcggg   7740
taagtttgga taaattgtga ggtaagtaat gagtttttgc tttttgttag tgatttgtaa   7800
aacttgttat aaatgtacat tatccgtaat ttcagtttag agataaccta tgtgctgacg   7860
acaattaaga ataaaaacta gctgaaaaaa tgaaaataac tatcgtgaca agtaaccatt   7920
tcaaaagact gctttgtgtc tcataggagc tagtttgatc atttcagtta attttttctt   7980
taatttttac gagtcatgaa aactacagga aaaaaaatct gaactgggtt ttaccactac   8040
tttttaggag ttgggagcat gcgaatggag ggagagctcc gtagaactgg gatgagagca   8100
gcaattaatg ctgcttgcta ggaacaaaaa ataattgatt gaaaattacg tgtgactttt   8160
tagtttgcat tatgcgtttg tagcagttgg tcctggatat cactttctct cgtttgaggt   8220
tttttaacct agttaacttt taagacaggt ttccttaaca ttcataagtg cccagaatac   8280
agctgtgtag tacagcatat aaagatttca gctctgaggt ttttcctatt gacttggaaa   8340
attgttttgt gcctgtcgct tgccacatgg ccaatcaagt aagcttatcg ataccggtgg   8400
cgcgccaatt gttaattaag atctggccca atgggccgta cgaatttgag gcggaaagaa   8460
ccagctgtgg aatgtgtgtc agttagggtg tggaaagtcc ccaggctccc cagcaggcag   8520
aagtatgcaa agcatgcatc tcaattagtc agcaaccagg tgtggaaagt ccccaggctc   8580
cccagcaggc agaagtatgc aaagcatgca tctcaattag tcagcaacca tagtcccgcc   8640
cctaactccg cccatcccgc ccctaactcc gcccagttcc gcccattctc cgccccatgg   8700
ctgactaatt ttttttattt atgcagaggc cgaggccgcc tcggcctctg agctattcca   8760
gaagtagtga ggaggctttt ttggaggcct aggcttttgc aaagatcgat caagagacag   8820
gatgaggatc gtttcgcatg attgaacaag atggattgca cgcaggttct ccggccgctt   8880
gggtggagag gctattcggc tatgactggg cacaacagac aatcggctgc tctgatgccg   8940
ccgtgttccg gctgtcagcg caggggcgcc cggttctttt tgtcaagacc gacctgtccg   9000
gtgccctgaa tgaactgcaa gacgaggcag cgcggctatc gtggctggcc acgacgggcg   9060
ttccttgcgc agctgtgctc gacgttgtca ctgaagcggg aagggactgg ctgctattgg   9120
gcgaagtgcc ggggcaggat ctcctgtcat ctcaccttgc tcctgccgag aaagtatcca   9180
tcatggctga tgcaatgcgg cggctgcata cgcttgatcc ggctacctgc ccattcgacc   9240
accaagcgaa acatcgcatc gagcgagcac gtactcggat ggaagccggt cttgtcgatc   9300
aggatgatca agagcatcag gggctcgcgc cagccgaact gttcgccagg ctcaaggcga   9360
gcatgcccga cggcgaggat ctcgtcgtga cccatggcga tgcctgcttg ccgaatatca   9420
tggtggaaaa tggccgcttt tctggattca tcgactgtgg ccggctgggt gtggcggacc   9480
gctatcagga catagcgttg gctacccgtg atattgctga agagcttggc ggcgaatggg   9540
ctgaccgctt cctcgtgctt tacggtatcg ccgctcccga ttcgcagcgc atcgccttct   9600
atcgccttct tgacgagttc ttctgagcgg gactctgggg ttcgaaatga ccgaccaagc   9660
gacgcccaac ctgccatcac gagatttcga ttccaccgcc gccttctatg aaaggttggg   9720
cttcggaatc gttttccggg acgccggctg gatgatcctc cagcgcgggg atctcatgct   9780
ggagttcttc gcccacccta gggggaggct aactgaaaca cggaaggaga caataccgga   9840
aggaacccgc gctatgacgg caataaaaag acagaataaa acgcacggtg ttgggtcgtt   9900
```

-continued

```
tgttcataaa cgcggggttc ggtcccaggg ctggcactct gtcgataccc caccgagacc   9960
ccattggggc caatacgccc gcgtttcttc cttttcccca ccccaccccc caagttcggg  10020
tgaaggccca gggctcgcag ccaacgtcgg ggcggcaggc cctgccatag cctcaaattc  10080
cttaggctcg agggccgcca ccgcggtgga gctccagctt ttgttccctt tagtgagggt  10140
taatttcgag cttggcgtaa tcatggtcat agctgtttcc tgtgtgaaat tgttatccgc  10200
tcacaattcc acacaacata cgagccggaa gcataaagtg taaagcctgg ggtgcctaat  10260
gagtgagcta actcacatta attgcgttgc gctcactgcc cgctttccag tcgggaaacc  10320
tgtcgtgcca gcatcgcgag cacttttcgg ggaaatgtgc gcggaacccc tatttgttta  10380
tttttctaaa tacattcaaa tatgtatccg ctcatgagac aataaccctg ataaatgctt  10440
caataatatt gaaaaaggaa gagtatgagt attcaacatt tccgtgtcgc ccttattccc  10500
ttttttgcgg cattttgcct tcctgttttt gctcacccag aaacgctggt gaaagtaaaa  10560
gatgctgaag atcagttggg tgcacgagtg ggttacatcg aactggatct caacagcggt  10620
aagatccttg agagttttcg ccccgaagaa cgttttccaa tgatgagcac ttttaaagtt  10680
ctgctatgtg gcgcggtatt atcccgtatt gacgccgggc aagagcaact cggtcgccgc  10740
atacactatt ctcagaatga cttggttgag tactcaccag tcacagaaaa gcatcttacg  10800
gatggcatga cagtaagaga attatgcagt gctgccataa ccatgagtga taacactgcg  10860
gccaacttac ttctgacaac gatcggagga ccgaaggagc taaccgcttt tttgcacaac  10920
atgggggatc atgtaactcg ccttgatcgt tgggaaccgg agctgaatga agccatacca  10980
aacgacgagc gtgacaccac gatgcctgta gcaatggcaa caacgttgcg caaactatta  11040
actggcgaac tacttactct agcttcccgg caacaattaa tagactggat ggaggcggat  11100
aaagttgcag gaccacttct gcgctcggcc cttccggctg gctggtttat tgctgataaa  11160
tctggagccg gtgagcgtgg gtctcgcggt atcattgcag cactggggcc agatggtaag  11220
ccctcccgta tcgtagttat ctacacgacg gggagtcagg caactatgga tgaacgaaat  11280
agacagatcg ctgagatagg tgcctcactg attaagcatt ggtaactgtc agactcgcga  11340
cactgcatta atgaatcggc caacgcgcgg ggagaggcgg tttgcgtatt gggcgctctt  11400
ccgcttcctc gctcactgac tcgctgcgct cggtcgttcg gctgcggcga gcggtatcag  11460
ctcactcaaa ggcggtaata cggttatcca cagaatcagg ggataacgca ggaaagaaca  11520
tgtgagcaaa aggccagcaa aaggccagga accgtaaaaa ggccgcgttg ctggcgtttt  11580
tccataggct ccgcccccct gacgagcatc acaaaaatcg acgctcaagt cagaggtggc  11640
gaaacccgac aggactataa agataccagg cgtttccccc tggaagctcc ctcgtgcgct  11700
ctcctgttcc gaccctgccg cttaccggat acctgtccgc ctttctccct tcgggaagcg  11760
tggcgctttc tcatagctca cgctgtaggt atctcagttc ggtgtaggtc gttcgctcca  11820
agctgggctg tgtgcacgaa ccccccgttc agcccgaccg ctgcgcctta tccggtaact  11880
atcgtcttga gtccaacccg gtaagacacg acttatcgcc actggcagca gccactggta  11940
acaggattag cagagcgagg tatgtaggcg gtgctacaga gttcttgaag tggtggccta  12000
actacggcta cactagaagg acagtatttg gtatctgcgc tctgctgaag ccagttacct  12060
tcggaaaaag agttggtagc tcttgatccg gcaaacaaac caccgctggt agcggtggtt  12120
tttttgtttg caagcagcag attacgcgca gaaaaaaagg atctcaagaa gatcctttga  12180
tcttttctac ggggtctgac gctcagtgga acgaaaactc a                      12221
```

<210> SEQ ID NO 13
<211> LENGTH: 11828
<212> TYPE: DNA
<213> ORGANISM: Artificial Sequence
<220> FEATURE:
<223> OTHER INFORMATION: Plasmid

<400> SEQUENCE: 13

```
cgttgtaaaa cgacggccag tgaattgtaa tacgactcac tatagggcga attgggtacc     60

gggccccccc tcgaagttta aacatttaaa tctagaagct tttaaccctc tatcccttta    120

aacttccttg atccagtgta agcacctcct agaaagtcag tagacaataa aacaaaagtt    180

ctgcttcacc gatttacatt tataaccaaa taccettcac caatacaata aaaaaacaaa    240

acaacaaaaa accccaacca tctgagaaat aatcttctcc tttcccagct ttattcccag    300

gattctacat gaccaaatta ccagagtcac cactcatttt aatcacaaca tagtgtcaaa    360

taactagaaa acatgagaca acaatggaga gctgagtaac tattagtagt agtactttac    420

cagagaatgg cctctatagg ctcacatgta ggaatggttg gtccccaggt ggtaggtaga    480

gctgtttgag gattacgtgg ccttcttgga tggggggtgg gggtggggtg ggagggttgg    540

gtggtgggta cttaagaggt ttcaaaagtc aatattgttt gcatttagct cttccttgta    600

cttgtggatc aaacacaacc tgtcagctac tgcttcaaat gtcatgcctg ctgccatctt    660

ctcagcagga tggtcatggc ctcaccctct tcaactgtaa atctttcttt cttttcttct    720

ttttcttttg gtttcgagac agggtttctc tgtatagtcc tggctgtcct ggaactcact    780

ttgtagacca ggctggcctt gaactcagaa atccgcctgc ctctgcctcc ctagcactgg    840

gattaaaggc gtgcgccacc acgcccagct ttcaactgga aatcttaata aactttccta    900

gaagtggcct tggttatggg agcttatcac agcaatagaa cagcaattat gactggagta    960

tgatagttaa aaacaagcaa gcaagcaagc aaacacacac accaaaacaa caaaacccca   1020

agacagagtc acatgtagcc caggctagcc tccaaattca ctatataact gaagaagacc   1080

cctaattccc attcctctag aatctatacc tcaagtactg aatggcttgg ttcacaatac   1140

cccactaaat gattggtctt actaagtgca acaaggtaaa cctaaaactt cagccctcag   1200

acatcccttt tccagtatca atttataaaa ttagatccca aggataaaaa ttaattgtaa   1260

agtaaaatca gagttctagc atcaactaca ggctcaacca tggggaccac aaataaacta   1320

aaagggataa gactggcttc cccataatta ttacatttag ataattttcc tgactactca   1380

acaaagctaa aatatcacca ctggtttatt ttctccttct agggtttaag ctcactctga   1440

ggaggggcat gcggcacaca ctcatagcat ccaggaaata gaaatatggt gactatcatg   1500

ggttcagggc caacctaggc tttagagaaa aaccttgtcc cacaaaccaa aaatgtctct   1560

tttttattct atcaggggtg gatggatttg ttaaagaagt gcttttaaaa accttgagat   1620

ggttatttag aagtccccat gggataccaa aataacccac tatttatatg cccaagcatt   1680

tcacctccac aacagtgcta tgcacccttt aacatttttg agacagtagc ccagtctagt   1740

ctttaacttg cagtgatttt tcctgattca gcttctccca gtgctggaat tataggtatg   1800

caccaccatg tgtaactaca gatgctactt aaaaattttt taaaggaatc acaaaaataa   1860

ccccctatca aatgcctagt ccctctaacc atcaccaagt gaaggatcac gcaggaaaaa   1920

aaaaatcacc agcagcacct cagaaccagg atactcagtc catcagcatc cagggccata   1980

cccacactca cagcatctcc acagtttacc agatgattca tgcttatcac tgtattgggt   2040

catctaagag tgaccatcag ggcttctgat cacagaatct agtccacttt gcagaccagt   2100
```

-continued

```
tgaagtcatg cactatatga gatagaaata ccctcttgct cattttggtc agaaattcaa   2160
ggataaaaac ccatgttttg ttaatgcaca cctccatatg attgagatca atgtgtccta   2220
attaatgtag aaaccacaac tgtaaatttc actcttttga catgaatctt tttctagaca   2280
gggtcttgga tgcagccccg actacccaga attttggaat ccaggctagc ctcaaactca   2340
aggcaatctg cttgcttcag cttctcacag gctggatcac aaacatacac cttcagaccc   2400
attttttttt cctccctccg tttttggttt ctctgtgtag ccctgggtgt ccgtggactc   2460
gctgtgtaga tctatctacc agcctctgtc ttggagtact gggattaaag ttgtgggcta   2520
ccactgcctg gctgacccag ttttatttat tttaaatata acttgacaaa aataaatttg   2580
tctaacttac tagaaatccc aagaaaacta acactggatt tagcaacagt cagaaatcgc   2640
tgaaaagaaa cagaattgat ctaacagtct tagatcactc ctagacagtt tgtaattctt   2700
gctcatggca acgtgagctc tatctaactc actctctgtg cactaatgaa tgctcagtgt   2760
ctccagaaca gcacagcttc cagggtaatc atgccaaccc acaagacttt tatagagctg   2820
tccacgactc ttccccatt  cagctcatta acaatatgat ggagctcctg tgtggaaatc   2880
aaggcacact ctggtagaaa cttgtttttt ctttccactt ttccttgggc tctgaagatt   2940
gagctgtttt ataacccaca aacatgcatt ttttacctca aaagcatcca gcaaaaactg   3000
tacaacgctt tttcaaaaaa atgtattgtg atcctcctta agaaaagcct tacttagtgt   3060
taattccttt ttctttagaa tgctggtaaa tacaaggact taggtaggct ggcttctaac   3120
agcaattcac ccacttatga tggattaaa  ggaaggcaca accatgtcca ccacaggttc   3180
tagctccccc acccacacgc ccagagaggg tttttctgtg tagctctgac tattctggaa   3240
ttcacactgc agaccaggct ggtctcgaac tcagagatcc accaccacat ggtttcttaa   3300
ttgtaatttt aaagaaaaaa aaaaatcctt cagttaagat tcttatgttc taggttttca   3360
caaacttacc aatgtagttt tattggaggc catttttttaa atttaatcgg agacttgaag  3420
agctattgca agaaaaaaaa tgtaggacag ttaaaatttc atgacacaca aaaggcagct   3480
acaagttttg tgtggatttc aacatgtaaa tttcgggtaa aaatgcagga aaacagttga   3540
gttcccgtgt tattagtatg ttactaataa tttcagtatg ttagtgaaaa taatcttact   3600
aaaacactgg tacctcagac aactttacat ggtgaggatt gttactttcc caatccatat   3660
agaattttaa caattttagt gtttattttg gatgaaagga aatgactatc ttttgttagc   3720
aaattaccat aagatctttt tctttagatt tctgaatact ccaaggagct catataattc   3780
catccttatt ttttcagagg ccctccctgt tcaatcacgg tataaaaaaa ggaacacatt   3840
aagatgtccc agtcctattt tctggctttt tttttccggg ggtggtggtg cggtaatcac   3900
tctctatagt ccagtctggg cttcaacgcc tggcaatccc cagcctcaag ctcccaagta   3960
ctgtcctgat aaggatagaa ggagtcgacc tccttcacgc tcccctccga ggagggctcc   4020
ttcccagctc cattccccgg tcgggagccc gtcccccacc cgagagcgcg ggcctcgtgg   4080
tcagcgcctc cgcggggaga aacaaaggcg gcggcggggg ctcaagggca ctgcgccacg   4140
ggcccgcgcc tcccccatcc ggcggcggcc acgtagccgg gagcgcgccg cagcccggag   4200
cctcgggcct cgcagctgca gagcctgaac cgctctctcc ctgcgggcct gcgacgaggc   4260
tgggggaggg gaggcccgcg ctttgtctgg agtctcggta gctgtcatcc ggctcccacc   4320
ctcatgcaca attgtcccat ctcccccacg caccggcgcg gcgcccgcct cagcgaggcc   4380
ccagccggtt tcccgcagcc cgcggcccac ggggctcgca gcctccccgc aagctcggac   4440
```

-continued

```
gcacggagca tcctaaaccc caccacacgc aagatcgaaa aaaagcaaag gcacgaactt   4500

caccgctccg atgctcaggg ccgcggatcc tgcagagtct cccgcctgcg cgcttcggtt   4560

cagccacatc cgaggggagg gggcgcgggc agctccgccg ggggggaggg ggagcaccgc   4620

ccacgccctg gccgcgcggg gcccgccggg aacgcgtcct gcggggggcg gcgcgcgcaa   4680

tgctcaccgt ccgcggcgtg gcgcccaggg ggtctcctgg ctggggggag gggggggaag   4740

gcgggcagga aggaccgcgg aggcctctct gcgtctcgga gcgcgccaaa gcggggctcc   4800

acccacctcc ttgcccggat cttgaaggcc ggggagataa acagcggggt tctttaagca   4860

ccacctctca ctaggcgcgg gatcccaagg cttgtggcat ccggggtggt acttggacta   4920

aaagtccttc tgggagggac cgagtgagaa cccctttggg acgtgtagaa atatttgtgt   4980

ggttcgagaa tatttgtgcg gacgggcttg gcaaaggcgt agctgcagag agcacgcttg   5040

ggtggagagg gccgcacgcc ccagcgccgg cctaagcccc tcccgacggc gttatttcaa   5100

actgcgcgac cgtttctccg ctccctacgc ggaggtgggg gccggaccta gttccggacg   5160

tagtaacacg ccgagcgcga gccttccgca attcacggaa cacagttgcg caagtgatgt   5220

aaagcagtcc cgctgtacct aaagggggag tgtcacgtac ttggcgtaag gagagtgtag   5280

gcccttcccg ccattggcgg cggttagggc gtttacgtaa cggcgtgacg taagcggaga   5340

cgcgttagtg gggggaaggt tctagaaaag cggcggtctc ggctccagcg gcagtagcag   5400

cggcgccggt cccgtgtgca ggagctcctt tgcggcccag tttcttggcc atcgcctgct   5460

ctccccacag cgccaggacg agtcccgtgc gcgtccgtcc gcggaggtct ttctcatctc   5520

gctcggctgc gggaaatcgg gctgaagcga ctgagtccgc gatggaggta acgggtttga   5580

aatcaatgag ttattaaaaa tggcatggcg aggccgtagg caccgcaatg gaaaccggcc   5640

acccgcctcc gtggtccggc ggaggggatg cggccactcg agtggcggtt ggccttggcg   5700

agtttctgag gggtcgttgg aggaggcctc tgattgtccg accgccttcc ccgccctcag   5760

ccgcccggcg ccatttccct cagttggggt gggggatggg aagtgcccgc cgcgaccggg   5820

ctggaccgct aaagtagcgc gtgagcgggc catcgctggc ctttcgatgt gcgcgggcct   5880

aggggctcgg ttgtgttcgc ggcggaacgt ttctggggcc cccccggctt cccggagcga   5940

gtctgcgaag ctagcttccc ctcccccctc tcccgggaac cggatttggc ggccgccatt   6000

ttcccgtctc cttcctcgcc acgattttgc tttcaacgct ttaggtttac tagtttggtt   6060

ttcttttttc accactgcgt agacgtgttt agcgattttc ctttcttttg gaagtcttca   6120

taccgtttcg aggtggattt agcgttttga gcttgggtct tcagcgtcct gcgcacctcg   6180

ctaaaggctc tctgccttcc cctcgacgaa atggcgccat tgctttctga agccaccgag   6240

gcgcggggtg ggggcggggt ggcggcgctc cacgagcttt actggaacag gcagagagaa   6300

cgtagtacaa ccgaggcctg ggcgggtggc tgaaggcagc gtcgctgcaa agagaccgtt   6360

ttatttttca taatacgtaa gattacgggt gctgtagtaa agcacttgag cattagtata   6420

gtaggaggaa gtcaaagtgg aaaaaatggg agcgctcatc aggaagctag ggaggctatg   6480

ttgagtgcag ggttactttc cttttattgc agaactttta tctgcttaaa ggatcctcgg   6540

atcgaaataa ttcaaattat aagcattttt aagggaatct tcgaatttgt tggtaaagtc   6600

aacggatcct tagcacgtgg tgttcacttt aaggaagtga aatagctgac ttttcatagt   6660

tagccttcgc ttaaagcctg gttcagtgga cgaaaatcca cgtcctggct atataaaaac   6720

ttagtttggg gtcacagtgt ttgagcgtgg tcattcggtt tttttatttt ttatttgttt   6780

gaaattatga tgcatcatta cactgataag cattagcttt cgaattgaaa ggggtctcct   6840
```

-continued

```
tggttatttt ctttgactct aagcacactt ataaataaaa taaccttgtt tataatcgat   6900
agtggacgtc tggtaagttt ggaaaaaacc cgaggtaagt aaagagcttt tgctttcgtt   6960
agtgatatga aaaaacaagg tgtatttaat acttgcaact tagtttaagg aaagccaatt   7020
tactgacatt ttagtagagc taccagaaac actatttgga gtcctgatta aggcttttgt   7080
aactattttg actatttaaa acaattttgg tcgtttttat taaacatttc aaaacctaaa   7140
aattgtaaac attggctttt tgagcacatt ttggagaaac ttacaaattt aggctataca   7200
gtaaaataac ggatttgttt tataattttg ctttttcatt tcgttgtgca gtcataggtc   7260
ctggatagta tgacctaatt tatgaacatc ttgataagtt tttgtactta gctattggaa   7320
agccagtatt aagtgcctga caaaaccaga tttaaggtga tatctggagt ttcagcattc   7380
ttcatggagc ttgtttcaga gttgcaggat tttttttttt catcttgaga tacttacaat   7440
taacaccaga gggggcagct cagggaaaag caaatatgcc acttttcaga aactgaatct   7500
tggaagtggt gaatttggaa acaggttttt taaatttttt ttaaatctaa aaagtagtaa   7560
attttggact tgggttgtag aatttaatga attacaaaag aattctttaa taccctttaa   7620
atgacctaag agctgggtat ggtttttctg aatttttttg aagaaaatct aagaaagttt   7680
acgtgaatta gaagttagat cgaatattag tgactttgaa acttgtatag ctcaggcaat   7740
ttttggtgta acacaactaa tatgcagttt aacatatggt ttaaatttga tgtaagtttt   7800
ttttctcccc cccagaaaac tttagaaact gttcctttgg agaggaaaaa ggtactctac   7860
cagcaggtca cctcatattt aagaatttaa tttcctgcat acaaagaaag tgtaaataaa   7920
aattgaaatg gtatttccct ttgcagagag aaaaggaaca gttccgaaag ctctttattg   7980
gtggcttaag cttatcgata ccggtggcgc gccaattgtt aattaagatc tggcccaatg   8040
ggccgtacga atttgaggcg gaaagaacca gctgtggaat gtgtgtcagt tagggtgtgg   8100
aaagtcccca ggctccccag caggcagaag tatgcaaagc atgcatctca attagtcagc   8160
aaccaggtgt ggaaagtccc caggctcccc agcaggcaga agtatgcaaa gcatgcatct   8220
caattagtca gcaaccatag tcccgcccct aactccgccc atcccgcccc taactccgcc   8280
cagttccgcc cattctccgc cccatggctg actaattttt tttatttatg cagaggccga   8340
ggccgcctcg gcctctgagc tattccagaa gtagtgagga ggcttttttg gaggcctagg   8400
cttttgcaaa gatcgatcaa gagacaggat gaggatcgtt tcgcatgatt gaacaagatg   8460
gattgcacgc aggttctccg gccgcttggg tggagaggct attcggctat gactgggcac   8520
aacagacaat cggctgctct gatgccgccg tgttccggct gtcagcgcag gggcgcccgg   8580
ttctttttgt caagaccgac ctgtccggtg ccctgaatga actgcaagac gaggcagcgc   8640
ggctatcgtg gctggccacg acgggcgttc cttgcgcagc tgtgctcgac gttgtcactg   8700
aagcgggaag ggactggctg ctattgggcg aagtgccggg gcaggatctc ctgtcatctc   8760
accttgctcc tgccgagaaa gtatccatca tggctgatgc aatgcggcgg ctgcatacgc   8820
ttgatccggc tacctgccca ttcgaccacc aagcgaaaca tcgcatcgag cgagcacgta   8880
ctcggatgga agccggtctt gtcgatcagg atgatcaaga gcatcagggg ctcgcgccag   8940
ccgaactgtt cgccaggctc aaggcgagca tgcccgacgg cgaggatctc gtcgtgaccc   9000
atggcgatgc ctgcttgccg aatatcatgg tggaaaatgg ccgcttttct ggattcatcg   9060
actgtggccg gctgggtgtg gcggaccgct atcaggacat agcgttggct acccgtgata   9120
ttgctgaaga gcttggcggc gaatgggctg accgcttcct cgtgctttac ggtatcgccg   9180
```

-continued

```
ctcccgattc gcagcgcatc gccttctatc gccttcttga cgagttcttc tgagcgggac   9240
tctggggttc gaaatgaccg accaagcgac gcccaacctg ccatcacgag atttcgattc   9300
caccgccgcc ttctatgaaa ggttgggctt cggaatcgtt ttccgggacg ccggctggat   9360
gatcctccag cgcggggatc tcatgctgga gttcttcgcc caccctaggg ggaggctaac   9420
tgaaacacgg aaggagacaa taccggaagg aacccgcgct atgacggcaa taaaaagaca   9480
gaataaaacg cacggtgttg ggtcgtttgt tcataaacgc ggggttcggt cccagggctg   9540
gcactctgtc gataccccac cgagacccca ttggggccaa tacgcccgcg tttcttcctt   9600
ttccccaccc caccccccaa gttcgggtga aggcccaggg ctcgcagcca acgtcggggc   9660
ggcaggccct gccatagcct caaattcctt aggctcgagg gccgccaccg cggtggagct   9720
ccagcttttg ttccctttag tgagggttaa tttcgagctt ggcgtaatca tggtcatagc   9780
tgtttcctgt gtgaaattgt tatccgctca caattccaca caacatacga gccggaagca   9840
taaagtgtaa agcctggggt gcctaatgag tgagctaact cacattaatt gcgttgcgct   9900
cactgcccgc tttccagtcg ggaaacctgt cgtgccagca tcgcgagcac ttttcgggga   9960
aatgtgcgcg gaacccctat ttgtttattt ttctaaatac attcaaatat gtatccgctc  10020
atgagacaat aaccctgata aatgcttcaa taatattgaa aaaggaagag tatgagtatt  10080
caacatttcc gtgtcgccct tattcccttt tttgcggcat tttgccttcc tgtttttgct  10140
cacccagaaa cgctggtgaa agtaaaagat gctgaagatc agttgggtgc acgagtgggt  10200
tacatcgaac tggatctcaa cagcggtaag atccttgaga gttttcgccc cgaagaacgt  10260
tttccaatga tgagcacttt taaagttctg ctatgtggcg cggtattatc ccgtattgac  10320
gccgggcaag agcaactcgg tcgccgcata cactattctc agaatgactt ggttgagtac  10380
tcaccagtca cagaaaagca tcttacggat ggcatgacag taagagaatt atgcagtgct  10440
gccataacca tgagtgataa cactgcggcc aacttacttc tgacaacgat cggaggaccg  10500
aaggagctaa ccgctttttt gcacaacatg ggggatcatg taactcgcct tgatcgttgg  10560
gaaccggagc tgaatgaagc cataccaaac gacgagcgtg acaccacgat gcctgtagca  10620
atggcaacaa cgttgcgcaa actattaact ggcgaactac ttactctagc ttcccggcaa  10680
caattaatag actggatgga ggcggataaa gttgcaggac cacttctgcg ctcggccctt  10740
ccggctggct ggtttattgc tgataaatct ggagccggtg agcgtgggtc tcgcggtatc  10800
attgcagcac tggggccaga tggtaagccc tcccgtatcg tagttatcta cacgacgggg  10860
agtcaggcaa ctatggatga acgaaataga cagatcgctg agataggtgc ctcactgatt  10920
aagcattggt aactgtcaga ctcgcgacac tgcattaatg aatcggccaa cgcgcgggga  10980
gaggcggttt gcgtattggg cgctcttccg cttcctcgct cactgactcg ctgcgctcgg  11040
tcgttcggct gcggcgagcg gtatcagctc actcaaaggc ggtaatacgg ttatccacag  11100
aatcagggga taacgcagga aagaacatgt gagcaaaagg ccagcaaaag gccaggaacc  11160
gtaaaaaggc cgcgttgctg gcgtttttcc ataggctccg cccccctgac gagcatcaca  11220
aaaatcgacg ctcaagtcag aggtggcgaa acccgacagg actataaaga taccaggcgt  11280
ttccccctgg aagctccctc gtgcgctctc ctgttccgac cctgccgctt accggatacc  11340
tgtccgcctt tctcccttcg ggaagcgtgg cgctttctca tagctcacgc tgtaggtatc  11400
tcagttcggt gtaggtcgtt cgctccaagc tgggctgtgt gcacgaaccc cccgttcagc  11460
ccgaccgctg cgccttatcc ggtaactatc gtcttgagtc caacccggta agacacgact  11520
tatcgccact ggcagcagcc actggtaaca ggattagcag agcgaggtat gtaggcggtg  11580
```

```
ctacagagtt cttgaagtgg tggcctaact acggctacac tagaaggaca gtatttggta  11640

tctgcgctct gctgaagcca gttaccttcg gaaaaagagt tggtagctct tgatccggca  11700

aacaaaccac cgctggtagc ggtggttttt ttgtttgcaa gcagcagatt acgcgcagaa  11760

aaaaaggatc tcaagaagat cctttgatct tttctacggg gtctgacgct cagtggaacg  11820

aaaactca                                                           11828
```

```
<210> SEQ ID NO 14
<211> LENGTH: 9209
<212> TYPE: DNA
<213> ORGANISM: Artificial Sequence
<220> FEATURE:
<223> OTHER INFORMATION: Plasmid

<400> SEQUENCE: 14

cgttgtaaaa cgacggccag tgaattgtaa tacgactcac tatagggcga attgggtacc     60

gggccccccc tcgaagttta aacatttaaa tctagaacta gtggatcccc cgggctgcag    120

gaattcgata tcaagctcat ggcacctgta ttgtactctt atcagtcatt atatggactt    180

taacttcccc agatattatt tgggctcctc cataagactg tgagcatctg accactggag    240

tgttgcttcc cattatatcc ctgttatcaa gcacaaggtc aggcacagag taagactcaa    300

aacatgtttt ggaatgtatg actggtatga actacaaacc agtaagctga tgttttcatt    360

ttgagtctat aaatctaatt ttgtggtggt tttgtgtatg gctcaaggct caaattgtaa    420

aatttaatat tatgtgacca aagaaagtta tacccagaac ctcaatttcc tcaccttcaa    480

aatggggcag tttctcactc attggtctgc tgtcacgatt ttaatgagct catgcacaaa    540

cagcccttta tataaggtaa gtgctggata aatgttggct actataataa aataagcctc    600

taagatactt ggtcagcaca agtactaccc aagagtatgc actgtaagta aactgacaaa    660

attgtgtatc taaaactggc cagatgaaag agaaactttt aaggggccct tctgcgtgcc    720

cgacactgtg ctaggcactc acactatccc gacccgagaa accgatctgc gacccagagg    780

aacttaccaa gcctccagca tcttgtgcag ccctactcat gggaccatct ggatacccac    840

ccttgtcttt acagggagca gaacacacct cttatgtgtc agaaaacaaa gtccaggaag    900

tatattttta cctgaggcaa tatctgaaaa ttgtatgcta cagcctccaa agtgagtctt    960

cctctcagta cctctcttct aggcacatgg agccctttct tccaagtatt atgtttaacc   1020

acttaatgaa tgaagtcctg aaactgctta cccatgctcc ctataatctc tgagtaatct   1080

tccttttcca caacctcagg cataatctca tcttctgttt ctattacaat ttcaaattct   1140

ggaaaaagga agttgtggtc tggaattata tggtccagat gatctgaaac aaaaaggaca   1200

gcactattag taatcattta gttttgaaga cagtctaata atttgctgtc tctaaagtac   1260

tatattccct atagttctgg cattttagat aaagggtcat aaattaaatg cctatatggt   1320

gacattattc agtgattcag acttcacagc cttttttttt tttttacaaa ggtgttccag   1380

gcatgaaaaa ttttaaagta ctataccttt cctaatttta cctttaaagt tgtcctggaa   1440

atatctgggt tgacaaaggc gatgaaactg aactgagact taaaaaaaag attacccacc   1500

tggttgtgca caagcctgct tatgtcccaa tctccagtct agggtctgat gctccttgct   1560

gcagtaatat gctttgtggc atctggagca cgttttgggg cctaaacagc cacaaaccct   1620

gcagagatga gcaccagact taagctggag acacactgat tctcctgttt ctgggggagg   1680

attctcagaa ggtggctcat atgagtaaaa atcgtttttc ctgggtagtt gattcctaaa   1740
```

-continued

```
aactaaaaaa gaatacagag aaaagtttta tcttcaaaca aaacagcaat tcacatattt   1800
tatcctctgc acgtaaaact gaaaataaca acaacaaaaa agaaatgaaa gtttttgctt   1860
tcaggaataa gcttttaaaa tccagaaact agatttcgtc cggtacacgc aactgagttg   1920
cctcctagag gtggtttgag ttaatcaaat taataagact gatcgttaag aacgactgcc   1980
aaaaatacga aaaagctact gggatccatc tttccaagac aatttctatt atctgaatta   2040
acaccatacc tggtacccac tgattaaaag ctgggggtta ccaatgcgcg tgggcacagt   2100
tagaagctta tgtagcaaaa atgagcacat cctggaaggg cccgggagaa ggtgctcctg   2160
gggcagcgcg gagagggagc tctgaggctg gggcggcagc ggtgcttgcc gccgtccccc   2220
tggtcgctcc cggaattaac gccgcgcacg cgtcggaggc atggccccgt cccgaccccg   2280
tttggcggct cacctcgcag gccggcacag cacggctgct cgcggcagca gaagaggaag   2340
atgcagcggt ggaaggcgtc cgggcggcca ggcagcggcg catacacctg cagcaggaag   2400
gagagcgggc ggccgcacag ctcgcaggcc agggcctggg gccccggcag cccggccgcg   2460
cccagccatg ccggccgccc gcccaccttg ctggggaact gctcgctgcg cagtcgccac   2520
gccggcgccg actcggcgaa gcccagctcc acaggcctgg ccccggcggc agccatgcgg   2580
ggcgcgggct ggcgtggggc gcagcccaca gctgggtcgg aaggcggaaa tcgggcgccg   2640
ggccggaagg caagaggcgg gcacctttcc ggaggacagg aggcggaaac gcgtctgacg   2700
ggagcggttg caggaccaat gcgagggaac ggggcagagg aaacctctcg gcatcagccc   2760
cgcccctggc gcctctgcct ccgagccgct ttcctggtgc ctccgggtgc tctgggatgg   2820
ttctggtctt tgggagagtg gcagctggtg acggcgctcc gctcacctct gcacatgtct   2880
tgctgtgggc ctgcgggtgg ccgccaggga ggcagagccc tcccgcaaac cttccctgct   2940
ggtgtccacc tcagggtgtg ggaaacctgt gcgctggccg agtgctaacc aagagtaggc   3000
agtgaaagac aaatgaaggt tgaacaggta aagtgaggac cctacagcgg aaaccaagaa   3060
tcctgtgtgc ctgagagtaa tgaagaagcc tctgcagaag agtcttttct gtcagtctta   3120
aggtctctgt tttaatgtta gtgctggctt gctgtacctg aattccaagg gaggagtgta   3180
taatgaggca tggccaaccc ccacttccca tcattgcctg aactagtttt tcaggttaac   3240
ttcagaatgc ccttggtacc gcgggccccc tctgtggtcc cacgccactg atcgctgcat   3300
gcccaccacc tgggtacaca cagtctgtga ttcccggagc agaacggacc ctgcccaccc   3360
ggtcttgtgt gctactcagt ggacagaccc aaggcaagaa agggtgacaa ggacagggtc   3420
ttcccaggct ggctttgagt tcctagcacc gccccgcccc caatcctctg tggcacatgg   3480
agtcttggtc cccagagtcc cccagcggcc tccagatggt ctgggagggc agttcagctg   3540
tggctgcgca tagcagacat acaacggacg gtgggcccag acccaggctg tgtagaccca   3600
gcccccccgc cccgcagtgc ctaggtcacc cactaacgcc ccaggcctgg tcttggctgg   3660
gcgtgactgt taccctcaaa agcaggcagc tccagggtaa aaggtgccct gccctgtaga   3720
gcccacttcc ttcccagggc tgcggctggg taggtttgta gccttcatca cgggccacct   3780
ccagccactg gaccgctggc ccctgccctg tcctggggag tgtggtcctg cgactctaat   3840
ggccgcaagc cacctgactc cccaacacc acactctacc tctcaagccc aggtctctcc   3900
ctagtgaccc acccagcaca tttagctagc tgagccccac agccagaggt cctcaggccc   3960
tgctttcagg gcagttgctc tgaagtcggc aagggggagt gactgcctgg ccactccatg   4020
ccctccaaga gctccttctg caggagcgta cagaacccag ggccctggca cccgtgcaga   4080
ccctggccca ccccacctgg gcgctcagtg cccaagagat gtccacacct aggatgtccc   4140
```

-continued

```
gcggtgggtg gggggcccga gagacgggca ggccgggggc aggcctggcc atgcggggcc   4200
gaaccgggca ctgcccagcg tggggcgcgg gggccacggc gcgcgccccc agcccccggg   4260
cccagcaccc caaggcggcc aacgccaaaa ctctccctcc tcctcttcct caatctcgct   4320
ctcgctcttt ttttttttcg caaaaggagg ggagaggggg taaaaaaatg ctgcactgtg   4380
cggcgaagcc ggtgagtgag cggcgcgggg ccaatcagcg tgcgccgttc cgaaagttgc   4440
cttttatggc tcgagcggcc gcggcggcgc cctataaaac ccagcggcgc gacgcgccac   4500
caccgccgag accgcgtccg cccgcgagca cagagcctcg cctttgccga tccgccgccc   4560
gtccacaccc gccgccaggt aagcccggcc agccgaccgg ggcatgcggc cgcggccctt   4620
cgcccgtgca gagccgccgt ctgggccgca gcggggggcg catggggcgg aaccggaccg   4680
ccgtgggggg cgcgggagaa gcccctgggc ctccggagat gggggacacc ccacgccagt   4740
tcgcaggcgc gaggccgcgc tcgggcgggc gcgctccggg ggtgccgctc tcggggcggg   4800
ggcaaccggc ggggtctttg tctgagccgg gctcttgcca atggggatcg cacggtgggc   4860
gcggcgtagc ccccgtcagg cccggtgggg gctggggcgc catgcgcgtg cgcgctggtc   4920
ctttgggcgc taactgcgtg cgcgctggga attggcgcta attgcgcgtg cgcgctggga   4980
ctcaatggcg ctaatcgcgc gtgcgttctg gggcccgggc gcttgcgcca cttcctgccc   5040
gagccgctgg cgcccgaggg tgtggccgct gcgtgcgcgc gcgcgacccg gtcgctgttt   5100
gaaccgggcg gaggcggggc tggcgcccgg ttgggagggg gttggggcct ggcttcctgc   5160
cgcgcgccgc ggggacgcct ccgaccagtg tttgcctttt atggtaataa cgcggccggc   5220
ccggcttcct ttgtccccaa tctgggcgcg cgccggcgcc ccctggcggc ctaaggactc   5280
ggcgcgccgg aagtggccag ggcgggggcg acttcggctc acagcgcgcc cggctattct   5340
cgcagctcac catgccggtc gccaccatga gcttatcgat accggtggcg cgccaattgt   5400
taattaagat ctggcccaat gggccgtacg aatttgaggc ggaaagaacc agctgtggaa   5460
tgtgtgtcag ttagggtgtg gaaagtcccc aggctcccca gcaggcagaa gtatgcaaag   5520
catgcatctc aattagtcag caaccaggtg tggaaagtcc ccaggctccc cagcaggcag   5580
aagtatgcaa agcatgcatc tcaattagtc agcaaccata gtcccgcccc taactccgcc   5640
catcccgccc ctaactccgc ccagttccgc ccattctccg ccccatggct gactaatttt   5700
ttttatttat gcagaggccg aggccgcctc ggcctctgag ctattccaga agtagtgagg   5760
aggctttttt ggaggcctag gcttttgcaa agatcgatca agagacagga tgaggatcgt   5820
ttcgcatgat tgaacaagat ggattgcacg caggttctcc ggccgcttgg gtggagaggc   5880
tattcggcta tgactgggca caacagacaa tcggctgctc tgatgccgcc gtgttccggc   5940
tgtcagcgca ggggcgcccg gttctttttg tcaagaccga cctgtccggt gccctgaatg   6000
aactgcaaga cgaggcagcg cggctatcgt ggctggccac gacgggcgtt ccttgcgcag   6060
ctgtgctcga cgttgtcact gaagcgggaa gggactggct gctattgggc gaagtgccgg   6120
ggcaggatct cctgtcatct caccttgctc ctgccgagaa agtatccatc atggctgatg   6180
caatgcggcg gctgcatacg cttgatccgg ctacctgccc attcgaccac caagcgaaac   6240
atcgcatcga gcgagcacgt actcggatgg aagccggtct tgtcgatcag gatgatcaag   6300
agcatcaggg gctcgcgcca gccgaactgt tcgccaggct caaggcgagc atgcccgacg   6360
gcgaggatct cgtcgtgacc catggcgatg cctgcttgcc gaatatcatg gtggaaaatg   6420
gccgcttttc tggattcatc gactgtggcc ggctgggtgt ggcggaccgc tatcaggaca   6480
```

-continued

```
tagcgttggc tacccgtgat attgctgaag agcttggcgg cgaatgggct gaccgcttcc   6540
tcgtgcttta cggtatcgcc gctcccgatt cgcagcgcat cgccttctat cgccttcttg   6600
acgagttctt ctgagcggga ctctggggtt cgaaatgacc gaccaagcga cgcccaacct   6660
gccatcacga gatttcgatt ccaccgccgc cttctatgaa aggttgggct tcggaatcgt   6720
tttccgggac gccggctgga tgatcctcca gcgcggggat ctcatgctgg agttcttcgc   6780
ccaccctagg gggaggctaa ctgaaacacg gaaggagaca ataccggaag gaacccgcgc   6840
tatgacggca ataaaaagac agaataaaac gcacggtgtt gggtcgtttg ttcataaacg   6900
cggggttcgg tcccagggct ggcactctgt cgatacccca ccgagacccc attggggcca   6960
atacgcccgc gtttcttcct tttccccacc ccacccccca agttcgggtg aaggcccagg   7020
gctcgcagcc aacgtcgggg cggcaggccc tgccatagcc tcaaattcct taggctcgag   7080
ggccgccacc gcggtggagc tccagctttt gttcccttta gtgagggtta atttcgagct   7140
tggcgtaatc atggtcatag ctgtttcctg tgtgaaattg ttatccgctc acaattccac   7200
acaacatacg agccggaagc ataaagtgta aagcctgggg tgcctaatga gtgagctaac   7260
tcacattaat tgcgttgcgc tcactgcccg ctttccagtc gggaaacctg tcgtgccagc   7320
atcgcgagca cttttcgggg aaatgtgcgc ggaaccccta tttgtttatt tttctaaata   7380
cattcaaata tgtatccgct catgagacaa taaccctgat aaatgcttca ataatattga   7440
aaaaggaaga gtatgagtat tcaacatttc cgtgtcgccc ttattccctt ttttgcggca   7500
ttttgccttc ctgtttttgc tcacccagaa acgctggtga aagtaaaaga tgctgaagat   7560
cagttgggtg cacgagtggg ttacatcgaa ctggatctca acagcggtaa gatccttgag   7620
agttttcgcc ccgaagaacg ttttccaatg atgagcactt ttaaagttct gctatgtggc   7680
gcggtattat cccgtattga cgccgggcaa gagcaactcg gtcgccgcat acactattct   7740
cagaatgact tggttgagta ctcaccagtc acagaaaagc atcttacgga tggcatgaca   7800
gtaagagaat tatgcagtgc tgccataacc atgagtgata acactgcggc caacttactt   7860
ctgacaacga tcggaggacc gaaggagcta accgcttttt tgcacaacat gggggatcat   7920
gtaactcgcc ttgatcgttg ggaaccggag ctgaatgaag ccataccaaa cgacgagcgt   7980
gacaccacga tgcctgtagc aatggcaaca acgttgcgca aactattaac tggcgaacta   8040
cttactctag cttcccggca acaattaata gactggatgg aggcggataa agttgcagga   8100
ccacttctgc gctcggccct tccggctggc tggtttattg ctgataaatc tggagccggt   8160
gagcgtgggt ctcgcggtat cattgcagca ctggggccag atggtaagcc ctcccgtatc   8220
gtagttatct acacgacggg gagtcaggca actatggatg aacgaaatag acagatcgct   8280
gagataggtg cctcactgat taagcattgg taactgtcag actcgcgaca ctgcattaat   8340
gaatcggcca acgcgcgggg agaggcggtt tgcgtattgg gcgctcttcc gcttcctcgc   8400
tcactgactc gctgcgctcg gtcgttcggc tgcggcgagc ggtatcagct cactcaaagg   8460
cggtaatacg gttatccaca gaatcagggg ataacgcagg aaagaacatg tgagcaaaag   8520
gccagcaaaa ggccaggaac cgtaaaaagg ccgcgttgct ggcgtttttc cataggctcc   8580
gcccccctga cgagcatcac aaaaatcgac gctcaagtca gaggtggcga aacccgacag   8640
gactataaag ataccaggcg tttccccctg gaagctccct cgtgcgctct cctgttccga   8700
ccctgccgct taccggatac ctgtccgcct ttctcccttc gggaagcgtg gcgctttctc   8760
atagctcacg ctgtaggtat ctcagttcgg tgtaggtcgt tcgctccaag ctgggctgtg   8820
tgcacgaacc ccccgttcag cccgaccgct gcgccttatc cggtaactat cgtcttgagt   8880
```

```
ccaacccggt aagacacgac ttatcgccac tggcagcagc cactggtaac aggattagca   8940

gagcgaggta tgtaggcggt gctacagagt tcttgaagtg gtggcctaac tacggctaca   9000

ctagaaggac agtatttggt atctgcgctc tgctgaagcc agttaccttc ggaaaaagag   9060

ttggtagctc ttgatccggc aaacaaacca ccgctggtag cggtggtttt tttgtttgca   9120

agcagcagat tacgcgcaga aaaaaaggat ctcaagaaga tcctttgatc ttttctacgg   9180

ggtctgacgc tcagtggaac gaaaactca                                     9209
```

```
<210> SEQ ID NO 15
<211> LENGTH: 7898
<212> TYPE: DNA
<213> ORGANISM: Artificial Sequence
<220> FEATURE:
<223> OTHER INFORMATION: Mouse hnRNP A2 HIndIII fragment

<400> SEQUENCE: 15
```

```
aagcttttaa ccctctatcc ctttaaactt ccttgatcca gtgtaagcac ctcctagaaa     60

gtcagtagac aataaaacaa aagttctgct tcaccgattt acatttataa ccaaataccc    120

ttcaccaata caataaaaaa acaaaacaac aaaaaacccc aaccatctga gaaataatct    180

tctcctttcc cagctttatt cccaggattc tacatgacca aattaccaga gtcaccactc    240

attttaatca caacatagtg tcaaataact agaaaacatg agacaacaat ggagagctga    300

gtaactatta gtagtagtac tttaccagag aatggcctct ataggctcac atgtaggaat    360

ggttggtccc caggtggtag gtagagctgt ttgaggatta cgtggccttc ttggatgggg    420

ggtgggggtg gggtgggagg gttgggtggt gggtacttaa gaggtttcaa aagtcaatat    480

tgtttgcatt tagctcttcc ttgtacttgt ggatcaaaca caacctgtca gctactgctt    540

caaatgtcat gcctgctgcc atcttctcag caggatggtc atggcctcac cctcttcaac    600

tgtaaatctt tctttctttt cttctttttc ttttggtttc gagacagggt ttctctgtat    660

agtcctggct gtcctggaac tcactttgta gaccaggctg gccttgaact cagaaatccg    720

cctgcctctg cctccctagc actgggatta aaggcgtgcg ccaccacgcc cagctttcaa    780

ctggaaatct taataaactt tcctagaagt ggccttggtt atgggagctt atcacagcaa    840

tagaacagca attatgactg gagtatgata gttaaaaaca agcaagcaag caagcaaaca    900

cacacaccaa aacaacaaaa ccccaagaca gagtcacatg tagcccaggc tagcctccaa    960

attcactata taactgaaga agacccctaa ttcccattcc tctagaatct atacctcaag   1020

tactgaatgg cttggttcac aataccccac taaatgattg gtcttactaa gtgcaacaag   1080

gtaaacctaa aacttcagcc ctcagacatc ccttttccag tatcaattta taaaattaga   1140

tcccaaggat aaaaattaat tgtaaagtaa aatcagagtt ctagcatcaa ctacaggctc   1200

aaccatgggg accacaaata aactaaaagg gataagactg gcttccccat aattattaca   1260

tttagataat tttcctgact actcaacaaa gctaaaatat caccactggt ttattttctc   1320

cttctagggt ttaagctcac tctgaggagg ggcatgcggc acacactcat agcatccagg   1380

aaatagaaat atggtgacta tcatgggttc agggccaacc taggctttag agaaaaacct   1440

tgtcccacaa accaaaaatg tctctttttt attctatcag gggtggatgg atttgttaaa   1500

gaagtgcttt taaaaacctt gagatggtta tttagaagtc cccatgggat accaaaataa   1560

cccactattt atatgcccaa gcatttcacc tccacaacag tgctatgcac cctttaacat   1620

ttttgagaca gtagcccagt ctagtcttta acttgcagtg atttttcctg attcagcttc   1680
```

-continued tcccagtgct ggaattatag gtatgcacca ccatgtgtaa ctacagatgc tacttaaaaa 1740
ttttttaaag gaatcacaaa aataaccccc tatcaaatgc ctagtccctc taaccatcac 1800
caagtgaagg atcacgcagg aaaaaaaaaa tcaccagcag cacctcagaa ccaggatact 1860
cagtccatca gcatccaggg ccatacccac actcacagca tctccacagt ttaccagatg 1920
attcatgctt atcactgtat tgggtcatct aagagtgacc atcagggctt ctgatcacag 1980
aatctagtcc actttgcaga ccagttgaag tcatgcacta tatgagatag aaataccctc 2040
ttgctcattt tggtcagaaa ttcaaggata aaaacccatg ttttgttaat gcacacctcc 2100
atatgattga gatcaatgtg tcctaattaa tgtagaaacc acaactgtaa atttcactct 2160
tttgacatga atctttttct agacagggtc ttggatgcag ccccgactac ccagaatttt 2220
ggaatccagg ctagcctcaa actcaaggca atctgcttgc ttcagcttct cacaggctgg 2280
atcacaaaca tacaccttca gacccatttt tttttcctcc ctccgttttt ggtttctctg 2340
tgtagccctg ggtgtccgtg gactcgctgt gtagatctat ctaccagcct ctgtcttgga 2400
gtactgggat taaagttgtg ggctaccact gcctggctga cccagtttta tttattttaa 2460
atataacttg acaaaaataa atttgtctaa cttactagaa atcccaagaa aactaacact 2520
ggatttagca acagtcagaa atcgctgaaa agaaacagaa ttgatctaac agtcttagat 2580
cactcctaga cagtttgtaa ttcttgctca tggcaacgtg agctctatct aactcactct 2640
ctgtgcacta atgaatgctc agtgtctcca gaacagcaca gcttccaggg taatcatgcc 2700
aacccacaag acttttatag agctgtccac gactcttccc ccattcagct cattaacaat 2760
atgatggagc tcctgtgtgg aaatcaaggc acactctggt agaaacttgt tttttcttc 2820 cacttttcct tgggctctga agattgagct gttttataac ccacaaacat gcatttttta 2880
cctcaaaagc atccagcaaa aactgtacaa cgctttttca aaaaaatgta ttgtgatcct 2940
ccttaagaaa agccttactt agtgttaatt cctttttctt tagaatgctg gtaaatacaa 3000
ggacttaggt aggctggctt ctaacagcaa ttcacccact tatgatggga ttaaaggaag 3060
gcacaaccat gtccaccaca ggttctagct cccccaccca cacgcccaga gagggttttt 3120
ctgtgtagct ctgactattc tggaattcac actgcagacc aggctggtct cgaactcaga 3180
gatccaccac cacatggttt cttaattgta attttaaaga aaaaaaaaaa tccttcagtt 3240
aagattctta tgttctaggt tttcacaaac ttaccaatgt agttttattg gaggccattt 3300
tttaaattta atcggagact tgaagagcta ttgcaagaaa aaaaatgtag gacagttaaa 3360
atttcatgac acacaaaagg cagctacaag ttttgtgtgg atttcaacat gtaaatttcg 3420
ggtaaaaatg caggaaaaca gttgagttcc cgtgttatta gtatgttact aataatttca 3480
gtatgttagt gaaaataatc ttactaaaac actggtacct cagacaactt tacatggtga 3540
ggattgttac tttcccaatc catatagaat tttaacaatt ttagtgttta ttttggatga 3600
aaggaaatga ctatcttttg ttagcaaatt accataagat ctttttcttt agatttctga 3660
atactccaag gagctcatat aattccatcc ttattttttc agaggccctc cctgttcaat 3720
cacggtataa aaaaaggaac acattaagat gtcccagtcc tattttctgg cttttttttt 3780
ccgggggtgg tggtgcggta atcactctct atagtccagt ctgggcttca acgcctggca 3840
atccccagcc tcaagctccc aagtactgtc ctgataagga tagaaggagt cgacctcctt 3900
cacgctcccc tccgaggagg gctccttccc agctccattc cccggtcggg agcccgtccc 3960
ccacccgaga gcgcgggcct cgtggtcagc gcctccgcgg ggagaaacaa aggcggcggc 4020
gggggctcaa gggcactgcg ccacgggccc gcgcctcccc catccggcgg cggccacgta 4080

-continued gccgggagcg cgccgcagcc cggagcctcg ggcctcgcag ctgcagagcc tgaaccgctc 4140
tctccctgcg ggcctgcgac gaggctgggg gaggggaggc ccgcgctttg tctggagtct 4200
cggtagctgt catccggctc ccaccctcat gcacaattgt cccatctccc ccacgcaccg 4260
gcgcggcgcc cgcctcagcg aggccccagc cggtttcccg cagcccgcgg cccacggggc 4320
tcgcagcctc cccgcaagct cggacgcacg gagcatccta aaccccacca cacgcaagat 4380
cgaaaaaaag caaaggcacg aacttcaccg ctccgatgct cagggccgcg gatcctgcag 4440
agtctcccgc ctgcgcgctt cggttcagcc acatccgagg ggaggggcg cgggcagctc 4500 cgccgggggg gagggggagc accgcccacg ccctggccgc gcggggcccg ccgggaacgc 4560
gtcctgcggg gggcggcgcg cgcaatgctc accgtccgcg gcgtggcgcc caggggggtct 4620 cctggctggg gggagggggg ggaaggcggg caggaaggac cgcggaggcc tctctgcgtc 4680
tcggagcgcg ccaaagcggg gctccaccca cctccttgcc cggatcttga aggccgggga 4740
gataaacagc ggggttcttt aagcaccacc tctcactagg cgcgggatcc caaggcttgt 4800
ggcatccggg gtggtacttg gactaaaagt ccttctggga gggaccgagt gagaacccct 4860
ttgggacgtg tagaaatatt tgtgtggttc gagaatattt gtgcggacgg gcttggcaaa 4920
ggcgtagctg cagagagcac gcttgggtgg agagggccgc acgccccagc gccggcctaa 4980
gcccctcccg acggcgttat ttcaaactgc gcgaccgttt ctccgctccc tacgcggagg 5040
tgggggccgg acctagttcc ggacgtagta acacgccgag cgcgagcctt ccgcaattca 5100
cggaacacag ttgcgcaagt gatgtaaagc agtcccgctg tacctaaagg gggagtgtca 5160
cgtacttggc gtaaggagag tgtaggccct tcccgccatt ggcggcggtt agggcgttta 5220
cgtaacggcg tgacgtaagc ggagacgcgt tagtgggggg aaggttctag aaaagcggcg 5280
gtctcggctc cagcggcagt agcagcggcg ccggtcccgt gtgcaggagc tcctttgcgg 5340
cccagtttct tggccatcgc ctgctctccc cacagcgcca ggacgagtcc cgtgcgcgtc 5400
cgtccgcgga ggtctttctc atctcgctcg gctgcgggaa atcgggctga agcgactgag 5460
tccgcgatgg aggtaacggg tttgaaatca atgagttatt aaaaatggca tggcgaggcc 5520
gtaggcaccg caatggaaac cggccacccg cctccgtggt ccggcggagg ggatgcggcc 5580
actcgagtgg cggttggcct tggcgagttt ctgaggggtc gttggaggag gcctctgatt 5640
gtccgaccgc cttccccgcc ctcagccgcc cggcgccatt tccctcagtt ggggtggggg 5700
atgggaagtg cccgccgcga ccgggctgga ccgctaaagt agcgcgtgag cgggccatcg 5760
ctggcctttc gatgtgcgcg ggcctagggg ctcggttgtg ttcgcggcgg aacgtttctg 5820
gggccccccc ggcttcccgg agcgagtctg cgaagctagc ttcccctccc ccctctcccg 5880
ggaaccggat ttggcggccg ccattttccc gtctccttcc tcgccacgat tttgctttca 5940
acgctttagg tttactagtt tggttttctt ttttcaccac tgcgtagacg tgtttagcga 6000
ttttcctttc ttttggaagt cttcataccg tttcgaggtg gatttagcgt tttgagcttg 6060
ggtcttcagc gtcctgcgca cctcgctaaa ggctctctgc cttcccctcg acgaaatggc 6120
gccattgctt tctgaagcca ccgaggcgcg gggtgggggc ggggtggcgg cgctccacga 6180
gctttactgg aacaggcaga gagaacgtag tacaaccgag gcctgggcgg gtggctgaag 6240
gcagcgtcgc tgcaaagaga ccgttttatt tttcataata cgtaagatta cgggtgctgt 6300
agtaaagcac ttgagcatta gtatagtagg aggaagtcaa agtggaaaaa atgggagcgc 6360
tcatcaggaa gctagggagg ctatgttgag tgcagggtta ctttcctttt attgcagaac 6420

-continued

```
ttttatctgc ttaaaggatc ctcggatcga aataattcaa attataagca tttttaaggg   6480

aatcttcgaa tttgttggta aagtcaacgg atccttagca cgtggtgttc actttaagga   6540

agtgaaatag ctgacttttc atagttagcc ttcgcttaaa gcctggttca gtggacgaaa   6600

atccacgtcc tggctatata aaaacttagt ttggggtcac agtgtttgag cgtggtcatt   6660

cggttttttt atttttattt tgtttgaaat tatgatgcat cattacactg ataagcatta   6720

gctttcgaat tgaaaggggt ctccttggtt attttctttg actctaagca cacttataaa   6780

taaaataacc ttgtttataa tcgatagtgg acgtctggta agtttggaaa aaacccgagg   6840

taagtaaaga gcttttgctt tcgttagtga tatgaaaaaa caaggtgtat ttaatacttg   6900

caacttagtt taaggaaagc caatttactg acattttagt agagctacca gaaacactat   6960

ttggagtcct gattaaggct tttgtaacta ttttgactat ttaaaacaat tttggtcgtt   7020

tttattaaac atttcaaaac ctaaaaattg taaacattgg ctttttgagc acattttgga   7080

gaaacttaca aatttaggct atacagtaaa ataacggatt tgttttataa ttttgctttt   7140

tcatttcgtt gtgcagtcat aggtcctgga tagtatgacc taatttatga acatcttgat   7200

aagtttttgt acttagctat tggaaagcca gtattaagtg cctgacaaaa ccagatttaa   7260

ggtgatatct ggagtttcag cattcttcat ggagcttgtt tcagagttgc aggatttttt   7320

tttttcatct tgagatactt acaattaaca ccagaggggg cagctcaggg aaaagcaaat   7380

atgccacttt tcagaaactg aatcttggaa gtggtgaatt tggaaacagg tttttttaaat   7440

ttttttaaa tctaaaaagt agtaaatttt ggacttgggt tgtagaattt aatgaattac   7500

aaaagaattc tttaataccc tttaaatgac ctaagagctg ggtatggttt ttctgaattt   7560

ttttgaagaa aatctaagaa agtttacgtg aattagaagt tagatcgaat attagtgact   7620

ttgaaacttg tatagctcag gcaatttttg gtgtaacaca actaatatgc agtttaacat   7680

atggtttaaa tttgatgtaa gttttttttc tccccccag aaaactttag aaactgttcc   7740

tttggagagg aaaaaggtac tctaccagca ggtcacctca tatttaagaa tttaatttcc   7800

tgcatacaaa gaaagtgtaa ataaaaattg aaatggtatt tccctttgca gagagaaaag   7860

gaacagttcc gaaagctctt tattggtggc ttaagctt                           7898
```